(12) United States Patent
Kharas et al.

(10) Patent No.: US 11,266,677 B2
(45) Date of Patent: Mar. 8, 2022

(54) METHODS FOR TREATMENT OR PREVENTION OF LEUKEMIA

(71) Applicant: MEMORIAL SLOAN KETTERING CANCER CENTER, New York, NY (US)

(72) Inventors: Michael Kharas, New York, NY (US); Ly Vu, New York, NY (US)

(73) Assignee: MEMORIAL SLOAN KETTERING CANCER CENTER, New York, NY (US)

(*) Notice: Subject to any disclaimer, the term of this patent is extended or adjusted under 35 U.S.C. 154(b) by 133 days.

(21) Appl. No.: 16/491,631

(22) PCT Filed: Mar. 8, 2018

(86) PCT No.: PCT/US2018/021626
§ 371 (c)(1),
(2) Date: Sep. 6, 2019

(87) PCT Pub. No.: WO2018/165482
PCT Pub. Date: Sep. 13, 2018

(65) Prior Publication Data
US 2021/0128602 A1  May 6, 2021

Related U.S. Application Data

(60) Provisional application No. 62/470,037, filed on Mar. 10, 2017.

(51) Int. Cl.
| | |
|---|---|
| *C07H 21/02* | (2006.01) |
| *C07H 21/04* | (2006.01) |
| *A61K 31/7105* | (2006.01) |
| *A61P 35/02* | (2006.01) |
| *A61K 45/06* | (2006.01) |
| *C12N 15/113* | (2010.01) |

(52) U.S. Cl.
CPC ......... *A61K 31/7105* (2013.01); *A61K 45/06* (2013.01); *A61P 35/02* (2018.01); *C12N 15/113* (2013.01); *C12N 2310/11* (2013.01); *C12N 2310/14* (2013.01); *C12N 2310/531* (2013.01)

(58) Field of Classification Search
CPC ........... C12N 15/113; C12N 2310/531; C12N 2310/11; C12N 2310/14; C12N 2310/20
See application file for complete search history.

(56) References Cited

U.S. PATENT DOCUMENTS

| | | |
|---|---|---|
| 2014/0010861 A1 | 1/2014 | Bancel et al. |
| 2014/0161721 A1 | 6/2014 | Hatchwell et al. |
| 2016/0298195 A1 | 10/2016 | Armstrong |
| 2016/0313300 A1* | 10/2016 | Trotter ................. C12Q 1/6886 |

OTHER PUBLICATIONS

Elbashir et al. (The EMBO Journal, vol. 20, No. 23, pp. 6877-6888, 2001).*
Siprashvili et al. (Nature Genetics, 48, 1, 2016, 53-61).*
Chen et al., "hnRNP Q Regulates Cdc42-Mediated Neuronal Morphogenesis," Molecular and Cellular Biology, vol. 32, No. 12, pp. 2224-2238 (Apr. 9, 2012).
International Search Report and Written Opinion, PCT/US2018/021626, Memorial Sloan Kettering Cancer Center (Aug. 7, 2018).

* cited by examiner

*Primary Examiner* — Amy H Bowman
(74) *Attorney, Agent, or Firm* — Foley & Lardner LLP

(57) ABSTRACT

The present disclosure relates generally to methods for preventing, ameliorating or treating leukemia. In particular, the present disclosure relates to administering a therapeutically effective amount of at least one agent to reduce the expression of synaptotagmin-binding, cytoplasmic RNA-interacting protein (SYNCRIP) to a subject diagnosed with, or at risk for acute myeloid leukemia (AML).

14 Claims, 124 Drawing Sheets
Specification includes a Sequence Listing.

Figure 15

| Symbol | BM.1 | BM.2 | BM.3 | BM.4 | BM.5 |
|---|---|---|---|---|---|
| Upf1 | 846.1513 | 13176.4116 | 100.3417 | 1108.5996 | 2406.2984 |
| Upf1 | 0.6657 | 0.9252 | 0.9122 | 64.3215 | 0.6821 |
| Bnip3l | 120.4583 | 76912.9716 | 218.357 | 21683.3832 | 186.2719 |
| Bnip3l | 149.3683 | 47031.1781 | 11406.3614 | 2273.1985 | 145307.197 |
| Bnip3l | 84230.8817 | 236.6392 | 138.1235 | 71162.0771 | 53.4752 |
| Bnip3l | 1.4455 | 62.6398 | 0.9141 | 0.8293 | 0.8913 |
| Bnip3l | 1.6061 | 391.4987 | 81.2491 | 36.8577 | 16.0426 |
| Spcs1 | 1461.7888 | 1521.1152 | 7025.4269 | 6902.1075 | 85062.2821 |
| Spcs1 | 0.865 | 0.9018 | 0.9956 | 0.8334 | 1.1102 |
| Cdk6 | 404.9639 | 906.1425 | 22524.9518 | 452.0843 | 64.2147 |
| Cdk6 | 41.0511 | 44.1531 | 0.921 | 15.1009 | 10.8532 |
| Cdk6 | 203.0367 | 699.4256 | 635.5002 | 214.2445 | 2226.7142 |
| Cdk6 | 0.9985 | 0.9031 | 0.921 | 0.8494 | 0.814 |
| Cdk6 | 1034.0447 | 1.0035 | 273.2344 | 0.8494 | 103.1054 |
| Mapk6 | 2309.5875 | 13.92 | 6334.3848 | 700.2962 | 0.8021 |
| Mapk6 | 88.3361 | 0.783 | 9.1405 | 0.8293 | 0.8021 |
| Atr | 0.9611 | 36.0739 | 51649.222 | 1634.3198 | 148805.4266 |
| Atr | 0.865 | 49.1006 | 1.1062 | 860.217 | 5.551 |
| Atr | 0.865 | 0.9018 | 0.9956 | 3093.6331 | 66.6119 |
| Atr | 0.865 | 3598.3695 | 7.7433 | 0.926 | 2904.2787 |
| Atr | 0.865 | 9.0185 | 338.4948 | 2.7779 | 0.9992 |
| Mylk | 1535.442 | 0.783 | 0.9141 | 596.1732 | 6.2388 |
| Mylk | 4248.1634 | 204.4493 | 4.0625 | 0.8293 | 1.7825 |
| Mylk | 12707.5497 | 20.0099 | 17.2654 | 0.8293 | 7.13 |
| Mylk | 1.6061 | 15.6599 | 1.0156 | 836.6697 | 0.8021 |
| Stk17b | 20123.93 | 12827.4857 | 823.7966 | 931.539 | 509.1958 |
| Stk17b | 0.9985 | 0.9031 | 0.921 | 3805.4358 | 28.0374 |
| Stk17b | 924.2052 | 138.4802 | 6.1401 | 790.9115 | 0.814 |
| Stk17b | 6484.9692 | 308166.7222 | 35812.1253 | 345852.9528 | 233866.4966 |
| Stk17b | 0.9985 | 1.0035 | 0.921 | 0.8494 | 0.9044 |
| Gpsm2 | 24.0917 | 112.2296 | 1.0156 | 47408.2128 | 16262.6914 |
| Gpsm2 | 1.6061 | 0.783 | 1515.2962 | 1.8429 | 0.8021 |
| Gpsm2 | 8586.269 | 4472.6556 | 19.2967 | 111.4945 | 1032.9621 |
| Gpsm2 | 49.7894 | 254.0392 | 0.9141 | 2.7643 | 0.8021 |
| Frmd6 | 25243.2455 | 2857.9408 | 1744.8249 | 18515.4641 | 201.4232 |
| Frmd6 | 1027.911 | 28.7099 | 84846.429 | 1705.5899 | 1036.5271 |
| Npepps | 0.9985 | 4.0139 | 21.4903 | 1606.362 | 10.8532 |
| Zcchc3 | 1.1095 | 0.9031 | 0.921 | 0.8494 | 0.9044 |
| Rrm2 | 1.4455 | 0.783 | 0.9141 | 0.8293 | 195.1844 |
| Rrm2 | 2908.6669 | 198.3594 | 1737.7156 | 70.0296 | 1174.6713 |
| Mycn | 17853.5291 | 381.9288 | 834.8347 | 316.0548 | 92550.3736 |
| Mycn | 79520.1583 | 1875.7139 | 22911.2374 | 6318.3307 | 1929.5625 |
| Mycn | 11380.9021 | 13678.9658 | 3644.0232 | 717.8036 | 935.8155 |
| Mycn | 1.6061 | 6.96 | 4631.2001 | 16839.3603 | 1697.8368 |
| Cdkn1a | 0.865 | 0.9018 | 0.9956 | 0.8334 | 0.9992 |
| Cdkn1a | 12338.2277 | 146584.2045 | 101.7697 | 6.4817 | 13.3224 |
| Cdkn1a | 0.865 | 0.9018 | 0.9956 | 0.8334 | 0.9992 |

Figure 15(cont'd)

| Symbol | BM.1 | BM.2 | BM.3 | BM.4 | BM.5 |
|---|---|---|---|---|---|
| Rrm2 | 1.4455 | 9395.0997 | 0.9141 | 3505.167 | 4.4563 |
| Rrm2 | 46.5772 | 58.2898 | 0.9141 | 26.7218 | 0.8021 |
| Rrm2 | 1.4455 | 180.0894 | 1.0156 | 9842.848 | 0.8021 |
| Rpl14 | 0.5408 | 1.0117 | 0.6237 | 0.6211 | 0.7143 |
| Rpl14 | 0.5408 | 0.9105 | 0.6237 | 0.6211 | 0.7143 |
| Rpl14 | 0.5408 | 72.8406 | 0.6237 | 0.6211 | 0.7143 |
| Rpl14 | 0.5408 | 1.0117 | 0.693 | 16.5623 | 0.7143 |
| Cdkn1a | 0.865 | 270.5541 | 7.7433 | 0.8334 | 0.9992 |
| Cdkn1a | 0.9611 | 2467.0525 | 163.7165 | 0.926 | 1.1102 |
| Hnrnpa1 | 1784.5641 | 100510.8957 | 636.1839 | 234432.6768 | 218054.1776 |
| Ilf2 | 513.7381 | 0.9105 | 0.6237 | 0.6211 | 0.7143 |
| Ilf3 | 144.97 | 36711.592 | 8285.7893 | 1360.5885 | 5327.9614 |
| Ilf3 | 0.6657 | 0.9252 | 1.0136 | 381.3885 | 0.6821 |
| Ilf3 | 14.7929 | 4.1118 | 37.5014 | 21.1883 | 0.7579 |
| Ltb | 9039.8325 | 679.3914 | 217.9199 | 0.926 | 4057.7747 |
| Ltb | 0.865 | 680.3934 | 1678.0936 | 120.3748 | 203.1663 |
| Ltb | 1489.6598 | 40119.164 | 4167.0262 | 32141.9312 | 10994.2936 |
| Slc25a24 | 0.865 | 1012.0727 | 0.9956 | 6797.474 | 1784.0886 |
| Slc25a24 | 0.865 | 17.0349 | 0.9956 | 5.5558 | 8.8816 |
| Slc25a24 | 0.9611 | 4860.9552 | 13201.2982 | 23435.1272 | 46864.8001 |
| Slc25a24 | 0.865 | 0.9018 | 0.9956 | 0.8334 | 0.9992 |
| Slc25a24 | 13720.2476 | 209489.0335 | 14.3805 | 323.1601 | 6763.3279 |
| Clcn3 | 0.865 | 1370.8074 | 2202.4288 | 0.8334 | 1942.847 |
| Clcn3 | 0.9611 | 714.4632 | 346.2382 | 0.8334 | 0.9992 |
| Csda | 0.6657 | 1.028 | 38.515 | 509.2748 | 0.7579 |
| Csda | 42405.9396 | 461.5548 | 22568.767 | 2437.4057 | 4739.8394 |
| Csda | 656.0631 | 1497.74 | 912.197 | 0.6811 | 862.478 |
| Csda | 0.6657 | 0.9252 | 0.9122 | 0.6811 | 0.6821 |
| Csda | 1.4793 | 0.9252 | 1750.4047 | 236.0977 | 0.6821 |
| Hnrnpa2b1 | 33570.9066 | 380.3458 | 245.2796 | 10.5941 | 42910.1735 |
| Hnrnpa2b1 | 0.6657 | 321.752 | 0.9122 | 8716.6957 | 19.7051 |
| Hnrnpa2b1 | 6189.3308 | 42.1464 | 132.7753 | 6501.0098 | 616.9218 |
| Ssb | 523.352 | 0.9105 | 0.6237 | 0.6211 | 0.7143 |
| Ssb | 1476.922 | 3.035 | 0.6237 | 155.9613 | 93.656 |
| Ssb | 407.3853 | 2.0233 | 13455.4973 | 1134.5153 | 1.5874 |
| Msi2 | 0.7396 | 292.9691 | 145.9515 | 612.9459 | 297.8505 |
| Msi2 | 1.4793 | 103.8241 | 291.903 | 267.1233 | 1473.3367 |
| Msi2 | 1883.1305 | 547.9035 | 0.9122 | 58128.4568 | 13.642 |
| RFP | 0.9031 | 0.8847 | 0.8733 | 0.7628 | 0.9984 |
| RFP | 0.9031 | 0.8847 | 0.8733 | 0.7628 | 0.9984 |
| RFP | 0.9031 | 0.8847 | 0.8733 | 0.7628 | 0.9984 |
| RFP | 0.9031 | 0.8847 | 0.8733 | 0.7628 | 0.9984 |
| RFP | 0.9031 | 0.8847 | 0.8733 | 0.7628 | 0.9984 |
| RFP | 0.9031 | 0.8847 | 0.8733 | 0.7628 | 0.9984 |
| lacZ | 2004.9536 | 569.2191 | 1882.8936 | 44.0129 | 1.9216 |
| lacZ | 2004.9536 | 569.2191 | 1882.8936 | 44.0129 | 1.9216 |
| lacZ | 2004.9536 | 569.2191 | 1882.8936 | 44.0129 | 1.9216 |
| lacZ | 2004.9536 | 569.2191 | 1882.8936 | 44.0129 | 1.9216 |
| lacZ | 2004.9536 | 569.2191 | 1882.8936 | 44.0129 | 1.9216 |

Figure 15(cont'd)

| Symbol | BM.1 | BM.2 | BM.3 | BM.4 | BM.5 |
|---|---|---|---|---|---|
| lacZ | 2004.9536 | 569.2191 | 1882.8936 | 44.0129 | 1.9216 |
| lacZ | 5163.4602 | 2999.7031 | 513.5229 | 949.1465 | 3058.8926 |
| lacZ | 5163.4602 | 2999.7031 | 513.5229 | 949.1465 | 3058.8926 |
| lacZ | 5163.4602 | 2999.7031 | 513.5229 | 949.1465 | 3058.8926 |
| lacZ | 5163.4602 | 2999.7031 | 513.5229 | 949.1465 | 3058.8926 |
| lacZ | 5163.4602 | 2999.7031 | 513.5229 | 949.1465 | 3058.8926 |
| lacZ | 5163.4602 | 2999.7031 | 513.5229 | 949.1465 | 3058.8926 |
| LUCIFERASE | 6149.914 | 749.7539 | 10.9873 | 343.6663 | 1.1509 |
| LUCIFERASE | 6149.914 | 749.7539 | 10.9873 | 343.6663 | 1.1509 |
| LUCIFERASE | 6149.914 | 749.7539 | 10.9873 | 343.6663 | 1.1509 |
| LUCIFERASE | 6149.914 | 749.7539 | 10.9873 | 343.6663 | 1.1509 |
| LUCIFERASE | 6149.914 | 749.7539 | 10.9873 | 343.6663 | 1.1509 |
| LUCIFERASE | 6149.914 | 749.7539 | 10.9873 | 343.6663 | 1.1509 |
| LUCIFERASE | 23013.5536 | 21168.921 | 373.2051 | 9377.7272 | 56693.9323 |
| LUCIFERASE | 23013.5536 | 21168.921 | 373.2051 | 9377.7272 | 56693.9323 |
| LUCIFERASE | 23013.5536 | 21168.921 | 373.2051 | 9377.7272 | 56693.9323 |
| LUCIFERASE | 23013.5536 | 21168.921 | 373.2051 | 9377.7272 | 56693.9323 |
| LUCIFERASE | 23013.5536 | 21168.921 | 373.2051 | 9377.7272 | 56693.9323 |
| LUCIFERASE | 23013.5536 | 21168.921 | 373.2051 | 9377.7272 | 56693.9323 |
| LUCIFERASE | 16987.9402 | 3632.376 | 31050.8723 | 8936.2058 | 7518.0908 |
| LUCIFERASE | 16987.9402 | 3632.376 | 31050.8723 | 8936.2058 | 7518.0908 |
| LUCIFERASE | 16987.9402 | 3632.376 | 31050.8723 | 8936.2058 | 7518.0908 |
| LUCIFERASE | 16987.9402 | 3632.376 | 31050.8723 | 8936.2058 | 7518.0908 |
| LUCIFERASE | 16987.9402 | 3632.376 | 31050.8723 | 8936.2058 | 7518.0908 |
| LUCIFERASE | 16987.9402 | 3632.376 | 31050.8723 | 8936.2058 | 7518.0908 |
| LUCIFERASE | 493.3644 | 2942.9214 | 67.5411 | 696.0734 | 2292.8136 |
| LUCIFERASE | 493.3644 | 2942.9214 | 67.5411 | 696.0734 | 2292.8136 |
| LUCIFERASE | 493.3644 | 2942.9214 | 67.5411 | 696.0734 | 2292.8136 |
| LUCIFERASE | 493.3644 | 2942.9214 | 67.5411 | 696.0734 | 2292.8136 |
| LUCIFERASE | 493.3644 | 2942.9214 | 67.5411 | 696.0734 | 2292.8136 |
| LUCIFERASE | 493.3644 | 2942.9214 | 67.5411 | 696.0734 | 2292.8136 |
| LUCIFERASE | 27109.0901 | 4769.9831 | 7796.2666 | 57389.3186 | 55493.3215 |
| LUCIFERASE | 27109.0901 | 4769.9831 | 7796.2666 | 57389.3186 | 55493.3215 |
| LUCIFERASE | 27109.0901 | 4769.9831 | 7796.2666 | 57389.3186 | 55493.3215 |
| LUCIFERASE | 27109.0901 | 4769.9831 | 7796.2666 | 57389.3186 | 55493.3215 |
| LUCIFERASE | 27109.0901 | 4769.9831 | 7796.2666 | 57389.3186 | 55493.3215 |
| LUCIFERASE | 27109.0901 | 4769.9831 | 7796.2666 | 57389.3186 | 55493.3215 |
| Zyx | 7.2104 | 0.9105 | 0.6237 | 4.8307 | 8032.1923 |
| Zyx | 105.7519 | 8.0934 | 1838.5576 | 63335.4887 | 119.8479 |
| Zyx | 97.9407 | 35.4086 | 0.6237 | 4063.9662 | 38.0974 |
| Atp5a1 | 516.2707 | 0.9252 | 8.1084 | 3.7836 | 48.5049 |
| Atp5a1 | 0.7396 | 225.1236 | 23.3117 | 56.7542 | 1.5158 |
| Atp5a1 | 0.6657 | 0.9252 | 31.4201 | 401.0633 | 138.6937 |
| Atp5a1 | 0.6657 | 17.4753 | 0.9122 | 0.6811 | 0.6821 |
| Acox1 | 1875.9376 | 43691.2589 | 78.2023 | 518.7721 | 1415.3096 |
| Acox1 | 342.1016 | 0.783 | 33989.5554 | 0.8293 | 4.4563 |
| Acox1 | 9.6367 | 14.79 | 9.1405 | 125.3162 | 8.0213 |
| Acox1 | 1.6061 | 50871.3457 | 6267.3543 | 2.7643 | 2403.709 |
| Acox1 | 1376.4371 | 9381.1797 | 127.9674 | 1407.964 | 6310.0704 |

Figure 15(cont'd)

| Symbol | BM.1 | BM.2 | BM.3 | BM.4 | BM.5 |
|---|---|---|---|---|---|
| Ybx1 | 75.7088 | 12.1401 | 0.6237 | 701.136 | 0.7143 |
| Ybx1 | 28167.8716 | 6149.9707 | 81349.7632 | 2070.2834 | 77.7821 |
| Peli1 | 0.9985 | 0.9031 | 0.921 | 0.8494 | 0.814 |
| Dyrk2 | 0.9985 | 0.9031 | 0.921 | 0.8494 | 0.814 |
| Dyrk2 | 616.8765 | 0.9031 | 20.467 | 11.3257 | 0.9044 |
| Dyrk2 | 0.9985 | 0.9031 | 0.921 | 0.8494 | 0.814 |
| Dyrk2 | 0.9985 | 0.9031 | 0.921 | 0.8494 | 0.814 |
| Dyrk2 | 0.9985 | 0.9031 | 185.2263 | 12.2695 | 42.5084 |
| Slc19a2 | 27.8711 | 50.1026 | 9.9557 | 10.1856 | 0.9992 |
| Slc19a2 | 1441.6063 | 4646.5161 | 0.9956 | 0.8334 | 114.3504 |
| Slc19a2 | 0.9611 | 0.9018 | 0.9956 | 0.8334 | 1.1102 |
| Slc40a1 | 1.6061 | 249.6892 | 0.9141 | 1653.9892 | 0.8021 |
| Ppp2r5c | 0.9985 | 714.4778 | 61.401 | 0.8494 | 0.9044 |
| Ppp2r5c | 23891.7582 | 40496.4417 | 433.9003 | 317.1196 | 2103.7113 |
| Ppp2r5c | 1006.3075 | 11.0383 | 223512.8937 | 253.8845 | 215.2551 |
| Ppp2r5c | 22.1898 | 53.1844 | 4.0934 | 0.8494 | 188.1221 |
| Mtmr9 | 1.1095 | 1268.3988 | 38.8873 | 569.1165 | 42754.3605 |
| E2f7 | 14.4234 | 80.2784 | 383.7562 | 0.8494 | 9897.2112 |
| E2f7 | 17.7518 | 0.9031 | 10.2335 | 0.8494 | 1709.3785 |
| E2f7 | 79.8833 | 0.9031 | 382.7328 | 48.1342 | 18.9931 |
| E2f7 | 130.9198 | 8123.1712 | 796.1661 | 25437.526 | 2760.3298 |
| E2f7 | 0.9985 | 308.0684 | 17.3969 | 0.9438 | 0.814 |
| Dst | 65.4599 | 0.9031 | 66.5177 | 271.8168 | 3505.5826 |
| Dst | 3381.7256 | 1.0035 | 2433.5258 | 19590.6325 | 20113.6872 |
| Krt6b | 3444.7494 | 0.9105 | 0.6237 | 0.6211 | 0.7143 |
| Krt6b | 1047.3048 | 0.9105 | 0.6237 | 26.9137 | 0.7143 |
| Krt6b | 11.4164 | 2.0233 | 0.6237 | 5.5208 | 0.7937 |
| Krt6b | 35.4509 | 132.5294 | 0.6237 | 383.0024 | 0.7143 |
| Krt6b | 285.4101 | 228.6385 | 0.693 | 12365.8025 | 472.2485 |
| Anln | 17800.5274 | 339.2989 | 10.1561 | 472.7 | 18.7163 |
| Anln | 11279.7171 | 3411.259 | 1710.2941 | 9664.0882 | 73580.0559 |
| Anln | 75.4872 | 5413.1225 | 1.0156 | 1688.0825 | 21053.1757 |
| Tubb2c | 0.5408 | 0.9105 | 0.6237 | 104.8944 | 11.9054 |
| Tubb2c | 0.5408 | 1936.3454 | 0.693 | 2685.1575 | 61.9082 |
| Tubb2c | 0.6009 | 224.5918 | 0.693 | 15.8722 | 373.8303 |
| Tubb2c | 0.5408 | 0.9105 | 0.6237 | 27.6038 | 0.7143 |
| Tubb2c | 0.5408 | 0.9105 | 0.6237 | 0.6211 | 0.7143 |
| Tjp1 | 0.865 | 39.08 | 65.2653 | 234.2679 | 979.1949 |
| Tjp1 | 0.865 | 1.0021 | 0.9956 | 0.8334 | 12.2122 |
| Tjp1 | 0.9611 | 20.041 | 0.9956 | 0.8334 | 0.9992 |
| Eps8 | 1.4455 | 0.783 | 0.9141 | 0.8293 | 0.8913 |
| Mybbp1a | 17181.0638 | 0.9018 | 402.654 | 0.926 | 0.9992 |
| Mybbp1a | 0.865 | 0.9018 | 0.9956 | 0.8334 | 153.2074 |
| Mybbp1a | 0.865 | 0.9018 | 0.9956 | 6817.8451 | 22.204 |
| Igf2bp3 | 0.865 | 0.9018 | 0.9956 | 0.8334 | 0.9992 |
| Igf2bp3 | 0.865 | 0.9018 | 0.9956 | 0.8334 | 0.9992 |
| Igf2bp3 | 0.865 | 1208.475 | 2642.6933 | 23.149 | 0.9992 |
| Igf2bp3 | 0.9611 | 1524.1214 | 542.0342 | 1.8519 | 8960.4103 |
| Igf2bp3 | 0.865 | 13.0267 | 721.2373 | 94.4479 | 13067.0338 |

Figure 15(cont'd)

| Symbol | BM.1 | BM.2 | BM.3 | BM.4 | BM.5 |
|---|---:|---:|---:|---:|---:|
| Mov10 | 16331.3126 | 0.9252 | 126309.8895 | 158366.2949 | 178.8619 |
| Mov10 | 1125.7363 | 0.9252 | 138.8567 | 2.2702 | 3196.019 |
| Mov10 | 0.6657 | 0.9252 | 0.9122 | 0.6811 | 0.6821 |
| Ube2k | 1.4455 | 0.783 | 0.9141 | 114.2589 | 0.8021 |
| Ube2k | 94.7605 | 0.87 | 2525.8321 | 15404.6745 | 2607.8059 |
| Ablim1 | 1988.3653 | 999.6268 | 26.406 | 387.0058 | 4184.4323 |
| Ablim1 | 53.0017 | 66560.875 | 2003.8065 | 151.1166 | 191.6194 |
| Ablim1 | 64.2444 | 7008.6974 | 10329.8105 | 11.0573 | 163.9905 |
| Ablim1 | 5202.1933 | 1142.3063 | 40571.7501 | 1104.8095 | 8427.6873 |
| Ablim1 | 9949.8572 | 325.3789 | 11.1718 | 1280.805 | 587.3357 |
| Mrpl22 | 0.6009 | 1.0117 | 586.9801 | 0.6211 | 0.7143 |
| Mrpl22 | 2949.0372 | 4932.926 | 5.5441 | 4443.5182 | 16.6676 |
| Atp10d | 464.1972 | 0.9018 | 23332.913 | 51.8538 | 0.9992 |
| Atp10d | 0.865 | 453.9296 | 19.9115 | 7432.6827 | 10716.744 |
| Atp10d | 86254.1879 | 8691.8008 | 71774.1775 | 21035.0383 | 19539.4898 |
| Atp10d | 0.865 | 961.9701 | 4361.716 | 4170.5248 | 0.9992 |
| Atp10d | 0.865 | 23.0472 | 21780.9253 | 108151.2278 | 3378.3334 |
| Caprin1 | 33335.7002 | 25.699 | 439.8817 | 354.9032 | 462.3124 |
| Caprin1 | 0.7396 | 0.9252 | 1.0136 | 8882.4181 | 29.5577 |
| Caprin1 | 0.6657 | 0.9252 | 0.9122 | 0.6811 | 0.6821 |
| Stau1 | 0.6657 | 1497.74 | 35.4743 | 0.7567 | 15.9157 |
| Stau1 | 6798.0568 | 402.9609 | 29.393 | 103.6711 | 0.6821 |
| Stau2 | 828.3999 | 1.028 | 1849.7328 | 2801.3896 | 39535.2926 |
| Stau2 | 188833.0212 | 22.6152 | 1.0136 | 3368.1754 | 0.7579 |
| Stau2 | 1653.1016 | 0.9252 | 6299.227 | 416.9545 | 2744.317 |
| Prpf19 | 0.6657 | 391.6534 | 1.0136 | 20.4315 | 18.1893 |
| Prpf19 | 0.6657 | 2.0559 | 0.9122 | 4575.1491 | 13.642 |
| Prpf19 | 0.7396 | 1.028 | 1.0136 | 0.7567 | 0.7579 |
| Prpf19 | 0.7396 | 0.9252 | 0.9122 | 0.6811 | 0.7579 |
| Prpf19 | 102.0707 | 0.9252 | 7.0949 | 10.5941 | 0.7579 |
| Pura | 14969.3079 | 26.3035 | 1486.5081 | 0.6211 | 0.7143 |
| Pura | 54.6786 | 1.0117 | 977.1452 | 621.7751 | 0.7143 |
| Pura | 0.5408 | 39.4553 | 2.772 | 4.1406 | 0.7937 |
| Pura | 97131.3583 | 502444.2061 | 502.4328 | 320.2038 | 196.0426 |
| Pura | 649.5332 | 22414.6652 | 443.5269 | 6824.344 | 49.2091 |
| Hnrnpab | 1105.2315 | 0.9018 | 0.9956 | 0.8334 | 0.9992 |
| Hnrnpab | 0.865 | 0.9018 | 0.9956 | 0.8334 | 7.7714 |
| Hnrnpab | 0.865 | 1.0021 | 0.9956 | 0.8334 | 0.9992 |
| Hnrnpab | 0.865 | 0.9018 | 0.9956 | 0.8334 | 333.0595 |
| Hnrnpab | 1.9221 | 0.9018 | 0.9956 | 0.8334 | 18943.3133 |
| Ddx56 | 0.6657 | 41.1185 | 0.9122 | 0.6811 | 0.6821 |
| Ddx21 | 213.0171 | 1.028 | 112548.8912 | 21.1883 | 0.6821 |
| Ddx21 | 0.6657 | 0.9252 | 35.4743 | 0.7567 | 0.6821 |
| Ddx21 | 245.5614 | 1034.1294 | 1776.757 | 9.0807 | 0.6821 |
| Rbmx | 24.6354 | 0.9105 | 81.0823 | 4.8307 | 4328.8119 |
| Rbmx | 2038.1284 | 31.3619 | 28.4134 | 136273.6418 | 749.248 |
| Rbmx | 21.0302 | 0.9105 | 180.1828 | 13.1118 | 61.1145 |
| Rbmx | 0.5408 | 2.0233 | 1.386 | 676.9827 | 0.7143 |
| Rbmx | 95.5373 | 929.7291 | 0.6237 | 10740.6301 | 688.1335 |

Figure 15(cont'd)

| Symbol | BM.1 | BM.2 | BM.3 | BM.4 | BM.5 |
|---|---|---|---|---|---|
| Rps24 | 147.8124 | 304.5141 | 2.079 | 41517.4625 | 21758.3517 |
| Rps24 | 0.6009 | 0.9105 | 0.6237 | 0.6901 | 0.7143 |
| Rps24 | 0.5408 | 1.0117 | 0.6237 | 0.6211 | 0.7937 |
| Rpl24 | 0.6657 | 0.9252 | 0.9122 | 1.5134 | 0.6821 |
| Rpl24 | 0.7396 | 1.028 | 7919.8969 | 2.2702 | 0.6821 |
| Rpl24 | 0.6657 | 1.028 | 0.9122 | 0.6811 | 0.6821 |
| Rpl24 | 0.6657 | 0.9252 | 0.9122 | 0.6811 | 0.6821 |
| Rpl24 | 0.6657 | 0.9252 | 1.0136 | 0.6811 | 0.6821 |
| Mrpl4 | 0.865 | 0.9018 | 0.9956 | 393.5331 | 51.0691 |
| Mrpl4 | 0.865 | 449.9214 | 0.9956 | 0.8334 | 0.9992 |
| Mrpl4 | 861.1195 | 24.0493 | 0.9956 | 12.0375 | 11633.7678 |
| Rpl26 | 0.5408 | 0.9105 | 0.6237 | 0.6211 | 0.7143 |
| Rpl26 | 0.5408 | 2.0233 | 0.6237 | 0.6211 | 1134.9837 |
| Rpl26 | 0.5408 | 0.9105 | 0.6237 | 0.6211 | 0.7937 |
| Rpl26 | 0.5408 | 0.9105 | 0.6237 | 0.6211 | 0.7143 |
| Rpl26 | 19.2276 | 55690.6703 | 54.7479 | 0.6901 | 9.5243 |
| Rps11 | 0.865 | 0.9018 | 0.9956 | 0.8334 | 0.9992 |
| Mrpl39 | 1.2017 | 322.7242 | 0.6237 | 162.8623 | 59.5271 |
| Mrpl39 | 0.6009 | 0.9105 | 0.6237 | 0.6211 | 7.9369 |
| Mrpl39 | 240483.5267 | 200.3116 | 39.5016 | 15.8722 | 48.4154 |
| Mrpl39 | 329.874 | 835.6433 | 2365.2458 | 19989.2759 | 38137.8331 |
| Rpl4 | 0.6009 | 0.9105 | 0.693 | 0.6211 | 0.7143 |
| Rpl4 | 0.5408 | 0.9105 | 0.693 | 0.6211 | 0.7143 |
| Rpl4 | 0.5408 | 0.9105 | 1.386 | 0.6211 | 0.7143 |
| Rpl4 | 0.5408 | 1.0117 | 0.6237 | 0.6211 | 0.7143 |
| Rpl4 | 0.5408 | 0.9105 | 0.6237 | 0.6211 | 0.7143 |
| Mrps9 | 476.33 | 2196.7539 | 99338.2518 | 1282.646 | 30223.8653 |
| Mrps9 | 1379.4338 | 791.5304 | 501.7083 | 1334.1032 | 3968.3081 |
| Rpl18 | 242.6028 | 13.3635 | 6351.9317 | 11.3508 | 0.6821 |
| Rpl18 | 0.6657 | 1.028 | 0.9122 | 0.6811 | 0.7579 |
| Rpl18 | 0.6657 | 0.9252 | 0.9122 | 0.6811 | 29.5577 |
| Rpl18 | 0.6657 | 0.9252 | 0.9122 | 0.6811 | 3226.3345 |
| Numb | 65404.0493 | 4226.4463 | 108.6707 | 0.9214 | 262.9196 |
| Numb | 72.275 | 8.7 | 0.9141 | 387.0058 | 298.5697 |
| Numb | 1.6061 | 64.3798 | 0.9141 | 0.8293 | 0.8021 |
| Snx14 | 1.1095 | 731.537 | 1602.5657 | 249.1654 | 101.2965 |
| Snx14 | 0.9985 | 0.9031 | 0.921 | 11.3257 | 47.0305 |
| Snx14 | 38.8322 | 145.5046 | 14.3269 | 66.0666 | 1931.8691 |
| Snx14 | 0.9985 | 0.9031 | 412.41 | 6.6067 | 15.3754 |
| Numbl | 6905.2942 | 17202.2302 | 13283.1565 | 16005.2224 | 2844.328 |
| Smc4 | 0.9985 | 30.1044 | 2449.8994 | 17.9324 | 927.0439 |
| Smc4 | 138969.1728 | 363334.0425 | 43102.469 | 793.7429 | 5337.964 |
| Ptbp1 | 5724.8351 | 1649.8783 | 4062.3172 | 8035.6447 | 517.6384 |
| Ptbp1 | 37.7218 | 52.426 | 24.3253 | 0.6811 | 253.135 |
| Crot | 4.8183 | 20.0099 | 2.0312 | 0.8293 | 838.669 |
| Crot | 14.455 | 26.0999 | 2354.1934 | 3.6858 | 0.8913 |
| Abcc5 | 63706.3901 | 47660.1861 | 269.1377 | 5391.3596 | 6842.1484 |
| Abcc5 | 25429.5544 | 852.5972 | 52188.3436 | 1771.0123 | 687.156 |
| Abcc5 | 1.4455 | 5.22 | 126.9518 | 19862.6129 | 141.7092 |

Figure 15(cont'd)

| Symbol | BM.1 | BM.2 | BM.3 | BM.4 | BM.5 |
|---|---|---|---|---|---|
| Pdia6 | 94.9364 | 105218.2182 | 428.2807 | 89.7123 | 34.9226 |
| Pdia6 | 116491.7754 | 1245.3716 | 2791.4474 | 10289.3083 | 73137.3965 |
| Pdia6 | 0.5408 | 51255.4883 | 410.2624 | 89.7123 | 4558.9834 |
| Pdia6 | 0.6009 | 0.9105 | 0.6237 | 0.6211 | 0.7937 |
| Hnrnpl | 35.5596 | 89.1826 | 5.531 | 298801.8075 | 3497.1246 |
| Syncrip | 6.6095 | 0.9105 | 3217.649 | 4.1406 | 0.7143 |
| Syncrip | 0.5408 | 0.9105 | 0.6237 | 0.6211 | 0.7143 |
| Hnrnpc | 1425.2478 | 1992.9992 | 0.693 | 193.9165 | 483.3602 |
| Hnrnpc | 0.5408 | 149.7279 | 177.4108 | 364.3699 | 0.7143 |
| Hnrnpc | 0.6009 | 0.9105 | 0.6237 | 129.7378 | 0.7937 |
| Hnrnpc | 58.8846 | 51.5954 | 0.6237 | 140.0892 | 0.7143 |
| Hnrnpr | 0.865 | 0.9018 | 0.9956 | 99.0777 | 281.9904 |
| Hnrnpr | 0.865 | 0.9018 | 0.9956 | 89.8181 | 0.9992 |
| Hnrnpa3 | 7992.6839 | 32.3736 | 0.6237 | 0.6901 | 0.7937 |
| Hnrnpa3 | 14.4207 | 217.5101 | 0.6237 | 0.6211 | 20.6361 |
| Hnrnpa3 | 3231.4429 | 3.035 | 6.9301 | 24.1533 | 0.7143 |
| Hnrnpa3 | 0.5408 | 21.2452 | 0.6237 | 35.1948 | 0.7143 |
| Hnrnpa3 | 1530.9997 | 0.9105 | 0.6237 | 0.6211 | 9.5243 |
| Asph | 1.4455 | 111.3596 | 0.9141 | 2.7643 | 0.8021 |
| Asph | 611.9283 | 0.783 | 0.9141 | 0.8293 | 0.8021 |
| Kif21a | 893.1395 | 0.9031 | 0.921 | 1.8876 | 4.5222 |
| Kif21a | 2.219 | 0.9031 | 1.0233 | 993.8303 | 0.814 |
| Cltc | 0.9985 | 2.007 | 6.1401 | 544.5775 | 1.8089 |
| Ap3s1 | 7006.2066 | 911.8675 | 0.9956 | 272.2323 | 583.9643 |
| Ap3s1 | 0.865 | 1705.4928 | 4.4248 | 0.8334 | 81.0445 |
| Crbn | 3461.1691 | 6344.0195 | 94.4521 | 9715.6889 | 60.6052 |
| Crbn | 1.4455 | 0.783 | 0.9141 | 0.8293 | 3.565 |
| Crbn | 1084.1249 | 802.1374 | 1734.6688 | 214.6961 | 57.9314 |
| Abca1 | 28867.8209 | 950.2956 | 17.3969 | 1277.9167 | 5519.7551 |
| Abca1 | 1471.1838 | 9.0313 | 129.9654 | 1.8876 | 12.6621 |
| Mrpl38 | 1279.1853 | 13137.9064 | 2225.6588 | 10029.0752 | 2950.907 |
| Mrpl38 | 4616.9844 | 2335.7837 | 0.9956 | 226.8603 | 48002.7533 |
| Mrpl38 | 0.865 | 10.0205 | 0.9956 | 0.8334 | 0.9992 |
| Cct3 | 0.7396 | 0.9252 | 0.9122 | 0.6811 | 0.6821 |
| Cct3 | 1974.8462 | 2401.3183 | 202.7104 | 511.5449 | 30882.4711 |
| Cct3 | 0.6657 | 0.9252 | 653.7412 | 0.7567 | 0.6821 |
| Sepp1 | 8371.1022 | 7.0244 | 0.921 | 6.6067 | 3219.7818 |
| Sepp1 | 210.8031 | 69493.0017 | 530.0952 | 51951.9375 | 774.1947 |
| Sepp1 | 13914.1144 | 40.1392 | 5175.0798 | 47405.6121 | 151.0403 |
| Sepp1 | 55.4745 | 1.0035 | 3219.4584 | 0.8494 | 165.5113 |
| Tmem50b | 0.9985 | 2.007 | 101.3116 | 5.6629 | 0.9044 |
| Tmem50b | 280.701 | 0.9031 | 140.1989 | 0.8494 | 0.814 |
| Aqp11 | 146030.8181 | 450.6585 | 159.4514 | 15589.8844 | 75195.0061 |
| Mrpl37 | 0.7396 | 89.4327 | 165.209 | 490.3567 | 4.5473 |
| Lst1 | 4531.1573 | 0.9031 | 0.921 | 22.6514 | 186.3132 |
| Lst1 | 24.4088 | 27.094 | 21.4903 | 18.8762 | 87.73 |
| Aqp11 | 1318.6171 | 21.7499 | 183.8261 | 23.0361 | 43.6714 |
| Mrpl37 | 81.3607 | 0.9252 | 0.9122 | 55.2408 | 0.6821 |
| Fastkd2 | 0.865 | 35.0718 | 178.097 | 13210.6745 | 43.2977 |

Figure 15(cont'd)

| Symbol | BM.1 | BM.2 | BM.3 | BM.4 | BM.5 |
|---|---|---|---|---|---|
| Fastkd2 | 0.865 | 13.0267 | 124378.0434 | 366.6802 | 345.2717 |
| Fastkd2 | 0.865 | 0.9018 | 0.9956 | 0.8334 | 0.9992 |
| Cyb5 | 1.4455 | 165.2995 | 0.9141 | 281.0399 | 0.8021 |
| Mrpl37 | 0.7396 | 78.1251 | 1.0136 | 32340.0836 | 139.4516 |
| Cyb5 | 73903.5884 | 14347.1237 | 2770.5951 | 283.8043 | 74.8652 |
| Ptcd3 | 15.0216 | 3401.2504 | 384065.1874 | 167.693 | 8884.6206 |
| Ptcd3 | 84.7217 | 0.9105 | 10033.41 | 13941.2881 | 0.7143 |
| Snx16 | 3.2122 | 3.48 | 2.0312 | 217776.4673 | 123.8842 |
| Snx16 | 19.2733 | 31444.3084 | 10.1561 | 0.8293 | 137.2529 |
| Tax1bp1 | 1.4455 | 0.783 | 0.9141 | 0.8293 | 0.8021 |
| Tax1bp1 | 1.4455 | 0.783 | 43.6714 | 1705.5899 | 0.8913 |
| Tax1bp1 | 16.0611 | 809.0974 | 222.4195 | 4607.2121 | 84.669 |
| Mrps27 | 0.5408 | 10.1167 | 0.6237 | 4828.5909 | 60.3208 |
| Snx16 | 1.4455 | 58.2898 | 0.9141 | 2.7643 | 0.8021 |
| Mrps27 | 101.5459 | 9699.9373 | 67568.5509 | 353.3284 | 20.6361 |
| Mrps27 | 0.5408 | 0.9105 | 0.6237 | 0.6211 | 188.8994 |
| Rabep1 | 163.095 | 0.9031 | 0.921 | 8.4943 | 35.2729 |
| Mrps28 | 85.0589 | 2.0559 | 116756.1464 | 1136.5984 | 39511.0402 |
| Fcho2 | 0.865 | 0.9018 | 1695.7927 | 2.7779 | 0.9992 |
| Baz2b | 1.1095 | 102622.8962 | 157.5959 | 59049.3772 | 134.7605 |
| Fcho2 | 1428.1513 | 598.2252 | 528.7599 | 15182.9697 | 3952.3059 |
| Fcho2 | 0.865 | 338.6936 | 32.0796 | 429.6455 | 2001.6875 |
| Rabep1 | 369.4602 | 6.0209 | 60685.6648 | 13407.7432 | 330932.9679 |
| Paip1 | 2538.1882 | 54962.5633 | 18785.3567 | 1013.0005 | 14861.1142 |
| Ttc3 | 781.081 | 36.1253 | 753.1854 | 46.2466 | 2753.9987 |
| Mrps28 | 250.7389 | 6.1678 | 14.1897 | 504.7344 | 21.2209 |
| Fcho2 | 0.865 | 0.9018 | 0.9956 | 0.8334 | 0.9992 |
| Baz2b | 45851.8942 | 60.2088 | 43058.465 | 18.8762 | 17161.6177 |
| Fcho2 | 48775.3074 | 72469.4174 | 90.7078 | 176.8584 | 17480.0719 |
| Baz2b | 4756.3837 | 1144.9708 | 45311.8812 | 9061.5052 | 35281.03 |
| Ict1 | 183692.5039 | 71868.9061 | 218579.6282 | 169138.2511 | 123635.9888 |
| Ict1 | 727.0689 | 0.9252 | 0.9122 | 0.6811 | 0.6821 |
| Sertad2 | 5037.9335 | 79.1621 | 1.1062 | 0.8334 | 0.9992 |
| Ict1 | 72.485 | 10126.4496 | 39.5285 | 14598.7059 | 29.5577 |
| Fastkd2 | 0.865 | 79.1621 | 613.9367 | 154.6354 | 54.3997 |
| Mrpl37 | 0.6657 | 2.0559 | 51.6912 | 241.3947 | 13.642 |
| Ptcd3 | 0.5408 | 27.3152 | 8.3161 | 86.2618 | 0.7143 |
| Aqp11 | 3170.463 | 16241.1075 | 13812.3511 | 7421.2973 | 434.9314 |
| Aqp11 | 70.6689 | 0.783 | 353.4337 | 5.5287 | 48.1277 |
| Mrps27 | 0.5408 | 0.9105 | 0.6237 | 0.6211 | 0.7143 |
| Mrps27 | 69.7001 | 64.7472 | 17.3253 | 17.9425 | 184.9309 |
| Tax1bp1 | 112.4278 | 956.1269 | 10167.3123 | 7612.9573 | 36.5414 |
| Ttc3 | 58.803 | 19.0661 | 1.0233 | 1.8876 | 126.6206 |
| Paip1 | 20177.6828 | 35152.9933 | 38162.5262 | 7134.5235 | 63564.4026 |
| Baz2b | 1264.8186 | 2.007 | 2.0467 | 64.179 | 33.464 |
| Mrps28 | 20780.264 | 133.635 | 531.1014 | 122382.5887 | 1211.107 |
| Mrpl37 | 75648.4448 | 8196.9657 | 37522.7162 | 67727.4918 | 105123.0282 |
| Cyb5 | 1.4455 | 25.2299 | 0.9141 | 0.8293 | 0.8021 |
| Sertad2 | 25594.2782 | 39466.8281 | 16.5929 | 1008.3707 | 567.3113 |

Figure 15(cont'd)

| Symbol | BM.1 | BM.2 | BM.3 | BM.4 | BM.5 |
|---|---|---|---|---|---|
| Sertad2 | 0.865 | 0.9018 | 8.8495 | 0.8334 | 11.102 |
| Tax1bp1 | 1068.0638 | 4318.6661 | 11.1718 | 104.123 | 1028.5058 |
| Ybx1 | 1.2017 | 2.0233 | 10.3952 | 2.7604 | 13285.6587 |
| Trip11 | 28.8467 | 0.9031 | 0.921 | 209.5255 | 0.814 |
| Trip11 | 93.1972 | 0.9031 | 0.921 | 25009.9808 | 53.3616 |
| Trip11 | 24520.839 | 119.4141 | 0.921 | 0.8494 | 117.5763 |
| Trip11 | 0.9985 | 61.2123 | 612.9865 | 0.8494 | 0.814 |
| Trip11 | 158.6571 | 1.0035 | 107.4517 | 619.1384 | 132.0472 |
| Sertad2 | 794.8056 | 0.9018 | 0.9956 | 93.522 | 0.9992 |
| Sertad2 | 0.865 | 1265.5919 | 6662.5959 | 1483.3883 | 2523.4807 |
| Mybbp1a | 0.865 | 0.9018 | 0.9956 | 0.8334 | 1.1102 |
| Mybbp1a | 0.9611 | 0.9018 | 0.9956 | 0.8334 | 0.9992 |
| Mybbp1a | 0.865 | 0.9018 | 0.9956 | 0.8334 | 8.8816 |
| Gpr65 | 1.4455 | 0.783 | 0.9141 | 66.3439 | 5.3475 |
| Gpr65 | 1.4455 | 0.783 | 425.5423 | 0.8293 | 1.7825 |
| Gpr65 | 6355.381 | 8259.7533 | 42.6558 | 15727.1793 | 230.8345 |
| Gpr65 | 6601.1159 | 8303.2532 | 62.9681 | 13809.6576 | 31.1939 |
| Gpr65 | 72997.7418 | 85.2597 | 6629.9285 | 48.8364 | 0.8913 |
| Mll3 | 0.9985 | 0.9031 | 0.921 | 0.8494 | 0.814 |
| Mll3 | 34.3942 | 0.9031 | 0.921 | 0.8494 | 0.814 |
| Mll3 | 0.9985 | 0.9031 | 480.9744 | 0.8494 | 2.7133 |
| Mll3 | 0.9985 | 0.9031 | 0.921 | 0.8494 | 0.814 |
| Mll3 | 0.9985 | 0.9031 | 0.921 | 0.8494 | 0.814 |
| Cenpf | 12.8489 | 221.8493 | 12802.8307 | 16.586 | 4480.3283 |
| Cenpf | 3734.2079 | 817.7974 | 4.0625 | 33.1719 | 5.3475 |
| Cenpf | 1.6061 | 0.783 | 0.9141 | 0.8293 | 0.8021 |
| Cenpf | 101.185 | 2434.2521 | 4.0625 | 382.3986 | 2.6738 |
| Cenpf | 1.6061 | 21.7499 | 558.5877 | 0.8293 | 1.7825 |
| Mns1 | 0.865 | 0.9018 | 0.9956 | 0.8334 | 0.9992 |
| Mns1 | 0.865 | 42.0862 | 47.5663 | 187.044 | 198.7255 |
| Mns1 | 0.865 | 0.9018 | 0.9956 | 666.6914 | 0.9992 |
| Mrps22 | 26641.6788 | 23242.2152 | 22749.4648 | 89169.1746 | 1320.7083 |
| Mrps22 | 0.5408 | 20.2335 | 155.2344 | 0.6901 | 0.7143 |
| Mrps22 | 11412.7979 | 111.2842 | 100528.1435 | 4102.6115 | 296.0482 |
| Mrps22 | 0.5408 | 0.9105 | 0.6237 | 0.6211 | 0.7143 |
| Mrps22 | 0.5408 | 0.9105 | 0.6237 | 0.6211 | 56.3523 |
| Mrps23 | 27740.3025 | 356.7027 | 4985.6633 | 6.0538 | 0.6821 |
| Mrps23 | 3170.109 | 0.9252 | 0.9122 | 0.6811 | 0.6821 |
| Mrps23 | 0.6657 | 0.9252 | 0.9122 | 0.6811 | 0.7579 |
| Mrps23 | 0.6657 | 1071.136 | 334.4722 | 4259.5954 | 0.6821 |
| Mrps23 | 0.6657 | 3509.4608 | 0.9122 | 0.6811 | 0.6821 |
| Cep70 | 530.0166 | 63.5098 | 1503.1088 | 53697.0574 | 37.4326 |
| Cep70 | 1.4455 | 0.783 | 10.1561 | 891.9563 | 44.5626 |
| Cep70 | 72.275 | 46.1099 | 223.4351 | 406.3561 | 263.8109 |
| Cep70 | 1.4455 | 11.31 | 19324.0885 | 372.2627 | 0.8021 |
| Cep70 | 443.2866 | 1206.6861 | 1001.3955 | 0.8293 | 21.3901 |
| Rwdd4a | 1821.3298 | 2751.8011 | 75.1554 | 849.5699 | 476.8203 |
| Rwdd4a | 9390.9306 | 11.31 | 0.9141 | 269.0612 | 6.2388 |
| Rwdd4a | 518.7738 | 109676.1957 | 85.3116 | 2439.0581 | 25374.861 |

Figure 15(cont'd)

| Symbol | BM.1 | BM.2 | BM.3 | BM.4 | BM.5 |
|---|---|---|---|---|---|
| Rwdd4a | 21467.2787 | 10420.8263 | 2021.072 | 2279.6486 | 5032.0138 |
| Rwdd4a | 2846.0286 | 0.87 | 4734.7927 | 3428.6873 | 0.8021 |
| Bex1 | 1.4455 | 0.783 | 3918.239 | 3.6858 | 0.8021 |
| Bex1 | 29223.1884 | 1820.0341 | 17.2654 | 4040.525 | 1376.0945 |
| Mrpl44 | 15.6224 | 1.0117 | 100757.5301 | 1794.2456 | 446.0565 |
| Mrpl44 | 828.5905 | 203.3466 | 0.6237 | 42.0958 | 0.7143 |
| Mrpl44 | 0.5408 | 119.3776 | 0.6237 | 24.1533 | 0.7143 |
| Mrpl44 | 0.5408 | 0.9105 | 0.6237 | 0.6211 | 0.7143 |
| Mrpl44 | 1051.5108 | 2668.7979 | 15763.2232 | 10042.9446 | 13.4928 |
| Lst1 | 346920.8878 | 707.4534 | 2479.5765 | 11746.6403 | 2801.0292 |
| Lst1 | 1.1095 | 0.9031 | 61.401 | 0.8494 | 0.814 |
| Lst1 | 0.9985 | 0.9031 | 3875.4256 | 324.6701 | 6.331 |
| Tnrc6a | 0.9985 | 2.007 | 1.0233 | 0.9438 | 0.9044 |
| Tnrc6a | 3624.7039 | 61980.9499 | 70998.9838 | 32465.1239 | 2096.4759 |
| Tnrc6a | 55.4745 | 0.9031 | 0.921 | 0.8494 | 66.0236 |
| Tnrc6a | 0.9985 | 4.0139 | 1.0233 | 0.8494 | 1.8089 |
| Iqgap2 | 0.9985 | 6.0209 | 1508.4176 | 13.2133 | 3.6177 |
| Iqgap2 | 7.7664 | 12.0418 | 3.07 | 0.8494 | 0.814 |
| Iqgap2 | 928.6431 | 0.9031 | 14.3269 | 2.8314 | 403.3772 |
| Iqgap2 | 365.0222 | 5.0174 | 0.921 | 0.8494 | 0.814 |
| Iqgap2 | 0.9985 | 36.1253 | 12.2802 | 0.8494 | 1466.086 |
| Mns1 | 0.865 | 1.0021 | 0.9956 | 1383.3846 | 1990.5855 |
| Mns1 | 39.4039 | 4061.3176 | 344560.0784 | 4240.8978 | 18417.0793 |
| Bex1 | 1.4455 | 0.783 | 0.9141 | 0.9214 | 1.7825 |
| Bex1 | 1.4455 | 0.783 | 2.0312 | 0.8293 | 0.8021 |
| Bex1 | 1.4455 | 14.79 | 0.9141 | 102.2801 | 0.8021 |
| Asph | 9707.3345 | 55.6798 | 1251.2365 | 2.7643 | 122.9929 |
| Asph | 70.6689 | 118.3196 | 16.2498 | 35.0148 | 0.8021 |
| Asph | 70.6689 | 0.783 | 0.9141 | 11.0573 | 41.8889 |
| Tnrc6a | 717.84 | 331.1484 | 86.9847 | 3.7752 | 8.1399 |
| Abca1 | 84432.1907 | 17.0592 | 401.1531 | 16.9886 | 538.1377 |
| Abca1 | 0.9985 | 11.0383 | 0.921 | 1123.1321 | 9.9488 |
| Abca1 | 0.9985 | 0.9031 | 0.921 | 31.1457 | 33058.8379 |
| Upf1 | 0.6657 | 0.9252 | 1.0136 | 0.6811 | 0.6821 |
| Upf1 | 2562.1226 | 1993.2175 | 13581.5996 | 0.6811 | 7338.6416 |
| Upf1 | 0.6657 | 0.9252 | 281.7675 | 0.6811 | 6.0631 |
| Upf1 | 0.6657 | 0.9252 | 57.7725 | 99.8875 | 1687.0615 |
| Snx16 | 81.9117 | 0.783 | 0.9141 | 2.7643 | 1516.0212 |
| Snx16 | 12.8489 | 0.783 | 0.9141 | 0.8293 | 0.8021 |
| Paip1 | 4320.0135 | 0.9018 | 69167.9886 | 2867.6988 | 3.3306 |
| Paip1 | 1.9221 | 898.8408 | 36661.4233 | 26.8528 | 19437.3515 |
| Paip1 | 1.9221 | 9870.2142 | 1710.1732 | 49.0759 | 11093.1012 |
| Spcs1 | 0.9611 | 0.9018 | 3482.2932 | 334.2716 | 44.4079 |
| Spcs1 | 41.326 | 1.0021 | 6.6372 | 0.8334 | 39.9671 |
| Ptbp1 | 273.6678 | 0.9252 | 4305.5698 | 50.7005 | 18.9472 |
| Ptbp1 | 30013.2248 | 146.9985 | 9501.0384 | 10221.0616 | 418.3549 |
| Hnrnpl | 0.865 | 0.9018 | 0.9956 | 0.8334 | 44.4079 |
| Hnrnpl | 46608.0926 | 24.0493 | 0.9956 | 0.8334 | 1.1102 |
| Hnrnpl | 64314.8622 | 326.669 | 2.2124 | 2.7779 | 12.2122 |

Figure 15(cont'd)

| Symbol | BM.1 | BM.2 | BM.3 | BM.4 | BM.5 |
|---|---|---|---|---|---|
| Ddx56 | 0.7396 | 0.9252 | 1266.9403 | 314.7969 | 120282.3289 |
| Ddx56 | 20475.5311 | 5049.3473 | 61.8267 | 9167.7027 | 914.7723 |
| Rps24 | 0.6009 | 0.9105 | 0.6237 | 0.6211 | 0.7143 |
| Rps11 | 0.865 | 0.9018 | 0.9956 | 0.8334 | 0.9992 |
| Rps11 | 0.865 | 0.9018 | 0.9956 | 0.926 | 0.9992 |
| Rps11 | 0.865 | 0.9018 | 0.9956 | 0.8334 | 0.9992 |
| Cyb5 | 1288.101 | 9641.3089 | 42.6558 | 0.9214 | 2630.0873 |
| Gpsm2 | 4400.744 | 36.5399 | 0.9141 | 0.8293 | 3099.7775 |
| Cyb5 | 379.0422 | 43237.9903 | 32.4996 | 363.9698 | 3.565 |
| Ptbp1 | 360.206 | 784303.849 | 187.5072 | 289.0683 | 124.2938 |
| Hnrnpl | 0.865 | 0.9018 | 3882.7348 | 1.8519 | 317.5167 |
| Hnrnpl | 0.865 | 0.9018 | 0.9956 | 0.8334 | 5.551 |
| Ptbp1 | 122.7807 | 0.9252 | 260.4829 | 612.9459 | 25.7682 |
| Rps24 | 24.6354 | 19.2218 | 15398.6995 | 359.5392 | 0.7143 |
| Rps24 | 0.5408 | 24.2802 | 0.6237 | 1837.0314 | 10738.6918 |
| Rps11 | 0.865 | 1.0021 | 14.3805 | 0.8334 | 0.9992 |
| Rps11 | 0.865 | 4275.7567 | 12.1681 | 29.6307 | 0.9992 |
| Spcs1 | 0.865 | 0.9018 | 115.044 | 197.2295 | 76.6037 |
| Ilf2 | 1606.7085 | 5124.1325 | 2.079 | 3.4505 | 244134.1979 |
| Ilf2 | 4.8069 | 96.1091 | 0.6237 | 11.7316 | 0.7143 |
| Ssb | 1.8026 | 0.9105 | 0.6237 | 0.6211 | 0.7143 |
| Ssb | 0.5408 | 0.9105 | 0.6237 | 8.2811 | 0.7143 |
| Tjp1 | 0.865 | 55.1129 | 0.9956 | 0.8334 | 0.9992 |
| Tjp1 | 0.9611 | 354.7265 | 61.9468 | 371.31 | 1.1102 |
| Mrps9 | 0.6657 | 0.9252 | 0.9122 | 31.0257 | 0.7579 |
| Mrps9 | 2699.6962 | 0.9252 | 31.4201 | 638.6745 | 0.7579 |
| Mrps9 | 0.6657 | 0.9252 | 3485.606 | 499.4374 | 130.357 |
| Hnrnpa2b1 | 992.6006 | 187.089 | 1173.6935 | 2306.4926 | 0.7579 |
| Hnrnpa2b1 | 136.0943 | 386.5136 | 0.9122 | 0.6811 | 31.8313 |
| Ilf3 | 117.6032 | 70.9293 | 121.6263 | 3921.3401 | 210.6932 |
| Ilf2 | 0.6009 | 1210.9746 | 483.0285 | 76.6005 | 0.7143 |
| Ilf2 | 0.5408 | 0.9105 | 0.6237 | 0.6901 | 0.7143 |
| Ilf2 | 0.5408 | 0.9105 | 0.6237 | 0.6901 | 0.7143 |
| Kif21a | 7.7664 | 42.1462 | 0.921 | 4897.4222 | 8.1399 |
| Mrpl22 | 10.8155 | 0.9105 | 0.693 | 0.6211 | 0.7937 |
| Abcc5 | 1.4455 | 2043.6234 | 132902.239 | 476.3857 | 2649.6948 |
| Abcc5 | 6175.4965 | 20.0099 | 4.0625 | 2094.4386 | 0.8021 |
| Ddx56 | 0.6657 | 1.028 | 0.9122 | 0.6811 | 236.4614 |
| Ddx56 | 0.6657 | 13.3635 | 1.0136 | 0.6811 | 114.4413 |
| Ddx56 | 0.6657 | 0.9252 | 0.9122 | 0.6811 | 0.6821 |
| Kif21a | 4744.1793 | 2673.2709 | 526.0018 | 475.6795 | 3973.1745 |
| Stau2 | 0.6657 | 2.0559 | 204.7375 | 0.6811 | 264.5033 |
| Stau2 | 0.6657 | 189.1449 | 0.9122 | 0.6811 | 0.6821 |
| Syncrip | 209335.9739 | 256.9654 | 63.064 | 6.9009 | 3.1748 |
| Syncrip | 20030.3796 | 2050.6647 | 0.6237 | 86.2618 | 0.7143 |
| Syncrip | 0.5408 | 40.467 | 0.6237 | 26.2236 | 0.7143 |
| Hnrnpr | 0.9611 | 133.2729 | 0.9956 | 8759.5837 | 66.6119 |
| Hnrnpr | 0.865 | 2117.3363 | 1.1062 | 0.8334 | 9878.5443 |
| Hnrnpr | 0.865 | 0.9018 | 86.283 | 236.1199 | 0.9992 |

Figure 15(cont'd)

| Symbol | BM.1 | BM.2 | BM.3 | BM.4 | BM.5 |
|---|---|---|---|---|---|
| Cltc | 0.9985 | 0.9031 | 8.1868 | 7.5505 | 0.814 |
| Ap3s1 | 0.865 | 0.9018 | 0.9956 | 0.8334 | 0.9992 |
| Ap3s1 | 1.9221 | 647.3257 | 1327.4307 | 602.8001 | 131920.421 |
| Ap3s1 | 583688.1287 | 1496.0639 | 1837.3853 | 467.6099 | 25.5346 |
| Anln | 1.4455 | 1.74 | 0.9141 | 52.5222 | 0.8021 |
| Ube2k | 1443.8937 | 21.7499 | 0.9141 | 7357.7178 | 0.8021 |
| Peli1 | 4.438 | 367.2737 | 1.0233 | 18.8762 | 27.133 |
| Peli1 | 0.9985 | 0.9031 | 0.921 | 7.5505 | 0.814 |
| Mrpl11 | 0.6657 | 14.3915 | 8.1084 | 289.0683 | 23.4946 |
| Mrpl11 | 0.6657 | 0.9252 | 0.9122 | 0.6811 | 483.5333 |
| Mrpl11 | 1568.7823 | 0.9252 | 0.9122 | 7.5672 | 0.6821 |
| Peli1 | 16.6424 | 241.8387 | 1655.7799 | 2475.6096 | 14.4709 |
| Peli1 | 60975.3527 | 5.0174 | 826.8666 | 131.1894 | 2280.9802 |
| Caprin1 | 22.1893 | 0.9252 | 0.9122 | 132.4266 | 43.1997 |
| Caprin1 | 53.2543 | 81.209 | 0.9122 | 1.5134 | 43.1997 |
| Npepps | 4937.2306 | 4.0139 | 2.0467 | 1.8876 | 8133.5667 |
| Hnrnpa1 | 0.5408 | 1.0117 | 0.6237 | 0.6211 | 0.7143 |
| Npepps | 0.9985 | 0.9031 | 0.921 | 0.8494 | 2.7133 |
| Npepps | 0.9985 | 15.0522 | 14.3269 | 2.8314 | 3047.035 |
| Npepps | 813.2562 | 2036.0611 | 1545.2582 | 9305.0078 | 0.814 |
| Hnrnpa1 | 48.6699 | 273.1522 | 0.6237 | 0.6211 | 0.7143 |
| Hnrnpa1 | 2.4035 | 0.9105 | 49.8968 | 0.6211 | 0.7143 |
| Hnrnpa1 | 0.5408 | 0.9105 | 0.6237 | 0.6211 | 0.7143 |
| Ddx21 | 0.6657 | 1019.7379 | 12.1626 | 0.6811 | 0.6821 |
| Ddx21 | 0.6657 | 0.9252 | 0.9122 | 0.6811 | 1630.2198 |
| Stau1 | 26474.0341 | 142.8867 | 900.0344 | 1311.4015 | 0.6821 |
| Stau1 | 0.6657 | 16.4474 | 0.9122 | 3.0269 | 1808.3237 |
| Stau1 | 0.6657 | 0.9252 | 0.9122 | 0.6811 | 0.6821 |
| Zyx | 88.9278 | 1305.0604 | 0.6237 | 69.6995 | 0.7143 |
| Zyx | 0.5408 | 0.9105 | 0.6237 | 0.6211 | 0.7143 |
| Kif21a | 319.5331 | 135.4698 | 0.921 | 1507.2621 | 0.814 |
| Ilf3 | 50.2957 | 1.028 | 4.0542 | 8.324 | 922.3512 |
| Crbn | 1.4455 | 0.783 | 223.4351 | 0.8293 | 0.8021 |
| Crbn | 5844.6377 | 28689.8973 | 10.1561 | 0.8293 | 3.565 |
| Dap3 | 15500.4711 | 868.0169 | 0.6237 | 111.7953 | 14.2865 |
| Dap3 | 11870.6558 | 4630.4352 | 921.0113 | 5465.5481 | 5778.8925 |
| Dap3 | 0.5408 | 0.9105 | 0.6237 | 0.6211 | 0.7937 |
| Dap3 | 0.5408 | 0.9105 | 34812.7034 | 431.9991 | 7.9369 |
| Dap3 | 0.5408 | 17247.0307 | 19.4043 | 2255.9188 | 8.7306 |
| Ddx21 | 0.6657 | 0.9252 | 1413.9053 | 0.6811 | 0.7579 |
| Stau1 | 0.6657 | 1.028 | 1.0136 | 0.7567 | 0.6821 |
| Zyx | 0.5408 | 57.6655 | 382.5419 | 3.4505 | 0.7143 |
| Hnrnpa1 | 97354.8795 | 68.7939 | 122.6629 | 407.8458 | 116522.3465 |
| Eps8 | 1.6061 | 0.783 | 307.7311 | 4585.0975 | 25.8463 |
| Slc40a1 | 1.4455 | 0.783 | 0.9141 | 0.8293 | 2749.5152 |
| Rpl18 | 0.6657 | 0.9252 | 706.4459 | 0.6811 | 0.6821 |
| Eps8 | 1.6061 | 340.1689 | 5.0781 | 0.8293 | 0.8021 |
| Eps8 | 1.6061 | 0.783 | 109116.558 | 5149.0203 | 18.7163 |
| Eps8 | 1.4455 | 7338.4263 | 0.9141 | 23.9575 | 0.8021 |

Figure 15(cont'd)

| Symbol | BM.1 | BM.2 | BM.3 | BM.4 | BM.5 |
|---|---|---|---|---|---|
| Slc40a1 | 73.8811 | 3084.14 | 85.3116 | 12.9002 | 0.8021 |
| Slc40a1 | 1829.3604 | 284.4891 | 191.9511 | 89.3799 | 90.0165 |
| Slc40a1 | 1.4455 | 0.783 | 32.4996 | 0.8293 | 0.8021 |
| Mrpl37 | 4.4379 | 121.2995 | 0.9122 | 31.0257 | 0.6821 |
| Ict1 | 16.2721 | 1601.5641 | 5.0678 | 82.4828 | 647.2374 |
| Irf6 | 0.865 | 0.9018 | 0.9956 | 585.2069 | 0.9992 |
| Irf6 | 1.9221 | 264.5418 | 929.2015 | 176896.3665 | 3922.3305 |
| Irf6 | 0.865 | 0.9018 | 11636.0362 | 12.0375 | 9.9918 |
| Irf6 | 0.865 | 20413.8075 | 691.3702 | 9384.6068 | 31108.866 |
| Mrps28 | 3392.7414 | 0.9252 | 49.6641 | 43.89 | 27655.3787 |
| Mrps28 | 0.6657 | 0.9252 | 0.9122 | 5.2971 | 0.6821 |
| Mrpl4 | 1.9221 | 136635.8302 | 6129.4112 | 19098.8555 | 438.5283 |
| Mrpl38 | 3233.0424 | 0.9018 | 67.4777 | 6.4817 | 34.4161 |
| Mrpl38 | 0.865 | 281.5767 | 0.9956 | 0.8334 | 0.9992 |
| Msi2 | 61055.2927 | 116.1597 | 1913.5866 | 1204.7035 | 132134.201 |
| Msi2 | 3277.3572 | 0.9252 | 0.9122 | 247.4485 | 0.6821 |
| Slc19a2 | 98.9903 | 13894.4558 | 95799.5668 | 2545.4646 | 11577.1477 |
| Numbl | 114.3674 | 505.0343 | 2.2124 | 4.6298 | 1182.3612 |
| Numbl | 0.865 | 1.0021 | 0.9956 | 12091.1886 | 118.7912 |
| Numbl | 0.865 | 0.9018 | 100.6635 | 0.926 | 0.9992 |
| Numbl | 0.865 | 0.9018 | 0.9956 | 7.4077 | 0.9992 |
| Crot | 1.4455 | 0.783 | 0.9141 | 0.8293 | 0.8021 |
| Crot | 19.2733 | 49.5898 | 503.7446 | 405.4347 | 82164.6037 |
| Crot | 486.6516 | 52.1998 | 2.0312 | 18707.1241 | 379259.2976 |
| Tmem50b | 9189.9059 | 14.0487 | 169.8761 | 0.8494 | 121.194 |
| Mov10 | 20.71 | 4528.1708 | 408.4615 | 2090.8265 | 419.8706 |
| Ube2k | 99.5789 | 28.7099 | 0.9141 | 0.8293 | 0.8021 |
| Numb | 19930.2305 | 554.1882 | 575.8532 | 997.0007 | 67.7352 |
| Numb | 1.6061 | 173.9994 | 302079.1651 | 2699.8263 | 17.8251 |
| Ltb | 0.865 | 41.0841 | 4365.0346 | 9.2596 | 0.9992 |
| Ltb | 27592.3445 | 3753.6876 | 2.2124 | 8491.9812 | 1713.0359 |
| Zcchc3 | 0.9985 | 0.9031 | 0.921 | 0.8494 | 0.814 |
| Zcchc3 | 13.3139 | 0.9031 | 0.921 | 0.8494 | 0.814 |
| Zcchc3 | 7.2104 | 0.9105 | 0.6237 | 97.3033 | 0.7143 |
| Zcchc3 | 0.9985 | 0.9031 | 0.921 | 0.8494 | 0.814 |
| Zcchc3 | 0.5408 | 1387.006 | 0.6237 | 3802.4204 | 10.318 |
| Cltc | 0.9985 | 0.9031 | 0.921 | 0.8494 | 268.6166 |
| Anln | 3.2122 | 227519.9251 | 166.5607 | 8644.0514 | 581.9881 |
| Mrpl39 | 76.9105 | 501.7907 | 12.4742 | 153.8911 | 0.7143 |
| Ybx1 | 23.4337 | 76.8873 | 0.6237 | 16.5623 | 0.7143 |
| Ybx1 | 3.6052 | 0.9105 | 0.6237 | 4625.7031 | 0.7937 |
| Mycn | 1.4455 | 0.783 | 0.9141 | 0.8293 | 0.8913 |
| Mtmr9 | 2.219 | 96.3341 | 1.0233 | 8245.1108 | 1830.5726 |
| Mtmr9 | 955.2709 | 257.8944 | 1.0233 | 42350.5739 | 8186.0238 |
| Mtmr9 | 3886.5436 | 22.0766 | 2.0467 | 17.9324 | 84.1123 |
| Mrpl22 | 1768.9416 | 0.9105 | 0.6237 | 14663.1269 | 101.5929 |
| Atp5a1 | 499.2589 | 2.0559 | 151899.0421 | 709.0497 | 77.3047 |
| Rabep1 | 49817.2115 | 1252.3431 | 184.203 | 12.2695 | 12.6621 |
| Rabep1 | 0.9985 | 6287.8061 | 2074.33 | 32461.3487 | 123.9073 |

Figure 15(cont'd)

| Symbol | BM.1 | BM.2 | BM.3 | BM.4 | BM.5 |
|---|---|---|---|---|---|
| Rabep1 | 142.0147 | 0.9031 | 145.3157 | 0.8494 | 72.3546 |
| Frmd6 | 1.4455 | 2273.3027 | 873.4281 | 4359.3441 | 141.7092 |
| Frmd6 | 1.4455 | 0.783 | 0.9141 | 0.8293 | 0.8021 |
| Ttc3 | 0.9985 | 0.9031 | 0.921 | 0.8494 | 0.814 |
| Ttc3 | 0.9985 | 0.9031 | 0.921 | 0.8494 | 0.814 |
| Cct3 | 0.6657 | 0.9252 | 4.0542 | 0.6811 | 0.6821 |
| Cct3 | 0.6657 | 0.9252 | 18.2439 | 0.6811 | 15.1578 |
| Frmd6 | 1.4455 | 0.783 | 0.9141 | 0.8293 | 0.8021 |
| Ttc3 | 0.9985 | 0.9031 | 0.921 | 0.8494 | 0.814 |
| 4932438A13Rik | 0.865 | 0.9018 | 996.6792 | 1175.0435 | 255.3456 |
| 4932438A13Rik | 0.865 | 2629.385 | 278.7604 | 47.224 | 26804.6273 |
| 4932438A13Rik | 0.9611 | 8540.4909 | 82.9644 | 2488.9811 | 9.9918 |
| 4932438A13Rik | 0.865 | 0.9018 | 587.3881 | 4.6298 | 2444.6566 |
| 4932438A13Rik | 26.91 | 0.9018 | 0.9956 | 0.8334 | 0.9992 |
| Ptcd3 | 49.8717 | 1986.9292 | 169.0946 | 2.0703 | 153.9768 |
| Ptcd3 | 444.6389 | 40883.799 | 79.6962 | 65568.6344 | 1373.8859 |
| Sepp1 | 0.9985 | 0.9031 | 816.6331 | 1604.4744 | 636.7209 |
| Mapk6 | 1.4455 | 0.783 | 0.9141 | 482.8358 | 762.9125 |
| Mapk6 | 2365.8014 | 11376.0833 | 60953.0928 | 293368.8396 | 4015.9855 |
| Mapk6 | 77.0933 | 0.783 | 334.137 | 2967.0446 | 2056.1204 |
| Baz2b | 32007.6777 | 4.0139 | 8456.9625 | 142815.2108 | 61457.1321 |
| Ybx1 | 10474.2494 | 980.3128 | 0.6237 | 757.7237 | 3498.6071 |
| Mtmr9 | 1259.2712 | 513.7818 | 346.9156 | 465.2976 | 1163.1009 |
| Hnrnpc | 0.6009 | 2017.2794 | 72.0731 | 0.6211 | 0.7143 |
| Hnrnpc | 0.5408 | 58.6771 | 6.9301 | 4.1406 | 1.5874 |
| Pdia6 | 551.5925 | 950.9742 | 37030.3379 | 2733.4641 | 20.6361 |
| Snx14 | 823.2416 | 6854.7724 | 3908.1728 | 8196.0328 | 756.1061 |
| Mrpl11 | 0.6657 | 0.9252 | 0.9122 | 0.6811 | 0.6821 |
| Mrpl11 | 0.6657 | 0.9252 | 3.0407 | 1320.4822 | 0.6821 |
| Caprin1 | 0.6657 | 0.9252 | 1.0136 | 0.6811 | 0.7579 |
| Cct3 | 0.6657 | 0.9252 | 0.9122 | 0.6811 | 0.6821 |
| Ptcd3 | 0.5408 | 0.9105 | 0.6237 | 0.6211 | 0.7143 |
| Mrpl22 | 0.5408 | 0.9105 | 0.6237 | 133.8783 | 0.7143 |
| Ppp2r5c | 13.3139 | 46.1601 | 156.5725 | 1989.5483 | 4645.1683 |
| Mrpl4 | 0.865 | 0.9018 | 0.9956 | 0.8334 | 0.9992 |
| Mov10 | 0.6657 | 0.9252 | 0.9122 | 6.8105 | 32.5892 |
| Tmem50b | 0.9985 | 18.0626 | 9209.1246 | 12.2695 | 0.814 |
| Tmem50b | 1.1095 | 13.0452 | 1.0233 | 0.9438 | 0.814 |
| Ube2k | 1.4455 | 8.7 | 0.9141 | 13.8216 | 378.7825 |
| Irf6 | 41.326 | 3385.9344 | 1.1062 | 0.926 | 233.1416 |
| Clcn3 | 0.865 | 1.0021 | 0.9956 | 0.8334 | 103.2484 |
| Clcn3 | 0.865 | 2.0041 | 0.9956 | 0.8334 | 0.9992 |
| Dst | 0.9985 | 22.0766 | 4723.7825 | 0.8494 | 7.2355 |
| Smc4 | 409.4018 | 221.7691 | 282.4445 | 6857.7124 | 4558.3427 |
| Ilf3 | 86.5382 | 13571.1488 | 130.7482 | 3.0269 | 87.9152 |
| Slc19a2 | 0.865 | 0.9018 | 1.1062 | 0.8334 | 1.1102 |
| Clcn3 | 20.1825 | 17216.2589 | 25.4424 | 147949.9241 | 143482.0259 |
| Smc4 | 0.9985 | 0.9031 | 0.921 | 0.8494 | 0.814 |
| Smc4 | 0.9985 | 1.0035 | 7.1634 | 0.8494 | 0.814 |

Figure 15(cont'd)

| Symbol | BM.1 | BM.2 | BM.3 | BM.4 | BM.5 |
|---|---|---|---|---|---|
| Dst | 1.1095 | 1.0035 | 232813.0964 | 72.6733 | 189.0265 |
| Dst | 1.1095 | 14.0487 | 63542.8574 | 201.975 | 987.6409 |
| Cltc | 305.1098 | 0.9031 | 6.1401 | 0.8494 | 0.814 |
| Cltc | 127.5914 | 1.0035 | 1.0233 | 0.8494 | 11566.7946 |
| Rpl14 | 77.5114 | 11.1284 | 8.3161 | 0.6211 | 0.7937 |
| Mylk | 1.4455 | 0.783 | 6.0937 | 0.8293 | 32.9764 |
| Rpl14 | 112.3614 | 5.0584 | 1194.0576 | 159702.3485 | 1096.8863 |

Figure 16

| Symbol | Spleen.1 | Spleen.2 | Spleen.3 | Spleen.4 | Spleen.5 |
|---|---:|---:|---:|---:|---:|
| Upf1 | 975.9612 | 115.5126 | 559.1414 | 339.572 | 27596.1232 |
| Upf1 | 0.9236 | 1.316 | 0.7863 | 771.0722 | 0.9541 |
| Bnip3l | 1580.9733 | 1011.1836 | 3182.5908 | 17205.2588 | 7164.8995 |
| Bnip3l | 1518.4018 | 9721.5662 | 35809.7226 | 4037.3829 | 26113.8497 |
| Bnip3l | 14410.2167 | 111.4126 | 2197.5669 | 22953.3292 | 625.8369 |
| Bnip3l | 1.0429 | 257.3567 | 0.803 | 0.3614 | 0.7632 |
| Bnip3l | 0.9386 | 2612.0072 | 1215.2197 | 585.0872 | 110.2423 |
| Spcs1 | 4564.7549 | 16306.4351 | 52785.1947 | 65201.2748 | 19521.3716 |
| Spcs1 | 0.9789 | 1.0226 | 1.1188 | 0.8861 | 0.7323 |
| Cdk6 | 69427.385 | 14269.8448 | 3998.4344 | 36.8822 | 949.7391 |
| Cdk6 | 199.8426 | 59.3179 | 1.0123 | 239.7341 | 435.8392 |
| Cdk6 | 1868.3396 | 1180.3659 | 1827.695 | 7895.5497 | 3833.3403 |
| Cdk6 | 0.8484 | 0.5393 | 1.0123 | 0.8298 | 0.8364 |
| Cdk6 | 2772.3444 | 0.5393 | 1547.6359 | 0.9221 | 1743.3567 |
| Mapk6 | 8465.9241 | 13.6823 | 1511.4406 | 18.0706 | 0.7632 |
| Mapk6 | 840.5438 | 13.0307 | 124.0202 | 2.0078 | 14.4163 |
| Atr | 1.0876 | 306.7896 | 7863.5819 | 12598.1957 | 37967.8962 |
| Atr | 0.9789 | 1497.5877 | 1.1188 | 560.2042 | 0.7323 |
| Atr | 0.9789 | 1.1363 | 1.2431 | 955.0055 | 14.6459 |
| Atr | 0.9789 | 14581.5958 | 68.3682 | 0.8861 | 5323.7885 |
| Atr | 0.9789 | 56.8129 | 4501.1113 | 12.799 | 0.7323 |
| Mylk | 9454.5538 | 19.5461 | 1.7845 | 4704.792 | 0.7632 |
| Mylk | 193.9717 | 272.9935 | 7.1379 | 16.8659 | 0.7632 |
| Mylk | 10506.7979 | 15.6369 | 20.5213 | 0.3614 | 68.6894 |
| Mylk | 1633.1162 | 18.243 | 0.8922 | 27.7083 | 0.7632 |
| Stk17b | 56945.7079 | 26903.9542 | 2090.8831 | 4169.5289 | 5639.889 |
| Stk17b | 0.9427 | 0.5393 | 48.3636 | 13474.8994 | 2.7879 |
| Stk17b | 14663.9204 | 708.8187 | 106.8499 | 18264.9707 | 6.5051 |
| Stk17b | 7329.1322 | 269980.2394 | 118352.5326 | 88483.0826 | 54117.4721 |
| Stk17b | 0.8484 | 14.3801 | 5.6237 | 22.1293 | 0.8364 |
| Gpsm2 | 35.4572 | 129.6556 | 0.803 | 1844.8117 | 6386.4195 |
| Gpsm2 | 0.9386 | 3.9092 | 11028.8771 | 169.0609 | 0.7632 |
| Gpsm2 | 932.3154 | 1925.9399 | 166.8473 | 1712.2937 | 29239.6421 |
| Gpsm2 | 544.3721 | 1430.7727 | 0.8922 | 38.5507 | 0.7632 |
| Frmd6 | 27639.9177 | 7710.9266 | 12534.9643 | 7368.003 | 2194.6692 |
| Frmd6 | 134.5287 | 461.9389 | 5646.0427 | 860.1625 | 1068.502 |
| Npepps | 0.8484 | 400.2459 | 482.5115 | 261.8634 | 32.5253 |
| Zcchc3 | 0.8484 | 0.5393 | 1.0123 | 0.8298 | 0.9293 |
| Rrm2 | 0.9386 | 0.6515 | 0.803 | 0.4016 | 410.4405 |
| Rrm2 | 1842.7307 | 554.457 | 6177.8129 | 186.73 | 8596.353 |
| Mycn | 10434.8406 | 2294.0577 | 8819.7112 | 6331.1497 | 68519.811 |
| Mycn | 32430.809 | 6903.6737 | 77868.6367 | 29116.2211 | 18431.6595 |
| Mycn | 25901.4728 | 26115.5108 | 11900.5875 | 386.3102 | 3878.8319 |
| Mycn | 16.6857 | 23.4553 | 131.1581 | 918.7917 | 3829.6469 |
| Cdkn1a | 0.9789 | 1.0226 | 1.1188 | 0.8861 | 0.7323 |
| Cdkn1a | 18331.8904 | 43535.716 | 100.6877 | 0.8861 | 0.8137 |
| Cdkn1a | 0.9789 | 1.0226 | 1.1188 | 0.8861 | 0.7323 |

Figure 16 (cont'd)

| Symbol | Spleen.1 | Spleen.2 | Spleen.3 | Spleen.4 | Spleen.5 |
|---|---|---|---|---|---|
| Rrm2 | 8.3429 | 16440.8552 | 0.803 | 31075.0787 | 0.848 |
| Rrm2 | 353.529 | 61.2444 | 0.803 | 1112.75 | 0.7632 |
| Rrm2 | 0.9386 | 59.2898 | 7.1379 | 12612.9064 | 0.7632 |
| Rpl14 | 0.8465 | 0.8563 | 0.3383 | 0.6498 | 0.7439 |
| Rpl14 | 0.9406 | 0.7706 | 0.3383 | 0.722 | 0.7439 |
| Rpl14 | 0.8465 | 18.8381 | 0.3383 | 0.6498 | 0.7439 |
| Rpl14 | 0.8465 | 0.7706 | 0.3383 | 12.2744 | 0.7439 |
| Cdkn1a | 0.9789 | 205.6627 | 266.0143 | 17.7218 | 0.7323 |
| Cdkn1a | 0.9789 | 19801.5639 | 2154.2187 | 0.8861 | 63.4656 |
| Hnrnpa1 | 7469.9233 | 17581.0701 | 1147.8825 | 44044.2659 | 43320.0613 |
| Ilf2 | 2350.4581 | 0.7706 | 0.3383 | 0.722 | 0.7439 |
| Ilf3 | 1441.8775 | 9701.5973 | 46474.2638 | 1089.0692 | 18.1284 |
| Ilf3 | 0.9236 | 1.316 | 0.7863 | 529.0569 | 0.8587 |
| Ilf3 | 109.8085 | 1.316 | 10.4839 | 69.4153 | 3.8165 |
| Ltb | 52712.75 | 6417.5838 | 1859.6141 | 0.8861 | 10861.5701 |
| Ltb | 0.9789 | 1664.6176 | 26825.1814 | 5313.5716 | 902.3508 |
| Ltb | 1648.8369 | 50002.1589 | 11175.0871 | 7822.1839 | 178213.0687 |
| Slc25a24 | 0.9789 | 7198.1929 | 1.2431 | 1882.4438 | 8049.5553 |
| Slc25a24 | 0.9789 | 443.1405 | 1.1188 | 6.8918 | 43.1241 |
| Slc25a24 | 140.3034 | 18148.3089 | 110673.1405 | 4370.3807 | 184730.499 |
| Slc25a24 | 0.9789 | 1.1363 | 1.1188 | 2.9536 | 0.7323 |
| Slc25a24 | 88664.1376 | 50736.1814 | 1.2431 | 916.6083 | 4680.1821 |
| Clcn3 | 51.1183 | 4439.3591 | 99.4446 | 0.9845 | 107479.8293 |
| Clcn3 | 34.8039 | 5227.9219 | 5512.9601 | 24.6135 | 46.3787 |
| Csda | 27.7087 | 1.316 | 469.1546 | 6.5663 | 0.8587 |
| Csda | 50770.5065 | 9956.0175 | 607.1927 | 21923.9659 | 23084.0717 |
| Csda | 9037.1337 | 1146.353 | 1185.5546 | 8.4424 | 9550.7794 |
| Csda | 2.0525 | 1.316 | 0.7863 | 0.8442 | 0.8587 |
| Csda | 31.8137 | 1.316 | 73.3873 | 40.3359 | 0.8587 |
| Hnrnpa2b1 | 1242.7855 | 462126.4848 | 4360.4296 | 15.0087 | 6878.2786 |
| Hnrnpa2b1 | 4.105 | 4244.723 | 45.4302 | 6145.1267 | 20.9907 |
| Hnrnpa2b1 | 13323.7687 | 1.316 | 164.2478 | 4482.9126 | 1834.7801 |
| Ssb | 166.479 | 2.5688 | 0.3383 | 0.6498 | 0.7439 |
| Ssb | 6497.3848 | 0.8563 | 0.7517 | 984.1205 | 576.124 |
| Ssb | 5533.3113 | 58.2268 | 83098.9521 | 8091.0156 | 0.7439 |
| Msi2 | 9.2362 | 5097.1768 | 1375.1385 | 6877.7391 | 3218.2596 |
| Msi2 | 0.9236 | 500.0673 | 1223.9956 | 450.2612 | 2803.2158 |
| Msi2 | 0.9236 | 1.316 | 0.8737 | 7830.7919 | 0.8587 |
| RFP | 11.0872 | 4.9106 | 3.3565 | 3.4665 | 2.6076 |
| RFP | 11.0872 | 4.9106 | 3.3565 | 3.4665 | 2.6076 |
| RFP | 11.0872 | 4.9106 | 3.3565 | 3.4665 | 2.6076 |
| RFP | 11.0872 | 4.9106 | 3.3565 | 3.4665 | 2.6076 |
| RFP | 11.0872 | 4.9106 | 3.3565 | 3.4665 | 2.6076 |
| RFP | 11.0872 | 4.9106 | 3.3565 | 3.4665 | 2.6076 |
| lacZ | 2362.3175 | 1520.956 | 676.2075 | 376.6063 | 10.3411 |
| lacZ | 2362.3175 | 1520.956 | 676.2075 | 376.6063 | 10.3411 |
| lacZ | 2362.3175 | 1520.956 | 676.2075 | 376.6063 | 10.3411 |
| lacZ | 2362.3175 | 1520.956 | 676.2075 | 376.6063 | 10.3411 |
| lacZ | 2362.3175 | 1520.956 | 676.2075 | 376.6063 | 10.3411 |

Figure 16 (cont'd)

| Symbol | Spleen.1 | Spleen.2 | Spleen.3 | Spleen.4 | Spleen.5 |
|---|---|---|---|---|---|
| lacZ | 2362.3175 | 1520.956 | 676.2075 | 376.6063 | 10.3411 |
| lacZ | 7899.9864 | 10308.6634 | 5254.3744 | 5571.0108 | 2094.6508 |
| lacZ | 7899.9864 | 10308.6634 | 5254.3744 | 5571.0108 | 2094.6508 |
| lacZ | 7899.9864 | 10308.6634 | 5254.3744 | 5571.0108 | 2094.6508 |
| lacZ | 7899.9864 | 10308.6634 | 5254.3744 | 5571.0108 | 2094.6508 |
| lacZ | 7899.9864 | 10308.6634 | 5254.3744 | 5571.0108 | 2094.6508 |
| lacZ | 7899.9864 | 10308.6634 | 5254.3744 | 5571.0108 | 2094.6508 |
| LUCIFERASE | 499.8757 | 4356.6762 | 92.9703 | 540.2586 | 20.7619 |
| LUCIFERASE | 499.8757 | 4356.6762 | 92.9703 | 540.2586 | 20.7619 |
| LUCIFERASE | 499.8757 | 4356.6762 | 92.9703 | 540.2586 | 20.7619 |
| LUCIFERASE | 499.8757 | 4356.6762 | 92.9703 | 540.2586 | 20.7619 |
| LUCIFERASE | 499.8757 | 4356.6762 | 92.9703 | 540.2586 | 20.7619 |
| LUCIFERASE | 499.8757 | 4356.6762 | 92.9703 | 540.2586 | 20.7619 |
| LUCIFERASE | 30365.8995 | 3839.4901 | 3151.3043 | 23921.2133 | 13668.3973 |
| LUCIFERASE | 30365.8995 | 3839.4901 | 3151.3043 | 23921.2133 | 13668.3973 |
| LUCIFERASE | 30365.8995 | 3839.4901 | 3151.3043 | 23921.2133 | 13668.3973 |
| LUCIFERASE | 30365.8995 | 3839.4901 | 3151.3043 | 23921.2133 | 13668.3973 |
| LUCIFERASE | 30365.8995 | 3839.4901 | 3151.3043 | 23921.2133 | 13668.3973 |
| LUCIFERASE | 30365.8995 | 3839.4901 | 3151.3043 | 23921.2133 | 13668.3973 |
| LUCIFERASE | 21372.1362 | 13092.5802 | 24120.3636 | 41498.4173 | 1315.4021 |
| LUCIFERASE | 21372.1362 | 13092.5802 | 24120.3636 | 41498.4173 | 1315.4021 |
| LUCIFERASE | 21372.1362 | 13092.5802 | 24120.3636 | 41498.4173 | 1315.4021 |
| LUCIFERASE | 21372.1362 | 13092.5802 | 24120.3636 | 41498.4173 | 1315.4021 |
| LUCIFERASE | 21372.1362 | 13092.5802 | 24120.3636 | 41498.4173 | 1315.4021 |
| LUCIFERASE | 21372.1362 | 13092.5802 | 24120.3636 | 41498.4173 | 1315.4021 |
| LUCIFERASE | 1119.1982 | 64.3461 | 40.3416 | 98.8824 | 3075.036 |
| LUCIFERASE | 1119.1982 | 64.3461 | 40.3416 | 98.8824 | 3075.036 |
| LUCIFERASE | 1119.1982 | 64.3461 | 40.3416 | 98.8824 | 3075.036 |
| LUCIFERASE | 1119.1982 | 64.3461 | 40.3416 | 98.8824 | 3075.036 |
| LUCIFERASE | 1119.1982 | 64.3461 | 40.3416 | 98.8824 | 3075.036 |
| LUCIFERASE | 1119.1982 | 64.3461 | 40.3416 | 98.8824 | 3075.036 |
| LUCIFERASE | 45329.1986 | 8677.3381 | 32901.4396 | 27171.2966 | 61989.5924 |
| LUCIFERASE | 45329.1986 | 8677.3381 | 32901.4396 | 27171.2966 | 61989.5924 |
| LUCIFERASE | 45329.1986 | 8677.3381 | 32901.4396 | 27171.2966 | 61989.5924 |
| LUCIFERASE | 45329.1986 | 8677.3381 | 32901.4396 | 27171.2966 | 61989.5924 |
| LUCIFERASE | 45329.1986 | 8677.3381 | 32901.4396 | 27171.2966 | 61989.5924 |
| LUCIFERASE | 45329.1986 | 8677.3381 | 32901.4396 | 27171.2966 | 61989.5924 |
| Zyx | 12.2273 | 0.7706 | 0.3383 | 322.7453 | 16871.2582 |
| Zyx | 3029.542 | 144.7107 | 9767.9015 | 6366.8192 | 176.8874 |
| Zyx | 362.1154 | 1581.5428 | 3.7586 | 1600.7301 | 95.0563 |
| Atp5a1 | 275.0343 | 1.316 | 67.2717 | 7.5044 | 1595.295 |
| Atp5a1 | 76.9685 | 902.1681 | 137.1644 | 795.4614 | 8.5871 |
| Atp5a1 | 0.9236 | 1.4622 | 179.9737 | 1833.8761 | 429.3557 |
| Atp5a1 | 0.9236 | 4.3866 | 0.7863 | 2.8141 | 0.9541 |
| Acox1 | 722.7008 | 704.9618 | 8.0301 | 4196.4046 | 1964.0084 |
| Acox1 | 357.7004 | 1.9546 | 29184.9017 | 3.6141 | 0.7632 |
| Acox1 | 738.3437 | 99.685 | 60.6718 | 155.0059 | 162.8194 |
| Acox1 | 93.8573 | 61278.2482 | 1589.957 | 0.3614 | 3221.6183 |
| Acox1 | 6972.5509 | 1257.4642 | 2463.452 | 1870.5122 | 25789.9071 |

Figure 16 (cont'd)

| Symbol | Spleen.1 | Spleen.2 | Spleen.3 | Spleen.4 | Spleen.5 |
|---|---|---|---|---|---|
| Ybx1 | 1225.549 | 42.8138 | 0.7517 | 4585.5827 | 2.4797 |
| Ybx1 | 28065.3538 | 12478.5182 | 1524.8721 | 22183.5056 | 77.6982 |
| Peli1 | 1.8853 | 4.7934 | 1.0123 | 0.8298 | 1.8586 |
| Dyrk2 | 0.8484 | 1.1983 | 4.4989 | 0.8298 | 0.8364 |
| Dyrk2 | 3411.4636 | 0.5393 | 199.0782 | 44.2586 | 0.8364 |
| Dyrk2 | 1.8853 | 0.5393 | 1.0123 | 10.1426 | 0.8364 |
| Dyrk2 | 0.8484 | 0.5393 | 1.0123 | 7.3764 | 3.7172 |
| Dyrk2 | 1884.3647 | 3.595 | 120.3467 | 121.7111 | 388.4452 |
| Slc19a2 | 30.4535 | 539.7224 | 2021.2115 | 568.0806 | 65.0929 |
| Slc19a2 | 16938.645 | 14.7714 | 2.4861 | 0.8861 | 790.8792 |
| Slc19a2 | 0.9789 | 11.3626 | 1.1188 | 0.8861 | 0.7323 |
| Slc40a1 | 11.4714 | 459.9843 | 14.2757 | 37499.7942 | 468.9537 |
| Ppp2r5c | 0.8484 | 7.7892 | 73.1078 | 0.8298 | 0.8364 |
| Ppp2r5c | 16489.8406 | 24185.5176 | 1904.177 | 4687.7233 | 541.7788 |
| Ppp2r5c | 1552.5506 | 633.9224 | 19268.967 | 1629.2697 | 8.3637 |
| Ppp2r5c | 98.9786 | 911.9375 | 1.0123 | 0.8298 | 2074.1856 |
| Mtmr9 | 22.6237 | 12137.397 | 37.1163 | 17342.9165 | 38620.5551 |
| E2f7 | 277.1402 | 4315.226 | 719.8307 | 0.8298 | 384.728 |
| E2f7 | 295.9933 | 8.3884 | 169.835 | 0.9221 | 17.6566 |
| E2f7 | 214.925 | 0.5393 | 846.9258 | 0.8298 | 181.2125 |
| E2f7 | 3120.1836 | 4036.0125 | 6827.1439 | 4866.6018 | 10005.7152 |
| E2f7 | 0.8484 | 9151.7303 | 70.8583 | 0.8298 | 0.8364 |
| Dst | 140.4554 | 32.3552 | 163.0866 | 3904.8993 | 2929.1366 |
| Dst | 4640.684 | 37.7477 | 19109.2545 | 4043.2075 | 82155.2201 |
| Krt6b | 402.5595 | 0.8563 | 0.3759 | 2.8881 | 0.7439 |
| Krt6b | 10738.3674 | 8.5628 | 0.3383 | 1781.9585 | 19.8378 |
| Krt6b | 106.2832 | 5.9939 | 54.1241 | 9.3863 | 0.7439 |
| Krt6b | 5681.9197 | 3835.2627 | 0.3383 | 5241.1817 | 0.8266 |
| Krt6b | 109324.9887 | 606.2438 | 0.7517 | 459.9301 | 2372.2753 |
| Anln | 2121.1739 | 117.928 | 28.5514 | 2900.1372 | 360.4074 |
| Anln | 44444.5371 | 8985.9822 | 7864.1309 | 36618.3484 | 37335.6648 |
| Anln | 584.0007 | 15765.2125 | 12.4912 | 1835.9772 | 4426.6512 |
| Tubb2c | 2.8217 | 0.7706 | 21.8 | 345.1281 | 0.8266 |
| Tubb2c | 69.6014 | 29812.1244 | 0.3759 | 2532.8648 | 1057.1917 |
| Tubb2c | 0.9406 | 216.638 | 0.7517 | 176.1742 | 1596.1197 |
| Tubb2c | 0.8465 | 11.1316 | 0.3383 | 14.4405 | 0.7439 |
| Tubb2c | 0.8465 | 0.7706 | 0.3383 | 71.4805 | 0.7439 |
| Tjp1 | 2.1752 | 431.7779 | 1189.6061 | 1356.6985 | 5466.993 |
| Tjp1 | 0.9789 | 1.0226 | 1.1188 | 0.9845 | 43.1241 |
| Tjp1 | 0.9789 | 698.7985 | 1.1188 | 0.8861 | 8.1366 |
| Eps8 | 0.9386 | 0.5864 | 0.803 | 0.4016 | 0.7632 |
| Mybbp1a | 89333.0259 | 35.224 | 10304.9469 | 0.8861 | 0.8137 |
| Mybbp1a | 0.9789 | 1.0226 | 300.8199 | 0.8861 | 1659.0562 |
| Mybbp1a | 0.9789 | 1.1363 | 1.1188 | 152.604 | 0.7323 |
| Igf2bp3 | 0.9789 | 1.0226 | 1.1188 | 0.8861 | 0.8137 |
| Igf2bp3 | 0.9789 | 1.0226 | 1.1188 | 0.8861 | 0.7323 |
| Igf2bp3 | 0.9789 | 6516.4382 | 1177.1755 | 3334.6428 | 30.9191 |
| Igf2bp3 | 1.0876 | 104835.6858 | 12234.1721 | 0.8861 | 177.3783 |
| Igf2bp3 | 2.1752 | 209.0714 | 448.7438 | 259.919 | 908.0465 |

Figure 16 (cont'd)

| Symbol | Spleen.1 | Spleen.2 | Spleen.3 | Spleen.4 | Spleen.5 |
|---|---|---|---|---|---|
| Mov10 | 3022.2983 | 10.2353 | 37424.0354 | 151606.6819 | 107.816 |
| Mov10 | 53.3649 | 17.5462 | 54.1668 | 0.8442 | 289.0995 |
| Mov10 | 0.9236 | 1.316 | 0.7863 | 0.8442 | 0.8587 |
| Ube2k | 0.9386 | 0.5864 | 0.803 | 1401.4787 | 1.696 |
| Ube2k | 7423.0657 | 44.956 | 20723.8676 | 58650.4764 | 126268.1041 |
| Ablim1 | 18659.8644 | 320.5556 | 275.6996 | 62775.4016 | 6050.6046 |
| Ablim1 | 19314.7795 | 14258.2102 | 14766.436 | 1217.5597 | 5036.3757 |
| Ablim1 | 2714.5603 | 540.1232 | 12888.2881 | 311.6182 | 8638.7539 |
| Ablim1 | 9989.5401 | 5832.5488 | 5283.7966 | 11784.4678 | 22977.0331 |
| Ablim1 | 3199.4894 | 165.4901 | 0.8922 | 2998.9234 | 14434.9532 |
| Mrpl22 | 1.8811 | 5.9939 | 1445.1894 | 3.6101 | 0.7439 |
| Mrpl22 | 32130.4518 | 4089.5768 | 70.6621 | 15178.4161 | 23.9707 |
| Atp10d | 5956.9127 | 379.5101 | 19503.5725 | 1866.6911 | 0.7323 |
| Atp10d | 1.0876 | 1462.3637 | 432.584 | 2207.3425 | 4312.407 |
| Atp10d | 515.5334 | 40657.5751 | 4478.7363 | 1014.078 | 10919.3401 |
| Atp10d | 0.9789 | 7464.0772 | 8884.1321 | 1468.9362 | 21.9689 |
| Atp10d | 35.8916 | 119.3071 | 22198.5213 | 75825.4644 | 1120.4122 |
| Caprin1 | 55566.1601 | 1.316 | 9654.8001 | 750.4353 | 1970.2657 |
| Caprin1 | 1.0262 | 1.316 | 0.7863 | 32474.1475 | 0.8587 |
| Caprin1 | 0.9236 | 1.316 | 0.7863 | 0.8442 | 0.8587 |
| Stau1 | 0.9236 | 242.7227 | 7.8629 | 0.938 | 143.1186 |
| Stau1 | 33240.1501 | 3608.6725 | 124.9332 | 88.1761 | 0.9541 |
| Stau2 | 778.9217 | 1.316 | 1379.5068 | 18409.1148 | 51395.7877 |
| Stau2 | 5678.2263 | 36.5546 | 1.7473 | 24015.8042 | 1.9082 |
| Stau2 | 98.5197 | 1.316 | 39289.2963 | 983.0702 | 1551.4053 |
| Prpf19 | 34.8924 | 440.1177 | 7.8629 | 553.446 | 170.7882 |
| Prpf19 | 1.0262 | 1.316 | 0.7863 | 1249.4747 | 51.5227 |
| Prpf19 | 0.9236 | 1.316 | 0.7863 | 0.938 | 0.8587 |
| Prpf19 | 0.9236 | 1.316 | 0.7863 | 0.8442 | 5.7247 |
| Prpf19 | 1560.9221 | 1.316 | 149.3956 | 319.873 | 0.8587 |
| Pura | 3172.5071 | 0.7706 | 62.3931 | 0.6498 | 0.7439 |
| Pura | 1485.1434 | 39.3887 | 1097.517 | 568.2339 | 0.7439 |
| Pura | 17.8706 | 10.2753 | 10.9 | 574.7321 | 0.7439 |
| Pura | 123973.2618 | 575989.8343 | 18.0414 | 1368.238 | 19.0113 |
| Pura | 4207.1225 | 14767.3454 | 4593.4094 | 42019.707 | 64.473 |
| Hnrnpab | 3694.6563 | 7.9538 | 8.7014 | 0.8861 | 0.7323 |
| Hnrnpab | 1.0876 | 2.2725 | 74.5835 | 0.8861 | 17.0869 |
| Hnrnpab | 0.9789 | 1.0226 | 1.1188 | 0.8861 | 0.8137 |
| Hnrnpab | 2.1752 | 1.0226 | 1.1188 | 0.8861 | 158.664 |
| Hnrnpab | 0.9789 | 44.3141 | 12.4306 | 0.8861 | 9462.072 |
| Ddx56 | 0.9236 | 1.316 | 0.8737 | 0.8442 | 0.8587 |
| Ddx21 | 241.1681 | 1.316 | 113901.4793 | 3.7522 | 0.8587 |
| Ddx21 | 99.546 | 1.4622 | 709.4107 | 9.3804 | 0.8587 |
| Ddx21 | 11.2887 | 1555.7648 | 1403.0955 | 57.2207 | 21.9448 |
| Rbmx | 348.9476 | 0.7706 | 12.4034 | 2.1661 | 12838.3902 |
| Rbmx | 34425.4169 | 215.7817 | 457.424 | 26686.0555 | 3185.6268 |
| Rbmx | 442.0629 | 0.8563 | 4.1345 | 15.1625 | 273.5969 |
| Rbmx | 19.7517 | 0.7706 | 3.7586 | 11872.2622 | 11.5721 |
| Rbmx | 1222.7273 | 1259.5828 | 0.3383 | 298.9185 | 3890.6968 |

Figure 16 (cont'd)

| Symbol | Spleen.1 | Spleen.2 | Spleen.3 | Spleen.4 | Spleen.5 |
|---|---|---|---|---|---|
| Rps24 | 1869.8322 | 3.4251 | 24.0552 | 7117.0035 | 54478.0209 |
| Rps24 | 0.8465 | 3.4251 | 27.4379 | 0.722 | 0.7439 |
| Rps24 | 0.8465 | 163.5488 | 0.3383 | 0.722 | 0.7439 |
| Rpl24 | 0.9236 | 43.8655 | 3.4946 | 5.6283 | 0.8587 |
| Rpl24 | 10.2625 | 1.316 | 1349.8024 | 0.8442 | 0.8587 |
| Rpl24 | 0.9236 | 1.316 | 0.7863 | 0.8442 | 0.8587 |
| Rpl24 | 1.0262 | 1.316 | 4.3683 | 0.8442 | 0.9541 |
| Rpl24 | 18.4725 | 1.316 | 0.7863 | 0.8442 | 0.8587 |
| Mrpl4 | 0.9789 | 6.8175 | 24.8612 | 1635.3238 | 0.7323 |
| Mrpl4 | 0.9789 | 874.9185 | 3.7292 | 0.8861 | 0.7323 |
| Mrpl4 | 0.9789 | 267.0206 | 113.1182 | 171.3103 | 2362.0599 |
| Rpl26 | 0.9406 | 0.7706 | 0.3383 | 0.6498 | 0.7439 |
| Rpl26 | 0.8465 | 0.8563 | 0.3759 | 0.6498 | 860.4664 |
| Rpl26 | 0.9406 | 0.7706 | 0.3383 | 0.6498 | 7.4392 |
| Rpl26 | 0.8465 | 0.7706 | 0.3383 | 0.6498 | 14.0518 |
| Rpl26 | 39.5035 | 2693.846 | 0.7517 | 0.722 | 0.7439 |
| Rps11 | 0.9789 | 1.0226 | 8.7014 | 0.8861 | 0.7323 |
| Mrpl39 | 7.5245 | 81.3463 | 0.3759 | 3610.8486 | 210.7771 |
| Mrpl39 | 15.049 | 18.8381 | 0.3383 | 0.6498 | 25.6239 |
| Mrpl39 | 35927.4904 | 90.7653 | 1.5034 | 425.9949 | 70.259 |
| Mrpl39 | 4782.7449 | 1585.8242 | 18.4172 | 83814.864 | 46244.4898 |
| Rpl4 | 0.8465 | 13.7004 | 13.1552 | 0.722 | 0.7439 |
| Rpl4 | 0.8465 | 0.7706 | 4.5103 | 7.2203 | 0.7439 |
| Rpl4 | 0.8465 | 0.7706 | 0.3383 | 0.6498 | 0.7439 |
| Rpl4 | 2.8217 | 101.8969 | 0.3383 | 10.1084 | 0.7439 |
| Rpl4 | 0.8465 | 0.7706 | 0.3383 | 1.4441 | 0.7439 |
| Mrps9 | 35.9187 | 2137.7144 | 73971.7913 | 2984.8562 | 6878.2786 |
| Mrps9 | 1998.1035 | 5493.4289 | 418.4824 | 15498.3641 | 9743.5124 |
| Rpl18 | 1303.3341 | 190.084 | 5933.0149 | 0.8442 | 0.8587 |
| Rpl18 | 0.9236 | 1.4622 | 0.7863 | 8.4424 | 0.8587 |
| Rpl18 | 18.4725 | 1.4622 | 0.7863 | 0.8442 | 41.0273 |
| Rpl18 | 0.9236 | 1.316 | 0.7863 | 0.938 | 1392.0667 |
| Numb | 6802.565 | 17489.1764 | 70.4863 | 1.6063 | 20438.0689 |
| Numb | 2179.574 | 41.0468 | 5.3534 | 4463.4485 | 563.9316 |
| Numb | 8.3429 | 18.8945 | 0.803 | 0.3614 | 0.7632 |
| Snx14 | 0.8484 | 841.8346 | 27956.4233 | 3928.8727 | 1666.2253 |
| Snx14 | 0.8484 | 65.3096 | 1.1247 | 130.0096 | 877.2541 |
| Snx14 | 469.4415 | 19.7726 | 662.4692 | 24.8955 | 5607.3637 |
| Snx14 | 0.8484 | 0.5393 | 10515.1513 | 8.2985 | 326.1824 |
| Numbl | 11384.1529 | 29364.3092 | 8432.9022 | 29297.9922 | 4021.9298 |
| Smc4 | 6.5986 | 364.8948 | 41.6152 | 218.5268 | 2036.0845 |
| Smc4 | 87418.8729 | 346005.3901 | 192814.5154 | 3247.4747 | 17328.5568 |
| Ptbp1 | 8808.2806 | 7695.4795 | 18959.2631 | 29668.4577 | 4251.5757 |
| Ptbp1 | 346.8716 | 766.1849 | 99.5971 | 0.8442 | 1592.4327 |
| Crot | 107.4144 | 9.773 | 74.0552 | 1.6063 | 131.4427 |
| Crot | 589.215 | 135.5195 | 1.7845 | 118.8647 | 36.4648 |
| Abcc5 | 33260.9242 | 174946.4926 | 215.9201 | 12277.9971 | 18307.849 |
| Abcc5 | 33219.2099 | 6425.4464 | 41060.5067 | 6745.5698 | 21477.7383 |
| Abcc5 | 76.1287 | 60.5928 | 1329.4254 | 2021.904 | 29884.1354 |

Figure 16 (cont'd)

| Symbol | Spleen.1 | Spleen.2 | Spleen.3 | Spleen.4 | Spleen.5 |
|---|---:|---:|---:|---:|---:|
| Pdia6 | 610.4231 | 15835.9785 | 658.1343 | 559.5696 | 161.1825 |
| Pdia6 | 70195.8339 | 9782.1033 | 2352.5202 | 35748.1951 | 26451.2828 |
| Pdia6 | 0.9406 | 40147.3823 | 10.9 | 569.678 | 5867.8684 |
| Pdia6 | 0.8465 | 5.1377 | 0.3759 | 0.722 | 0.7439 |
| Hnrnpl | 90.2727 | 724.9324 | 718.4872 | 208006.0963 | 0.7323 |
| Syncrip | 484.3881 | 80.49 | 258.5931 | 0.722 | 0.8266 |
| Syncrip | 0.8465 | 0.7706 | 0.3759 | 9.3863 | 0.7439 |
| Hnrnpc | 1013.9231 | 8336.7085 | 0.3759 | 1989.1797 | 55.3806 |
| Hnrnpc | 2.8217 | 245.7514 | 918.6067 | 1888.0962 | 18.1847 |
| Hnrnpc | 31.979 | 7.7065 | 0.3383 | 1273.6526 | 0.7439 |
| Hnrnpc | 647.1049 | 1179.0928 | 4.1345 | 1266.4324 | 0.7439 |
| Hnrnpr | 15.2267 | 1.0226 | 31.0764 | 4388.1024 | 2044.7319 |
| Hnrnpr | 0.9789 | 1.1363 | 1.1188 | 153.5885 | 0.7323 |
| Hnrnpa3 | 75958.6417 | 0.8563 | 0.3759 | 7.9423 | 0.7439 |
| Hnrnpa3 | 34.8007 | 746.6732 | 1.5034 | 2.1661 | 75.2185 |
| Hnrnpa3 | 2361.7448 | 17.9818 | 90.5827 | 659.9311 | 0.8266 |
| Hnrnpa3 | 0.8465 | 104.4657 | 0.3383 | 1313.364 | 0.7439 |
| Hnrnpa3 | 864.3741 | 0.7706 | 0.3383 | 8.6643 | 0.8266 |
| Asph | 0.9386 | 4.5608 | 0.803 | 34.535 | 0.7632 |
| Asph | 259.6717 | 0.6515 | 0.803 | 0.3614 | 0.848 |
| Kif21a | 2742.1795 | 0.5393 | 1.0123 | 0.8298 | 4.6465 |
| Kif21a | 0.9427 | 0.5393 | 1.1247 | 23.0514 | 0.8364 |
| Cltc | 0.8484 | 0.5393 | 23.6194 | 2472.9492 | 0.8364 |
| Ap3s1 | 9648.3061 | 6203.9674 | 36.0487 | 7560.2958 | 1294.5358 |
| Ap3s1 | 1.0876 | 6035.8012 | 218.7781 | 0.8861 | 665.5753 |
| Crbn | 15973.4613 | 8633.5013 | 0.803 | 22418.4382 | 2840.0105 |
| Crbn | 0.9386 | 0.6515 | 0.803 | 0.3614 | 132.2907 |
| Crbn | 3922.1903 | 2420.4556 | 6815.7586 | 740.4947 | 3245.3628 |
| Abca1 | 1314.0592 | 1897.573 | 194.5792 | 27355.5026 | 477.6574 |
| Abca1 | 223.4089 | 44.9378 | 711.9575 | 46.1027 | 154.2629 |
| Mrpl38 | 3754.4756 | 45216.2412 | 3942.9785 | 147.6813 | 4027.6254 |
| Mrpl38 | 17895.7535 | 48.8591 | 1.1188 | 5154.0759 | 1811.211 |
| Mrpl38 | 0.9789 | 17.0439 | 1.1188 | 0.8861 | 0.7323 |
| Cct3 | 0.9236 | 1.316 | 1.7473 | 0.8442 | 27.6696 |
| Cct3 | 8507.5901 | 5709.8323 | 512.8375 | 5043.8629 | 3126.6638 |
| Cct3 | 12.315 | 1.316 | 243.7507 | 4.6902 | 0.8587 |
| Sepp1 | 11433.4463 | 3.595 | 1.1247 | 7.3764 | 1504.528 |
| Sepp1 | 4216.4898 | 63750.5437 | 1520.6423 | 24516.4979 | 9576.381 |
| Sepp1 | 9100.3785 | 63.5121 | 31813.141 | 26954.409 | 418.1826 |
| Sepp1 | 783.3452 | 52.1278 | 1576.879 | 0.9221 | 646.7891 |
| Tmem50b | 1892.8486 | 0.5393 | 97.852 | 98.6598 | 15.798 |
| Tmem50b | 22.6237 | 0.5393 | 39.3657 | 1.8441 | 1.8586 |
| Aqp11 | 151623.2612 | 497.1218 | 2436.685 | 58168.1911 | 10126.1765 |
| Mrpl37 | 13.3412 | 767.6471 | 1143.619 | 4480.0985 | 19.0825 |
| Lst1 | 147.9966 | 0.5393 | 1.0123 | 189.0211 | 4.6465 |
| Lst1 | 473.2121 | 6.5909 | 557.8688 | 1021.636 | 2210.7919 |
| Aqp11 | 331.629 | 123.1403 | 689.6952 | 491.5215 | 1963.1604 |
| Mrpl37 | 104.6772 | 1.316 | 0.8737 | 226.0686 | 48.6603 |
| Fastkd2 | 1.0876 | 251.113 | 4120.7357 | 652.7512 | 29.2918 |

Figure 16 (cont'd)

| Symbol | Spleen.1 | Spleen.2 | Spleen.3 | Spleen.4 | Spleen.5 |
|---|---|---|---|---|---|
| Fastkd2 | 2.1752 | 32.9515 | 3505.4222 | 810.2778 | 2520.724 |
| Fastkd2 | 0.9789 | 1.0226 | 1.1188 | 0.8861 | 0.7323 |
| Cyb5 | 1.0429 | 115.9734 | 0.803 | 37.346 | 0.7632 |
| Mrpl37 | 0.9236 | 339.2269 | 3.4946 | 4671.4594 | 20.0366 |
| Cyb5 | 11846.8709 | 12738.8286 | 14701.3031 | 4.0157 | 9545.2846 |
| Ptcd3 | 68026.9038 | 2244.3008 | 373926.6791 | 275.0916 | 41771.883 |
| Ptcd3 | 79.9476 | 0.8563 | 49006.0142 | 28891.8428 | 76.8716 |
| Snx16 | 125.143 | 121.8372 | 26.767 | 13632.8937 | 10.1762 |
| Snx16 | 301.3861 | 286.6758 | 29.4436 | 15.2597 | 680.11 |
| Tax1bp1 | 0.9386 | 26.0614 | 4.4612 | 0.3614 | 0.7632 |
| Tax1bp1 | 0.9386 | 1.3031 | 48929.0988 | 8625.7197 | 0.7632 |
| Tax1bp1 | 946.9154 | 1678.3563 | 2617.8081 | 31983.0281 | 3481.9597 |
| Mrps27 | 21.6329 | 1414.5689 | 0.3759 | 6719.1675 | 13.2252 |
| Snx16 | 0.9386 | 190.2485 | 0.803 | 0.3614 | 0.7632 |
| Mrps27 | 1409.8986 | 3737.6471 | 115765.1178 | 4807.9665 | 15.705 |
| Mrps27 | 0.8465 | 0.7706 | 0.3383 | 0.6498 | 951.3898 |
| Rabep1 | 727.7286 | 0.5393 | 4.4989 | 1169.1647 | 227.6772 |
| Mrps28 | 127.2547 | 1.4622 | 16812.6841 | 12654.2144 | 49555.2829 |
| Fcho2 | 159.8806 | 1.1363 | 78.3126 | 0.8861 | 0.7323 |
| Baz2b | 4.7133 | 50173.9392 | 35.9915 | 7315.5776 | 13.0101 |
| Fcho2 | 27.1906 | 426.0967 | 2798.1225 | 17042.417 | 9835.5427 |
| Fcho2 | 0.9789 | 361.33 | 1485.4537 | 877.2267 | 846.2082 |
| Rabep1 | 2586.6417 | 2.9959 | 12875.9709 | 64310.511 | 317051.1623 |
| Paip1 | 23914.6607 | 16623.451 | 14694.183 | 13136.74 | 17984.3647 |
| Ttc3 | 4827.3294 | 665.6784 | 1615.12 | 822.4723 | 4875.0796 |
| Mrps28 | 193.9607 | 40.9412 | 127.5541 | 1202.5725 | 9.5412 |
| Fcho2 | 0.9789 | 1.0226 | 1.1188 | 0.8861 | 0.7323 |
| Baz2b | 44513.9913 | 6.5909 | 3557.5381 | 7.3764 | 473.9403 |
| Fcho2 | 923.3922 | 162789.3764 | 1971.4892 | 3995.2703 | 24713.347 |
| Baz2b | 12519.3833 | 1966.4776 | 73824.2578 | 72444.8727 | 106095.7081 |
| Ict1 | 294552.4741 | 118460.3777 | 175860.4663 | 120909.1898 | 469576.8079 |
| Ict1 | 6406.8619 | 4.3866 | 0.7863 | 64.725 | 0.9541 |
| Sertad2 | 168.5816 | 471.547 | 53.4515 | 13.7836 | 0.7323 |
| Ict1 | 297.6117 | 5880.908 | 371.3049 | 1352.6595 | 49.6144 |
| Fastkd2 | 1.0876 | 1401.0058 | 19015.0509 | 2838.4338 | 286.4089 |
| Mrpl37 | 2.0525 | 49.7143 | 189.5839 | 46.9022 | 45.7979 |
| Ptcd3 | 0.8465 | 48.8078 | 0.7517 | 101.0835 | 0.7439 |
| Aqp11 | 5981.8355 | 25852.9418 | 87026.5037 | 37074.5318 | 9793.7537 |
| Aqp11 | 1271.2443 | 26.0614 | 3857.118 | 148.5808 | 1511.1671 |
| Mrps27 | 0.8465 | 0.7706 | 0.3383 | 0.6498 | 0.7439 |
| Mrps27 | 612.3042 | 122.4475 | 8.269 | 108.3038 | 605.8808 |
| Tax1bp1 | 2931.4748 | 838.5266 | 84696.8866 | 20629.8462 | 1545.9358 |
| Ttc3 | 1002.0408 | 395.4525 | 5.6237 | 346.6924 | 44.6061 |
| Paip1 | 1037.5926 | 1525.9942 | 7046.8931 | 8302.6402 | 42419.4394 |
| Baz2b | 3686.7185 | 7.19 | 5.6237 | 919.288 | 468.3645 |
| Mrps28 | 16513.3453 | 678.4538 | 11204.6702 | 206652.9837 | 1042.8573 |
| Mrpl37 | 16073.0852 | 12279.4294 | 52571.5264 | 40307.7535 | 9404.7985 |
| Cyb5 | 1.0429 | 1.3031 | 0.803 | 1.6063 | 0.848 |
| Sertad2 | 144368.9392 | 8385.5823 | 207.5906 | 28724.0044 | 407.6445 |

Figure 16 (cont'd)

| Symbol | Spleen.1 | Spleen.2 | Spleen.3 | Spleen.4 | Spleen.5 |
|---|---|---|---|---|---|
| Sertad2 | 1.0876 | 14.7714 | 364.2159 | 39.3817 | 13.0186 |
| Tax1bp1 | 6879.7365 | 1058.7457 | 137.4037 | 1189.0482 | 29910.4239 |
| Ybx1 | 0.8465 | 0.8563 | 14.6586 | 34.6572 | 18262.3869 |
| Trip11 | 679.6533 | 4.1942 | 186.7061 | 993.0523 | 0.9293 |
| Trip11 | 87.6668 | 0.5393 | 22.4947 | 10291.9684 | 11.1515 |
| Trip11 | 861.5854 | 16.7768 | 14.6216 | 0.8298 | 2187.5595 |
| Trip11 | 0.8484 | 1479.9512 | 571.3656 | 0.8298 | 0.8364 |
| Trip11 | 579.732 | 54.5245 | 644.4734 | 9029.6763 | 936.729 |
| Sertad2 | 4414.6629 | 11.3626 | 1.1188 | 73.8406 | 0.7323 |
| Sertad2 | 0.9789 | 5661.9724 | 87834.4446 | 34220.7008 | 10817.6324 |
| Mybbp1a | 0.9789 | 1.1363 | 1.1188 | 0.8861 | 0.7323 |
| Mybbp1a | 0.9789 | 1.0226 | 3.7292 | 41.3508 | 0.7323 |
| Mybbp1a | 0.9789 | 1.0226 | 1.1188 | 0.8861 | 78.9252 |
| Gpr65 | 0.9386 | 0.5864 | 0.803 | 534.4894 | 80.5617 |
| Gpr65 | 0.9386 | 0.5864 | 1307.1196 | 1.6063 | 5.9361 |
| Gpr65 | 30201.1778 | 12770.1023 | 163.2784 | 31.724 | 5743.6223 |
| Gpr65 | 450.5148 | 10248.0071 | 1231.2799 | 29487.2716 | 322.2466 |
| Gpr65 | 2984.6606 | 28.6676 | 2874.7708 | 543.324 | 14.4163 |
| Mll3 | 0.8484 | 0.5393 | 1.0123 | 0.8298 | 3.7172 |
| Mll3 | 222.4663 | 0.5393 | 1.0123 | 0.8298 | 3.7172 |
| Mll3 | 0.8484 | 2.9959 | 6035.3302 | 14.7529 | 0.8364 |
| Mll3 | 0.8484 | 0.5393 | 1.0123 | 0.8298 | 0.9293 |
| Mll3 | 0.8484 | 0.5393 | 1.0123 | 0.8298 | 0.8364 |
| Cenpf | 538.1149 | 1289.3894 | 97387.9915 | 116.0537 | 21950.932 |
| Cenpf | 21011.51 | 4798.5614 | 0.803 | 367.0348 | 0.848 |
| Cenpf | 0.9386 | 25.4099 | 0.803 | 0.3614 | 0.848 |
| Cenpf | 282.6146 | 1136.93 | 0.803 | 4712.8234 | 230.6607 |
| Cenpf | 47.9715 | 151.8078 | 4772.5478 | 0.3614 | 54.2731 |
| Mns1 | 0.9789 | 1.0226 | 1.1188 | 0.8861 | 0.8137 |
| Mns1 | 23.9277 | 106.8082 | 1587.3845 | 1972.037 | 877.1273 |
| Mns1 | 106.5871 | 1.0226 | 2.4861 | 38.3971 | 13.0186 |
| Mrps22 | 11989.3115 | 202.9375 | 151374.6589 | 163979.1681 | 18021.853 |
| Mrps22 | 12.2273 | 17.1255 | 324.3689 | 0.6498 | 19.0113 |
| Mrps22 | 31747.6441 | 1603.806 | 2043.5617 | 4132.8729 | 6.6126 |
| Mrps22 | 0.8465 | 5.9939 | 0.3383 | 0.6498 | 0.7439 |
| Mrps22 | 0.8465 | 0.7706 | 5.6379 | 5.0542 | 405.8492 |
| Mrps23 | 7035.9515 | 4158.4541 | 70356.5925 | 2207.2177 | 0.8587 |
| Mrps23 | 329.4254 | 1.316 | 3.4946 | 0.938 | 0.8587 |
| Mrps23 | 12.315 | 1.316 | 0.8737 | 0.8442 | 0.8587 |
| Mrps23 | 0.9236 | 1003.0589 | 480.5122 | 623.7993 | 21.9448 |
| Mrps23 | 0.9236 | 12981.2782 | 2.621 | 3.7522 | 0.8587 |
| Cep70 | 4210.0192 | 187.6423 | 6648.9113 | 9923.9949 | 8.4802 |
| Cep70 | 2.0857 | 0.5864 | 137.4037 | 10435.9964 | 59.3612 |
| Cep70 | 160.6002 | 517.3195 | 3748.2657 | 9741.2806 | 1844.438 |
| Cep70 | 0.9386 | 602.0191 | 26559.9557 | 3754.2762 | 35.6167 |
| Cep70 | 167.9002 | 331.6317 | 4958.132 | 5.2204 | 708.0946 |
| Rwdd4a | 5681.4923 | 319362.0161 | 41.9349 | 820.4071 | 524.0748 |
| Rwdd4a | 1863.5879 | 9.773 | 0.8922 | 313.626 | 161.1233 |
| Rwdd4a | 1317.1301 | 2849.1662 | 36.5815 | 76194.6602 | 19125.3378 |

Figure 16 (cont'd)

| Symbol | Spleen.1 | Spleen.2 | Spleen.3 | Spleen.4 | Spleen.5 |
|---|---|---|---|---|---|
| Rwdd4a | 18128.0067 | 22246.0395 | 1852.2732 | 7073.6523 | 20543.223 |
| Rwdd4a | 7.3 | 34.5314 | 24970.8909 | 28690.9587 | 0.7632 |
| Bex1 | 0.9386 | 0.5864 | 662.036 | 0.4016 | 0.7632 |
| Bex1 | 33680.1533 | 1908.3485 | 34.797 | 17006.8833 | 2324.4159 |
| Mrpl44 | 524.8322 | 5.9939 | 16880.3379 | 14166.1366 | 1595.2931 |
| Mrpl44 | 6180.4162 | 48.8078 | 0.3383 | 352.3484 | 0.7439 |
| Mrpl44 | 0.8465 | 750.9545 | 0.3383 | 490.2552 | 0.7439 |
| Mrpl44 | 0.8465 | 0.7706 | 0.3383 | 0.722 | 0.7439 |
| Mrpl44 | 3382.2518 | 17.1255 | 12047.8803 | 35426.8939 | 32.2365 |
| Lst1 | 68154.8026 | 16899.6042 | 20731.123 | 1785.0968 | 32509.5137 |
| Lst1 | 10.3692 | 0.5992 | 2189.8598 | 0.8298 | 0.8364 |
| Lst1 | 19.7957 | 0.5393 | 7782.0443 | 7872.4984 | 107.7982 |
| Tnrc6a | 0.8484 | 7.7892 | 1065.1244 | 0.8298 | 7.4344 |
| Tnrc6a | 45833.7065 | 37312.7442 | 18282.574 | 45935.8158 | 13961.7224 |
| Tnrc6a | 40.5341 | 0.5393 | 43.8647 | 0.8298 | 1028.7291 |
| Tnrc6a | 0.8484 | 41.3428 | 2.2495 | 330.0954 | 0.8364 |
| Iqgap2 | 16.0251 | 225.8873 | 5326.7469 | 302.4338 | 0.8364 |
| Iqgap2 | 0.8484 | 0.5992 | 3.3742 | 0.9221 | 3.7172 |
| Iqgap2 | 4140.1349 | 45.537 | 122.5962 | 0.8298 | 3154.9552 |
| Iqgap2 | 426.0795 | 90.4747 | 1.0123 | 0.8298 | 0.8364 |
| Iqgap2 | 0.8484 | 1062.9285 | 1.0123 | 0.8298 | 11298.364 |
| Mns1 | 0.9789 | 1.0226 | 1.1188 | 77.7788 | 12139.8326 |
| Mns1 | 2.1752 | 10875.123 | 66465.0427 | 12300.8641 | 48731.8269 |
| Bex1 | 7.3 | 0.5864 | 0.803 | 0.3614 | 83.9537 |
| Bex1 | 0.9386 | 0.5864 | 4.4612 | 0.3614 | 0.7632 |
| Bex1 | 0.9386 | 385.7092 | 0.803 | 96.3768 | 0.7632 |
| Asph | 22260.8543 | 652.1874 | 16665.9975 | 20.4801 | 5097.433 |
| Asph | 79.2572 | 65.8051 | 42.8271 | 33.3303 | 29.6806 |
| Asph | 118.8859 | 0.5864 | 15.1679 | 257.4063 | 5151.7061 |
| Tnrc6a | 2646.0288 | 5418.8981 | 7.8731 | 210.2283 | 97.5759 |
| Abca1 | 11258.1127 | 170.1644 | 4890.3495 | 82.9849 | 6847.0428 |
| Abca1 | 9.4265 | 187.5404 | 76.482 | 16472.4974 | 0.8364 |
| Abca1 | 0.8484 | 10.1859 | 1.0123 | 20.2852 | 3318.5111 |
| Upf1 | 0.9236 | 1.316 | 6.9893 | 0.8442 | 0.8587 |
| Upf1 | 16768.8809 | 519.0757 | 13458.7092 | 0.938 | 7845.7602 |
| Upf1 | 98.5197 | 23.395 | 2458.475 | 0.8442 | 67.7428 |
| Upf1 | 0.9236 | 1.316 | 133.6698 | 589.0917 | 326.3103 |
| Snx16 | 838.4581 | 24.1068 | 0.803 | 28.913 | 21214.0048 |
| Snx16 | 587.1293 | 0.5864 | 1.7845 | 5.2204 | 0.7632 |
| Paip1 | 39394.8029 | 1.0226 | 19220.1554 | 31690.4286 | 24.4099 |
| Paip1 | 133.7777 | 321.5609 | 33543.9073 | 6.8918 | 14017.7639 |
| Paip1 | 0.9789 | 3636.0248 | 125.5488 | 252.0427 | 1130.9898 |
| Spcs1 | 0.9789 | 1.0226 | 1146.099 | 436.152 | 65.9066 |
| Spcs1 | 0.9789 | 1.0226 | 211.3198 | 0.8861 | 668.8299 |
| Ptbp1 | 6865.5944 | 57.0252 | 426.3453 | 0.8442 | 131.6691 |
| Ptbp1 | 50297.4065 | 1469.4959 | 7111.5802 | 53933.7816 | 3181.0488 |
| Hnrnpl | 0.9789 | 1.0226 | 1.1188 | 0.8861 | 0.7323 |
| Hnrnpl | 692.816 | 334.0598 | 1.1188 | 0.8861 | 0.7323 |
| Hnrnpl | 198204.1164 | 84.0831 | 1.2431 | 41.3508 | 0.7323 |

Figure 16 (cont'd)

| Symbol | Spleen.1 | Spleen.2 | Spleen.3 | Spleen.4 | Spleen.5 |
|---|---|---|---|---|---|
| Ddx56 | 0.9236 | 23.395 | 13524.2335 | 4628.3094 | 14289.9124 |
| Ddx56 | 41244.879 | 450.353 | 551.2785 | 48812.061 | 2708.7575 |
| Rps24 | 0.8465 | 0.7706 | 0.3759 | 0.6498 | 14.8784 |
| Rps11 | 0.9789 | 1.0226 | 1.1188 | 0.8861 | 0.7323 |
| Rps11 | 0.9789 | 1.0226 | 1.1188 | 0.8861 | 0.7323 |
| Rps11 | 0.9789 | 1.0226 | 1.1188 | 0.8861 | 0.7323 |
| Cyb5 | 2248.4026 | 31559.7442 | 543.3692 | 30.9209 | 22087.4628 |
| Gpsm2 | 133.4859 | 0.6515 | 0.803 | 8.8345 | 42520.4436 |
| Cyb5 | 1421.4159 | 10560.7443 | 0.803 | 2252.4051 | 2.5441 |
| Ptbp1 | 367.3965 | 236388.5201 | 2489.0531 | 466.2079 | 2045.6415 |
| Hnrnpl | 0.9789 | 1.0226 | 96110.7216 | 174.2639 | 2007.3034 |
| Hnrnpl | 0.9789 | 1.0226 | 1.1188 | 0.8861 | 69.9749 |
| Ptbp1 | 496.7037 | 2.9244 | 942.6775 | 5157.3663 | 0.8587 |
| Rps24 | 56.4336 | 88.1965 | 185.6758 | 10844.0981 | 9.0923 |
| Rps24 | 0.8465 | 451.2577 | 0.3383 | 12514.8647 | 14991.6226 |
| Rps11 | 0.9789 | 1.0226 | 1.1188 | 0.8861 | 0.8137 |
| Rps11 | 0.9789 | 52151.9586 | 1.2431 | 871.3194 | 0.7323 |
| Spcs1 | 1.0876 | 1.0226 | 780.6401 | 5204.2875 | 371.0297 |
| Ilf2 | 27.2762 | 375.9054 | 28.1896 | 23.8268 | 267373.6102 |
| Ilf2 | 3.7622 | 498.353 | 0.3383 | 508.3058 | 0.7439 |
| Ssb | 17.8706 | 0.7706 | 0.3383 | 0.6498 | 0.7439 |
| Ssb | 0.8465 | 0.7706 | 19.9207 | 12.9965 | 0.7439 |
| Tjp1 | 0.9789 | 299.972 | 1.1188 | 0.8861 | 0.7323 |
| Tjp1 | 0.9789 | 2517.9472 | 989.4738 | 22.6445 | 0.7323 |
| Mrps9 | 0.9236 | 1.316 | 0.7863 | 313.3067 | 6.6789 |
| Mrps9 | 8285.9207 | 1.316 | 481.3858 | 3436.0554 | 166.9717 |
| Mrps9 | 0.9236 | 1.316 | 49623.8027 | 5013.8455 | 1728.8724 |
| Hnrnpa2b1 | 27402.8554 | 3387.8826 | 1807.5994 | 363.0231 | 11.4495 |
| Hnrnpa2b1 | 2205.4054 | 2849.7985 | 5.242 | 0.938 | 94.4583 |
| Ilf3 | 1439.825 | 947.4959 | 678.8327 | 36534.9403 | 1652.5425 |
| Ilf2 | 0.8465 | 414.4379 | 1190.7308 | 18.7727 | 0.7439 |
| Ilf2 | 0.8465 | 5.9939 | 0.3383 | 0.6498 | 0.7439 |
| Ilf2 | 0.8465 | 0.7706 | 0.3383 | 1.4441 | 0.7439 |
| Kif21a | 17.9104 | 220.4947 | 6.7484 | 2913.6911 | 0.8364 |
| Mrpl22 | 1.8811 | 0.7706 | 1.1276 | 0.6498 | 3.3063 |
| Abcc5 | 20.8572 | 2620.4771 | 735.199 | 4321.2928 | 416.3766 |
| Abcc5 | 80104.0355 | 609.186 | 0.803 | 1072.1914 | 262.0374 |
| Ddx56 | 0.9236 | 1.316 | 34.9463 | 2.8141 | 62.9722 |
| Ddx56 | 16.42 | 1.316 | 219.2883 | 18.7609 | 144.0727 |
| Ddx56 | 0.9236 | 1.316 | 0.7863 | 0.8442 | 0.8587 |
| Kif21a | 13920.1667 | 12663.4687 | 2577.8936 | 678.6319 | 7304.2557 |
| Stau2 | 26.6824 | 36.5546 | 6676.4982 | 3.7522 | 644.0336 |
| Stau2 | 30.7874 | 2779.6136 | 16.5995 | 0.8442 | 0.8587 |
| Syncrip | 30284.1336 | 26.5446 | 37.5862 | 0.722 | 0.7439 |
| Syncrip | 1266.9336 | 226.057 | 0.3383 | 465.7063 | 19.0113 |
| Syncrip | 0.8465 | 263.7332 | 0.3383 | 251.2648 | 0.7439 |
| Hnrnpr | 0.9789 | 495.4084 | 1.1188 | 1719.0098 | 0.7323 |
| Hnrnpr | 0.9789 | 5723.3303 | 12.4306 | 0.9845 | 51172.812 |
| Hnrnpr | 0.9789 | 1.0226 | 2060.9894 | 0.8861 | 0.7323 |

Figure 16 (cont'd)

| Symbol | Spleen.1 | Spleen.2 | Spleen.3 | Spleen.4 | Spleen.5 |
|---|---|---|---|---|---|
| Cltc | 7.5412 | 1.1983 | 7.8731 | 0.8298 | 0.8364 |
| Ap3s1 | 0.9789 | 1.0226 | 1.2431 | 0.8861 | 0.7323 |
| Ap3s1 | 1.0876 | 5074.5271 | 42895.429 | 19902.5107 | 12270.8322 |
| Ap3s1 | 68403.8911 | 4851.8206 | 233.6948 | 4176.4259 | 54.5153 |
| Anln | 0.9386 | 0.5864 | 0.8922 | 500.356 | 13.5683 |
| Ube2k | 665.3436 | 17.5915 | 0.803 | 1505.8868 | 0.7632 |
| Peli1 | 6.5986 | 46.1361 | 1.0123 | 287.6809 | 102.2224 |
| Peli1 | 0.8484 | 10.7851 | 1.0123 | 93.1275 | 0.8364 |
| Mrpl11 | 1.0262 | 42.4034 | 18.3468 | 209.1838 | 105.9077 |
| Mrpl11 | 0.9236 | 1.316 | 13.9785 | 0.8442 | 1165.9393 |
| Mrpl11 | 1479.8486 | 71.6471 | 0.7863 | 15.0087 | 0.8587 |
| Peli1 | 32.0502 | 1062.3293 | 2387.8133 | 4958.8072 | 33.4546 |
| Peli1 | 242491.9992 | 0.5992 | 4935.339 | 2496.0006 | 6869.3458 |
| Caprin1 | 37.9712 | 43.8655 | 0.7863 | 2.8141 | 119.2655 |
| Caprin1 | 28.7349 | 1.316 | 0.7863 | 8.4424 | 4.7706 |
| Npepps | 562.7642 | 0.5992 | 50.6131 | 59.0115 | 30999.4099 |
| Hnrnpa1 | 9.4056 | 0.7706 | 0.3759 | 0.722 | 0.7439 |
| Npepps | 0.8484 | 0.5393 | 39.3657 | 24.8955 | 22.3031 |
| Npepps | 0.8484 | 26.9627 | 1.0123 | 1.8441 | 2259.1152 |
| Npepps | 2704.4734 | 198.3254 | 1096.617 | 4076.4014 | 0.8364 |
| Hnrnpa1 | 189.993 | 2907.9152 | 11.6517 | 6.4982 | 0.7439 |
| Hnrnpa1 | 7.5245 | 3.4251 | 83.4414 | 0.6498 | 0.7439 |
| Hnrnpa1 | 0.8465 | 12.8441 | 0.3383 | 0.6498 | 0.7439 |
| Ddx21 | 0.9236 | 1914.0001 | 13.9785 | 4.6902 | 0.8587 |
| Ddx21 | 0.9236 | 1.316 | 0.8737 | 0.938 | 2108.6136 |
| Stau1 | 54236.1436 | 2108.4707 | 5100.4183 | 16983.2878 | 65.8345 |
| Stau1 | 0.9236 | 73.1092 | 0.7863 | 25.3272 | 7129.2132 |
| Stau1 | 0.9236 | 1.316 | 0.7863 | 0.8442 | 0.8587 |
| Zyx | 1830.3287 | 210.644 | 8.269 | 85.921 | 0.7439 |
| Zyx | 1127.7308 | 17.1255 | 0.3383 | 0.6498 | 0.7439 |
| Kif21a | 7170.7664 | 6236.7658 | 202.4524 | 121866.0532 | 0.8364 |
| Ilf3 | 70.8111 | 1.316 | 1065.8634 | 101.3088 | 7643.4859 |
| Crbn | 0.9386 | 0.5864 | 4292.5271 | 0.3614 | 0.7632 |
| Crbn | 1544.4732 | 13511.5501 | 0.8922 | 36.9444 | 52.5771 |
| Dap3 | 25126.1055 | 1604.6623 | 18.0414 | 85.199 | 36.3694 |
| Dap3 | 38898.7177 | 1131.9976 | 14021.9075 | 9620.9873 | 1540.7391 |
| Dap3 | 0.8465 | 0.7706 | 0.3383 | 0.6498 | 0.7439 |
| Dap3 | 0.8465 | 2.5688 | 1598.1652 | 197.1129 | 0.7439 |
| Dap3 | 4.7028 | 7039.4495 | 0.3759 | 1042.6045 | 0.7439 |
| Ddx21 | 0.9236 | 1.316 | 18913.8328 | 0.8442 | 0.8587 |
| Stau1 | 48.2336 | 1.316 | 6.1156 | 31.8935 | 0.8587 |
| Zyx | 0.9406 | 381.8993 | 2974.5718 | 25.9929 | 0.8266 |
| Hnrnpa1 | 60574.8511 | 19.6944 | 790.0619 | 265.7053 | 15162.724 |
| Eps8 | 9.3857 | 4.5608 | 1872.7945 | 2674.0534 | 796.2884 |
| Slc40a1 | 136.6144 | 5.8638 | 0.803 | 0.3614 | 4786.2106 |
| Rpl18 | 1.0262 | 1.316 | 0.7863 | 3.7522 | 0.8587 |
| Eps8 | 0.9386 | 731.6747 | 0.803 | 3.6141 | 5.0881 |
| Eps8 | 9.3857 | 3.9092 | 8339.6905 | 20800.9149 | 0.848 |
| Eps8 | 0.9386 | 846.345 | 17.8446 | 720.8178 | 29.6806 |

Figure 16 (cont'd)

| Symbol | Spleen.1 | Spleen.2 | Spleen.3 | Spleen.4 | Spleen.5 |
|---|---|---|---|---|---|
| Slc40a1 | 960.4725 | 719.2956 | 1597.0949 | 331.6967 | 0.7632 |
| Slc40a1 | 181.4574 | 895.8618 | 1771.9723 | 1647.2394 | 3156.321 |
| Slc40a1 | 0.9386 | 0.5864 | 820.8532 | 0.3614 | 6.7841 |
| Mrpl37 | 26.6824 | 1634.7228 | 1.7473 | 838.6114 | 0.8587 |
| Ict1 | 61.5748 | 5285.7987 | 37.5673 | 423.0579 | 775.7027 |
| Irf6 | 0.9789 | 31.8152 | 1.1188 | 13307.0658 | 0.7323 |
| Irf6 | 5.4381 | 649.9394 | 12840.7842 | 98672.7393 | 2014.6264 |
| Irf6 | 0.9789 | 1.1363 | 7788.9984 | 0.8861 | 54.5153 |
| Irf6 | 0.9789 | 69159.4647 | 2406.5594 | 441.0747 | 12396.1361 |
| Mrps28 | 2549.1983 | 1.316 | 220.1619 | 250.4578 | 9091.8459 |
| Mrps28 | 0.9236 | 1.316 | 0.8737 | 90.0522 | 0.8587 |
| Mrpl4 | 1.0876 | 8975.3 | 944.7237 | 49119.7705 | 1205.033 |
| Mrpl38 | 26072.5053 | 1.0226 | 476.091 | 79.7479 | 298.6138 |
| Mrpl38 | 0.9789 | 3324.6902 | 1.1188 | 0.8861 | 19.5279 |
| Msi2 | 5017.3231 | 928.4875 | 15442.7876 | 240.1393 | 112343.309 |
| Msi2 | 550.0686 | 1.316 | 0.7863 | 2151.8731 | 0.8587 |
| Slc19a2 | 746.1096 | 4083.7104 | 28845.1498 | 17069.9842 | 17560.4469 |
| Numbl | 30.4535 | 55.6766 | 124.3058 | 72.8561 | 85.4345 |
| Numbl | 26.103 | 1.0226 | 1.1188 | 3306.0911 | 0.7323 |
| Numbl | 0.9789 | 1.0226 | 2721.0529 | 5.9073 | 0.7323 |
| Numbl | 0.9789 | 47.7228 | 41.0209 | 190.0166 | 1.6273 |
| Crot | 0.9386 | 0.5864 | 0.803 | 0.3614 | 0.7632 |
| Crot | 15806.604 | 404.6038 | 613.8555 | 409.1996 | 62097.7747 |
| Crot | 4516.6195 | 291.8881 | 12.4912 | 95292.9191 | 20647.5292 |
| Tmem50b | 43576.0509 | 207.9122 | 2178.6125 | 30.4278 | 1088.204 |
| Mov10 | 5.1312 | 780.8068 | 6502.6402 | 1536.5162 | 1392.0667 |
| Ube2k | 531.8578 | 171.3539 | 8.9223 | 20.8816 | 0.7632 |
| Numb | 3024.2892 | 5.8638 | 75.8397 | 7196.9343 | 2377.841 |
| Numb | 107.4144 | 7392.3256 | 94294.6239 | 227.2885 | 2050.5062 |
| Ltb | 0.9789 | 44.3141 | 34445.124 | 0.8861 | 11.3913 |
| Ltb | 164300.7235 | 6794.8214 | 63.3959 | 19803.072 | 2814.4558 |
| Zcchc3 | 0.9427 | 156.3835 | 1.0123 | 0.8298 | 0.8364 |
| Zcchc3 | 0.8484 | 0.5393 | 1.0123 | 0.8298 | 0.8364 |
| Zcchc3 | 264.2972 | 0.7706 | 0.3383 | 3050.5569 | 0.7439 |
| Zcchc3 | 0.8484 | 0.5393 | 1.0123 | 0.8298 | 0.8364 |
| Zcchc3 | 0.8465 | 26.5446 | 0.3759 | 3387.7428 | 0.7439 |
| Cltc | 0.8484 | 7.19 | 1.0123 | 11.0646 | 1990.5491 |
| Anln | 214.8288 | 19474.406 | 939.5201 | 2318.2626 | 16309.0718 |
| Mrpl39 | 796.6539 | 12.8441 | 252.9551 | 938.6329 | 0.7439 |
| Ybx1 | 65.8392 | 3.4251 | 0.3383 | 192.7808 | 3.3063 |
| Ybx1 | 17.8706 | 1.7126 | 25.5586 | 7570.4354 | 0.8266 |
| Mycn | 0.9386 | 0.5864 | 0.803 | 0.3614 | 0.7632 |
| Mtmr9 | 26.3943 | 1940.7133 | 8.9979 | 4881.3547 | 8009.5903 |
| Mtmr9 | 399.6852 | 2388.8928 | 28.1184 | 9402.1862 | 41083.1858 |
| Mtmr9 | 17411.7558 | 0.5393 | 39.3657 | 504.3636 | 5277.4641 |
| Mrpl22 | 251.1294 | 0.8563 | 0.3383 | 2137.1949 | 0.7439 |
| Atp5a1 | 2053.5208 | 1.316 | 42101.603 | 8753.8272 | 25222.2631 |
| Rabep1 | 2145.4797 | 898.7558 | 1741.0904 | 486.8446 | 205.3741 |
| Rabep1 | 16.9678 | 6654.3877 | 39101.4264 | 11827.1886 | 30.6667 |

Figure 16 (cont'd)

| Symbol | Spleen.1 | Spleen.2 | Spleen.3 | Spleen.4 | Spleen.5 |
|---|---|---|---|---|---|
| Rabep1 | 773.9187 | 0.5393 | 2379.9401 | 0.9221 | 795.4762 |
| Frmd6 | 105.3287 | 1894.6662 | 9353.2658 | 123.6835 | 3228.4025 |
| Frmd6 | 0.9386 | 0.5864 | 0.803 | 0.3614 | 0.7632 |
| Ttc3 | 0.8484 | 0.5393 | 1.0123 | 0.8298 | 22.3031 |
| Ttc3 | 0.8484 | 0.5393 | 1.0123 | 0.8298 | 0.9293 |
| Cct3 | 0.9236 | 1.316 | 11.3576 | 0.8442 | 0.8587 |
| Cct3 | 0.9236 | 29.2437 | 137.1644 | 0.8442 | 442.7135 |
| Frmd6 | 0.9386 | 0.5864 | 0.803 | 0.3614 | 0.7632 |
| Ttc3 | 0.8484 | 0.5393 | 1.0123 | 0.8298 | 0.8364 |
| 4932438A13Rik | 0.9789 | 1.1363 | 33153.5872 | 26396.5478 | 5.6956 |
| 4932438A13Rik | 22.8401 | 7093.6572 | 7439.6993 | 128.975 | 47850.6312 |
| 4932438A13Rik | 2.1752 | 257.9305 | 191.4309 | 17898.9683 | 14.6459 |
| 4932438A13Rik | 0.9789 | 10.2263 | 64271.0462 | 145.7122 | 16822.4558 |
| 4932438A13Rik | 0.9789 | 2.2725 | 1.1188 | 0.8861 | 11.3913 |
| Ptcd3 | 463.6958 | 1775.0613 | 16.1621 | 33.9352 | 847.2412 |
| Ptcd3 | 4625.6714 | 169570.1577 | 1100.5239 | 100020.0001 | 166817.2414 |
| Sepp1 | 22.6237 | 0.5393 | 10327.3205 | 2746.7993 | 266.7076 |
| Mapk6 | 129.3144 | 0.5864 | 0.803 | 1529.5794 | 13670.0415 |
| Mapk6 | 15191.3176 | 31871.1783 | 84373.0064 | 18152.562 | 51269.4397 |
| Mapk6 | 3.1286 | 0.5864 | 2976.4852 | 148.5808 | 2166.6846 |
| Baz2b | 1068.0266 | 1.1983 | 35778.958 | 42490.0994 | 7227.1243 |
| Ybx1 | 12002.4793 | 126.7289 | 0.3383 | 8259.2475 | 961.3088 |
| Mtmr9 | 9601.8702 | 18797.1772 | 4006.3075 | 3878.1598 | 8138.7623 |
| Hnrnpc | 32.9196 | 5856.0753 | 429.6103 | 1.4441 | 0.7439 |
| Hnrnpc | 3.7622 | 531.7477 | 6.3897 | 6.4982 | 0.8266 |
| Pdia6 | 6148.4372 | 3658.0134 | 82458.1074 | 1711.922 | 2.4797 |
| Snx14 | 21599.0234 | 8579.5225 | 1464.4055 | 5985.9756 | 9510.4011 |
| Mrpl11 | 0.9236 | 2.9244 | 0.7863 | 0.8442 | 0.8587 |
| Mrpl11 | 0.9236 | 13.1597 | 27.9571 | 187.6088 | 0.9541 |
| Caprin1 | 0.9236 | 1.4622 | 5.242 | 0.8442 | 0.8587 |
| Cct3 | 69.7848 | 1.316 | 5.242 | 0.8442 | 0.8587 |
| Ptcd3 | 0.8465 | 0.7706 | 0.3383 | 10.8304 | 0.8266 |
| Mrpl22 | 0.8465 | 0.7706 | 0.3759 | 3908.323 | 12.3987 |
| Ppp2r5c | 137.6274 | 1433.2159 | 906.5367 | 297.8235 | 7063.5684 |
| Mrpl4 | 0.9789 | 1.0226 | 3.7292 | 7.8763 | 0.7323 |
| Mov10 | 0.9236 | 1.316 | 3.4946 | 17.8228 | 345.3928 |
| Tmem50b | 0.8484 | 631.5257 | 8302.7968 | 274.7721 | 0.8364 |
| Tmem50b | 0.8484 | 214.503 | 1.0123 | 0.8298 | 63.192 |
| Ube2k | 0.9386 | 184.3846 | 366.7073 | 461.4037 | 10645.1632 |
| Irf6 | 28.2782 | 23062.6237 | 1.1188 | 0.8861 | 1209.915 |
| Clcn3 | 0.9789 | 1.0226 | 1162.2588 | 5.9073 | 480.8741 |
| Clcn3 | 0.9789 | 65.9029 | 1.2431 | 0.8861 | 0.8137 |
| Dst | 0.8484 | 0.5393 | 871.6699 | 0.8298 | 8.3637 |
| Smc4 | 6503.3676 | 538.6543 | 108270.4044 | 82947.9915 | 1419.9622 |
| Ilf3 | 812.7879 | 593.6471 | 3134.6867 | 4.6902 | 3015.0313 |
| Slc19a2 | 85.9222 | 1.1363 | 1.1188 | 0.8861 | 0.8137 |
| Clcn3 | 329.5499 | 80456.1393 | 1.1188 | 91021.8657 | 11855.8647 |
| Smc4 | 0.8484 | 3.595 | 1.0123 | 0.8298 | 0.9293 |
| Smc4 | 31.1076 | 0.5393 | 121.4714 | 0.9221 | 5.5758 |

Figure 16 (cont'd)

| Symbol | Spleen.1 | Spleen.2 | Spleen.3 | Spleen.4 | Spleen.5 |
|---|---|---|---|---|---|
| Dst | 0.9427 | 6.5909 | 18500.7727 | 3.6882 | 227.6772 |
| Dst | 22.6237 | 0.5393 | 62748.9883 | 1653.2431 | 3161.4603 |
| Cltc | 582.56 | 0.5393 | 1.0123 | 0.8298 | 0.8364 |
| Cltc | 82.0109 | 95.8673 | 1.0123 | 15.6749 | 38938.3738 |
| Rpl14 | 34.8007 | 333.9479 | 0.3383 | 13.7185 | 3.3063 |
| Mylk | 1.0429 | 0.5864 | 35.6893 | 0.3614 | 2179.4049 |
| Rpl14 | 1417.4231 | 103.6095 | 7231.2089 | 13488.1548 | 1028.2615 |

Figure 17

| Differentially Expressed Upregulated Genes (n=225) | Differentially Expressed Downregulated Genes (n=57) |
|---|---|
| Anxa1 | Slc25a23 |
| Clec4a3 | 4922501C03Rik |
| Ppbp | Ccar1 |
| 3110043O21Rik | Kif15 |
| Clec4n | Nefh |
| Klra2 | Cbs |
| Cmklr1 | Rock1 |
| Trim30b | Brca2 |
| Slfn1 | Uaca |
| Slfn1 | Chd5 |
| Thbs1 | Cenpf |
| Clec4b2 | Sned1 |
| S100a6 | Slc22a3 |
| Chi3l3 | Bod1l |
| Arg2 | Tmem86b |
| Slc19a2 | Sp9 |
| Ifitm6 | Ccdc176 |
| Fam214b | Leprel4 |
| Il18 | Ccdc102a |
| Jag1 | Slc7a3 |
| Cd38 | Arhgdig |
| C5ar1 | Tespa1 |
| Clec4a1 | Eltd1 |
| Socs1 | Hirip3 |
| P2ry13 | Golga4 |
| Abcg3 | Gata2 |
| Naaa | Purb |
| Mgst1 | Cyp26a1 |
| Ptplad2 | Zfp820 |
| I830012O16Rik | Kcnip3 |
| Lgmn | Soat2 |
| Id3 | Ptprf |
| Serpinb10 | Myo6 |
| Derl3 | Prpf40b |
| Mpeg1 | Chdh |

Figure 17 (cont'd)

| Differentially Expressed Upregulated Genes (n=225) | Differentially Expressed Downregulated Genes (n=57) |
|---|---|
| Mgl2 | Mss51 |
| Dusp6 | Slc6a9 |
| 6430548M08Rik | Eml5 |
| Gpr34 | Cenpe |
| Lrg1 | Gm16586 |
| Ly6a | Pdgfrb |
| Clec4a2 | Gm13776 |
| P2ry12 | Hoxa3 |
| Gm19705 | Armcx4 |
| Acvrl1 | Sltm |
| 1-Mar | 9430002A10Rik |
| Rgag4 | Kmt2a |
| Cxcl3 | Cep290 |
| 1100001G20Rik | Syncrip |
| Sirpb1c | Nkx6-1 |
| Sirpb1c | Gm6484 |
| Sirpb1c | Dlk1 |
| Sirpb1c | Ccdc40 |
| Mmp8 | Epx |
| Gm13986 | Angpt1 |
| P2ry6 | Hspa2 |
| Ltc4s | Prg3 |
| Serpinb2 | |
| Abcg1 | |
| Msr1 | |
| Camk1d | |
| Adrb2 | |
| Rnase4 | |
| AA467197 | |
| Clec4d | |
| Adtrp | |
| Hs3st3b1 | |
| Hs3st3b1 | |
| Dse | |
| Crispld2 | |
| Ptafr | |
| Tgfbi | |

Figure 17 (cont'd)

| Differentially Expressed Upregulated Genes (n=225) | Differentially Expressed Downregulated Genes (n=57) |
|---|---|
| 4933430I17Rik | |
| Cyp4v3 | |
| Ifit3 | |
| Ms4a7 | |
| Tmem243 | |
| Ifi202b | |
| Kmo | |
| Pgap1 | |
| Sdcbp | |
| Raet1e | |
| Tbc1d9 | |
| D630023F18Rik | |
| Tlr4 | |
| Mgst2 | |
| Slc40a1 | |
| Xdh | |
| Irf5 | |
| 9030619P08Rik | |
| Ms4a4c | |
| Slc11a1 | |
| Rbpms | |
| Dlg2 | |
| Cd274 | |
| Hsd11b1 | |
| Fbxo8 | |
| C920021L13Rik | |
| Mapre3 | |
| Mylip | |
| Cxcr2 | |
| C3ar1 | |
| KCTD12 | |
| Abcc3 | |
| Oasl2 | |
| Il1f9 | |
| Gm7676 | |
| Gm7676 | |
| Gm7676 | |

Figure 17 (cont'd)

| Differentially Expressed Upregulated Genes (n=225) | Differentially Expressed Downregulated Genes (n=57) |
|---|---|
| Hspb11 | |
| Fcgrt | |
| S100a10 | |
| S100a8 | |
| Fcnb | |
| Fcnb | |
| Gsap | |
| Gm1673 | |
| Trp53inp1 | |
| Ifi204 | |
| Kcnn3 | |
| Sez6 | |
| Ly96 | |
| Creb5 | |
| Klf6 | |
| Agpat9 | |
| Gm7665 | |
| Sell | |
| Gm11965 | |
| Lrrc57 | |
| Ifi27l2a | |
| Ifi27l2a | |
| Cd200r4 | |
| Cd200r4 | |
| Pnpla1 | |
| Ankrd22 | |
| Gm15830 | |
| 2210408F21Rik | |
| Smox | |
| Fcgr4 | |
| Fcgr4 | |
| Fcgr1 | |
| Fcgr1 | |
| Tlr3 | |
| Ces2g | |
| Ube2l6 | |
| Rab32 | |

Figure 17 (cont'd)

| Differentially Expressed Upregulated Genes (n=225) | Differentially Expressed Downregulated Genes (n=57) |
|---|---|
| Cd52 | |
| Lyz2 | |
| Spint1 | |
| Gm6977 | |
| Tmem86a | |
| Rnase6 | |
| Rbm47 | |
| Gbp9 | |
| Gm12164 | |
| Tarm1 | |
| Pde8b | |
| Ccl2 | |
| Tlr8 | |
| Plxdc1 | |
| Fn1 | |
| Ctss | |
| Gm22767 | |
| Gm13392 | |
| 2010012P19Rik | |
| Ear6 | |
| Ear6 | |
| Bst1 | |
| Itm2c | |
| Ceacam10 | |
| Oas1g | |
| H2-T23 | |
| Clec7a | |
| Tnfrsf11a | |
| Gm5548 | |
| Lyz1 | |
| Irf4 | |
| Ifit2 | |
| Kcnk13 | |
| Mctp1 | |
| Lpar6 | |
| Zfp36l1 | |
| 5031414D18Rik | |

Figure 17 (cont'd)

| Differentially Expressed Upregulated Genes (n=225) | Differentially Expressed Downregulated Genes (n=57) |
|---|---|
| Smug1 | |
| Tlr7 | |
| 9530053A07Rik | |
| St3gal5 | |
| Zc3h12d | |
| Gad1-ps | |
| Dfna5 | |
| Prickle1 | |
| Ccdc109b | |
| Fpr2 | |
| Kcnj2 | |
| A530064D06Rik | |
| Ednrb | |
| Pglyrp1 | |
| Calcrl | |
| Ccr1 | |
| Gbp2 | |
| Rcbtb2 | |
| Fam89a | |
| Adora2b | |
| Sirpb1b | |
| Sirpb1b | |
| Sirpb1b | |
| Sirpb1b | |
| Gm25820 | |
| Gm25820 | |
| Adam8 | |
| Pfn1 | |
| Ahrr | |
| Stard3nl | |
| Cib2 | |
| Slc7a8 | |
| Lsp1 | |
| Lsp1 | |
| Samd5 | |
| Ptplb | |
| Cxcl16 | |

Figure 17 (cont'd)

| Differentially Expressed Upregulated Genes (n=225) | Differentially Expressed Downregulated Genes (n=57) |
|---|---|
| Ptprj | |
| Slc9a9 | |
| Rdh12 | |
| Ctsl | |
| 2310058D17Rik | |

Figure 18

Homo sapiens synaptotagmin binding cytoplasmic RNA interacting protein (SYNCRIP), transcript variant 7, mRNA NCBI Reference Sequence: NM_001253771.1 (SEQ ID NO: 5)

```
   1 ctccactcgc gccggacaca gggagcagcg agcacgcgtt tcccgcaacc cgataccatc
  61 ggacaggatt tctccgcctc agcccaacgg ggagggctag ttgcacatag tgatttagat
 121 gaaagagcta ttgaagcttt aaaagaattc aatgaagacg gtgcattggc agttcttcaa
 181 cagtttaaag acagtgatct ctctcatgtt cagaacaaaa gtgcctttt atgtggagtc
 241 atgaagactt acaggcagag agaaaaacaa gggaccaaag tagcagattc tagtaaagga
 301 ccagatgagg caaaaattaa ggcactcttg gaaagaacag gctacacact tgatgtgacc
 361 actggacaga ggaagtatgg aggaccacct ccagattccg tttattcaga tatttgtggg
 421 aaagatccca agagatctat ttgaggatga acttgttcca ttatttgaga aagctggacc
 481 tatatgggat cttcgtctaa tgatggatcc actcactggt ctcaatagag gttatgcgtt
 541 tgtcactttt tgtacaaaag aagcagctca ggaggctgtt aaactgtata ataatcatga
 601 aattcgttct ggaaaacata ttggtgtctg catctcagtt gccaacaata ggctttttgt
 661 gggctctatt cctaagagta aaaccaagga acagattctt gaagaattta gcaaagtaac
 721 agagggtctt acagacgtca ttttatacca ccaaccggat gacaagaaaa aaaacagagg
 781 cttttgcttt cttgaatatg aagatcacaa aacagctgcc caggcaaggc gtaggttaat
 841 gagtggtaaa gtcaaggtct gggggaatgt tggaactgtt gaatgggctg atcctataga
 901 agatcctgat cctgaggtta tggcaaaggt aaaagtgctg tttgtacgca accttgccaa
 961 tactgtaaca gaagagattt tagaaaaggc atttagtcag tttgggaaac tggaacgagt
1021 gaagaagtta aaagattatg cgttcattca ttttgatgag cgagatggtg ctgtcaaggc
1081 tatggaagaa atgaatggca aagacttgga gggagaaaat attgaaattg ttttgccaa
1141 gccaccagat cagaaaagga agaaagaaa agctcagagg caagcagcaa aaaatcaaat
1201 gtatgacgat tactactatt atggtccacc tcatatgccc cctccaacaa gaggtcgagg
1261 gcgtggaggt agaggtggtt atggatatcc tccagattat tatggatatg aagattatta
1321 tgattattat ggttatgatt accataacta tcgtggtgga tatgaagatc catactatgg
1381 ttatgaagat tttcaagttg gagctagagg aaggggtggt agaggagcaa ggggtgctgc
1441 tccatccaga ggtcgtgggg ctgctcctcc ccgcggtaga gccggttatt cacagagagg
1501 aggtcctgga tcagcaagag gcgttcgagg tgcgagagga ggtgcccaac aacaaagagg
1561 ccgcgggcag ggaaaagggg tcgaggccgg tcctgacctg ttacaatgaa gactgacttg
1621 ctatgtggga ttacaccaga agcttgcagt ggagtaatgg taaggaaatc aagcaacctt
1681 aaatatgtcg gctgtatagg agcatattct attgcagaag accttcctat gaagatcatg
1741 gaatcaaata cgggacattg aactaatact tggactttga tatgaatttc tttaacaatt
1801 ttctctgcag tgcaagttat taaactaaag ctactctatt tcaaaatgt gttccaacag
1861 aaatccttca taactcctag catggtatct taataaagaa taaagttctt ttaaaaatct
1921 gctctaagta gatttttccc ctttttaaa ttaaggatcc caacagtggt attttgaaat
1981 attctcttga atttgtgcat ttaaatttta ttgcagtggt atagatgaat gccactgatg
2041 gtatccttaa attttatttc tgctcaccaa ggttaatcat gattgtctat atctttttta
2101 tagtgatcac ttttgaattg tgttcagata tgcagtttca ggtgtaatca tcagagctgg
2161 ttagtcaggc attccagata gtggttcttt tcagaaccct tttaaaggg ttggttaact
2221 acctcagtag cagaggattg aactataccc tgtctgtact gtacatagaa aatctttgta
2281 gataaaagca aggcttgtta aatatgatat gagggtaaga ttttaatata ccaaatgtaa
2341 cattcttagt tgcctttagt ttcagaggct tgtaagactt cctcatgacc atcataacag
2401 gccttgcttt tgtcgtattt tgtggctgaa aaagcagcct tgcttcttca gatattgtag
2461 ttatttggat gtataatagt ttagcaagat gttacttttg taagacatca gatgttcaaa
2521 aaagtgcatc cgaacttgta ctaaatactg cagtgtccct ttataaaag tcagactaaa
2581 actgacaatt gtacagcgaa gcctgacatt tggatatttt gaagttttt cataaatcat
2641 agaaattagt atatggctgt agtttagctt tttaggtaaa aggtatgttt cattagtgca
2701 tttcttcctg ctgatcactg taaacatgtg aatcagcttt ccatttctta tgcaggtcat
2761 gataacttgt agagtagagt acaatcattt gtgctatgtt tttaattttc taaagcacct
2821 tgatgacagt gagtgtccag tggtgaagca tcctctattg aaccaccctc aaaaattttt
2881 ttgccaagtc ctaagttgat agcttaaagt aaaaagtgaa aattatagtt tcattaggac
```

Figure 18 (cont'd)

```
2941 ttggtgtaaa gaaatccect cecccttcc ccaaagggat actgcagtta tatcacatac
3001 ccaataggca ccacgatgaa gatcagagct tatacttaat taaggtttta tacacaccag
3061 ttccccagta aatgcaaatt taacaagaaa atcagacatg tcatatgttc aaaatgctca
3121 tggcaaacaa tcatttttgca ttcctgcaaa taaaattgtt ttatactgta agctggaggc
3181 gagtgtaact tatttttgta ataaagtttt tattttttt atgtgtcatt aatataaatg
3241 tgtgttagtg tagaaatctt ctggtttaaa aacttagaat tgcacacatt tcagtatgtt
3301 tatttgtact tacataattt tagaatagtg gttgccaata gcctgtatgt ttcacattaa
3361 ttggtttttt gttatctaaa taaatcattt tagtatgttg tatgtcagtt actgggatag
3421 ctgggacata gagtgtaatt taaaatttgt caataagtat tcattggaat atatgtaaat
3481 gtgccttgcc ggttattgaa acttatctac aaaatgagta tggggtgaca aaaattagtt
3541 cctggtgctt aatgaaactt tctgccactg attttatata ttaccccgtg cttttttaaa
3601 gtacatctct ctcaaaactt agtgtaagtt tgagggctac acaaaacatt tacatttcat
3661 tctaacataa tgaatataat aggttgtgga aagtgggtaa actaaatgta gccttcagta
3721 aaattgaatc tcagtgtaat ccttggtgct ggcatttctc agttccgagg agttaaatga
3781 tcccatctaa gaggtcattg ccatgcctat tggcacttta ctgtcatagc attttaagg
3841 gacactgtca aggtgtttaa gttctcagaa ttacttgttg ggattttagg acaggtttgt
3901 ttacttaaag taagaactgc attgtcaaag ttgaaagagg aacactttg tgagttcaca
3961 aatgtgttct taagaaaaca ttaaaatatg gagctctggg ttttcaagac tatttggcat
4021 tcttaatttg gggacttggg agggaaactg ataaaagaa attgaagaat tgatggttat
4081 acttaaagaa gggtaatgta aacagtggtg atgaaatata tacacatcaa gtgaaattac
4141 ttgacagtgt tcatttgaat gactttgaat tcaagccatt ataattactt ttaaaattaa
4201 atatcatttg cactgttctg ataatgggtg cagttttga gcaatataat cagagctaaa
4261 tatgcatgta gtgattagtg atgtgaacaa ttaacgttct gagaagaaat actaactgtg
4321 gtattttcaa acttaaattt ctgtagtaaa atcagtatca aagtcttatc agatcaagga
4381 aaaacaggca atgcatataa acatactttt gaatgttgtg tggcctataa agcaataatg
4441 caatttatat ggaatgtcat gggatatgag aaatggaaat gcaaaataa ctaatccttt
4501 agtaaaaatg tcaacatgtt aaagggggaa tgttaactaa tgtaggttat tgctatttgt
4561 gatttgttta tgggttcttg gctttgacag cttcaaagaa tggacagtga taagttaaaa
4621 gaaattttgt atattgtcaa ggaaagggtc ttaaatccga gtcaagtccc ttccttgggg
4681 taaaaaatgt attcttaaag cattctgatg ttaaaagaa aacttaagtt atctaaccaa
4741 aacagacgca agattttgtt tctgcagact acttggcaat caaaagtgat cataaattta
4801 ggttatcagt tttcagaaag ttgctttgtg agaaaatttt gttagatata ttctcccaag
4861 catgcttttt gtggaaggtt ttcagccatt gccactgaat cagatgttaa aaatgaaggg
4921 aaaattgagt gtgcacacac acaactgttg tacactcatg attgcagttt ttagcttaag
4981 aaacttttct accagttact gtgaatctga cttaaaatgt aaagtttcct catgataaaa
5041 taggaacaac atagaaatgg attgatgggg tgatctgagt tattgtatat aaaagttttt
5101 aaagaataga atgaacatca agctagatag gcaaaaattg acacattcag aacagctttt
5161 ttgactgcga agccaaaagt tgtcagaaac agcaaaagat cccttattat tacagagtat
5221 tttacgtagt ctctatttta aggagagaaa ttaaatagaa gggcttcatg catttagggg
5281 agggtgctaa aacttctcaa gttcgtcaaa cttacaggaa tacccaccat gatcattttc
5341 tctctaatta tgtataccac aaaattttca tctggccata ggaattcact ggtgggtgta
5401 aaattaatga ctaaagaaat taagtgacaa atacataaaa gaaacagact tgtggggata
5461 ttgttttaag gtgtattaat tactcagtga tgataccact caataggca tgccactact
5521 tttcttaaga tgctaattat gaagcagtgc tcacaggcat ttttaacta gcaaattagt
5581 agatggactt tggggtctg tcactttta aaagtattta agacttaaat tctattagca
5641 ccacagtctg ccttcagtaa tacacctaaa atatttttca ggaccagaag cattcagttt
5701 gaaaatttgc agatgcaaac cagtattatt actaacgctc tgggtcaaag attaggtttt
5761 taatattaac agtagtctgg taaatattta gaagtctggc attgagaaac aaaagcttgt
5821 acctgactag tatttttatt taaaaaatt agttctgtta gcttatttaa attgtgtttt
5881 atttatccgt agaatttata tttatttcat tcctttcatc tcactgaaaa ctgtctgcag
5941 gcccttttgat ttggattaga tgtgtgaagt actgtctttt gccaaaaacc tcaaattacc
6001 tgttcttttc aacgtagtgg gtttgtgctt gtttggagat cagttcaaaa actatctgta
6061 ctatctgtac tgcctctgat gttaagattt tatgtatagc ataaggaagc tagctctgac
6121 tatattttcc taagaataaa gacctatttt tgtagcatgt cttaggatct ccaggagtcc
6181 aagaattatt gtgggtgtcc tccaattcat cactcttcac ttaacagctt ttaagtagac
6241 acttggaatc tttagaggtc tgtcgccctt tgattatcca tacattcgaa gtaactagcc
6301 aatggtgaaa aattcctcaa gatatcctca gttgcaatca cattactgga agatgaatag
```

Figure 18 (cont'd)

```
6361 aataaatgta ttaggctggt cttaattttt gatggaaata ttctgttgtc ccgtacttgc
6421 cattggattt gataaagtta gtggtaattt ggaaagaatc ggggacttgc caatatattt
6481 gtgggtttta gcttataccc ctaggatttc ttggttgcgg gacgagcagt tttggccact
6541 tccatcagga caagactttt taggtcactt agtgcaggtt ttagtttcta ttttggatta
6601 acaacattta tattgattat cgaaaagaag ctttcatcat ttcagaacag tcctggaagt
6661 ttgactttga gtgtgggaga agtcctaata aaccattttg gaaattaaaa aaaaaa
```

Figure 19

Homo sapiens synaptotagmin binding cytoplasmic RNA interacting protein (SYNCRIP), transcript variant 6, mRNA NCBI Reference Sequence: NM_001159677.1 (SEQ ID NO: 6)

```
   1 agcgcggag agagaaagag aggagccgac tcggcaggga ctgggggacc gggccgagag
  61 tgcgagcgag cgagggaggg agtgagggag cgtgcgagcc agaaggggaa aggcggccac
 121 tcgtgcctga gcgaccgcag aggggagtgg gagcagtggg gtaaaggagc gggggcggg
 181 aataagaaag gccgagagaa ggcggacaga ggctagtggt ggtggtggtg gtaggggag
 241 aaggaggagc tggaggaggg cagggctga gggagtgagt gaagcggacg cgcgagggag
 301 gggagggaag ggaagggaag ggaaggggg gtcacgcggg ggcgcgcgcg cgcaccggga
 361 gcgcgctcgg aggcgagtgg aactggatcg ggtttgctgc cagcggcgtg agcttcggcc
 421 gccattttac aacagctcca ctcgcgccgg acacagggag cagcgagcac gcgtttcccg
 481 caacccgata ccatcggaca ggatttctcc gcctcagccc aacggggaga tctctggaaa
 541 catggctaca gaacatgtta atggaaatgg tactgaagag cccatggata ctacttctgc
 601 agttatccat tcagaaaatt ttcagacatt gcttgatgct ggtttaccac agaaagttgc
 661 tgaaaaacta gatgaaattt acgttgcagg gctagttgca catagtgatt tagatgaaag
 721 agctattgaa gctttaaaag aattcaatga agacggtgca ttggcagttc ttcaacagtt
 781 taaagacagt gatctctctc atgttcagaa caaaagtgcc tttttatgtg gagtcatgaa
 841 gacttacagg cagagagaaa acaagggac caaagtagca gattctagta aaggaccaga
 901 tgaggcaaaa attaaggcac tcttggaaag aacaggctac acacttgatg tgaccactgg
 961 acagaggaag tatggaggac cacctccaga ttccgtttat tcaggtcagc agccttctgt
1021 tggcactgag atatttgtgg gaaagatccc aagagatcta tttgaggatg aacttgttcc
1081 attatttgag aaagctggac ctatatggga tcttcgtcta atgatggatc cactcactgg
1141 tctcaataga ggttatgcgt tgtcactttt tgtacaaaa gaagcagctc aggaggctgt
1201 taaactgtat aataatcatg aaattcgttc tggaaaacat attggtgtct gcatctcagt
1261 tgccaacaat aggcttttg tgggctctat tcctaagagt aaaaccaagg aacagattct
1321 tgaagaattt agcaaagtaa cagagggtct tacagacgtc attttatacc accaaccgga
1381 tgacaagaaa aaaaacagag gcttttgctt tcttgaatat gaagatcaca aaacagctgc
1441 ccaggcaagg cgtaggttaa tgagtggtaa agtcaaggtc tgggggaatg ttggaactgt
1501 tgaatgggct gatcctatag aagatcctga tcctgaggtt atggcaaagg taaaagtgct
1561 gtttgtacgc aaccttgcca atactgtaac agaagagatt ttagaaaagg catttagtca
1621 gtttgggaaa ctggaacgag tgaagaagtt aaaagattat gcgttcattc attttgatga
1681 gcgagatggt gctgtcaagg ctatggaaga aatgaatggc aaagacttgg agggagaaaa
1741 tattgaaatt gtttttgcca agccaccaga tcagaaaagg aaagaagaa aagctcagag
1801 gcaagcagca aaaaatcaaa tgtatgacga ttactactat tatggtccac ctcatatgcc
1861 ccctccaaca agaggtcgag ggcgtggagg tagaggtggt tatggatatc tccagatta
1921 ttatggatat gaagattatt atgattatta tggttatgat taccataact atcgtggtgg
1981 atatgaagat ccatactatg gttatgaaga ttttcaagtt ggagctagag aaggggtgg
2041 tagaggagca aggggtgctg ctccatccag aggtcgtggg gctgctcctc ccgcggtag
2101 agccggttat tcacagagag gaggtcctgg atcagcaaga ggcgttcgag gtgcgagagg
2161 aggtgcccaa caacaaagag gccgcgggca gggaaaaggg gtcgaggccg gtcctgacct
2221 gttacaatga agactgactt gctatgtggg attacaccag aagcttgcag tggagtaatg
2281 gtaaggaaat caagcaacct taaatatgtc ggctgtatag gagcatattc tattgcagaa
2341 gaccttccta tgaagatcat ggaatcaaat acgggacatt gaactaatac ttggactttg
2401 atatgaattt ctttaacaat tttctctgca gtgcaagtta ttaaactaaa gctactctat
2461 tttcaaaatg tgttccaaca gaaatccttc ataactccta gcatggtatc ttaataaga
2521 ataaagttct tttaaaaatc tgctctaagt agattttttcc ccttttttaa attaaggatc
2581 ccaacagtgg tattttgaaa tattctcttg aatttgtgca tttaaatttt attgcagtgg
2641 tatagatgaa tgccactgat ggtatcctta aatttattt ctgctcacca aggttaatca
2701 tgattgtcta tatctttttt atagtgatca cttttgaatt gtgttcagat atgcagtttc
2761 aggtgtaatc atcagagctg gttagtcagg cattccagat agtggttctt ttcagaacct
2821 ttttaaaagg gttggttaac tacctcagta gcagaggatt gaactatacc ctgtctgtac
2881 tgtacataga aaatctttgt agataaaagc aaggcttgtt aaatatgata tgagggtaag
```

Figure 19 (cont'd)

```
2941 atttaatat accaaatgta acattcttag ttgcctttag tttcagaggc ttgtaagact
3001 tcctcatgac catcataaca ggccttgctt ttgtcgtatt ttgtggctga aaaagcagcc
3061 ttgcttcttc agatattgta gttatttgga tgtataatag tttagcaaga tgttactttt
3121 gtaagacatc agatgttcaa aaaagtgcat ccgaacttgt actaaatact gcagtgtccc
3181 tttataaaaa gtcagactaa aactgacaat tgtacagcga agcctgacat ttggatattt
3241 tgaagttttt tcataaatca tagaaattag tatatggctg tagtttagct ttttaggtaa
3301 aaggtatgtt tcattagtgc atttcttcct gctgatcact gtaaacatgt gaatcagctt
3361 tccatttctt atgcaggtca tgataacttg tagagtagag tacaatcatt tgtgctatgt
3421 ttttaatttt ctaaagcacc ttgatgacag tgagtgtcca gtggtgaagc atcctctatt
3481 gaaccaccct caaaaatttt tttgccaagt cctaagttga tagcttaaag taaaaagtga
3541 aaattatagt ttcattagga cttggtgtaa agaaatcccc tcccccttc cccaaaggga
3601 tactgcagtt atatcacata cccataggc accacgatga agatcagagc ttatacttaa
3661 ttaaggtttt atacacacca gttccccagt aaatgcaaat ttaacaagaa aatcagacat
3721 gtcatatgtt caaaatgctc atggcaaaca atcatttgc attcctgcaa ataaaattgt
3781 tttatactgt aagctggagg cgagtgtaac ttatttttgt aataaagttt ttatttttt
3841 tatgtgtcat taatataaat gtgtgttagt gtagaaatct tctggtttaa aaacttagaa
3901 ttgcacacat ttcagtatgt ttatttgtac ttacataatt ttagaatagt ggttgccaat
3961 agcctgtatg tttcacatta attggttttt tgttatctaa ataaatcatt ttagtatgtt
4021 gtatgtcagt tactgggata gctgggacat agagtgtaat ttaaaatttg tcaataagta
4081 ttcattggaa tatatgtaaa tgtgccttgc cggttattga aacttatcta caaaatgagt
4141 atggggtgac aaaaattagt tcctggtgct taatgaaact ttctgccact gattttatat
4201 attacccgt gcttttttaa agtacatctc tctcaaaact tagtgtaagt tgagggcta
4261 cacaaaacat ttacatttca ttctaacata atgaatataa taggttgtgg aaagtgggta
4321 aactaaatgt agccttcagt aaaattgaat ctcagtgtaa tccttggtgc tggcatttct
4381 cagttccgag gagttaaatg atcccatcta agaggtcatt gccatgccta ttggcacttt
4441 actgtcatag cattttaag ggacactgtc aaggtgttta agttctcaga attacttgtt
4501 gggattttag dacaggtttg tttacttaaa gtaagaactg cattgtcaaa gttgaaagag
4561 gaacactttt gtgagttcac aaatgtgttc ttaagaaaac attaaatat ggagctctgg
4621 gttttcaaga ctatttggca ttcttaattt ggggacttgg gagggaaact gataaaaga
4681 aattgaagaa ttgatggtta tacttaaaga agggtaatgt aaacagtggt gatgaaatat
4741 atacacatca agtgaaatta cttgacagtg ttcatttgaa tgactttgaa ttcaagccat
4801 tataattact tttaaaatta aatatcattt gcactgttct gataatgggt gcagttttg
4861 agcaatataa tcagagctaa atatgcatgt agtgattagt gatgtgaaca attaacgttc
4921 tgagaagaaa tactaactgt ggtattttca aacttaaatt tctgtagtaa aatcagtatc
4981 aaagtcttat cagatcaagg aaaacaggc aatgcatata aacatacttt gaatgttgt
5041 gtggcctata aagcaataat gcaatttata tggaatgtca tgggatatga gaaatggaaa
5101 tgcaaaaata actaatcctt tagtaaaaat gtcaacatgt taaggggga atgttaacta
5161 atgtaggtta ttgctatttg tgatttgttt atgggttctt ggctttgaca gcttcaaaga
5221 atggacagtg ataagttaaa agaaattttg tatattgtca aggaagggt cttaaatccg
5281 agtcaagtcc cttccttggg gtaaaaatg tattcttaaa gcattctgat gttaaaaga
5341 aaacttaagt tatctaacca aaacagacgc aagatttgt ttctgcagac tacttggcaa
5401 tcaaaagtga tcataaattt aggttatcag ttttcagaaa gttgctttgt gagaaaattt
5461 tgttagatat attctcccaa gcatgctttt tgtggaaggt tttcagccat tgccactgaa
5521 tcagatgtta aaaatgaagg gaaaattgag tgtgcacaca cacaactgtt gtacactcat
5581 gattgcagtt tttagcttaa gaaacttttc taccagttac tgtgaatctg acttaaaatg
5641 taaagtttcc tcatgataaa ataggaacaa catagaaatg gattgatggg gtgatctgag
5701 ttattgtata taaaagtttt taaagaatag aatgaacatc aagctagata ggcaaaaatt
5761 gacacattca gaacagcttt tttgactgcg aagccaaaag ttgtcagaaa cagcaaaaga
5821 tcccttatta ttacagagta ttttacgtag tctctatttt aaggagagaa attaaataga
5881 agggcttcat gcatttaggg gagggtgcta aaacttctca agttcgtcaa acttacagga
5941 atacccacca tgatcatttt ctctctaatt atgtatacca caaaattttc atctggccat
6001 aggaattcac tggtgggtgt aaaattaatg actaaagaaa ttaagtgaca aatacataaa
6061 agaaacagac ttgtggggat attgttttaa ggtgtattaa ttactcagtg atgataccac
6121 tcaatagggc atgccactac ttttcttaag atgctaatta tgaagcagtg ctcacaggca
6181 ttttttaact agcaaattag tagatggact tttggggtct gtcactttt aaaagtattt
6241 aagacttaaa ttctattagc accacagtct gccttcagta atacacctaa aatatttttc
6301 aggaccagaa gcattcagtt tgaaaatttg cagatgcaaa ccagtattat tactaacgct
```

Figure 19 (cont'd)

```
6361 ctgggtcaaa gattaggttt ttaatattaa cagtagtctg gtaaatattt agaagtctgg
6421 cattgagaaa caaaagcttg tacctgacta gtatttttat ttaaaaaaat tagttctgtt
6481 agcttattta aattgtgttt tatttatccg tagaatttat atttatttca ttcctttcat
6541 ctcactgaaa actgtctgca ggcccttga tttggattag atgtgtgaag tactgtcttt
6601 tgccaaaaac ctcaaattac ctgttctttt caacgtagtg ggtttgtgct tgtttggaga
6661 tcagttcaaa aactatctgt actatctgta ctgcctctga tgttaagatt ttatgtatag
6721 cataaggaag ctagctctga ctatattttc ctaagaataa agacctattt ttgtagcatg
6781 tcttaggatc tccaggagtc caagaattat tgtgggtgtc ctccaattca tcactcttca
6841 cttaacagct tttaagtaga cacttggaat ctttagaggt ctgtcgccct ttgattatcc
6901 atacattcga agtaactagc caatggtgaa aaattcctca agatatcctc agttgcaatc
6961 acattactgg aagatgaata gaataaatgt attaggctgg tcttaatttt tgatggaaat
7021 attctgttgt cccgtacttg ccattggatt tgataaagtt agtggtaatt tggaaagaat
7081 cggggacttg ccaatatatt tgtgggtttt agcttatacc cctaggattt cttggttgcg
7141 ggacgagcag ttttggccac ttccatcagg acaagacttt ttaggtcact tagtgcaggt
7201 tttagtttct attttggatt aacaacattt atattgatta tcgaaaagaa gctttcatca
7261 tttcagaaca gtcctggaag tttgactttg agtgtgggag aagtcctaat aaaccatttt
7321 ggaaattaaa aaaaaa
```

Figure 20

Homo sapiens synaptotagmin binding cytoplasmic RNA interacting protein (SYNCRIP), transcript variant 2, mRNA NCBI Reference Sequence: NM_001159673.1 (SEQ ID NO: 7)

```
   1 cggcgtgagc ttcggccgcc attttacaac agctccactc gcgccggaca cagggagcag
  61 cgagcacgcg tttcccgcaa cccgatacca tcggacagga tttctccgcc tcagcccaac
 121 ggggagggct agttgcacat agtgatttag atgaaagagc tattgaagct ttaaaagaat
 181 tcaatgaaga cggtgcattg gcagttcttc aacagtttaa agacagtgat ctctctcatg
 241 ttcagaacaa aagtgccttt ttatgtggag tcatgaagac ttacaggcag agagaaaaac
 301 aagggaccaa agtagcagat tctagtaaag gaccagatga ggcaaaaatt aaggcactct
 361 tggaagaac aggctacaca cttgatgtga ccactggaca gaggaagtat ggaggaccac
 421 ctccagattc cgtttattca ggtcagcagc cttctgttgg cactgagata tttgtgggaa
 481 agatcccaag agatctattt gaggatgaac ttgttccatt atttgagaaa gctggaccta
 541 tatgggatct tcgtctaatg atggatccac tcactggtct caatagaggt tatgcgtttg
 601 tcacttttg tacaaaagaa gcagctcagg aggctgttaa actgtataat aatcatgaaa
 661 ttcgttctgg aaaacatatt ggtgtctgca tctcagttgc caacaatagg cttttgtgg
 721 gctctattcc taagagtaaa accaaggaac agattcttga agaatttagc aaagtaacag
 781 agggtcttac agacgtcatt ttataccacc aaccggatga caagaaaaaa aacagaggct
 841 tttgctttct tgaatatgaa gatcacaaaa cagctgccca ggcaaggcgt aggttaatga
 901 gtggtaaagt caaggtctgg gggaatgttg gaactgttga atgggctgat cctatagaag
 961 atcctgatcc tgaggttatg gcaaggtaa aagtgctgtt tgtacgcaac cttgccaata
1021 ctgtaacaga agagatttta gaaaaggcat ttagtcagtt tgggaaactg aacgagtga
1081 agaagttaaa agattatgcg ttcattcatt ttgatgagcg agatggtgct gtcaaggcta
1141 tggaagaaat gaatggcaaa gacttggagg gagaaaatat tgaaattgtt tttgccaagc
1201 caccagatca gaaaaggaaa gaagaaaaag ctcagaggca agcagcaaaa aatcaaatgt
1261 atgacgatta ctactattat ggtccacctc atatgccccc tcaacaaga ggtcgagggc
1321 gtggaggtag aggtggttat ggatatcctc cagattatta tggatatgaa gattattatg
1381 attattatgg ttatgattac cataactatc gtggtggata tgaagatcca tactatggtt
1441 atgaagattt tcaagttgga gctagaggaa ggggtggtag aggagcaagg ggtgctgctc
1501 catccagagg tcgtggggct gctcctcccc gcggtagagc cggttattca cagagaggag
1561 gtcctggatc agcaagaggc gttcgaggtg cgagaggagg tgcccaacaa caaagaggcc
1621 gcgggcaggg aaaagggtc gaggccggtc ctgacctgtt acaatgaaga ctgacttgct
1681 atgtgggatt acaccagaag cttgcagtgg agtaatggta aggaaatcaa gcaaccttaa
1741 atatgtcggc tgtataggag catattctat tgcagaagac cttcctatga agatcatgga
1801 atcaaatacg ggacattgaa ctaatacttg gactttgata tgaatttctt taacaatttt
1861 ctctgcagtg caagttatta aactaaagct actctatttt caaaatgtgt tccaacagaa
1921 atccttcata actcctagca tggtatctta ataaagaata agttcttttt aaaaatctgc
1981 tctaagtaga ttttccct ttttaaatt aaggatccca acagtggtat tttgaaatat
2041 tctcttgaat ttgtgcattt aaattttatt gcagtggtat agatgaatgc cactgatggt
2101 atccttaaat tttattctg ctcaccaagg ttaatcatga ttgtctatat cttttttata
2161 gtgatcactt ttgaattgtg ttcagatatg cagtttcagg tgtaatcatc agagctggtt
2221 agtcaggcat tccagatagt ggttctttc agaacctttt taaagggtt ggttaactac
2281 ctcagtagca gaggattgaa ctataccctg tctgtactgt acatagaaaa tctttgtaga
2341 taaaagcaag gcttgttaaa tatgatatga gggtaagatt ttaatatacc aaatgtaaca
2401 ttcttagttg cctttagttt cagaggcttg taagacttcc tcatgaccat cataacaggc
2461 cttgcttttg tcgtattttg tggctgaaaa agcagccttg cttcttcaga tattgtagtt
2521 atttggatgt ataatagttt agcaagatgt tacttttgta agacatcaga tgttcaaaaa
2581 agtgcatccg aacttgtact aaatactgca gtgtcccttt ataaaagtc agactaaaac
2641 tgacaattgt acagcgaagc ctgacatttg gatattttga agttttttca taaatcatag
2701 aaattagtat atggctgtag tttagctttt taggtaaaag gtatgtttca ttagtgcatt
2761 tcttcctgct gatcactgta aacatgtgaa tcagctttcc atttcttatg caggtcatga
2821 taacttgtag agtagagtac aatcatttgt gctatgtttt taattttcta aagcaccttg
2881 atgacagtga gtgtccagtg gtgaagcatc ctctattgaa ccaccctcaa aaatttttt
```

Figure 20 (cont'd)

```
2941 gccaagtcct aagttgatag cttaaagtaa aaagtgaaaa ttatagtttc attaggactt
3001 ggtgtaaaga aatcccctcc cccttcccc aaagggatac tgcagttata tcacataccc
3061 aataggcacc acgatgaaga tcagagctta tacttaatta aggttttata cacaccagtt
3121 ccccagtaaa tgcaaattta acaagaaaat cagacatgtc atatgttcaa aatgctcatg
3181 gcaaacaatc attttgcatt cctgcaaata aaattgtttt atactgtaag ctggaggcga
3241 gtgtaactta ttttgtaat aaagttttta ttttttttat gtgtcattaa tataaatgtg
3301 tgttagtgta gaaatcttct ggtttaaaaa cttagaattg cacacatttc agtatgttta
3361 tttgtactta cataatttta gaatagtggt tgccaatagc ctgtatgttt cacattaatt
3421 ggttttttgt tatctaaata aatcatttta gtatgttgta tgtcagttac tgggatagct
3481 gggacataga gtgtaattta aaatttgtca ataagtattc attggaatat atgtaaatgt
3541 gccttgccgg ttattgaaac ttatctacaa aatgagtatg gggtgacaaa aattagttcc
3601 tggtgcttaa tgaaactttc tgccactgat tttatatatt accccgtgct ttttaaagt
3661 acatctctct caaaacttag tgtaagtttg agggctacac aaaacattta catttcattc
3721 taacataatg aatataatag gttgtggaaa gtgggtaaac taaatgtagc cttcagtaaa
3781 attgaatctc agtgtaatcc ttggtgctgg catttctcag ttccgaggag ttaaatgatc
3841 ccatctaaga ggtcattgcc atgcctattg cactttact gtcatagcat ttttaaggga
3901 cactgtcaag gtgtttaagt tctcagaatt acttgttggg attttaggac aggtttgttt
3961 acttaaagta agaactgcat tgtcaaagtt gaaagaggaa cacttttgtg agttcacaaa
4021 tgtgttctta agaaaacatt aaaatatgga gctctgggtt ttcaagacta tttggcattc
4081 ttaatttggg gacttgggag ggaaactgat aaaaagaaat tgaagaattg atggttatac
4141 ttaaagaagg gtaatgtaaa cagtggtgat gaaatatata cacatcaagt gaaattactt
4201 gacagtgttc atttgaatga ctttgaattc aagccattat aattacttt aaaattaaat
4261 atcatttgca ctgttctgat aatgggtgca gttttgagc aatataatca gagctaaata
4321 tgcatgtagt gattagtgat gtgaacaatt aacgttctga gaagaaatac taactgtggt
4381 attttcaaac ttaaatttct gtagtaaaat cagtatcaaa gtcttatcag atcaaggaaa
4441 aacaggcaat gcatataaac atacttttga atgttgtgtg gcctataaag caataatgca
4501 atttatatgg aatgtcatgg gatatgagaa atggaaatgc aaaaataact aatcctttag
4561 taaaaatgtc aacatgttaa aggggaatg ttaactaatg taggttattg ctatttgtga
4621 tttgtttatg ggttcttggc tttgacagct tcaaagaatg gacagtgata agttaaaaga
4681 aattttgtat attgtcaagg aaagggtctt aaatccgagt caagtcccct ccttggggta
4741 aaaaatgtat tcttaaagca ttctgatgtt aaaagaaaa cttaagttat ctaaccaaaa
4801 cagacgcaag attttgtttc tgcagactac ttggcaatca aaagtgatca taaatttagg
4861 ttatcagttt tcagaaagtt gctttgtgag aaaattttgt tagatatatt ctcccaagca
4921 tgctttttgt ggaaggtttt cagccattgc cactgaatca gatgttaaaa atgaagggaa
4981 aattgagtgt gcacacacac aactgttgta cactcatgat tgcagttttt agcttaagaa
5041 acttttctac cagttactgt gaatctgact taaaatgtaa agttcctca tgataaaata
5101 ggaacaacat agaaatggat tgatggggtg atctgagtta ttgtatataa aagttttaa
5161 agaatagaat gaacatcaag ctagataggc aaaaattgac acattcagaa cagcttttt
5221 gactgcgaag ccaaaagttg tcagaaacag caaaagatcc cttattatta cagagtattt
5281 tacgtagtct ctattttaag gagagaaatt aaatagaagg gcttcatgca tttaggggag
5341 ggtgctaaaa cttctcaagt tcgtcaaact tacaggaata ccaccatga tcattttctc
5401 tctaattatg tataccacaa aattttcatc tggccatagg aattcactgg tgggtgtaaa
5461 attaatgact aaagaaatta agtgacaaat acataaaaga aacagacttg tggggatatt
5521 gttttaaggt gtattaatta ctcagtgatg ataccactca ataggcatg ccactactttt
5581 tcttaagatg ctaattatga agcagtgctc acaggcattt tttaactagc aaattagtag
5641 atggactttt ggggtctgtc acttttaaa agtatttaag acttaaattc tattagcacc
5701 acagtctgcc ttcagtaata cacctaaaat atttttcagg accagaagca ttcagtttga
5761 aaatttgcag atgcaaacca gtattattac taacgctctg ggtcaaagat taggttttta
5821 atattaacag tagtctggta aatatttaga agtctggcat tgagaaacaa aagcttgtac
5881 ctgactagta ttttattta aaaaattag ttctgttagc ttatttaaat tgtgttttat
5941 ttatccgtag aatttatatt tatttcattc ctttcatctc actgaaaact gtctgcaggc
6001 cctttgattt ggattagatg tgtgaagtac tgtctttgc caaaacctc aaattacctg
6061 ttcttttcaa cgtagtgggt ttgtgcttgt tggagatca gttcaaaaac tatctgtact
6121 atctgtactg cctctgatgt taagatttta tgtatagcat aaggaagcta gctctgacta
6181 tattttccta agaataaaga cctattttg tagcatgtct taggatctcc aggagtccaa
6241 gaattattgt gggtgtcctc caattcatca ctcttcactt aacagctttt aagtagacac
6301 ttggaatctt tagaggtctg tcgccctttg attatccata cattcgaagt aactagccaa
```

Figure 20 (cont'd)

```
6361 tggtgaaaaa ttcctcaaga tatcctcagt tgcaatcaca ttactggaag atgaatagaa
6421 taaatgtatt aggctggtct taatttttga tggaaatatt ctgttgtccc gtacttgcca
6481 ttggatttga taaagttagt ggtaatttgg aaagaatcgg ggacttgcca atatatttgt
6541 gggttttagc ttatacccct aggatttctt ggttgcggga cgagcagttt tggccacttc
6601 catcaggaca agactttta ggtcacttag tgcaggtttt agtttctatt ttggattaac
6661 aacatttata ttgattatcg aaaagaagct ttcatcattt cagaacagtc ctggaagttt
6721 gactttgagt gtgggagaag tcctaataaa ccatttgga aattaaaaaa aaaa
```

Figure 21

Homo sapiens synaptotagmin binding cytoplasmic RNA interacting protein (SYNCRIP), transcript variant 5, mRNA NCBI Reference Sequence: NM_001159676.1 (SEQ ID NO: 8)

```
   1 atctctggaa acatggctac agaacatgtt aatggaaatg gtactgaaga gcccatggat
  61 actacttctg cagttatcca ttcagaaaat tttcagacat tgcttgatgc tggtttacca
 121 cagaaagttg ctgaaaaact agatgaaatt tacgttgcag ggctagttgc acatagtgat
 181 ttagatgaaa gagctattga agctttaaaa gaattcaatg aagacggtgc attggcagtt
 241 cttcaacagt ttaaagacag tgatctctct catgttcaga acaaaagtgc cttttatgt
 301 ggagtcatga agacttacag gcagagagaa aaacaaggga ccaaagtagc agattctagt
 361 aaaggaccag atgaggcaaa aattaaggca ctcttggaaa gaacaggcta cacacttgat
 421 gtgaccactg gacagaggaa gtatggagga ccacctccag attccgttta ttcaggtcag
 481 cagccttctg ttggcactga gatatttgtg ggaaagatcc aagagatct atttgaggat
 541 gaacttgttc cattatttga gaaagctgga cctatatggg atcttcgtct aatgatggat
 601 ccactcactg gtctcaatag aggttatgcg tttgtcactt tttgtacaaa agaagcagct
 661 caggaggctg ttaaactgta taataatcat gaaattcgtt ctggaaaaca tattggtgtc
 721 tgcatctcag ttgccaacaa taggcttttt gtgggctcta ttcctaagag taaaaccaag
 781 gaacagattc ttgaagaatt tagcaaagta acagagggtc ttacagacgt cattttatac
 841 caccaaccgg atgacaagaa aaaaaacaga ggcttttgct ttcttgaata tgaagatcac
 901 aaaacagctg cccaggcaag gcgtaggtta atgagtggta aagtcaaggt ctgggggaat
 961 gttggaactg ttgaatgggc tgatcctata gaagatcctg atcctgaggt tatggcaaag
1021 gtaaaagtgc tgtttgtacg caaccttgcc aatactgtaa cagaagagat tttagaaaag
1081 gcatttagtc agtttgggaa actggaacga gtgaagaagt taaaagatta tgcgttcatt
1141 cattttgatg agcgagatgg tgctgtcaag gctatggaag aaatgaatgg caaagacttg
1201 gagggagaaa atattgaaat tgtttttgcc aagccaccag atcagaaaag gaaagaaaga
1261 aaagctcaga ggcaagcagc aaaaaatcaa atgtatgacg attactacta ttatggtcca
1321 cctcatatgc cccctccaac aagaggtcga gggcgtggag gtagaggtgg ttatggatat
1381 cctccagatt attatggata tgaagattat tatgattatt atggttatga ttaccataac
1441 tatcgtggtg gatatgaaga tccatactat ggttatgaag attttcaagt tggagctaga
1501 ggaaggggtg gtagaggagc aaggggtgct gctccatcca gaggtcgtgg ggctgctcct
1561 ccccgcggta gagccggtta ttcacagaga ggaggtcctg gatcagcaag aggcgttcga
1621 ggtgcgagag gaggtgccca acaacaaaga ggccgcgggg gaaaaggggt cgaggccggt
1681 cctgacctgt acaatgaag actgacttgc tatgtgggat tacaccagaa gcttgcagtg
1741 gagtaatggt aaggaaatca agcaacctta aatatgtcgg ctgtatagga gcatattcta
1801 ttgcagaaga ccttcctatg aagatcatgg aatcaaatac gggacattga actaatactt
1861 ggactttgat atgaatttct ttaacaattt tctctgcagt gcaagttatt aaactaaagc
1921 tactctattt tcaaaatgtg ttccaacaga aatccttcat aactcctagc atggtatctt
1981 aataaagaat aaagttcttt taaaaatctg ctctaagtag attttttccc tttttaaat
2041 taaggatccc aacagtggta ttttgaaata ttctcttgaa tttgtgcatt taaatttat
2101 tgcagtggta tagatgaatg ccactgatgg tatccttaaa ttttatttct gctcaccaag
2161 gttaatcatg attgtctata tctttttat agtgatcact tttgaattgt gttcagatat
2221 gcagtttcag gtgtaatcat cagagctggt tagtcaggca ttccagatag tggttctttt
2281 cagaaccttt ttaaagggt tggttaacta cctcagtagc agaggattga actataccct
2341 gtctgtactg tacatagaaa atctttgtag ataaaagcaa ggcttgttaa atatgatatg
2401 agggtaagat tttaatatac caatgtaac attcttagtt gcctagtt tcagaggctt
2461 gtaagacttc ctcatgacca tcataacagg ccttgctttt gtcgtatttt gtggctgaaa
2521 aagcagcctt gcttcttcag atattgtagt tatttggatg tataatagtt tagcaagatg
2581 ttactttgt aagacatcag atgttcaaaa aagtgcatcc gaacttgtac taaatactgc
2641 agtgtccctt tataaaagt cagactaaaa ctgacaattg tacagcgaag cctgacattt
2701 ggatattgg aagtttttc ataaatcata gaaattagta tatggctgta gtttagcttt
2761 ttaggtaaaa ggtatgtttc attagtgcat ttcttcctgc tgatcactgt aaacatgtga
2821 atcagctttc catttcttat gcaggtcatg ataacttgta gagtagagta caatcatttg
2881 tgctatgttt ttaattttct aaagcacctt gatgacagtg agtgtccagt ggtgaagcat
```

Figure 21 (cont'd)

```
2941 cctctattga accaccctca aaaattttt  tgccaagtcc taagttgata gcttaaagta
3001 aaaagtgaaa attatagttt cattaggact tggtgtaaag aaatcccctc cccccttccc
3061 caaagggata ctgcagttat atcacatacc caataggcac cacgatgaag atcagagctt
3121 atacttaatt aaggttttat acacaccagt tccccagtaa atgcaaattt aacaagaaaa
3181 tcagacatgt catatgttca aaatgctcat ggcaaacaat cattttgcat tcctgcaaat
3241 aaaattgttt tatactgtaa gctggaggcg agtgtaactt attttttgtaa taaagttttt
3301 attttttta  tgtgtcatta atataaatgt gtgttagtgt agaaatcttc tggtttaaaa
3361 acttagaatt gcacacattt cagtatgttt atttgtactt acataatttt agaatagtgg
3421 ttgccaatag cctgtatgtt tcacattaat tggttttttg ttatctaaat aaatcatttt
3481 agtatgttgt atgtcagtta ctgggatagc tgggacatag agtgtaattt aaaatttgtc
3541 aataagtatt cattggaata tatgtaaatg tgccttgccg gttattgaaa cttatctaca
3601 aaatgagtat ggggtgacaa aaattagttc ctggtgctta atgaactttt ctgccactga
3661 ttttatatat tacccccgtgc ttttttaaag tacatctctc tcaaaactta gtgtaagttt
3721 gagggctaca caaaacattt acatttcatt ctaacataat gaatataata ggttgtggaa
3781 agtgggtaaa ctaaatgtag ccttcagtaa aattgaatct cagtgtaatc cttggtgctg
3841 gcatttctca gttccgagga gttaaatgat cccatctaag aggtcattgc catgcctatt
3901 ggcactttac tgtcatagca tttttaaggg acactgtcaa ggtgtttaag ttctcagaat
3961 tacttgttgg gatttttagga caggtttgtt tacttaaagt aagaactgca ttgtcaaagt
4021 tgaaagagga acactttgt  gagttcacaa atgtgttctt aagaaaacat taaaatatgg
4081 agctctgggt tttcaagact atttggcatt cttaatttgg ggacttggga gggaaactga
4141 taaaagaaa  ttgaagaatt gatggttata cttaaagaag ggtaatgtaa acagtggtga
4201 tgaaatatat acacatcaag tgaaattact tgacagtgtt catttgaatg actttgaatt
4261 caagccatta taattacttt taaaattaaa tatcatttgc actgttctga taatgggtgc
4321 agttttgag  caatataatc agagctaaat atgcatgtag tgattagtga tgtgaacaat
4381 taacgttctg agaagaaata ctaactgtgg tattttcaaa cttaaattc  tgtagtaaaa
4441 tcagtatcaa agtcttatca gatcaaggaa aaacaggcaa tgcatataaa catactttttg
4501 aatgttgtgt ggcctataaa gcaataatgc aatttatatg gaatgtcatg ggatatgaga
4561 aatggaaatg caaaaataac taatcccttta gtaaaaatgt caacatgtta aagggggaat
4621 gttaactaat gtaggttatt gctatttgtg atttgtttat gggttcttgg ctttgacagc
4681 ttcaaagaat ggacagtgat aagttaaaag aaatttttgta tattgtcaag gaagggtct
4741 taaatccgag tcaagtccct tccttggggt aaaaaatgta ttcttaaagc attctgatgt
4801 taaaagaaa  acttaagtta tctaaccaaa acagacgcaa gatttttgttt ctgcagacta
4861 cttggcaatc aaaagtgatc ataaatttag gttatcagtt ttcagaaagt tgctttgtga
4921 gaaaatttttg ttagatatat tctcccaagc atgcttttg  tggaaggttt tcagccattg
4981 ccactgaatc agatgttaaa aatgaaggga aaattgagtg tgcacacaca caactgttgt
5041 acactcatga ttgcagtttt tagcttaaga aacttttcta ccagttactg tgaatctgac
5101 ttaaaatgta aagtttcctc atgataaaat aggaacaaca tagaaatgga ttgatggggt
5161 gatctgagtt attgtatata aagttttta  aagaatagaa tgaacatcaa gctagatagg
5221 caaaaattga cacattcaga acagcttttt tgactgcgaa gccaaaagtt gtcagaaaca
5281 gcaaaagatc ccttattatt acagagtatt ttacgtagtc tctattttaa ggagagaaat
5341 taaatagaag ggcttcatgc atttagggga gggtgctaaa acttctcaag ttcgtcaaac
5401 ttacaggaat acccaccatg atcattttct ctctaattat gtataccaca aaattttcat
5461 ctggccatag gaattcactg gtgggtgtaa aattaatgac taaagaaatt aagtgacaaa
5521 tacataaaag aaacagactt gtggggatat tgttttaagg tgtattaatt actcagtgat
5581 gataccactc aataggggcat gccactactt ttcttaagat gctaattatg aagcagtgct
5641 cacaggcatt ttttaactag caaattagta gatggacttt tggggtctgt cactttttaa
5701 aagtatttaa gacttaaatt ctattagcac cacagtctgc cttcagtaat acacctaaaa
5761 tatttttcag gaccagaagc attcagtttg aaaatttgca gatgcaaacc agtattatta
5821 ctaacgctct gggtcaaaga ttaggtttttt aatattaaca gtagtctggt aaatatttag
5881 aagtctggca ttgagaaaca aaagcttgta cctgactagt attttttattt aaaaaaatta
5941 gttctgttag cttatttaaa ttgtgtttta tttatccgta gaatttatat ttatttcatt
6001 cctttcatct cactgaaaac tgtctgcagg cccttttgatt tggattagat gtgtgaagta
6061 ctgtcttttg ccaaaaacct caaattacct gttcttttca acgtagtggg tttgtgcttg
6121 tttggagatc agttcaaaaa ctatctgtac tatctgtact gcctctgatg ttaagatttt
6181 atgtatagca taaggaagct agctctgact atattttcct aagaataaag acctattttt
6241 gtagcatgtc ttaggatctc caggagtcca agaattattg tgggtgtcct ccaattcatc
6301 actcttcact taacagcttt taagtagaca cttggaatct ttagaggtct gtcgcccttt
```

Figure 21 (cont'd)

```
6361 gattatccat acattcgaag taactagcca atggtgaaaa attcctcaag atatcctcag
6421 ttgcaatcac attactggaa gatgaataga ataaatgtat taggctggtc ttaattttg
6481 atggaaatat tctgttgtcc cgtacttgcc attggatttg ataaagttag tggtaatttg
6541 gaaagaatcg gggacttgcc aatatatttg tgggttttag cttatacccc taggatttct
6601 tggttgcggg acgagcagtt ttggccactt ccatcaggac aagactttt aggtcactta
6661 gtgcaggttt tagtttctat tttggattaa caacatttat attgattatc gaaaagaagc
6721 tttcatcatt tcagaacagt cctggaagtt tgactttgag tgtgggagaa gtcctaataa
6781 accattttgg aaattaaaaa aaaaa
```

Figure 22

Homo sapiens synaptotagmin binding cytoplasmic RNA interacting protein (SYNCRIP), transcript variant 1, mRNA NCBI Reference Sequence: NM_006372.4 (SEQ ID NO: 9)

```
   1 agcgcgggag agagaaagag aggagccgac tcggcaggga ctgggggacc gggccgagag
  61 tgcgagcgag cgagggaggg agtgagggag cgtgcgagcc agaaggggaa aggcggccac
 121 tcgtgcctga gcgaccgcag aggggagtgg gagcagtggg gtaaaggagc ggggggcggg
 181 aataagaaag gccgagagaa ggcggacaga ggctagtggt ggtggtggtg gtaggggag
 241 aaggaggagc tggaggaggg caggggctga gggagtgagt gaagcggacg cgcgagggag
 301 gggagggaag ggaagggaag ggaaggggg gtcacgcggg ggcgcgcgcg cgcaccggga
 361 gcgcgctcgg aggcgagtgg aactggatcg ggtttgctgc cagcggcgtg agcttcggcc
 421 gccattttac aacagctcca ctcgcgccgg acacagggag cagcgagcac gcgtttcccg
 481 caacccgata ccatcggaca ggatttctcc gcctcagccc aacggggaga tctctggaaa
 541 catggctaca gaacatgtta atggaaatgg tactgaagag cccatggata ctacttctgc
 601 agttatccat tcagaaaatt ttcagacatt gcttgatgct ggtttaccac agaaagttgc
 661 tgaaaaacta gatgaaattt acgttgcagg gctagttgca catagtgatt tagatgaaag
 721 agctattgaa gctttaaaag aattcaatga agacggtgca ttggcagttc ttcaacagtt
 781 taaagacagt gatctctctc atgttcagaa caaaagtgcc ttttatgtg gagtcatgaa
 841 gacttacagg cagagagaaa aacaagggac caaagtagca gattctagta aaggaccaga
 901 tgaggcaaaa attaaggcac tcttggaaag aacaggctac acacttgatg tgaccactgg
 961 acagaggaag tatggaggac cacctccaga ttccgtttat tcaggtcagc agccttctgt
1021 tggcactgag atatttgtgg gaaagatccc aagagatcta tttgaggatg aacttgttcc
1081 attatttgag aaagctggac ctatatggga tcttcgtcta atgatggatc cactcactgg
1141 tctcaataga ggttatgcgt tgtcactt ttgtacaaaa gaagcagctc aggaggctgt
1201 taaactgtat aataatcatg aaattcgttc tggaaaacat attggtgtct gcatctcagt
1261 tgccaacaat aggcttttg tgggctctat tcctaagagt aaaaccaagg aacagattct
1321 tgaagaattt agcaaagtaa cagagggtct tacagacgtc attttatacc accaaccgga
1381 tgacaagaaa aaaacagag gcttttgctt tcttgaatat gaagatcaca aaacagctgc
1441 ccaggcaagg cgtaggttaa tgagtggtaa agtcaaggtc tgggggaatg ttggaactgt
1501 tgaatgggct gatcctatag aagatcctga tcctgaggtt atggcaaagg taaaagtgct
1561 gtttgtacgc aaccttgcca atactgtaac agaagagatt ttagaaaagg catttagtca
1621 gtttgggaaa ctggaacgag tgaagaagtt aaaagattat gcgttcattc attttgatga
1681 gcgagatggt gctgtcaagg ctatggaaga aatgaatggc aaagacttgg agggagaaaa
1741 tattgaaatt gttttgcca agccaccaga tcagaaaagg aaagaagaa aagctcagag
1801 gcaagcagca aaaaatcaaa tgtatgacga ttactactat tatggtccac ctcatatgcc
1861 ccctccaaca agaggtcgag ggcgtggagg tagaggtggt tatggatatc ctccagatta
1921 ttatggatat gaagattatt atgattatta tggttatgat taccataact atcgtggtgg
1981 atatgaagat ccatactatg gttatgaaga ttttcaagtt ggagctagag aaggggtgg
2041 tagaggagca aggggtgctg ctccatccag aggtcgtggg gctgctcctc cccgcggtag
2101 agccggttat tcacagagag gaggtcctgg atcagcaaga ggcgttcgag gtgcgagagg
2161 aggtgcccaa caacaaagag gccgcgggt acgtggtgcg aggggtggcc gcggtggaaa
2221 tgtaggagga aagcgcaaag ctgatgggta caaccagcca gattccaagc ggcgccagac
2281 caataatcag aactggggct cccaacccat tgctcagcaa ccgctccaag tggtgatca
2341 ttctggtaac tatggttaca aatctgaaaa ccaggagttt tatcaggata cttttgggca
2401 acagtggaag tagaaacagt agggcctctg taaaattgga gactgatagg ttgatcagaa
2461 actcacccta aatctgaacg ggtgccgcta taatttgtga catctggcaa gatttccctt
2521 tatgtatata ttttaacaat ccgcttggac acgaacaaag ccacacttct aactgcttct
2581 ggcgaactga ttttattttt aattttttc aataaagata ttcttagata ctgaaagaaa
2641 tagttaatga gtttgcattt gtgcttgaga aaatttggct caagtccatt tggctgtagt
2701 gtcaacgatg tttccagtag tgtttagatt tggtgtcttc aaaggtagtt gattaaaacc
2761 aagtgtgtct ttaatatctt gtatcagaat aactttgtat gttaccaact taaattgcta
2821 gaataaggta aattgataca caactgctat ttttaattta gaactttgac ctaatttggg
2881 ttttcaaaac cattttggct acttgtattc tttatgctgt tgtttatttc aataaaaaat
```

Figure 22 (cont'd)

```
2941 tcacacctaa atgtatactt actaaaattg tgtttacaat tcgtttttca caaaatttcc
3001 tgcaaatttg gttcaaattg tatagcatgt caaggccaat taaagggttt tgtgccttgt
3061 taattcttgt gtggaatatg tctgcacatt acacaacact gatttattgc agttttctgc
3121 ttctggttta aagtgctatt ttacaacaga cttcatgttc ccatcaaaaa taaaagata
3181 atacatgtag taag
```

Figure 23

Homo sapiens synaptotagmin binding cytoplasmic RNA interacting protein (SYNCRIP), transcript variant 3, mRNA NCBI Reference Sequence: NM_001159674.1 (SEQ ID NO: 10)

```
   1 ctccactcgc gccggacaca gggagcagcg agcacgcgtt tcccgcaacc cgataccatc
  61 ggacaggatt tctccgcctc agcccaacgg ggagatctct ggaaacatgg ctacagaaca
 121 tgttaatgga aatggtactg aagagcccat ggatactact tctgcagtta tccattcaga
 181 aaattttcag acattgcttg atgctggttt accacagaaa gttgctgaaa aactagatga
 241 aatttacgtt gcagggctag ttgcacatag tgatttagat gaaagagcta ttgaagcttt
 301 aaaagaattc aatgaagacg gtgcattggc agttcttcaa cagtttaaag acagtgatct
 361 ctctcatgtt cagaacaaaa gtgccttttt atgtggagtc atgaagactt acaggcagag
 421 agaaaaacaa gggaccaaag tagcagattc tagtaaagga ccagatgagg caaaaattaa
 481 ggcactcttg gaaagaacag gctacacact tgatgtgacc actggacaga ggaagtatgg
 541 aggaccacct ccagattccg tttattcagg tcagcagcct tctgttggca ctgagatatt
 601 tgtgggaaag atcccaagag atctatttga ggatgaactt gttccattat ttgagaaagc
 661 tggacctata tgggatcttc gtctaatgat ggatccactc actggtctca atagaggtta
 721 tgcgtttgtc acttttttgta caaaagaagc agctcaggag gctgttaaac tgtataataa
 781 tcatgaaatt cgttctggaa aacatattgg tgtctgcatc tcagttgcca acaataggct
 841 ttttgtgggc tctattccta agagtaaaac caaggaacag attcttgaag aatttagcaa
 901 agtaacagag ggtcttacag acgtcatttt ataccaccaa ccggatgaca agaaaaaaaa
 961 cagaggcttt tgctttcttg aatatgaaga tcacaaaaca gctgcccagg taaaagtgct
1021 gtttgtacgc aaccttgcca atactgtaac agaagagatt ttagaaaagg catttagtca
1081 gtttgggaaa ctggaacgag tgaagaagtt aaaagattat gcgttcattc attttgatga
1141 gcgagatggt gctgtcaagg ctatggaaga aatgaatggc aaagacttgg agggagaaaa
1201 tattgaaatt gtttttgcca agccaccaga tcagaaaagg aaagaaagaa aagctcagag
1261 gcaagcagca aaaaatcaaa tgtatgacga ttactactat tatggtccac ctcatatgcc
1321 ccctccaaca agaggtcgag ggcgtggagg tagaggtggt tatggatatc ctccagatta
1381 ttatggatat gaagattatt atgattatta tggttatgat taccataact atcgtggtgg
1441 atatgaagat ccatactatg gttatgaaga ttttcaagtt ggagctagag aaggggtgg
1501 tagaggagca aggggtgctg ctccatccag aggtcgtggg gctgctcctc ccgcggtag
1561 agccggttat tcacagagag gaggtcctgg atcagcaaga ggcgttcgag gtgcgagagg
1621 aggtgcccaa caacaaagag gccgcgggca gggaaaaggg gtcgaggccg gtcctgacct
1681 gttacaatga agactgactt gctatgtggg attacaccag aagcttgcag tggagtaatg
1741 gtaaggaaat caagcaacct taaatatgtc ggctgtatag gagcatattc tattgcagaa
1801 gaccttccta tgaagatcat ggaatcaaat acgggacatt gaactaatac ttggactttg
1861 atatgaattt ctttaacaat tttctctgca gtgcaagtta ttaaactaaa gctactctat
1921 tttcaaaatg tgttccaaca gaaatccttc ataactccta gcatggtatc ttaataaaga
1981 ataaagttct tttaaaaatc tgctctaagt agattttcc ccttttttaa attaaggatc
2041 ccaacagtgg tattttgaaa tattctcttg aatttgtgca tttaaatttt attgcagtgg
2101 tatagatgaa tgccactgat ggtatcctta aattttattt ctgctcacca aggttaatca
2161 tgattgtcta tatctttttt atagtgatca cttttgaatt gtgttcagat atgcagtttc
2221 aggtgtaatc atcagagctg gttagtcagg cattccagat agtggttctt ttcagaacct
2281 ttttaaaagg gttggttaac tacctcagta gcagaggatt gaactatacc ctgtctgtac
2341 tgtacataga aaatctttgt agataaaagc aaggcttgtt aaatatgata tgagggtaag
2401 attttaatat accaaatgta acattcttag ttgcctttag tttcagaggc ttgtaagact
2461 tcctcatgac catcataaca ggccttgctt ttgtcgtatt ttgtggctga aaaagcagcc
2521 ttgcttcttc agatattgta gttatttgga tgtataatag tttagcaaga tgttactttt
2581 gtaagcatc agatgttcaa aaaagtgcat ccgaacttgt actaaatact gcagtgtccc
2641 tttataaaaa gtcagactaa aactgacaat tgtacagcga agcctgacat tggatattt
2701 tgaagttttt tcataaatca tagaaattag tatatggctg tagtttagct ttttaggtaa
2761 aaggtatgtt tcattagtgc atttcttcct gctgatcact gtaaacatgt gaatcagctt
2821 tccatttctt atgcaggtca tgataacttg tagagtagag tacaatcatt tgtgctatgt
2881 ttttaatttt ctaaagcacc ttgatgacag tgagtgtcca gtggtgaagc atcctctatt
```

Figure 23 (cont'd)

```
2941 gaaccaccct caaaaatttt tttgccaagt cctaagttga tagcttaaag taaaaagtga
3001 aaattatagt ttcattagga cttggtgtaa agaaatcccc tcccccttc cccaaaggga
3061 tactgcagtt atatcacata cccaataggc accacgatga agatcagagc ttatacttaa
3121 ttaaggtttt atacacacca gttccccagt aaatgcaaat ttaacaagaa aatcagacat
3181 gtcatatgtt caaaatgctc atggcaaaca atcattttgc attcctgcaa ataaaattgt
3241 tttatactgt aagctggagg cgagtgtaac ttattttgt aataaagttt ttattttttt
3301 tatgtgtcat taatataaat gtgtgttagt gtagaaatct tctggtttaa aaacttagaa
3361 ttgcacacat ttcagtatgt ttatttgtac ttacataatt ttagaatagt ggttgccaat
3421 agcctgtatg tttcacatta attggttttt tgttatctaa ataaatcatt ttagtatgtt
3481 gtatgtcagt tactgggata gctgggacat agagtgtaat ttaaaatttg tcaataagta
3541 ttcattggaa tatatgtaaa tgtgccttgc cggttattga aacttatcta caaaatgagt
3601 atggggtgac aaaaattagt tcctggtgct taatgaaact ttctgccact gatttatat
3661 attacccccgt gctttttaa agtacatctc tctcaaaact tagtgtaagt ttgagggcta
3721 cacaaaacat ttacatttca ttctaacata atgaatataa taggttgtgg aaagtgggta
3781 aactaaatgt agccttcagt aaaattgaat ctcagtgtaa tccttggtgc tggcatttct
3841 cagttccgag gagttaaatg atcccatcta agaggtcatt gccatgccta ttggcacttt
3901 actgtcatag cattttaag ggacactgtc aaggtgttta agttctcaga attacttgtt
3961 gggattttag gacaggtttg tttacttaaa gtaagaactg cattgtcaaa gttgaaagag
4021 gaacactttt gtgagttcac aaatgtgttc ttaagaaaac attaaatat ggagctctgg
4081 gttttcaaga ctatttggca ttcttaattt ggggacttgg gagggaaact gataaaaaga
4141 aattgaagaa ttgatggtta tacttaaaga agggtaatgt aaacagtggt gatgaaatat
4201 atacacatca agtgaaatta cttgacagtg ttcatttgaa tgactttgaa ttcaagccat
4261 tataattact tttaaaatta aatatcattt gcactgttct gataatgggt gcagttttg
4321 agcaatataa tcagagctaa atatgcatgt agtgattagt gatgtgaaca attaacgttc
4381 tgagaagaaa tactaactgt ggtattttca aacttaaatt tctgtagtaa aatcagtatc
4441 aaagtcttat cagatcaagg aaaaacaggc aatgcatata aacatacttt tgaatgttgt
4501 gtggcctata aagcaataat gcaatttata tggaatgtca tgggatatga gaaatggaaa
4561 tgcaaaaata actaatcctt tagtaaaaat gtcaacatgt taaggggga atgttaacta
4621 atgtaggtta ttgctatttg tgatttgttt atgggttctt ggctttgaca gcttcaaaga
4681 atggacagtg ataagttaaa agaaattttg tatattgtca aggaagggt cttaaatccg
4741 agtcaagtcc cttccttggg gtaaaaatg tattcttaaa gcattctgat gttaaaaaga
4801 aaacttaagt tatctaacca aaacagacgc aagattttgt ttctgcagac tacttggcaa
4861 tcaaaagtga tcataaattt aggttatcag ttttcagaaa gttgctttgt gagaaaattt
4921 tgttagatat attctcccaa gcatgctttt tgtggaaggt tttcagccat tgccactgaa
4981 tcagatgtta aaaatgaagg gaaaattgag tgtgcacaca cacaactgtt gtacactcat
5041 gattgcagtt tttagcttaa gaaacttttc taccagttac tgtgaatctg acttaaaatg
5101 taaagtttcc tcatgataaa ataggaacaa catagaaatg gattgatggg gtgatctgag
5161 ttattgtata taaaagtttt taaagaatag aatgaacatc aagctagata ggcaaaaatt
5221 gacacattca gaacagcttt tttgactgcg aagccaaaag ttgtcagaaa cagcaaaaga
5281 tcccttatta ttacagagta ttttacgtag tctctatttt aaggagagaa attaaataga
5341 agggcttcat gcatttaggg gagggtgcta aaacttctca agttcgtcaa acttacagga
5401 atacccacca tgatcatttt ctctctaatt atgtataacca caaaattttc atctggccat
5461 aggaattcac tggtgggtgt aaaattaatg actaaagaaa ttaagtgaca aatacataaa
5521 agaaacagac ttgtggggat attgttttaa ggtgtattaa ttactcagtg atgataccac
5581 tcaataggc atgccactac ttttcttaag atgctaatta tgaagcagtg ctcacaggca
5641 ttttttaact agcaaattag tagatggact tttggggtct gtcactttt aaaagtattt
5701 aagacttaaa ttctattagc accacagtct gccttcagta atacacctaa aatatttttc
5761 aggaccagaa gcattcagtt tgaaaatttg cagatgcaaa ccagtattat tactaacgct
5821 ctgggtcaaa gattaggttt ttaatattaa cagtagtctg gtaaatattt agaagtctgg
5881 cattgagaaa caaaagcttg tacctgacta gtatttttat ttaaaaaaat tagttctgtt
5941 agcttattta aattgtgttt tatttatccg tagaatttat atttatttca ttcctttcat
6001 ctcactgaaa actgtctgca ggcccttga tttggattag atgtgtgaag tactgtcttt
6061 tgccaaaaac ctcaaattac ctgttcttt caacgtagtg ggtttgtgct tgtttggaga
6121 tcagttcaaa aactatctgt actatctgta ctgcctctga tgttaagatt ttatgtatag
6181 cataaggaag ctagctctga ctatattttc ctaagaataa agacctattt ttgtagcatg
6241 tcttaggatc tccaggagtc caagaattat tgtgggtgtc ctccaattca tcactcttca
6301 cttaacagct tttaagtaga cacttggaat ctttagaggt ctgtcgccct ttgattatcc
```

Figure 23 (cont'd)

```
6361 atacattcga agtaactagc caatggtgaa aaattcctca agatatcctc agttgcaatc
6421 acattactgg aagatgaata gaataaatgt attaggctgg tcttaatttt tgatggaaat
6481 attctgttgt cccgtacttg ccattggatt tgataaagtt agtggtaatt tggaaagaat
6541 cggggacttg ccaatatatt tgtgggtttt agcttatacc cctaggattt cttggttgcg
6601 ggacgagcag ttttggccac ttccatcagg acaagacttt ttaggtcact tagtgcaggt
6661 tttagtttct attttggatt aacaacattt atattgatta tcgaaaagaa gctttcatca
6721 tttcagaaca gtcctggaag tttgactttg agtgtgggag aagtcctaat aaaccatttt
6781 ggaaattaaa aaaaaaa
```

Figure 24

Homo sapiens synaptotagmin binding cytoplasmic RNA interacting protein (SYNCRIP), transcript variant 4, mRNA NCBI Reference Sequence: NM_001159675.1 (SEQ ID NO: 11)

```
   1 atctctggaa acatggctac agaacatgtt aatggaaatg gtactgaaga gcccatggat
  61 actacttctg cagttatcca ttcagaaaat tttcagacat tgcttgatgc tggtttacca
 121 cagaaagttg ctgaaaaact agatgaaatt tacgttgcag ggctagttgc acatagtgat
 181 ttagatgaaa gagctattga agctttaaaa gaattcaatg aagacggtgc attggcagtt
 241 cttcaacagt ttaaagacag tgatctctct catgttcaga acaaaagtgc ctttttatgt
 301 ggagtcatga agacttacag gcagagagaa aaacaaggga ccaaagtagc agattctagt
 361 aaaggaccag atgaggcaaa aattaaggca ctcttggaaa gaacaggcta cacacttgat
 421 gtgaccactg gacagaggaa gtatggagga ccacctccag attccgttta ttcaggtcag
 481 cagccttctg ttggcactga gatatttgtg ggaaagatcc caagagatct atttgaggat
 541 gaacttgttc cattatttga gaaagctgga cctatatggg atcttcgtct aatgatggat
 601 ccactcactg gtctcaatag aggttatgcg tttgtcactt tttgtacaaa agaagcagct
 661 caggaggctg ttaaactgta taataatcat gaaattcgtt ctggaaaaca tattggtgtc
 721 tgcatctcag ttgccaacaa taggcttttt gtgggctcta ttcctaagag taaaaccaag
 781 gaacagattc ttgaagaatt tagcaaagta acagagggtc ttacagacgt cattttatac
 841 caccaaccgg atgacaagaa aaaaaacaga ggcttttgct ttcttgaata tgaagatcac
 901 aaaacagctg cccaggtaaa agtgctgttt gtacgcaacc ttgccaatac tgtaacagaa
 961 gagattttag aaaaggcatt tagtcagttt gggaaactgg aacgagtgaa gaagttaaaa
1021 gattatgcgt tcattcattt tgatgagcga gatggtgctg tcaaggctat ggaagaaatg
1081 aatggcaaag acttggaggg agaaaatatt gaaattgttt ttgccaagcc accagatcag
1141 aaaaggaaag aagaaaaagc tcagaggcaa gcagcaaaaa atcaaatgta tgacgattac
1201 tactattatg gtccacctca tatgccccct ccaacaagag gtcgagggcg tggaggtaga
1261 ggtggttatg gatatcctcc agattattat ggatatgaag attattatga ttattatggt
1321 tatgattacc ataactatcg tggtggatat gaagatccat actatggtta tgaagatttt
1381 caagttggag ctagaggaag gggtggtaga ggagcaaggg gtgctgctcc atccagaggt
1441 cgtggggctg ctcctccccg cggtagagcc ggttattcac agagaggagg tcctggatca
1501 gcaagaggcg ttcgaggtgc gagaggaggt gcccaacaac aaagaggccg cggggtacgt
1561 ggtgcgaggg gtggccgcgg tggaaatgta ggaggaaagc gcaaagctga tgggtacaac
1621 cagccagatt ccaagcggcg ccagaccaat aatcagaact ggggctccca acccattgct
1681 cagcaaccgc tccaaggtgg tgatcattct ggtaactatg gttacaaatc tgaaaaccag
1741 gagttttatc aggatacttt tgggcaacag tggaagtaga aacagtaggg cctctgtaaa
1801 attggagact gataggttga tcagaaactc accctaaatc tgaacgggtg ccgctataat
1861 ttgtgacatc tggcaagatt tccctttatg tatatatttt aacaatccgc ttggacacga
1921 acaaagccac acttctaact gcttctggcg aactgatttt attttttaatt ttttttcaata
1981 aagatattct tagatactga aagaaatagt taatgagttt gcatttgtgc ttgagaaaat
2041 ttggctcaag tccatttggc tgtagtgtca acgatgtttc cagtagtgtt tagatttggt
2101 gtcttcaaag gtagttgatt aaaaccaagt gtgtctttaa tatcttgtat cagaataact
2161 ttgtatgtta ccaacttaaa ttgctagaat aaggtaaatt gatacacaac tgctattttt
2221 aatttagaac tttgacctaa tttgggtttt caaaaccatt ttggctactt gtattcttta
2281 tgctgttgtt tatttcaata aaaaattcac acctaaatgt atacttacta aaattgtgtt
2341 tacaattcgt ttttcacaaa atttcctgca aatttggttc aaattgtata gcatgtcaag
2401 gccaattaaa gggttttgtg ccttgttaat tcttgtgtgg aatatgtctg cacattacac
2461 aacactgatt tattgcagtt ttctgcttct ggtttaaagt gctattttac aacagacttc
2521 atgttcccat caaaaataaa aagataatac atgtagtaag
```

METHODS FOR TREATMENT OR PREVENTION OF LEUKEMIA

CROSS-REFERENCE TO RELATED APPLICATIONS

This application is a National Stage Application of PCT/US2018/021626, filed Mar. 8, 2018, which claims the benefit of and priority to U.S. Provisional Appl. No. 62/470,037, filed Mar. 10, 2017, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Mar. 28, 2018, is named 115872-0608_SL.txt and is 57,662 bytes in size.

TECHNICAL FIELD

The present technology relates generally to methods for treating, preventing, and/or ameliorating leukemia in a subject in need thereof. Also disclosed herein are methods for reducing the expression and/or activity of synaptotagmin-binding, cytoplasmic RNA-interacting protein (SYNCRIP; also known as NSAP1 or hnRNPQ1 in humans) to treat, prevent, and/or ameliorate leukemia.

BACKGROUND

The following description of the background of the present technology is provided simply as an aid in understanding the present technology and is not admitted to describe or constitute prior art to the present technology.

Acute myeloid leukemia (AML) is a genetically complex and heterogeneous set of diseases characterized by a diverse set of mutations (Lindsley, R. C. & Ebert, B. L., *Blood* 122, 3741-3748 (2013)). Overall survival of adult patients with AML has only improved modestly in the past 30 years (Maynadié, M. et al., *Haematologica* 96, 55-61 (2011)). Leukemia stem cells (LSCs) are a subpopulation characterized by a self-renewal capacity and an ability to recapitulate the phenotypic heterogeneity of the disease. While somatic alterations in genetic and epigenetic mechanisms in leukemogenesis are intensively studied, how post-transcriptional and translational regulation of mRNA/protein expression influences leukemia progression and LSC function remains poorly defined.

SUMMARY OF THE PRESENT TECHNOLOGY

In one aspect, the present disclosure provides a method for treating or preventing AML in a subject in need thereof, comprising administering to the subject a therapeutically effective amount of at least one SYNCRIP-specific inhibitory nucleic acid that inhibits synaptotagmin-binding, cytoplasmic RNA-interacting protein (SYNCRIP) expression levels or activity in the subject. The AML may be T-cell acute lymphoblastic leukemia or B-cell acute lymphoblastic leukemia.

In some embodiments, the at least one SYNCRIP-specific inhibitory nucleic acid comprises a nucleic acid sequence selected from the group consisting of: SEQ ID NO: 1, SEQ ID NO: 2, SEQ ID NO: 18, SEQ ID NO: 19, SEQ ID NO: 20, SEQ ID NO: 21, and any complement thereof. The at least one SYNCRIP-specific inhibitory nucleic acid may be a siRNA, a shRNA, an antisense oligonucleotide, or a sgRNA.

Additionally or alternatively, in some embodiments of the methods of the present technology, the subject displays elevated expression levels of SYNCRIP protein in leukemic cells prior to treatment. In certain embodiments, treatment with the at least one SYNCRIP-specific inhibitory nucleic acid results in a decrease in SYNCRIP and/or HOXA9 levels in the subject compared to that observed prior to treatment.

In some embodiments of the methods of the present technology, the subject has been diagnosed as having AML. Signs or symptoms of AML may comprise one or more of leukemic cell proliferation, enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite.

In any of the above embodiments of the methods disclosed herein, the subject may harbor one or more point mutations in NRAS, DNMT3A, FLT3, KIT, IDH1, IDH2, CEBPA and NPM1 and/or one or more gene fusions selected from the group consisting of CBFB-MYH11, DEK-NUP214, MLL-MLLT3, PML-RARA, RBM15-MKL1, RPN1-EVI1 and RUNX1-RUNX1T1. In certain embodiments, the subject is human.

Additionally or alternatively, in some embodiments of the methods of the present technology, the at least one SYNCRIP-specific inhibitory nucleic acid is administered orally, topically, intranasally, systemically, intravenously, subcutaneously, intraperitoneally, intradermally, intraocularly, iontophoretically, transmucosally, or intramuscularly. In some embodiments, the at least one SYNCRIP-specific inhibitory nucleic acid is administered daily for 6 weeks or more. In other embodiments, the at least one SYNCRIP-specific inhibitory nucleic acid is administered daily for 12 weeks or more.

Additionally or alternatively, in some embodiments, the methods further comprise separately, sequentially or simultaneously administering one or more additional therapeutic agents to the subject. Examples of additional therapeutic agents include cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacnne, etoposide phosphate, teniposide, azacitidine (Vidaza), decitabine, accatin III, 10-deacetyl-taxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, or combinations thereof.

In another aspect, the present disclosure provides a method for inhibiting leukemic cell proliferation in a subject in need thereof, comprising administering to the subject a therapeutically effective amount of an SYNCRIP-specific inhibitory nucleic acid, wherein the subject suffers from a disease or condition characterized by elevated expression levels and/or increased activity of SYNCRIP.

Also disclosed herein are methods for monitoring the therapeutic efficacy of an SYNCRIP-specific inhibitory nucleic acid that targets SYNCRIP expression and/or activity in a subject diagnosed with AML comprising: (a) detecting SYNCRIP protein levels in a test sample obtained from the subject after the subject has been administered the SYNCRIP-specific inhibitory nucleic acid; and (b) determining that the SYNCRIP-specific inhibitory nucleic acid is effective when the SYNCRIP protein levels in the test sample are reduced compared to that observed in a control sample obtained from the subject prior to administration of the SYNCRIP-specific inhibitory nucleic acid. The SYNCRIP-specific inhibitory nucleic acid may be a siRNA, a shRNA, an antisense oligonucleotide, or a sgRNA. The test sample may be tissues, cells or biological fluids (blood, plasma, saliva, urine, serum etc.) present within a subject. In certain embodiments, the method further comprises detecting HOXA9 levels in the subject. Additionally or alternatively, in some embodiments, the SYNCRIP-specific inhibitory nucleic acid comprises a nucleic acid sequence selected from the group consisting of: SEQ ID NO: 1, SEQ ID NO: 2, SEQ ID NO: 18, SEQ ID NO: 19, SEQ ID NO: 20, and SEQ ID NO: 21, and any complement thereof.

Also provided herein are kits comprising one or more SYNCRIP-specific inhibitory nucleic acids comprising a nucleic acid sequence selected from the group consisting of SEQ ID NOs: 1-2, 18-21, and any complement thereof.

BRIEF DESCRIPTION OF THE DRAWINGS

FIG. 13(L) shows mRNA stability of Syncrip, Hoxa9, Myc and Ikzf2 in dsRed cells transduced with control and SYNCRIP shRNAs 4 days after transduction.

Figure 13A:
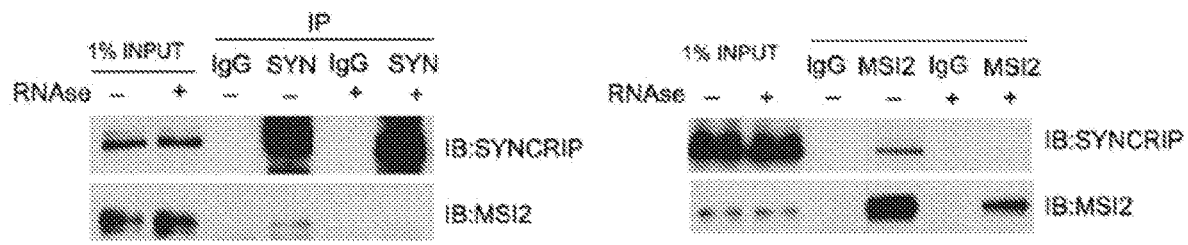
FIG. 13(A) shows MOLM13 human myeloid leukemia cells carrying the MLL-AF9 translocation overexpressing MSI2 were immunoprecipitated for endogenous MSI2 and SYNCRIP.
Figure 13B:
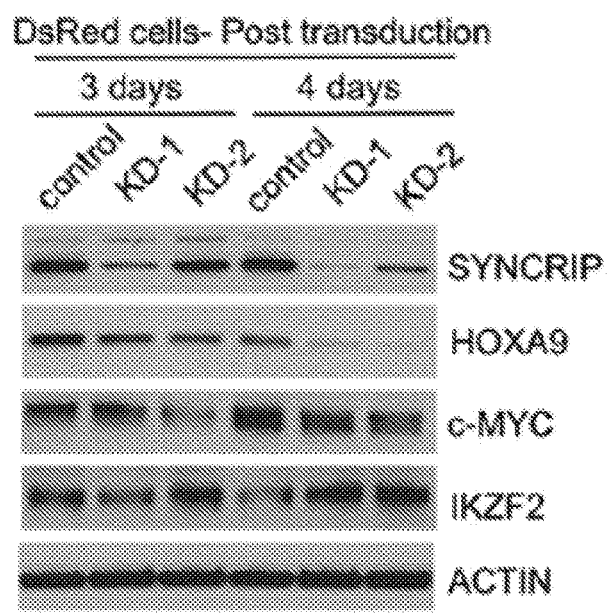
FIG. 13(B) shows immunoblots showing protein expression of HOXA9, MYC and IKZF2 upon SYNCRIP knockdown in dsRed MLL-AF9 cells 3 and 4 days after transduction. Actin serves as a loading control.
Figure 13C:
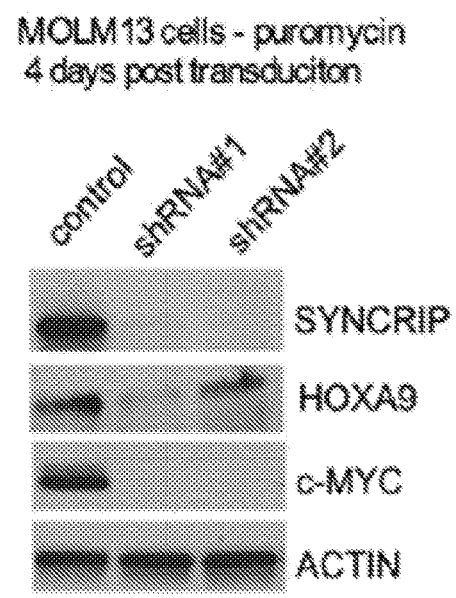
FIG. 13(C) shows immunoblots showing protein expression of HOXA9 and MYC upon SYNCRIP knockdown in MOLM13 cells after 2 days of puromycin selection (4 days after transduction).
Figure 13D:
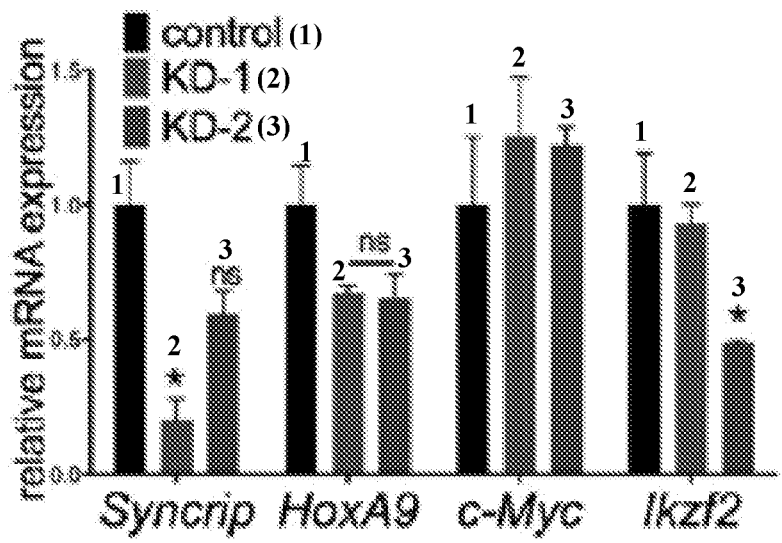
FIG. 13(D) shows qPCR measuring the mRNA expression of Syncrip, Hoxa9, Myc and Ikzf2 in dsRed tertiary MLL-AF9 leukemia cells 3 days after transduction.
Figure 13E:
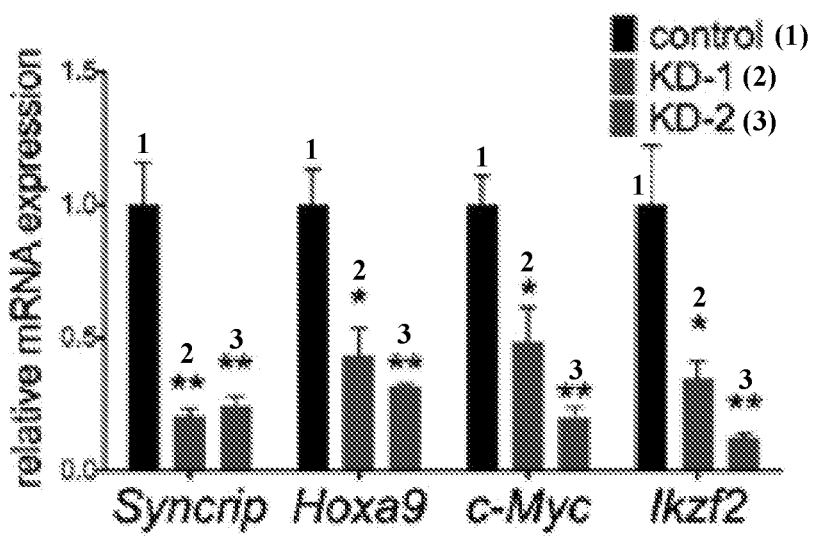
FIG. 13(E) shows qPCR measuring the mRNA expression of Syncrip, Hoxa9, Myc and Ikzf2 in dsRed tertiary MLL-AF9 leukemia cells 4 days after transduction.
Figure 13F:
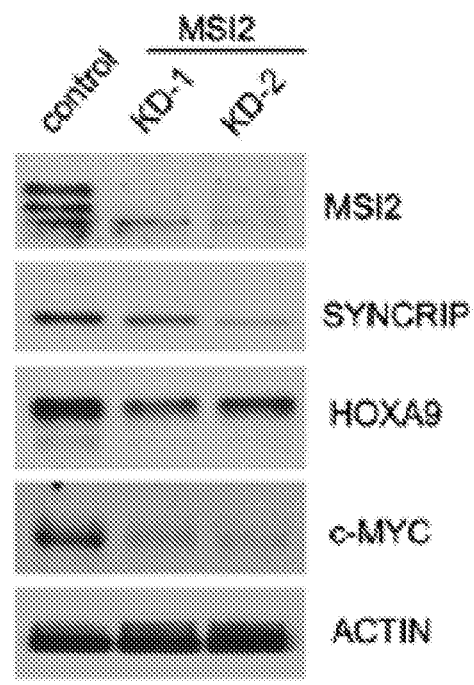
FIG. 13(F) shows immunoblots showing protein expression of HOXA9, MYC and SYNCRIP upon MSI2 knockdown in dsRed MLL-AF9 cells at 4 days after transduction.
Figure 13G:
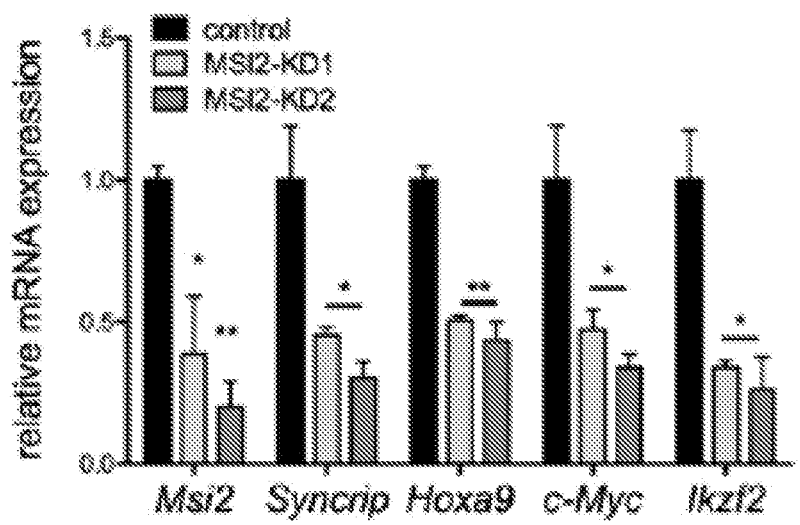
FIG. 13(G) shows qPCR measuring mRNA expression of Syncrip, Hoxa9, Myc and Ikzf2 upon MSI2 knockdown in dsRed MLL-AF9 cells at 4 days after transduction.
Figure 13H:
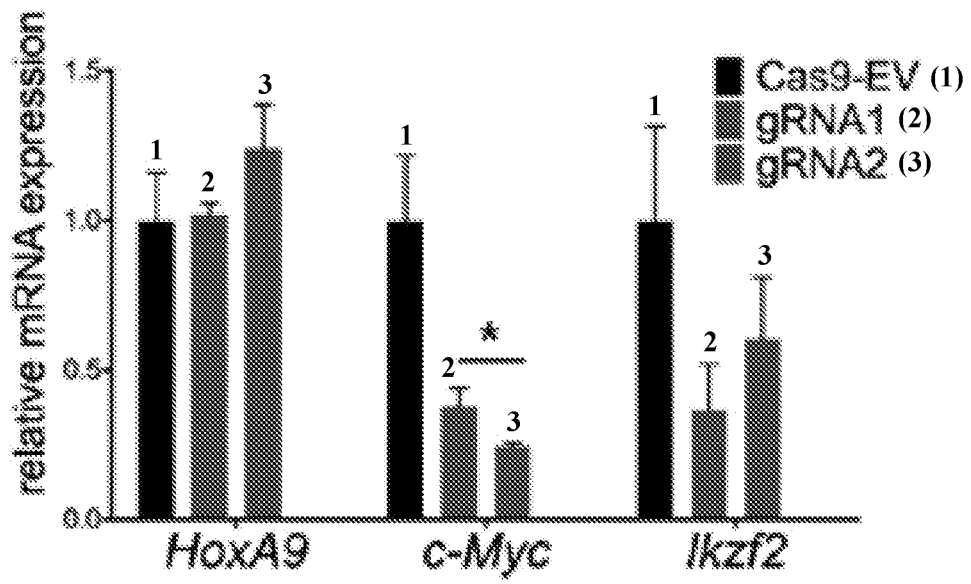
FIG. 13(H) shows qPCR measuring mRNA expression of Syncrip, Hoxa9, Myc and Ikzf2 in RN2 cells 24 hours after induction.
Figure 13I:
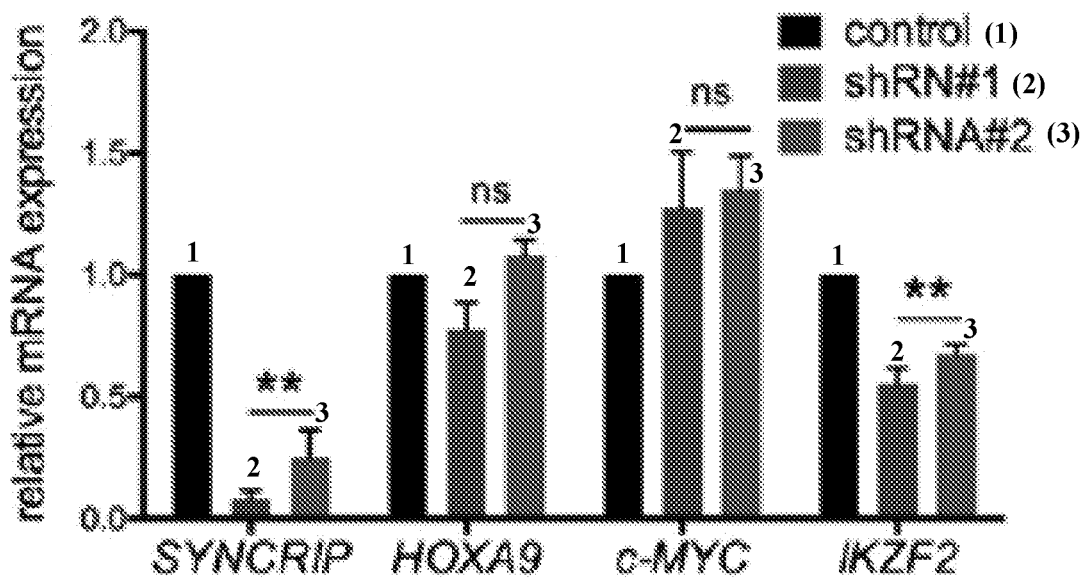
FIG. 13(I) shows qPCR measuring mRNA expression of Syncrip, Hoxa9, Myc and Ikzf2 in human MOLM13 leukemia cells 3 days after transduction.
Figure 13J:
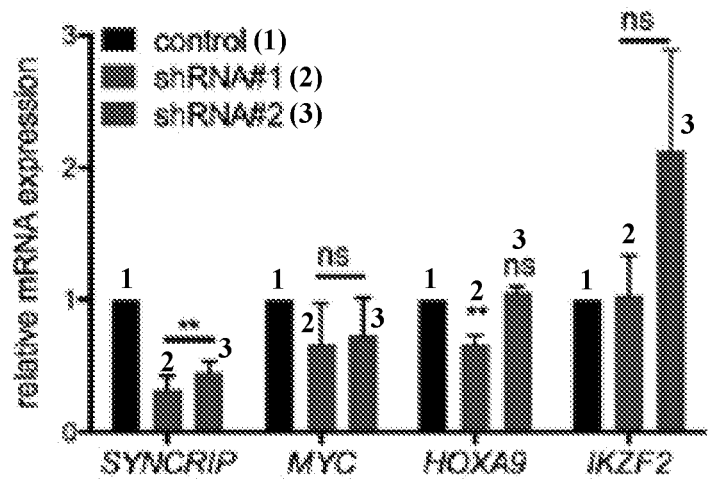
FIG. 13(J) shows qPCR measuring mRNA expression of Syncrip, Hoxa9, Myc and Ikzf2 in human MOLM13 leukemia cells 4 days after transduction.
Figure 13K:
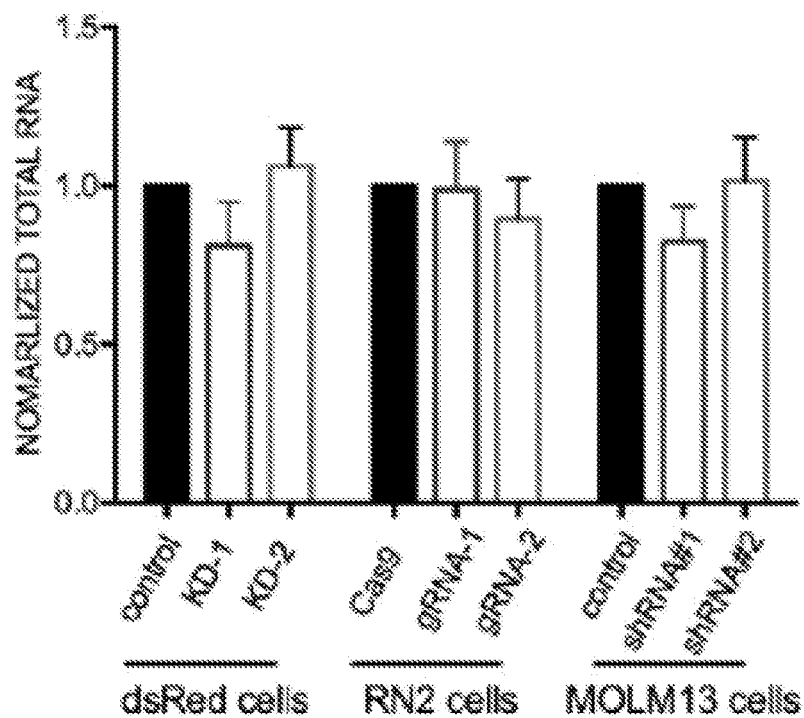
FIG. 13(K) shows normalized total RNA levels in dsRed MLL-AF9, RN2 and MOLM13 cells upon SYNCRIP depletion.
Figure 13L:
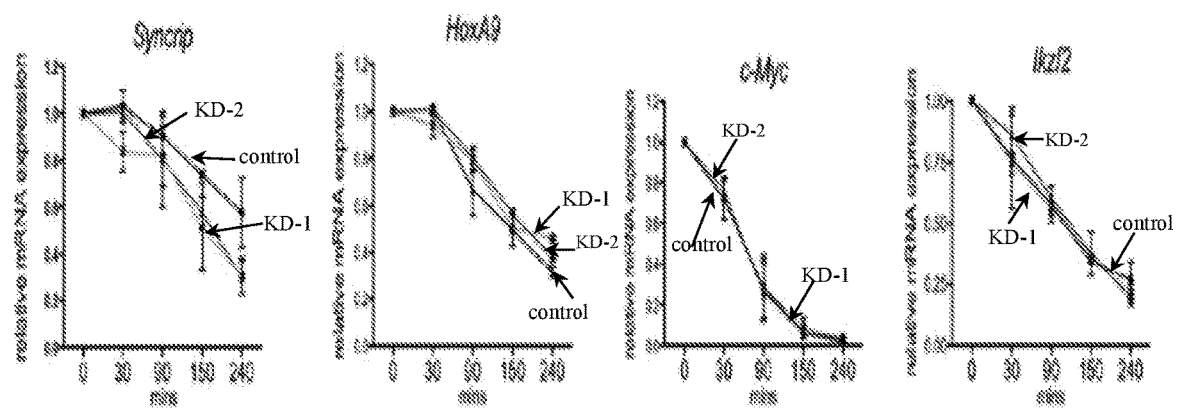
Figure 13M:
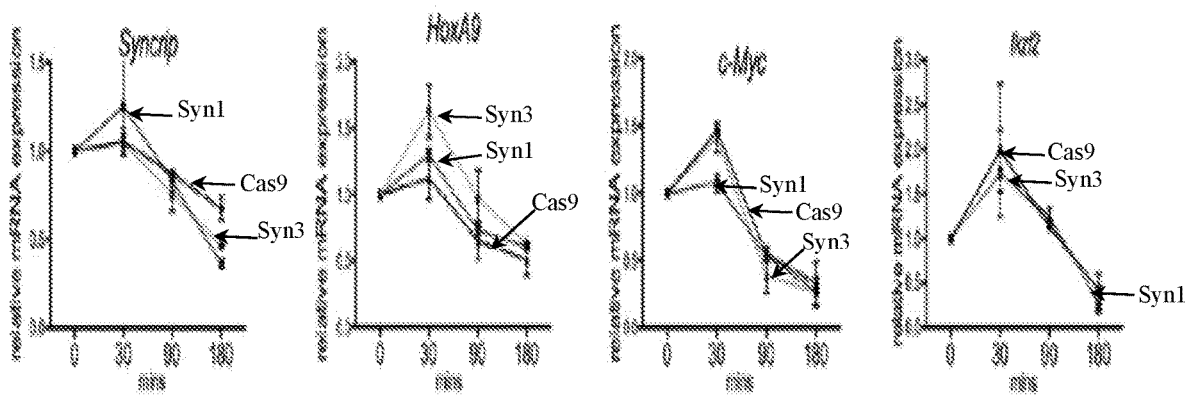

FIG. 13(M) shows mRNA stability of Syncrip, Hoxa9, Myc and Ikzf2 in RN2 cells expressing Cas9-EV or gRNA1 and gRNA3 targeting Syncrip after 24 hours of doxycycline induction. Actin served as a loading control. β-actin served as a control housekeeping gene. All data represent the means+s.e.m. of at least three independent experiments. *p<0.05, p<0.01, *p<0.001, two-tailed t test.

Figure 14A:
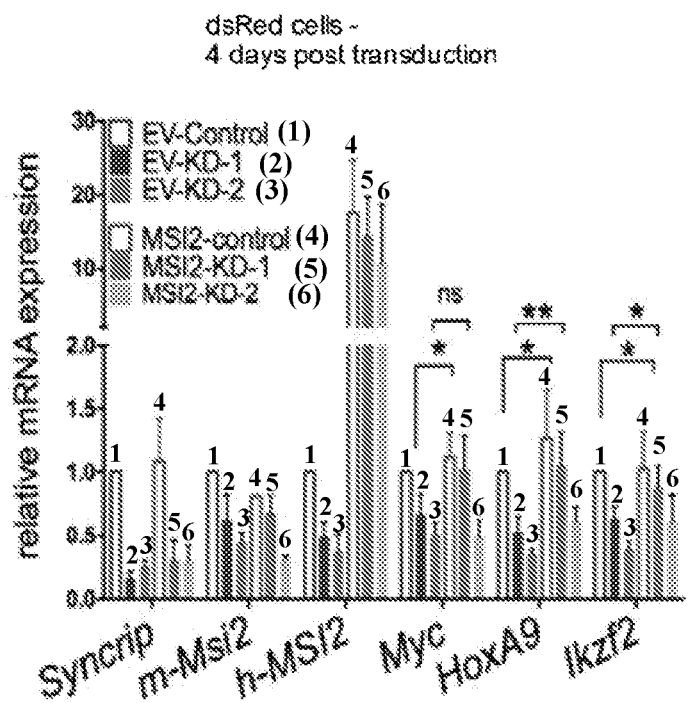

FIG. 14(A) shows qPCR measuring mRNA expression showing that MSI2 overexpression increased the mRNA levels of Hoxa9, Myc and Ikzf2. All data represent the means+s.e.m. of at least three independent replicates. *p<0.05, p<0.01, *p<0.001, ****p<0.0001, two-tailed t test.

Figure 14B:
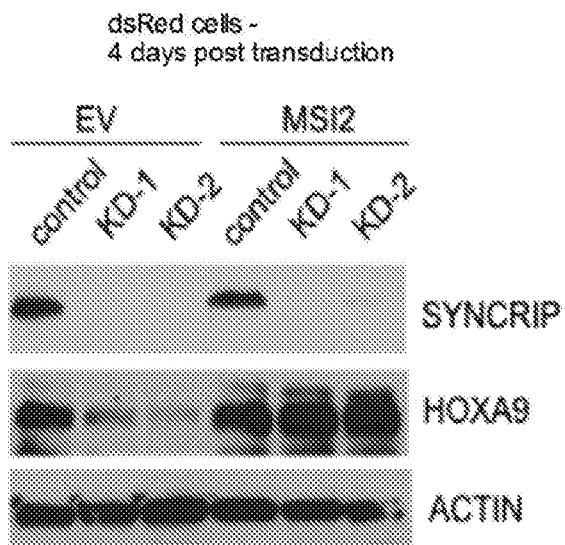

FIG. 14(B) shows immunoblots that show depletion of SYNCRIP, and protein expression of HOXA9 for the cells in FIG. 14(A). Actin served as a loading control. β-actin served as a control housekeeping gene.

Figure 14C:
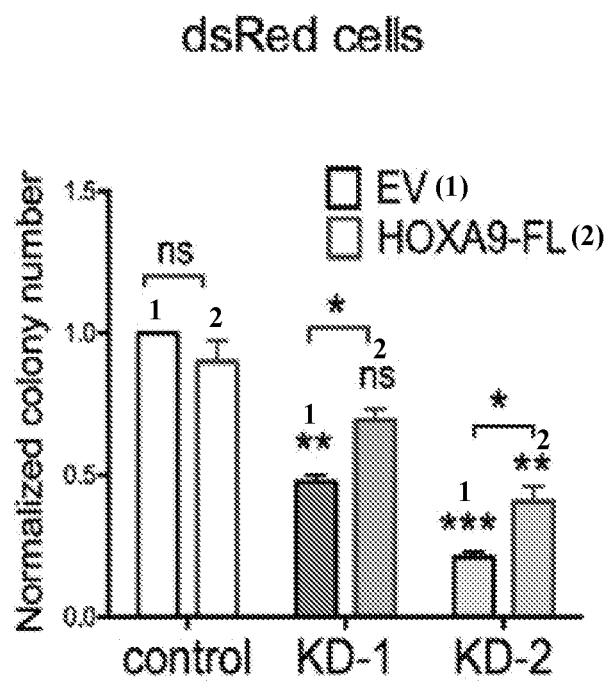

FIG. 14(C) shows that colony formation was rescued in dsRed SYNCRIP-KD leukemia cells overexpressing full-length HOXA9. All data represent the means+s.e.m. of at least three independent replicates. *p<0.05, p<0.01, *p<0.001, ****p<0.0001, two-tailed t test.

Figure 14D:
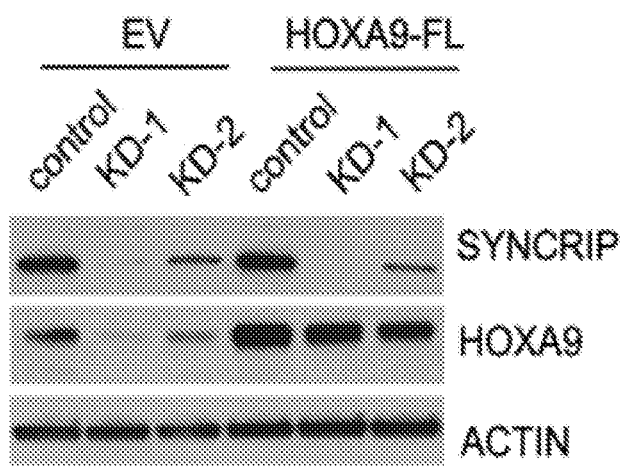

FIG. 14(D) shows immunoblots that show depletion of SYNCRIP, and protein expression of HOXA9 for the cells in FIG. 14(C). Actin served as a loading control. β-actin served as a control housekeeping gene.

Figure 14E:
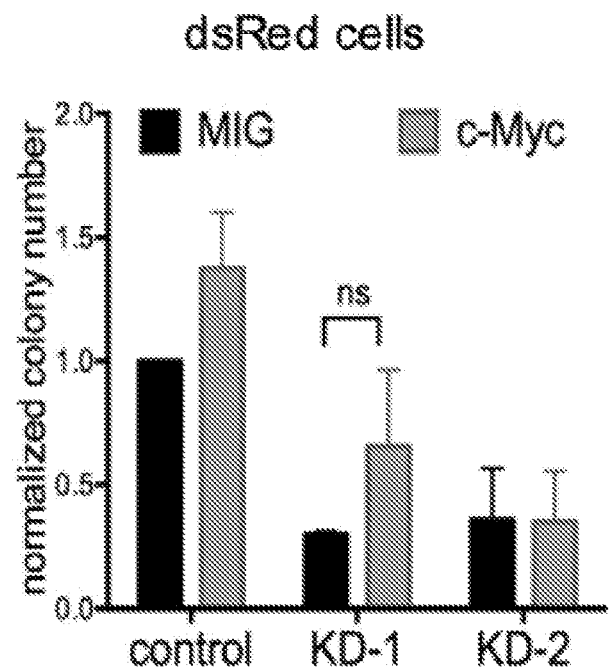

FIG. 14(E) shows that colony formation was not rescued in dsRed SYNCRIP-KD leukemia cells overexpressing MYC. All data represent the means+s.e.m. of at least three independent replicates. *p<0.05, p<0.01, *p<0.001, ****p<0.0001, two-tailed t test.

Figure 14F:
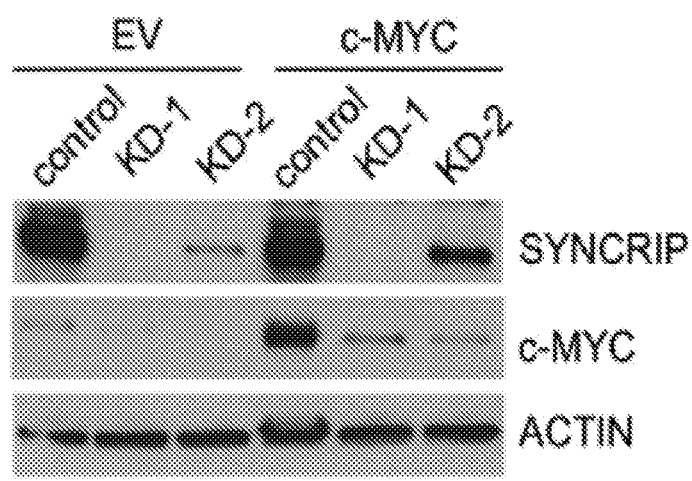

FIG. 14(F) shows immunoblots that show depletion of SYNCRIP, and protein expression of MYC for the cells in FIG. 14(E). Actin served as a loading control. β-actin served as a control housekeeping gene.

Figure 14G:
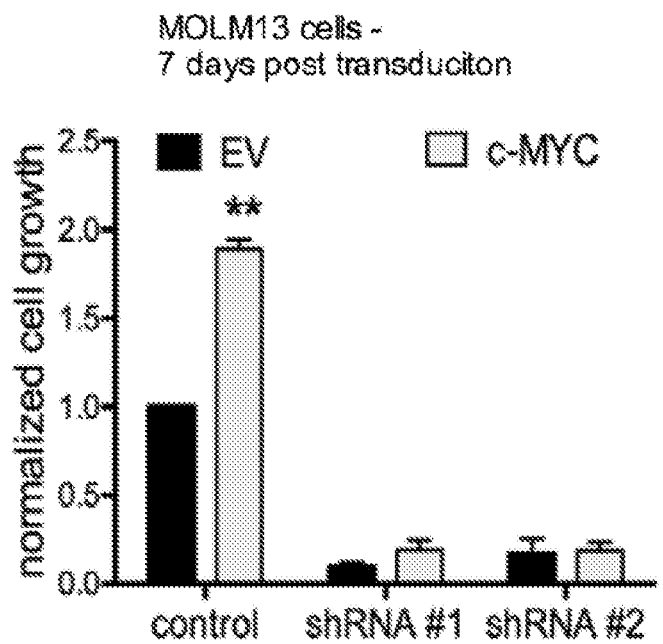

FIG. 14(G) shows that cell growth was not rescued in MOLM13 SYNCRIP-KD cells overexpressing MYC. All data represent the means+s.e.m. of at least three independent replicates. *p<0.05, p<0.01, *p<0.001, ****p<0.0001, two-tailed t test.

Figure 14H:
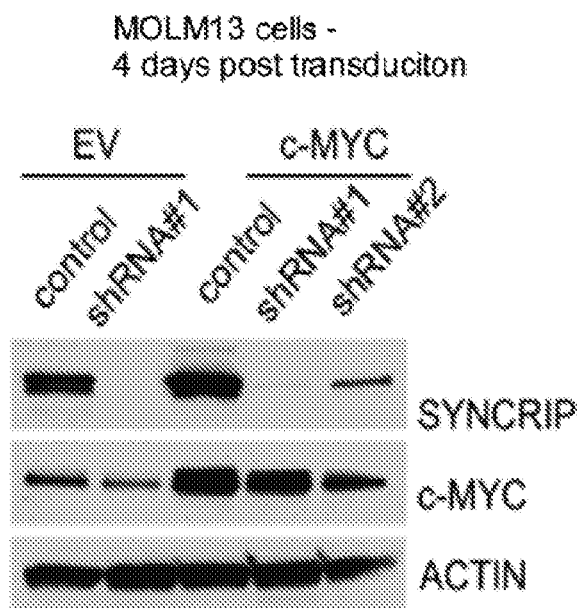

FIG. 14(H) shows immunoblots that show depletion of SYNCRIP, and protein expression of MYC for the cells in FIG. 14(G). Actin served as a loading control. β-actin served as a control housekeeping gene.

FIG. 15 shows raw normalized read counts of all target sequences in the in vivo shRNA screen in bone marrow.

FIG. 16 shows raw normalized read counts of all target sequences in the in vivo shRNA screen in spleen.

FIG. 17 shows a list of differentially expressed genes in Syncrip-shRNA leukemia cells with log 2(fold change)>1.5.

FIG. 18 shows the nucleic acid sequence of *Homo sapiens* synaptotagmin binding cytoplasmic RNA interacting protein (SYNCRIP), transcript variant 7, mRNA (SEQ ID NO: 5).

FIG. 19 shows the nucleic acid sequence of *Homo sapiens* synaptotagmin binding cytoplasmic RNA interacting protein (SYNCRIP), transcript variant 6, mRNA (SEQ ID NO: 6).

FIG. 20 shows the nucleic acid sequence of *Homo sapiens* synaptotagmin binding cytoplasmic RNA interacting protein (SYNCRIP), transcript variant 2, mRNA (SEQ ID NO: 7).

FIG. 21 shows the nucleic acid sequence of *Homo sapiens* synaptotagmin binding cytoplasmic RNA interacting protein (SYNCRIP), transcript variant 5, mRNA (SEQ ID NO: 8).

FIG. 22 shows the nucleic acid sequence of *Homo sapiens* synaptotagmin binding cytoplasmic RNA interacting protein (SYNCRIP), transcript variant 1, mRNA (SEQ ID NO: 9).

FIG. 23 shows the nucleic acid sequence of *Homo sapiens* synaptotagmin binding cytoplasmic RNA interacting protein (SYNCRIP), transcript variant 3, mRNA (SEQ ID NO: 10).

FIG. 24 shows the nucleic acid sequence of *Homo sapiens* synaptotagmin binding cytoplasmic RNA interacting protein (SYNCRIP), transcript variant 4, mRNA (SEQ ID NO: 11).

Figure 25A:
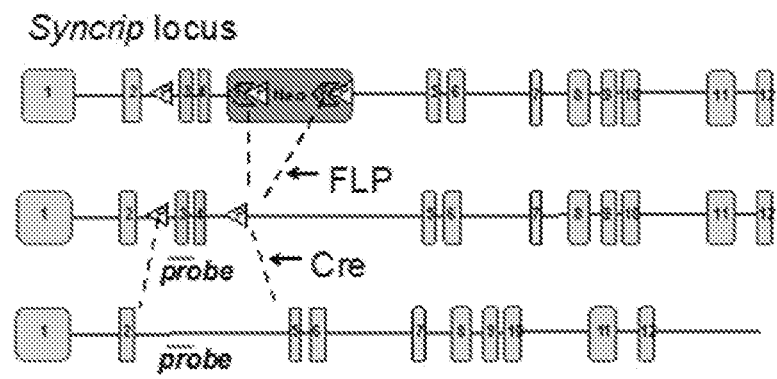

FIG. 25(A) shows the targeting scheme for SYNCRIP conditional knockout mice.

Figure 25B:
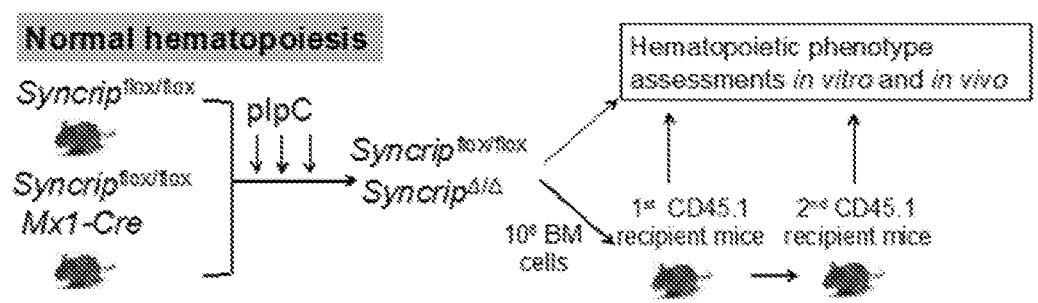

FIG. 25(B) shows the experimental schemes for studying the effects of SYNCRIP depletion in normal hematopoiesis.

Figure 25C:
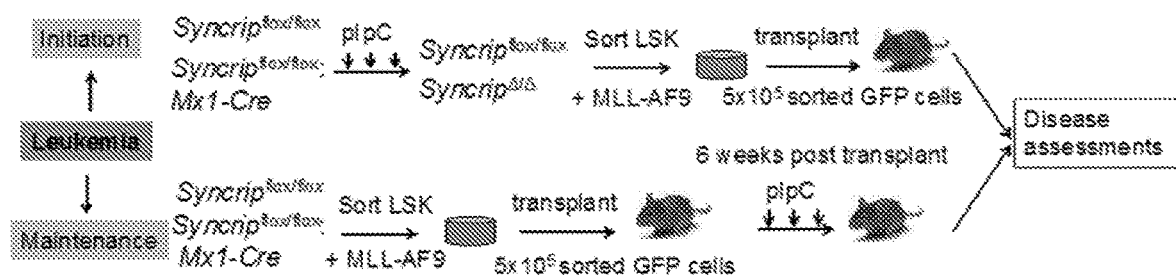

FIG. 25(C) shows the experimental schemes for studying the effects of SYNCRIP depletion in leukemia.

DETAILED DESCRIPTION

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning. A Laboratory Manual,* 3rd edition; the series Ausubel et al. eds. (2007) *Current Protocols in Molecular Biology*; the series Methods in Enzymology (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular*

*Biology* (Academic Press, London); and Herzenberg et al. eds (1996) *Weir's Handbook of Experimental Immunology*.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of AML. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning. A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning. A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention", "prevent", or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample. As used herein, preventing AML, includes preventing or delaying the initiation of symptoms of AML. As used herein, prevention of AML also includes preventing a recurrence of one or more signs or symptoms of AML.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

The term "specific" as used herein in reference to an oligonucleotide means that the nucleotide sequence of the oligonucleotide has at least 12 bases of sequence identity with a portion of a target nucleic acid when the oligonucleotide and the target nucleic acid are aligned. An oligonucleotide that is specific for a target nucleic acid is one that, under the stringent hybridization or washing conditions, is capable of hybridizing to the target nucleic acid of interest and not substantially hybridizing to nucleic acids which are not of interest. Higher levels of sequence identity are desirable and include at least 75%, at least 80%, at least 85%, at least 90%, at least 95% or at least 98% sequence identity.

The term "stringent hybridization conditions" as used herein refers to hybridization conditions at least as stringent as the following: hybridization in 50% formamide, 5×SSC, 50 mM NaH$_2$PO$_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

As used herein, the terms "subject," "individual," or "patient" are used interchangeably and refer to an individual organism, a vertebrate, a mammal, or a human. In certain embodiments, the individual, patient or subject is a human.

As used herein, the terms "target sequence" and "target nucleic acid sequence" refer to a specific nucleic acid sequence to be modulated (e.g., inhibited or downregulated).

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

SYNCRIP-Specific Inhibitory Nucleic Acids of the Present Technology

FIGS. 18-24 show the nucleic acid sequences of seven human SYNCRIP transcript variants, represented by SEQ ID NOs: 5-11.

In one aspect, the present disclosure provides SYNCRIP-specific inhibitory nucleic acids comprising a nucleic acid molecule which is complementary to a portion of a SYN-CRIP nucleic acid sequence selected from the group consisting of SEQ ID NOs: 5-11.

The present disclosure also provides an antisense nucleic acid comprising a nucleic acid sequence that is complementary to and specifically hybridizes with a portion of any one of SEQ ID NOs: 5-11 (SYNCRIP mRNA), thereby reducing or inhibiting SYNCRIP expression. The antisense nucleic acid may be antisense RNA, or antisense DNA Antisense nucleic acids based on the known SYNCRIP gene sequence can be readily designed and engineered using methods known in the art. In some embodiments, the antisense nucleic acid comprises the nucleic acid sequence of SEQ ID NO: 1, SEQ ID NO: 2, SEQ ID NO: 18, SEQ ID NO: 19, SEQ ID NO: 20, SEQ ID NO: 21, or a complement thereof.

Antisense nucleic acids are molecules which are complementary to a sense nucleic acid strand, e.g., complementary to the coding strand of a double-stranded DNA molecule (or cDNA) or complementary to an mRNA sequence. Accordingly, an antisense nucleic acid can form hydrogen bonds with a sense nucleic acid. The antisense nucleic acid can be complementary to an entire SYNCRIP coding strand, or to a portion thereof, e.g., all or part of the protein coding region (or open reading frame). In some embodiments, the antisense nucleic acid is an oligonucleotide which is complementary to only a portion of the coding region of SYNCRIP mRNA. In certain embodiments, an antisense nucleic acid molecule can be complementary to a noncoding region of the SYNCRIP coding strand. In some embodiments, the noncoding region refers to the 5' and 3' untranslated regions that flank the coding region and are not translated into amino acids. For example, the antisense oligonucleotide can be complementary to the region surrounding the translation start site of SYNCRIP. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or modified nucleotides designed to increase the biological stability of the molecules or to increase the physical stability of the duplex formed between the antisense and sense nucleic acids, e.g., phosphorothioate derivatives and acridine substituted nucleotides Examples of modified nucleotides which can be used to generate the antisense nucleic acid include 5-fluorouracil, 5-bromouracil, 5-chlorouracil, 5-hodouracil, hypoxanthine, xanthine, 4-acetylcytosine, 5-(carboxyhydroxylmethyl)uracil, 5-carboxymethylaminomethyl-2-thiouridine, 5-carboxymethylaminometh-yluracil, dihydrouracil, beta-D-galactosylqueosine, inosine, N6-isopentenyladenine, l-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules may be administered to a subject or generated in situ such that they hybridize with or bind to cellular mRNA and/or genomic DNA encoding the protein of interest to thereby inhibit expression of the protein, e.g., by inhibiting transcription and/or translation. The hybridization can occur via Watson-Crick base pairing to form a stable duplex, or in the case of an antisense nucleic acid molecule which binds to DNA duplexes, through specific interactions in the major groove of the double helix In some embodiments, the antisense nucleic acid molecules are modified such that they specifically bind to receptors or antigens expressed on a selected cell surface, e.g., by linking the antisense nucleic acid molecules to peptides or antibodies which bind to cell surface receptors or antigens. In some embodiments, the antisense nucleic acid molecule is an alpha-anomeric nucleic acid molecule. An alpha-anomeric nucleic acid molecule forms specific double-stranded hybrids with complementary RNA in which, contrary to the usual β-units, the strands run parallel to each other (Gaultier et al., *Nucleic Acids. Res.* 15:6625-

6641(1987)). The antisense nucleic acid molecule can also comprise a 2'-O-methylribonucleotide (Inoue et al., *Nucleic Acids Res.* 15 6131-6148 (1987)) or a chimeric RNA-DNA analogue (Inoue et al., *FEBS Lett.* 215:327-330 (1987)).

The present disclosure also provides a short hairpin RNA (shRNA) or small interfering RNA (siRNA) comprising a nucleic acid sequence that is complementary to and specifically hybridizes with a portion of any one of SEQ ID NOs: 5-11 (SYNCRIP mRNA), thereby reducing or inhibiting SYNCRIP expression. In some embodiments, the shRNA or siRNA is about 18, 19, 20, 21, 22, 23, 24, 25, 26, 27, 28 or 29 base pairs in length. Double-stranded RNA (dsRNA) can induce sequence-specific post-transcriptional gene silencing (e.g., RNA interference (RNAi)) in many organisms such as *C. elegans, Drosophila*, plants, mammals, oocytes and early embryos. RNAi is a process that interferes with or significantly reduces the number of protein copies made by an mRNA. For example, a double-stranded siRNA or shRNA molecule is engineered to complement and hydridize to a mRNA of a target gene Following intracellular delivery, the siRNA or shRNA molecule associates with an RNA-induced silencing complex (RISC), which then binds and degrades a complementary target mRNA (such as SYNCRIP mRNA). In some embodiments, the shRNA or siRNA comprises the nucleic acid sequence of SEQ ID NO: 1, SEQ ID NO: 2, SEQ ID NO: 18, SEQ ID NO: 19, SEQ ID NO: 20, or SEQ ID NO: 21.

The present disclosure also provides a ribozyme comprising a nucleic acid sequence that is complementary to and specifically hybridizes with a portion of any one of SEQ ID NOs: 5-11 (SYNCRIP mRNA), thereby reducing or inhibiting SYNCRIP expression. Ribozymes are catalytic RNA molecules with ribonuclease activity which are capable of cleaving a complementary single-stranded nucleic acid, such as an mRNA. Thus, ribozymes (e.g., hammerhead ribozymes (described in Haselhoff and Gerlach, *Nature* 334:585-591 (1988))) can be used to catalytically cleave SYNCRIP transcripts, thereby inhibiting translation of SYNCRIP.

A ribozyme having specificity for a SYNCRIP-encoding nucleic acid can be designed based upon a SYNCRIP nucleic acid sequence disclosed herein. For example, a derivative of a Tetrahymena L-19 IVS RNA can be constructed in which the nucleotide sequence of the active site is complementary to the nucleotide sequence to be cleaved in a SYNCRIP-encoding mRNA. See, e.g., U.S. Pat. Nos. 4,987,071 and 5,116,742. Alternatively, SYNCRIP mRNA can be used to select a catalytic RNA having a specific ribonuclease activity from a pool of RNA molecules. See, e.g., Bartel and Szostak (1993) *Science* 261:1411-1418, incorporated herein by reference.

The present disclosure also provides a synthetic guide RNA (sgRNA) comprising a nucleic acid sequence that is complementary to and specifically hybridizes with a portion of any one of SEQ ID NOs: 5-11 (SYNCRIP mRNA). Guide RNAs for use in CRISPR-Cas systems are typically generated as a single guide RNA comprising a crRNA segment and a tracrRNA segment. The crRNA segment and a tracrRNA segment can also be generated as separate RNA molecules. The crRNA segment comprises the targeting sequence that binds to a portion of any one of SEQ ID NOs: 5-11, and a stem portion that hybridizes to a tracrRNA. The tracrRNA segment comprises a nucleotide sequence that is partially or completely complementary to the stem sequence of the crRNA and a nucleotide sequence that binds to the CRISPR enzyme. In some embodiments, the crRNA segment and the tracrRNA segment are provided as a single guide RNA. In some embodiments, the crRNA segment and the tracrRNA segment are provided as separate RNAs. The combination of the CRISPR enzyme with the crRNA and tracrRNA make up a functional CRISPR-Cas system. Exemplary CRISPR-Cas systems for targeting nucleic acids, are described, for example, in WO2015/089465.

In some embodiments, a synthetic guide RNA is a single RNA represented as comprising the following elements:
5'-X1-X2-Y-Z-3'
where X1 and X2 represent the crRNA segment, where X1 is the targeting sequence that binds to a portion of any one of SEQ ID NOs: 5-11, X2 is a stem sequence the hybridizes to a tracrRNA, Z represents a tracrRNA segment comprising a nucleotide sequence that is partially or completely complementary to X2, and Y represents a linker sequence. In some embodiments, the linker sequence comprises two or more nucleotides and links the crRNA and tracrRNA segments. In some embodiments, the linker sequence comprises 2, 3, 4, 5, 6, 7, 8, 9, 10 or more nucleotides. In some embodiments, the linker is the loop of the hairpin structure formed when the stem sequence hybridized with the tracrRNA.

In some embodiments, a synthetic guide RNA is provided as two separate RNAs where one RNA represents a crRNA segment: 5'-X1-X2-3' where X1 is the targeting sequence that binds to a portion of any one of SEQ ID NOs: 5-11, X2 is a stem sequence the hybridizes to a tracrRNA, and one RNA represents a tracrRNA segment, Z, that is a separate RNA from the crRNA segment and comprises a nucleotide sequence that is partially or completely complementary to X2 of the crRNA.

Exemplary crRNA stem sequences and tracrRNA sequences are provided, for example, in WO/2015/089465, which is incorporated by reference herein. In general, a stem sequence includes any sequence that has sufficient complementarity with a complementary sequence in the tracrRNA to promote formation of a CRISPR complex at a target sequence, wherein the CRISPR complex comprises the stem sequence hybridized to the tracrRNA. In general, degree of complementarity is with reference to the optimal alignment of the stem and complementary sequence in the tracrRNA, along the length of the shorter of the two sequences. Optimal alignment may be determined by any suitable alignment algorithm, and may further account for secondary structures, such as self-complementarity within either the stem sequence or the complementary sequence in the tracrRNA. In some embodiments, the degree of complementarity between the stem sequence and the complementary sequence in the tracrRNA along the length of the shorter of the two when optimally aligned is about or more than about 25%, 30%, 40%, 50%, 60%, 70%, 80%, 90%, 95%, 97.5%, 99%, or higher. In some embodiments, the stem sequence is about or more than about 5, 6, 7, 8, 9, 10, 11, 12, 13, 14, 15, 16, 17, 18, 19, 20, 25, 30, 40, 50, or more nucleotides in length. In some embodiments, the stem sequence and complementary sequence in the tracrRNA are contained within a single RNA, such that hybridization between the two produces a transcript having a secondary structure, such as a hairpin. In some embodiments, the tracrRNA has additional complementary sequences that form hairpins. In some embodiments, the tracrRNA has at least two or more hairpins. In some embodiments, the tracrRNA has two, three, four or five hairpins. In some embodiments, the tracrRNA has at most five hairpins.

In a hairpin structure, the portion of the sequence 5' of the final "N" and upstream of the loop corresponds to the crRNA stem sequence, and the portion of the sequence 3' of the loop corresponds to the tracrRNA sequence. Further non-limiting examples of single polynucleotides comprising a guide sequence, a stem sequence, and a tracr sequence are as follows (listed 5' to 3'), where "N" represents a base of a guide sequence (e.g. a modified oligonucleotide provided herein), the first block of lower case letters represent stem sequence, and the second block of lower case letters represent the tracrRNA sequence, and the final poly-T sequence represents the transcription terminator:

(a)
(SEQ ID NO: 12)
NNNNNNNNNNNNNNNNNNNNNgttttttgtactctcaagatttaGA

AAtaaatcttgcagaagctacaaagataaggcttcatgccgaaa tcaacaccctgtcattttatggcagggtgttttcgttatttaaT

TTTTT;

(b)
(SEQ ID NO: 13)
NNNNNNNNNNNNNNNNNNNNNgttttttgtactctcaGAAAtgcag aagctacaaagataaggcttcatgccgaaatcaacaccctgtca ttttatggcagggtgttttcgttatttaaTTTTTT;

(c)
(SEQ ID NO: 14)
NNNNNNNNNNNNNNNNNNNNNgttttttgtactctcaGAAAtgcag aagctacaaagataaggcttcatgccgaaatcaacaccctgtca ttttatggcagggtgtTTTTTT;

(d)
(SEQ ID NO: 15)
NNNNNNNNNNNNNNNNNNNNNgttttagagctaGAAAtagcaagt taaaataaggctagtccgttatcaacttgaaaaagtggcaccga gtcggtgcTTTTTT;

(e)
(SEQ ID NO: 16)
NNNNNNNNNNNNNNNNNNNNNgttttagagctaGAAATAGcaagt taaaataaggctagtccgttatcaacttgaaaaagtGTTTTTTT;
and (f)
(SEQ ID NO: 17)
NNNNNNNNNNNNNNNNNNNNNgttttagagctagAAATAGcaagt taaaataaggctagtccgttatcaTTTTTTTT.

Selection of suitable oligonucleotides for use in as a targeting sequence in a CRISPR Cas system depends on several factors including the particular CRISPR enzyme to be used and the presence of corresponding proto-spacer adjacent motifs (PAMs) downstream of the target sequence in the target nucleic acid. The PAM sequences direct the cleavage of the target nucleic acid by the CRISPR enzyme. In some embodiments, a suitable PAM is 5'-NRG or 5'-NNGRR (where N is any Nucleotide) for SpCas9 or SaCas9 enzymes (or derived enzymes), respectively. Generally the PAM sequences should be present between about 1 to about 10 nucleotides of the target sequence to generate efficient cleavage of the target nucleic acid. Thus, when the guide RNA forms a complex with the CRISPR enzyme, the complex locates the target and PAM sequence, unwinds the DNA duplex, and the guide RNA anneals to the complementary sequence on the opposite strand. This enables the Cas9 nuclease to create a double-strand break. In some embodiments, the sgRNA comprises the nucleic acid sequence of SEQ ID NO: 1 or SEQ ID NO: 2.

A variety of CRISPR enzymes are available for use in conjunction with the disclosed guide RNAs of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any chimeras, mutants, homologs or orthologs. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Cs2, Cs3, Csf4, homologues thereof, or modified variants thereof. In some embodiments, the CRISPR enzyme cleaves both strands of the target nucleic acid at the Protospacer Adjacent Motif (PAM) site. In some embodiments, the CRISPR enzyme is a nickase, which cleaves only one strand of the target nucleic acid.

Therapeutic Methods

The following discussion is presented by way of example only, and is not intended to be limiting.

One aspect of the present technology includes methods of treating a disease or condition characterized by elevated expression levels and/or increased activity of SYNCRIP. Additionally or alternatively, in some embodiments, the present technology includes methods of treating AML. In one aspect, the present disclosure provides a method for inhibiting leukemic cell proliferation in a subject in need thereof, comprising administering to the subject a therapeutically effective amount of at least one SYNCRIP-specific inhibitory nucleic acid, wherein the at least one SYNCRIP-specific inhibitory nucleic acid is selected from the group consisting of antisense oligonucleotide, sgRNA, shRNA, and siRNA, and wherein the subject suffers from a disease or condition characterized by elevated expression levels and/or increased activity of SYNCRIP. The AML may be T-cell acute lymphoblastic leukemia or B-cell acute lymphoblastic leukemia.

In some embodiments, the subject is diagnosed as having, suspected as having, or at risk of having a disease or condition characterized by elevated expression levels and/or increased activity of SYNCRIP. Additionally or alternatively, in some embodiments, the subject is diagnosed as having AML.

In therapeutic applications, compositions or medicaments comprising an SYNCRIP-specific inhibitory nucleic acid disclosed herein are administered to a subject suspected of, or already suffering from such a disease or condition (such as, a subject diagnosed with a disease or condition characterized by elevated expression levels and/or increased activity of SYNCRIP and/or a subject diagnosed with AML), in an amount sufficient to cure, or at least partially arrest, the symptoms of the disease, including its complications and intermediate pathological phenotypes in development of the disease.

Subjects suffering from a disease or condition characterized by elevated expression levels and/or increased activity of SYNCRIP and/or a subject diagnosed with AML can be identified by any or a combination of diagnostic or prognostic assays known in the art. For example, typical symptoms of AML include, but are not limited to, enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite.

In some embodiments, the subject may exhibit one or more point mutations in NRAS, DNMT3A, FLT3, KIT, IDH1, IDH2, CEBPA, and NPM1 and/or one or more chromosomal alterations (e.g., an inversion, translocation, or gene fusion) such as CBFB-MYH11, DEK-NUP214, MLL-MLLT3, PML-RARA, RBM15-MKL1, RPN1-EVI1 and RUNX1-RUNX1T1, and are detectable using techniques known in the art. See Naoe & Kiyoi, *Int J Hematol.* 97(2):165-74 (2013); Shih et al., *Nat Rev Cancer.* 12(9): 599-612 (2012).

In some embodiments, subjects with a disease or condition characterized by elevated expression levels and/or increased activity of SYNCRIP, and/or subjects suffering from AML that are treated with the SYNCRIP-specific inhibitory nucleic acid will show amelioration or elimination of one or more of the following symptoms: enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite.

In certain embodiments, subjects with a disease or condition characterized by elevated expression levels and/or increased activity of SYNCRIP, and/or subjects suffering from AML that are treated with the SYNCRIP-specific inhibitory nucleic acid will show reduced leukemic cell proliferation and/or increased survival compared to untreated AML subjects. In certain embodiments, subjects with a disease or condition characterized by elevated expression levels and/or increased activity of SYNCRIP, and/or subjects suffering from AML that are treated with the SYNCRIP-specific inhibitory nucleic acid will show reduced SYNCRIP and/or HOXA9 expression levels compared to untreated AML subjects.

In one aspect, the present disclosure provides a method for monitoring the therapeutic efficacy of an SYNCRIP-specific inhibitory nucleic acid in a subject diagnosed with AML comprising: (a) detecting SYNCRIP protein levels in a test sample obtained from the subject after the subject has been administered the SYNCRIP-specific inhibitory nucleic acid; and (b) determining that the SYNCRIP-specific inhibitory nucleic acid is effective when the SYNCRIP protein levels in the test sample are reduced compared to that observed in a control sample obtained from the subject prior to administration of the SYNCRIP-specific inhibitory nucleic acid. The SYNCRIP-specific inhibitory nucleic acid may be an antisense oligonucleotide, a sgRNA, a shRNA, or a siRNA. The test sample may be tissues, cells or biological fluids (blood, plasma, saliva, urine, serum etc.) present within a subject. Alternatively, HOXA9 expression levels may be used to determine efficacy of the SYNCRIP-specific inhibitory nucleic acid in the subject (see Example 9 described herein). Accordingly, in certain embodiments, the method further comprises detecting expression levels of HOXA9 in the subject, wherein a decrease in HOXA9 expression levels relative to those observed in the subject prior to treatment is indicative of the therapeutic efficacy of the SYNCRIP-specific inhibitory nucleic acid.

Prophylactic Methods

In one aspect, the present technology provides a method for preventing or delaying the onset of a disease or condition characterized by elevated expression levels and/or increased activity of SYNCRIP. Additionally or alternatively, in some aspects, the present technology provides a method for preventing or delaying the onset AML. The AML may be T-cell acute lymphoblastic leukemia or B-cell acute lymphoblastic leukemia.

Subjects at risk or susceptible to a disease or condition characterized by elevated expression levels and/or increased activity of SYNCRIP, and/or subjects at risk or susceptible to AML include those that exhibit one or more point mutations in NRAS, DNMT3A, FLT3, KIT, IDH1, IDH2, CEBPA, and NPM1 and/or one or more chromosomal alterations (e.g., an inversion, translocation, or gene fusion) such as CBFB-MYH11, DEK-NUP214, MLL-MLLT3, PML-RARA, RBM15-MKL1, RPN1-EVI1 and RUNX1-RUNX1T1. Such subjects can be identified by, e.g., any or a combination of diagnostic or prognostic assays known in the art.

In prophylactic applications, pharmaceutical compositions or medicaments comprising an SYNCRIP-specific inhibitory nucleic acid disclosed herein are administered to a subject susceptible to, or otherwise at risk of a disease or condition characterized by elevated expression levels and/or increased activity of SYNCRIP, and/or a subject susceptible to, or otherwise at risk of AML, in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic SYNCRIP-specific inhibitory nucleic acid can occur prior to the manifestation of symptoms characteristic of the disease or disorder, such that the disease or disorder is prevented or, alternatively, delayed in its progression.

In some embodiments, treatment with the SYNCRIP-specific inhibitory nucleic acid will prevent or delay the onset of one or more of the following symptoms: leukemic cell proliferation, enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite. In certain embodiments, (a) subjects with a disease or condition characterized by elevated expression levels and/or increased activity of SYNCRIP, and/or (b) subjects with AML that are treated with the SYNCRIP-specific inhibitory nucleic acid will show SYNCRIP and/or HOXA9 expression levels that resemble those observed in healthy control subjects.

For therapeutic and/or prophylactic applications, a composition comprising an SYNCRIP-specific inhibitory nucleic acid disclosed herein, is administered to the subject. In some embodiments, the SYNCRIP-specific inhibitory nucleic acid is administered one, two, three, four, or five times per day. In some embodiments, the SYNCRIP-specific inhibitory nucleic acid is administered more than five times per day. Additionally or alternatively, in some embodiments, the SYNCRIP-specific inhibitory nucleic acid is administered every day, every other day, every third day, every fourth day, every fifth day, or every sixth day. In some embodiments, the SYNCRIP-specific inhibitory nucleic acid is administered weekly, bi-weekly, tri-weekly, or monthly. In some embodiments, the SYNCRIP-specific inhibitory nucleic acid is administered for a period of one, two, three, four, or five weeks. In some embodiments, the SYNCRIP-specific inhibitory nucleic acid is administered for six weeks or more. In some embodiments, the SYNCRIP-specific inhibitory nucleic acid is administered for twelve weeks or more. In some embodiments, the SYNCRIP-specific inhibitory nucleic acid is administered for a period of less than one year. In some embodiments, the SYNCRIP-specific inhibitory nucleic acid is administered for a period of more than one year. In some embodiments, the SYNCRIP-specific inhibitory nucleic acid is administered throughout the subject's life.

In some embodiments of the methods of the present technology, the SYNCRIP-specific inhibitory nucleic acid is administered daily for 1 week or more. In some embodiments of the methods of the present technology, the SYNCRIP-specific inhibitory nucleic acid is administered daily for 2 weeks or more. In some embodiments of the methods of the present technology, the SYNCRIP-specific inhibitory nucleic acid is administered daily for 3 weeks or more. In some embodiments of the methods of the present technology, the SYNCRIP-specific inhibitory nucleic acid is administered daily for 4 weeks or more. In some embodiments of the methods of the present technology, the SYNCRIP-specific inhibitory nucleic acid is administered daily for 6 weeks or more. In some embodiments of the methods of the present technology, the SYNCRIP-specific inhibitory nucleic acid is administered daily for 12 weeks or more. In some embodiments, the SYNCRIP-specific inhibitory nucleic acid is administered daily throughout the subject's life.

Determination of the Biological Effect of SYNCRIP-Specific Inhibitory Nucleic Acids In various embodiments, suitable in vitro or in vivo assays are performed to determine the effect of a specific SYNCRIP-specific inhibitory nucleic acid and whether its administration is indicated for treatment. In various embodiments, in vitro assays can be performed with representative animal models, to determine if a given SYNCRIP-specific inhibitory nucleic acid exerts the desired effect on reducing or eliminating signs and/or symptoms of AML. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. In some embodiments, in vitro or in vivo testing is directed to the biological function of one or more SYNCRIP-specific inhibitory nucleic acids.

Animal models of AML may be generated using techniques known in the art. Such models may be used to demonstrate the biological effect of SYNCRIP-specific inhibitory nucleic acids in the prevention and treatment of conditions arising from disruption of a particular gene, and for determining what comprises a therapeutically effective amount of the one or more SYNCRIP-specific inhibitory nucleic acids disclosed herein in a given context.

Modes of Administration and Effective Dosages

Any method known to those in the art for contacting a cell, organ or tissue with one or more SYNCRIP-specific inhibitory nucleic acids disclosed herein may be employed. Suitable methods include in vitro, ex vivo, or in vivo methods. In vivo methods typically include the administration of one or more SYNCRIP-specific inhibitory nucleic acids to a mammal, suitably a human. When used in vivo for therapy, the one or more SYNCRIP-specific inhibitory nucleic acids described herein are administered to the subject in effective amounts (i.e., amounts that have desired therapeutic effect). The dose and dosage regimen will depend upon the degree of the disease state of the subject, the characteristics of the particular SYNCRIP-specific inhibitory nucleic acid used, e.g., its therapeutic index, and the subject's history.

The effective amount may be determined during preclinical trials and clinical trials by methods familiar to physicians and clinicians. An effective amount of one or more SYNCRIP-specific inhibitory nucleic acids useful in the methods may be administered to a mammal in need thereof by any of a number of well-known methods for administering pharmaceutical compounds. The SYNCRIP-specific inhibitory nucleic acids may be administered systemically or locally.

The one or more SYNCRIP-specific inhibitory nucleic acids described herein can be incorporated into pharmaceutical compositions for administration, singly or in combination, to a subject for the treatment or prevention of AML. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™

(BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having one or more SYNCRIP-specific inhibitory nucleic acids disclosed herein can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, Chemical Biology, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods,* 4(3): 201-9 (1994); and Gregoriadis, "Engineering Liposomes for Drug Delivery: Progress and Problems," *Trends Biotechnol.,* 13(12):527-37 (1995). Mizguchi, et al., *Cancer Lett.,* 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the one or more SYNCRIP-specific inhibitory nucleic acids disclosed herein sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, one or more SYNCRIP-specific inhibitory nucleic acid concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of one or more SYNCRIP-specific inhibitory nucleic acids may be defined as a concentration of inhibitor at the target tissue of $10^{-32}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, one or more of the SYNCRIP-specific inhibitory nucleic acids disclosed herein may be combined with one or more additional therapies for the prevention or treatment of AML. Additional therapeutic agents include, but are not limited to, chemotherapeutic agents, arsenic trioxide (Trisenox), all-trans retinoic acid (ATRA), and stem cell transplants.

In some embodiments, the one or more SYNCRIP-specific inhibitory nucleic acids disclosed herein may be separately, sequentially or simultaneously administered with at least one additional therapeutic agent selected from the group consisting of alkylating agents, topoisomerase inhibitors, endoplasmic reticulum stress inducing agents, antimetabolites, mitotic inhibitors, nitrogen mustards, nitrosoureas, alkylsulfonates, platinum agents, taxanes, vinca agents, antiestrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, phenphormin and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent.

Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacnne, etoposide phosphate, teniposide, azacitidine (Vidaza), decitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, or combinations thereof.

Examples of antimetabolites include 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof.

Examples of taxanes include accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, and mixtures thereof.

Examples of DNA alkylating agents include cyclophosphamide, chlorambucil, melphalan, bendamustine, uramustine, estramustine, carmustine, lomustine, nimustine, ranimustine, streptozotocin; busulfan, mannosulfan, and mixtures thereof.

Examples of topoisomerase I inhibitor include SN-38, ARC, NPC, camptothecin, topotecan, 9-nitrocamptothecin, exatecan, lurtotecan, lamellarin D9-aminocamptothecin, rubifen, gimatecan, diflomotecan, BN80927, DX-8951f, MAG-CPT, and mixtures thereof. Examples of topoisomerase II inhibitors include amsacrine, etoposide, etoposide phosphate, teniposide, daunorubicin, mitoxantrone, amsacrine, ellipticines, aurintricarboxylic acid, doxorubicin, and HU-331 and combinations thereof.

In certain embodiments, an additional therapeutic agent is administered to a subject in combination with the one or more SYNCRIP-specific inhibitory nucleic acids disclosed herein such that a synergistic therapeutic effect is produced. For example, administration of one or more SYNCRIP-specific inhibitory nucleic acids with one or more additional therapeutic agents for the prevention or treatment of AML will have greater than additive effects in the prevention or treatment of the disease. For example, lower doses of one or more of the therapeutic agents may be used in treating or preventing AML resulting in increased therapeutic efficacy and decreased side-effects. In some embodiments, the one or more SYNCRIP-specific inhibitory nucleic acids disclosed herein are administered in combination with any of the at least one additional therapeutic agents described above, such that a synergistic effect in the prevention or treatment of AML results.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits for the prevention and/or treatment of AML comprising one or more SYNCRIP-specific inhibitory nucleic acids comprising a nucleic acid sequence selected from the group consisting of SEQ ID NOs: 1-2, 18-21 or any complement thereof. Optionally, the above described components of the kits of the present technology are packed in suitable containers and labeled for the prevention and/or treatment of AML.

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way. The following Examples demonstrate the preparation, characterization, and use of illustrative compositions of the present technology that inhibit SYNCRIP expression and/or activity.

Example 1: Experimental Materials and Methods

Pool description for gene prioritization used for in vivo shRNA screen. The number of genes used in the screen was determined based on previous studies that included approximately 100 genes (Cho S, et al., *Mol Cell Biol.* 27:368-83

(2007)). Therefore, the genes in each pool were prioritized based on the following criteria. Pool 1 is made up of two sub-pools, 1a and 1b. Pool 1a was composed of differentially expressed genes prioritized based on Msi2 gene expression and other hematopoietic gene sets with a matrix score of 6 or more. Pool 1b was selected based on genes found in the leading edge taken from the GSEA with MSI2 overexpression in LSK cells overlapped with genes upregulated after shRNA depletion in CML/AML cell lines or leading edge genes in the rank list of Msi2 KO LSKs. Genes previously determined as canonical targets Numb, Numbl and CDKN1A, were added.

Pool 2 genes were chosen based on an intestinal CLIP-CHIP (UV-crosslinked mouse intestine) and immunoprecipitation for MSI1. MSI1 bound targets were ranked for the top 1000 genes, binding of the 3'UTR and their fold enrichment over the IgG control. These genes were ranked if they were MSI2-hematopoietic relevant genes. A combined score of 3 or more were included into the screen.

Pool 3 included MSI2 direct protein-protein interactors. A matrix score of 3 or more were chosen based on their ability to interact with MSI2 and was included in a MSI2 or hematopoietic relevant gene set.

Intestinal MSI-1 CLIP-CHIP used for pool 2 gene prioritization. UV-crosslinked mouse intestine was immunoprecipitated for MSI1. Similar CLIP protocol was performed as in Park et al., *J Exp Med.* 211:71-87 (2014), with the exception that RNA was random primed and hybridized to Affymetric arrays 1.0ST array. Fold enrichment was ranked over IgG.

Mass Spectrometry Methods and Analysis (used for Pool 3). K562 cells were grown with either MSCV-IRES-GFP or with FLAG-MSI2 and immunoprecipitated with FLAG antibody as previously described in Park et al., *J Clin Invest.* 125:1286-98 (2015). 150 million cells per experiment were then stained, and the gel was cut into nine slices. Control and MSI2 interacting proteins were considered to be represented if there were two or more peptides found and there was high confidence with a MASCOT score of either equal or greater than 20 or 77. Pairwise analysis was performed for two independent immunoprecipitation experiments and mass spectrometry analyses. TOPGENE was performed with 234 MSI2 direct binding targets.

Lentiviral production, infection, and in vivo shRNA screen. Lentiviruses expressing shRNAs in the pLKO.1 vectors were obtained from RNAi consortium at the Broad Institute (Boston, Mass.). Virus production and preparation of pooled and titered lentiviruses for screening was performed as described in Miller et al., *Cancer Cell.* 24(1):45-58 (2013). Pooled titered virus was thawed and kept on ice. L-GMPs (c-kit high cells top 50% were sorted). Infection, 12 well dishes were re-suspended into 600 µL virus+600 µL of cells (2*10⁶ cells) per replicate (1.2 mL/well). Cells were spinfected (2500 RPM, 90 minutes) and then cells were split for day 0 sequencing or injected into sub-lethally irradiated mice. Five pools representing a random set of ~100 shRNAs per pool with a total of titered 627 shRNA viruses were generated and used to transduce leukemia cells. Each transducing well was split: half was kept for sequencing and half was transplanted (1 million cells) into a sub-lethally irradiated recipient mice. There were five replicates per pool with five mice per pool with an experiment representing 25 total mice. After two weeks, cells were harvested from bone marrow and spleen and previously frozen cells for sequencing analysis. The sequences of the SYNCRIP shRNAs described herein are provided below:

| Gene | shRNA ID | Sequence |
|---|---|---|
| Mouse SYNCRIP | KD-1 | 5' GCAGCACAAGAGGCTGTTAAA 3' (SEQ ID NO: 18) |
| Mouse SYNCRIP | KD-2 | 5' GCAACCTTAAATATCTCGGAT 3' (SEQ ID NO: 19) |
| Human SYNCRIP | shRNA#1 | 5' GCACATAGTGATTTAGATGAA 3' (SEQ ID NO: 20) |
| Human SYNCRIP | shRNA#2 | 5' CCAAAGTAGCAGATTCTAGTA 3' (SEQ ID NO: 21) |

Isolation, infection and selection of murine leukemia and normal cells. Tibia and femurs, pelvis, and arm bones from leukemia or C57Bl/6 wild-type mice (6-8 weeks old) were harvested, crushed, filtered, and subjected to red blood cell lysis (QIAGEN, Hilden, Germany). To isolate c-kit positive cells, bone marrow cells were incubated with CD117 microbeads (Miltenyi Biotec, Somerville Mass.), according to manufacturer's instructions, and then subjected to positive selection using autoMACS Pro Separator. Cells were spinfected in RPMI with 10% FBS and cytokines: SCF (10 ng/ml), IL-3 (10 ng/ml), and IL-6 (10 ng/ml) and GM-CSF (10 ng/ml). 48 hours post-transduction, cells were treated with 2 µg/ml puromycin. Two days after puromycin selection, cells were harvested for further analysis.

Colony forming assay. 10,000 cells were plated on methocult GFM3434 (STEMCELL Technologies, Cambridge Mass.). Colonies were scored every five days for leukemia cells and every seven days for normal c-kit-enriched bone marrow cells.

In vivo transplantation of leukemia cells. MLL-AF9 tertiary mouse leukemia cells were transduced with lentiviruses expressing puromycin and shRNAs against Syncrip or a control shRNA. Transduced cells were selected by 2 µg/ml puromycin for 2 days. 50,000 selected cells were injected retro-orbitally into female C57Bl/6 (6-8 weeks old) recipient mice that had been sub-lethally irradiated with 475 cGy.

CRISPR/Cas9 approach to create SYNCRIP-CRISPR-knock out (CR-KO). The CRISPR gRNAs used for deleting exon 3 and 4 of the Syncrip gene were designed using the approach reported in Romanienko et al., *PLoS One* 11(2): e0148362 (2016). The sequence for the 5'-gRNA is GTACCTGTATTACCCAATGC (SEQ ID NO: 1) and sequence for the 3'-gRNA is CAATTTGGAATTGACCGCAC (SEQ ID NO: 2). Both sgRNAs were produced by in vitro transcription using the pU6T7 promoter in the hybrid plasmid described in Romanienko et al., *PLoS One* 11(2):e0148362 (2016). To initiate cleavage of the target locus in mice, gRNA (C67) and gRNA (C69) in conjunction with Cas9 mRNA were co-injected into the pronucleus of mouse zygotes at a concentration of 50 ng/µl each, using conventional techniques. Deleted samples were assayed using PCR primers:

(SEQ ID NO: 3)
CAGTGTTCAGGACTACTTGGACAC (SYNCRIPA)
and (SEQ ID NO: 4)
GTCTATGCTTTCCATAGATGGTTGTAG (SYNCRIPD), which are located outside of the gRNA cleavage sites (outside SYNCRIP exon 3-4) thereby revealing the size of the deletion based on the nucleotide length of the amplicon obtained (~900 bp for wild-type vs.~300 bp for deletion).

Isolation of fetal liver cells, PCR genotyping and bone marrow transplantation. Fetal liver cells were isolated and single cell suspended based on standard protocols (Hemann M. Cold Spring Harb Protoc. 2015(7):679-84 (2015). ~200,000 fetal liver cells after red blood cell lysis were used for DNA extracting using HotSHOT genomic DNA preparation methods. 2 μl supernatant containing DNA was used for PCR reactions with specific primers for detection of Syncrip exon 3-4. DNA was resolved in 1.5% agarose gel. 500,000 cells from confirmed wild-type and Syncrip-CR-KO fetal livers were retro-orbitally injected into lethally irradiated CD45.1 recipient mice. For secondary transplantation, 1 million bone marrow cells were retro-orbitally injected into lethally irradiated CD45.1 recipient mice.

Generation of MLL-AF9 primary leukemia and transplantation. Bone marrow cells from 6- to 10-week-old transplanted $WT^{fl/fl}$ or CR-SYNCRIP $KO^{\Delta/\Delta}$ mice were isolated and subsequently enriched for c-kit positive cells. c-kit enriched cells were stained with Lineage antibody cocktail (CD3, CD4, CD8, Gr1, B220, CD19, TER119 conjugated with PeCy5), Sca-Pac Blue, CD34-FITC, SLAM-APC, CD48-PE, and c-KIT-APC-Cy7. Lin-Sca*Kit* cells were sorted using a BD FACS Aria. Sorted cells were grown overnight in SFEM medium with 10 ng/ml IL-3, 10 ng/ml IL-6, 50 ng/ml SCF, 10 ng/ml thrombopoietin (TPO), and 20 ng/ml FLT3L. Cells were transduced twice with supernatant containing retroviruses expressing MLL-AF9 and GFP on retronectin-coated 96 well flat-bottom plates. The cells were expanded for one week in GFM3434 methylcellulose (STEMCELL Technologies, Cambridge Mass.). MLL-AF9 transformed cells were sorted based on GFP positivity. 200,000 GFP+ sorted cells and 250,000 helper cells were injected retro-orbitally into each lethally irradiated 6-8 week-old C57Bl/6 mouse.

Proliferation assay of human leukemia cells. Human leukemia cells were infected with viruses expressing scramble and hairpins against SYNCRIP by spinfection of cells in RPMI with 10% FBS together with viral supernatant. After 48 hours of infection, cells were treated with 3 μg/ml puromycin. Two days after puromycin selection, cells were plated at 250,000 cells/ml for proliferation assay. Cells were counted everyday using MUSE cell analyzer (EMD Millipore, Billerica Mass.) after plating. Cell growth was calculated based on normalization of cell number to cell number at plating. All cell lines were purchased from ATCC (Manassas, Va.), and tested negative for mycoplasma contamination.

Intracellular staining and flow cytometry. For intracellular staining, cells were fixed with 1.5% paraformaldehyde at room temperature for 15 minutes and permeabilized with ice-cold methanol. Cells were washed 3 times with PBS and incubated with SYNCRIP antibody (MAB11004, EMD Millipore, Billerica Mass.) in 2% FBS PBS for 1 hour at room temperature. Cells were then washed twice with PBS and incubated with secondary antibody conjugated with Alexa Fluor 647 (Molecular Probes, Eugene Oreg.) for 30 min at room temperature. Cells were washed with PBS and re-suspended prior to analysis using BD Fortessa instrument.

Cells were stained for Mac1-PB, Gr1-APC, F480-PE-Cy7, CD115-APC and c-Kit-APC-Cy7 and analyzed on a BD FACS LSR Fortessa instrument to assess differentiation status of wild-type and knockdown leukemia cells. For stem and progenitor cells analysis of fetal liver hematopoietic cells, $10^6$ cells were stained with stem/progenitor cells' antibody panel including: lineage antibody cocktail (CD3, CD4, CD8, Gr1, B220, CD19, TER119 conjugated with PeCy5), Sca-Pac Blue, KIT-APC-Cy7, CD34-FITC, CD16/32-PE-CY7, CD48-PE and SLAM-CD150-APC. For analysis of engraftment in recipient mice, $10^6$ bone marrow cells were stained with stem/progenitor cells' antibody panel and CD45.1-PE-Texas Red and CD45.2-A700.

To measure apoptosis, cells were washed with PBS and incubated with anti-ANNEXIN-V-PE (BD Biosciences, Franklin Lakes N.J.) in the ANNEXIN-V binding buffer (10 mM HEPES, pH 7.4, 140 mM NaCl, 4 mM KCl, 0.75 mM $MgCl_2$, 1 mM $CaCl_2$) in a reaction volume of 100 μl for 15 minutes. DAPI was added prior to analysis using a BD Fortessa instrument.

O-Propargyl-puromycin (OP-puro)flow analysis. Cells were plated at 100,000 cells/ml density and treated with 50 μM OP-Puro (NU-931-05, Jena Bioscience, Jena, Germany). Control cells were treated with cyclohexamide (CHX) at 150 μg/ml for 15 minutes. Cells were washed twice prior to collection and processed using Click-iT® Flow Cytometry Assay Kit (C10418, Invitrogen, Carlsbad Calif.) following the manufacturer's instructions. Labelled cells were analyzed using BD Fortessa instrument.

Immunoprecipitation and immunoblot analysis. K562 cells were collected by spinning down at 1,500 rpm for five minutes at 4° C., washed twice with PBS, and then re-suspended thoroughly at $2 \times 10^7$ per ml in 1× Ripa buffer (BP-115—Boston BioProducts, Ashland Mass.) with freshly added DTT (1 mM) and proteinase inhibitor cocktail. The cells were incubated for 30 min on ice. Supernatant was then collected after the mix was spun at 14,000 rpm for 30 min at 4° C. For each immunoprecipitation assay, 250 μl of cell extract was mixed with 750 μl of 1× Ripa buffer 2 μg of anti-mouse/anti-SYNCRIP antibody or 2 μg anti-rabbit/anti-MSI2 and 50 μl agarose beads. For RNA independent assay, lysates were treated with RNase A (1 μg/ml) for 30 min at 37° C. prior to co-immunoprecipitation reactions. After rotating at 4° C. overnight, beads were washed 5 times with 1× Ripa buffer and boiled with 1× Lamine protein running buffer.

For immunoblot analysis, cells were counted and washed twice with cold PBS prior to collection. ~250,000 cells were re-suspended and lysed in 40 μl 1× Lamine protein running buffer and boiled for 5 minutes. Whole cell lysates were run on 4%-15% gradient SDS-PAGE and transferred to nitrocellulose membrane. Membranes were blotted for SYNCRIP (MAB11004 or 05-1517; EMD Millipore, Billerica Mass.), IKZF2 (sc-9864; Santa Cruz Biotechnology, Dallas Tex.), HOXA9 (07-178; EMD Millipore, Billerica Mass. and ab140631; Abcam, Cambridge, UK), MYC (5605S; Cell Signaling Technology, Danvers Mass.), MSI2 (ab76148; Abcam, Cambridge, UK), and Actin (A3854; Sigma-Aldrich, St. Louis Mo.).

RNA immunoprecipitation. $30 \times 10^6$ RN2 leukemia cells were used for RNA-IP using the Magna RIP RNA-binding protein immunoprecipitation kit (03-115; EMD Millipore, Billerica Mass.). First, cells were washed with cold PBS and then lysed. Anti-rabbit antibody or anti-MSI2 antibody (EMD Millipore, Billerica Mass.); anti-mouse or anti-SYNCRIP (18E4; EMD Millipore, Billerica Mass.) incubated with magnetic beads was used to immunoprecipitate MSI2 and SYNCRIP. After washing, the immunoprecipitated complexes were treated with proteinase K. RNA extraction was performed by the phenol/chloroform method, and purified RNA was converted to cDNA using the Verso cDNA kit (Thermo Fisher Scientific, Waltham Mass.). Quantitative PCR was used for validating target mRNAs bound by MSI2 and SYNCRIP.

mRNA stability analysis. Control and SYNCRIP depleted cells were treated with 5 μg/ml of Actinomycin D and harvested at indicated time points. Total RNA was isolated using RNeasy RNA extraction kit. 200 ng of RNA was used for reverse transcription reaction and quantitative RT-PCR for Syncrip, Hoxa9, Ikzf2, Myc and β-actin was performed. β-actin served as a housekeeping gene control. Relative mRNA levels were normalized to the starting point of treatment.

Metabolic labeling and capture of newly synthesized protein. Newly synthesized proteins were labeled using the Click-iT Protein Labeling Kit (Invitrogen, Carlsbad Calif.). 48 hours after infection with corresponding shRNA-expressing plasmids, 1×10$^7$ MOLM13 selected cells were cultured at 1×10$^6$ cells/mL in fresh media for 14 hours. After one wash with PBS, cells were re-suspended in methionine-free RPMI 1640 medium (Gibco, Thermo Fisher Scientific, Waltham Mass.) supplemented with 10% dialyzed FBS (Gibco, Thermo Fisher Scientific, Waltham Mass.) for 30 min, at which point the methionine analog L-azidohomoalanine (AHA) was added (50 μM, 14 hours) to allow incorporation of AHA into nascent proteins. Cells were harvested and lysed in 50 mM Tris-HCl, pH 8.0, 1% SDS, with protease and phosphatase inhibitor mixes (complete and PhosSTOP, Roche, Basel, Switzerland). 150 μg of total protein (up to 50 μL of lysate) were used in the crosslinking of AHA-labeled nascent proteins to an alkyne-derivatized biotin in the Click-iT Protein Reaction Buffer (Invitrogen, Carlsbad Calif.) according to manufacturer's instructions. The resulting precipitated total protein pellet was re-solubilized in 100 μL of 1% SDS PBS with protease inhibitors by pipetting, vortexing and incubating at 70° C. for 10 minutes. The SDS was then quenched with 100 μL of 6% NP-40 in PBS with protease inhibitors. After centrifuging at 15,000×g for 5 minutes at room temperature to remove any insoluble particles, biotin-crosslinked nascent proteins were then captured overnight with streptavidin-coated Dynabeads M-280 (Invitrogen, Carlsbad Calif.) and then eluted from the beads by boiling the samples for 5 min in 2% SDS loading buffer for Western Blotting. Beads were thoroughly washed with PBS with 0.1% bovine serum albumin and 2% NP-40, first, and finally with PBS. The whole volume of AHA-labeled, biotin-crosslinked, streptavidin-pulled down protein was separated by SDS-PAGE together with lysate depleted of nascent protein after streptavidin incubation and input lysates.

RNA purification and quantitative Real time PCR (qRT-PCR). Total RNA was isolated using TRIzol and the Qiagen RNeasy Plus® mini kit (QIAGEN, Hilden, Germany). cDNA was generated from RNA using iScript™ cDNA Synthesis (Biorad Kit #1708891, Biorad Laboratories, Hercules Calif.) with random hexamers according to the manufacturer's instructions. Real-time PCR reactions were performed using an ABI 7500 sequence detection system. Quantitative PCR for actin was performed to normalize for cDNA loading. Relative quantification of the genes was calculated using the method ($2^{-\Delta\Delta Ct}$) as described by the manufacturer.

RNA sequencing. Total RNA was isolated from 9 individually transduced and processed MLL-AF9 murine leukemia cells (n=3 for each group including shRNA against luciferase, two shRNAs against SYNCRIP) using TRIzol and the Qiagen RNeasy Plus® mini kit (QIAGEN, Hilden, Germany). RNA was denatured and the first chain of cDNA was synthesized using oligo-dT primer containing illumina-compatible linker sequence. After removal of RNA, the second cDNA chain was synthesized with random decamer containing another illumina-compatible linker sequence. Illumina compatible annealing sequences and external barcodes were introduced during amplification of the libraries.

Differential expression and pathway analysis. Quality Control of raw reads was done using FastQC (v0.11.2) to make sure there were no major flaws in sequencing. The raw reads were then mapped to mm10 genome using STAR (v2.3.0e_r291) and default parameters. The mapped reads were counted using htseq-count (v0.6.0, parameters -t exon) and gene models from Ensembl (Mus_musculus.GRCm38.75.gtf). Differential expression was performed using DESeq2 (v1.2.10, default parameters).

Statistical analysis. Student's t test was used for significance testing in the bar graphs, except where stated otherwise. A two-sample equal variance with normal distribution was used. P values less than 0.05 were considered significant. Graphs and error bars reflect mean+s.e.m, except where stated otherwise.

For animal study, survival probabilities were estimated using the Kaplan-Meier method and compared with the log-rank test. Ten mice per group were chosen to have an estimated 80% power in detecting a greater than 1.50 s.d. difference in means at a significance level of α=0.05 using a two-sided test. All animals were randomly assigned to the experimental groups. All statistical analyses were carried out using GraphPad Prism 4.0 and the R statistical environment.

Syncrip conditional knockout (cKO) mouse model. A Syncrip cKO mouse was generated by targeting the Syncrip locus in embryonic stem cells with a construct containing loxP sites flanking Syncrip exons 3 and 4 (FIG. 25(A)). The neomycin resistance selection cassette was removed and a Syncrip$^{flox/flox}$ mouse colony was established. The Syncrip-$^{flox/flox}$ mice were crossed with Mx-1 Cre mice and an inducible Syncrip loss of function strain (Syncrip$^{flox/flox}$: Mx1-Cre) was generated.

Example 2: Identification of Novel Regulators of Leukemia Using Pooled In Vivo shRNA Screening of the RNA-Binding Protein Musashi2 (MSI2) Interactome To identify which RBPs are required for the survival of myeloid leukemia, an in vivo pooled short hairpin (shRNAs) screen in MLL-AF9 driven leukemia cells enriched for LSCs was conducted. The mixed lineage leukemia (MLL) gene has been shown to be involved in chromosomal translocations in over 70% of childhood leukemia and 5-10% of leukemia in adult.

Figure 1A:
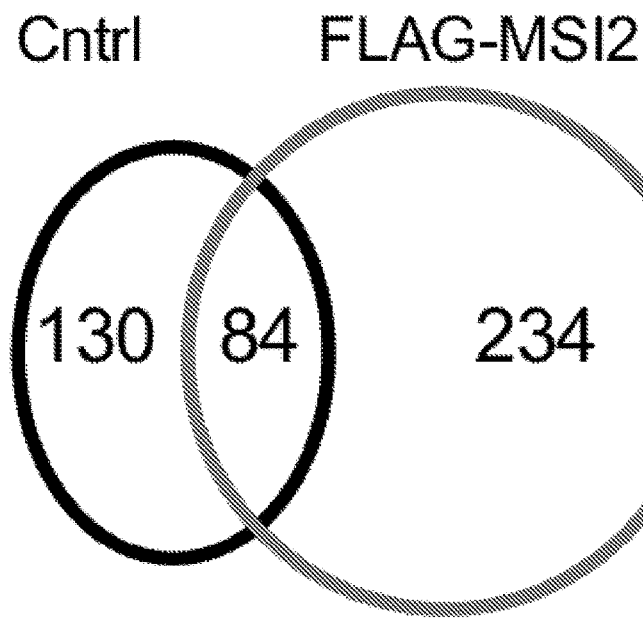
FIG. 1(A) shows a Venn diagram showing mass spectrometry analysis of Flag-MSI2 immunoprecipitation in K562 cells transduced with FLAG-MSI2 or empty vector.
Figure 8A:
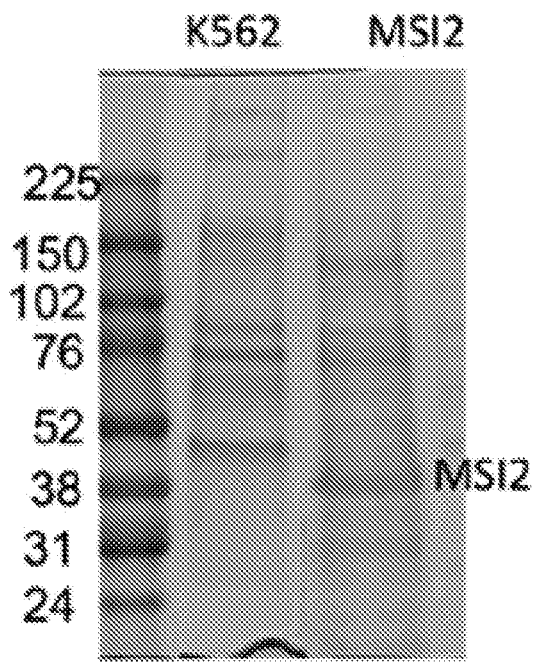
FIG. 8(A) shows Coomassie blue staining of Flag-MSI2 immunoprecipitated complexes.
Figure 8B:
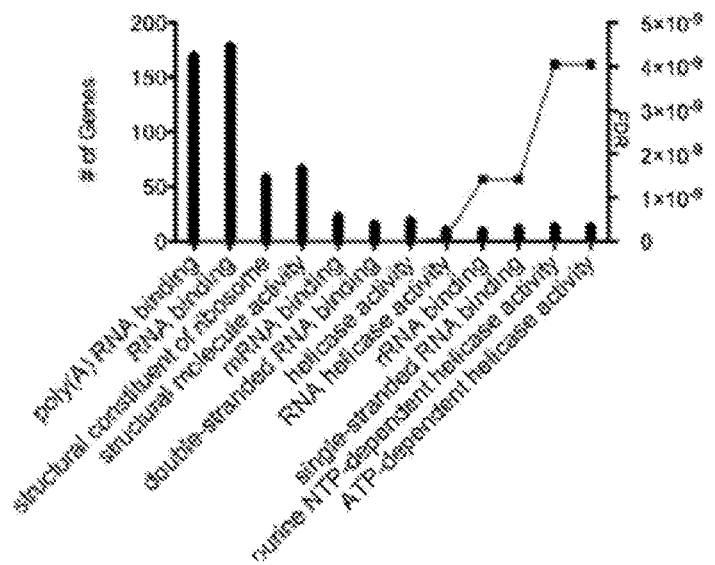
FIG. 8(B) shows GO analysis of MSI2 interacting proteins.
Figure 8C:
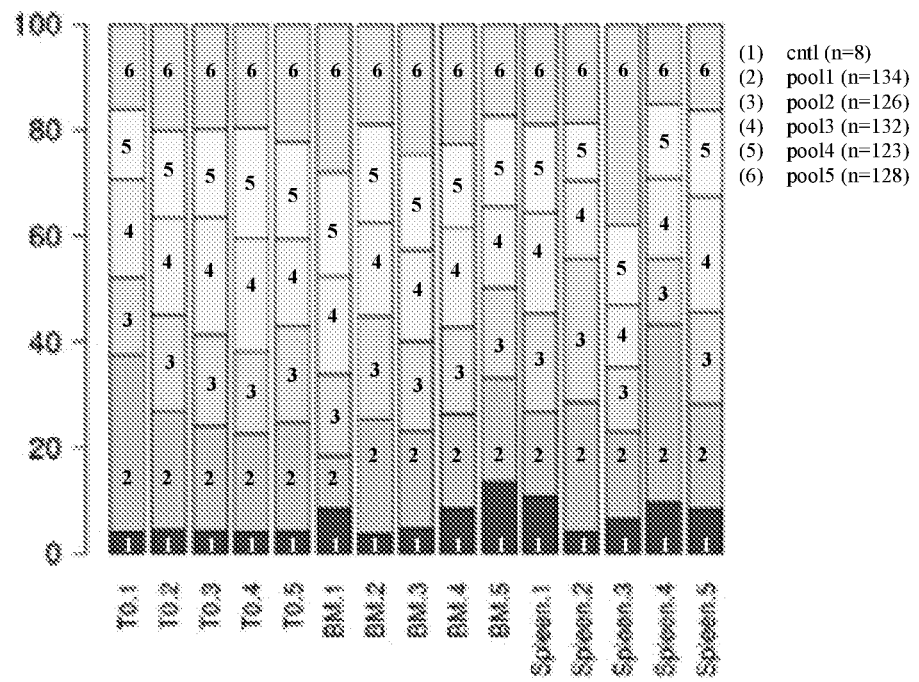
FIG. 8(C) shows the proportion of total read counts sequenced per pool. cntl=Control pool.
Figure 8D:
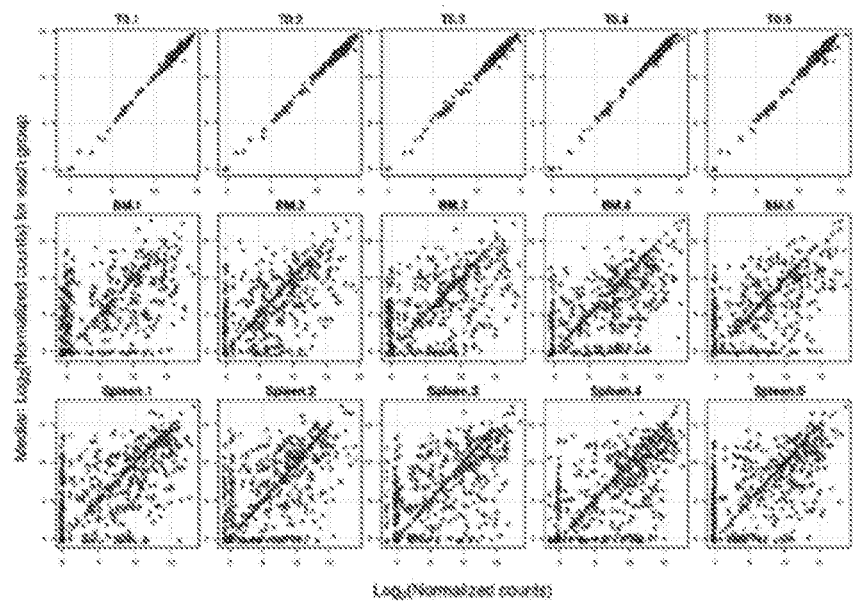
FIG. 8(D) shows a scatterplot depicting concordance of shRNA abundance ($\log_2$ normalized read counts) between each one of the replicates against their respective groups (median of $\log_2$ normalized read counts).
Figure 8E:
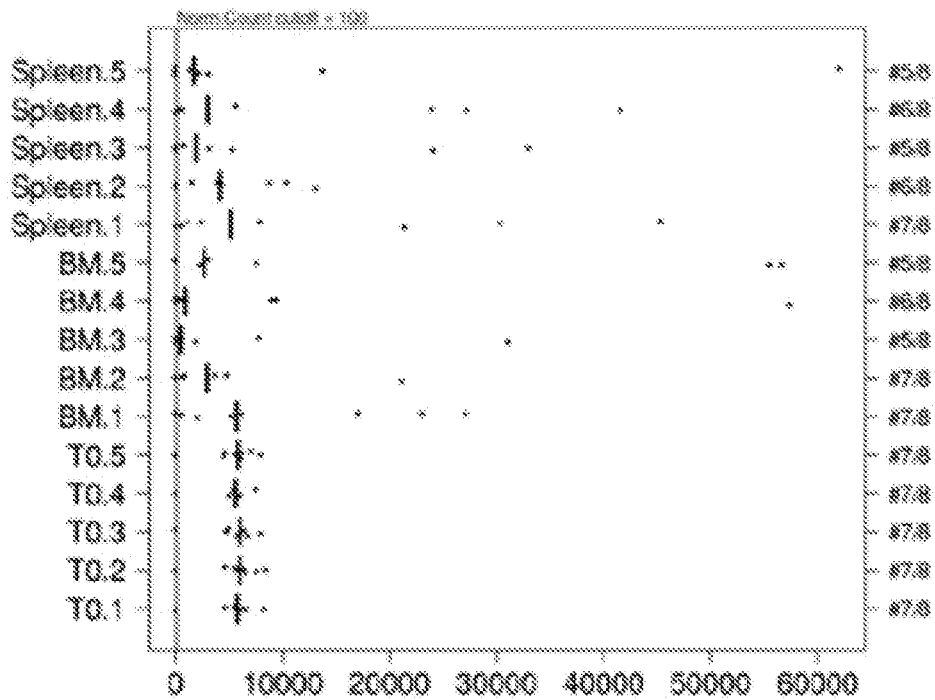
FIG. 8(E) shows number of control hairpins represented with a minimum arbitrary threshold (normalized counts>100).
Figure 8F:
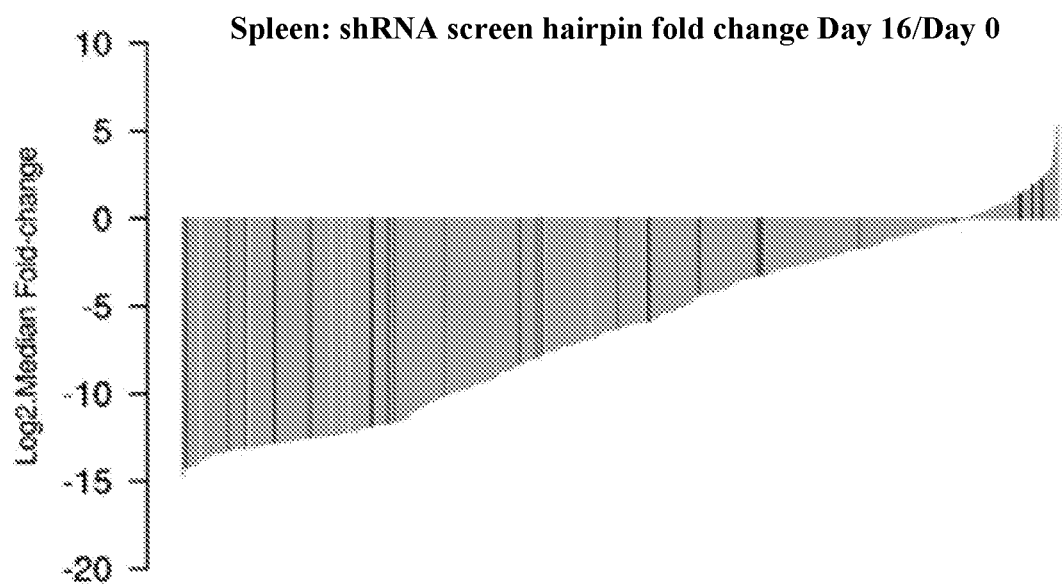
FIG. 8(F) shows a Waterfall plot depicting normalized depletion levels of all shRNAs in spleen (SP), generated from the data in FIG. 16. Top candidate genes included SYNCRIP, Caprin1, Dyrk2, Hnrnpr, Cct3, Mybbp1a, and Hnrnpa3, and control shRNAs include RFP, lacZ and luciferase.

T(9;11) MLL-AF9 translocation is the most common translocation in acute myeloid leukemia (AML). Expression of the fusion protein MLL-AF9 in granulocyte-monocyte progenitor cells (GMPs) results in an established, robust, and short latency leukemia model, where LSCs can be enriched after serial transplantations (Miller P G, et al., Cancer Cell 24:45-58 (2013). MSI2 was used as a founding factor and mass spectrometry analysis was performed on FLAG-MSI2 immunoprecipitated complexes in a leukemia cell line (K562) (FIG. 8(A)). A group of 234 proteins of multiple RBP classes were identified in association with MSI2 (FIG. 1(A)). Functional GO term analysis linked these 234 proteins to RNA binding functions, including polyA binding and helicase activity (FIG. 8(B)).

To obtain a comprehensive assessment of MSI2 functional networks, data generated from MSI2 associated genomic studies was used to prioritize genes in different candidate pools for functional screening. 51 genes with differential expression found in MSI2 depleted CML/AML cell lines, MSI2 overexpressing LSK cells, and MSI2 KO LSK cells were prioritized based on their associations with hematopoietic/leukemic gene sets, and Gene set enrichment analysis leading edge genes were included in Pool 1. Genes identified as MSI1 binding mRNA targets were ranked and evaluated for their relevance to MSI2 and hematopoietic system, and 19 genes were included in Pool 2. Similarly, 58 genes discovered from MSI2 protein-protein interactions and had relevance to hematopoietic/leukemic gene sets were selected for Pool 3.

Figure 1B:
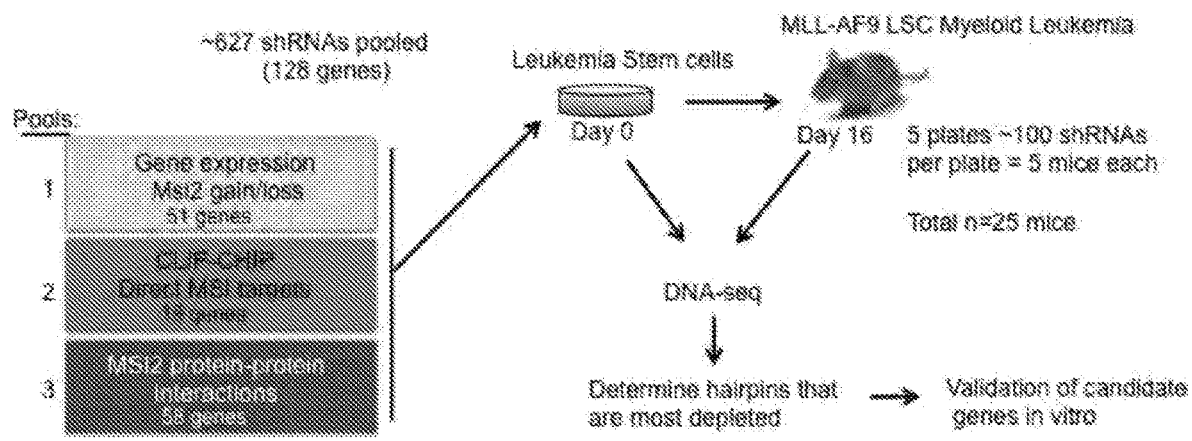
FIG. 1(B) shows a summary of the pooled shRNA screening strategy from primary leukemia cells.
Figure 1C:
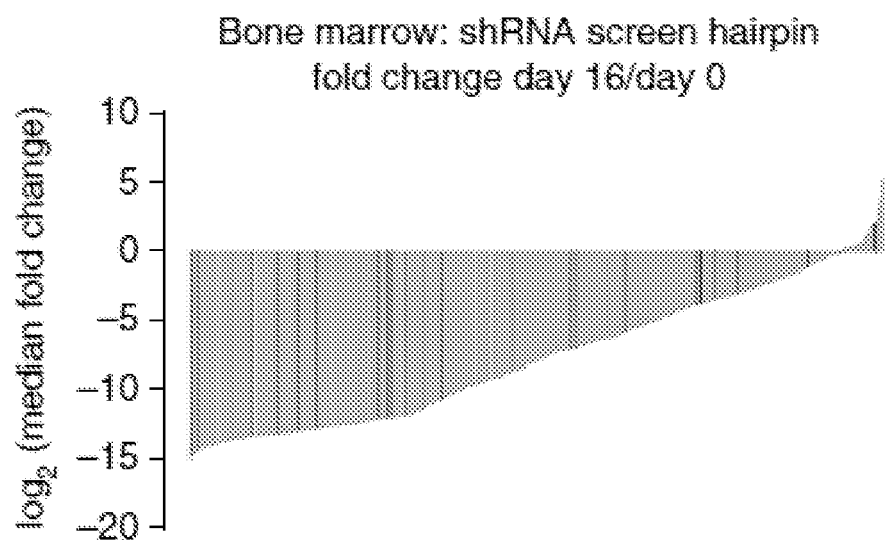
FIG. 1(C) shows a Waterfall plot depicting normalized depletion levels of all shRNAs in bone marrow (BM), generated from the data in FIG. 15. Top candidate genes included SYNCRIP, Caprin1, Dyrk2, Hnrnpr, Cct3, Mybbp1a, and Hnrnpa3.
Figure 1D:
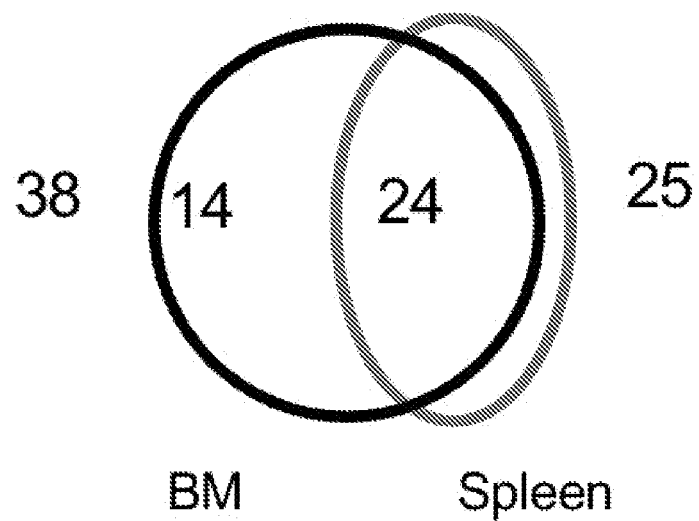
FIG. 1(D) shows a Venn diagram showing score of 24 hits in bone marrow and spleen samples.
Figure 1E:
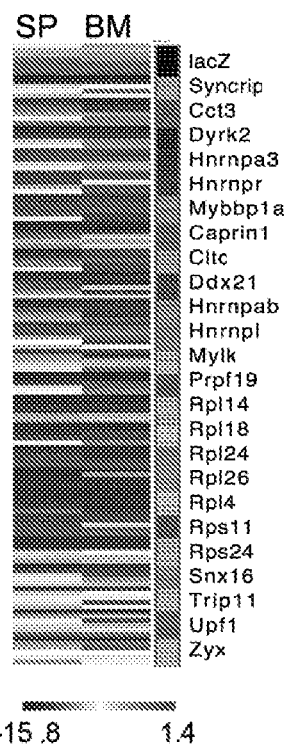
FIG. 1(E) shows a heatmap depicting normalized depletion levels of all shRNAs targeting top 24 genes scored both in bone marrow (BM) and spleen (SP), generated from the data in FIG. 15 and FIG. 16.

A total of 128 genes were selected and 5-7 hairpins targeting each gene were obtained. Using a pooled library of titered shRNAs lentiviruses, LSC enriched cells (a tertiary transplant of c-kit enriched MLL-AF9-dsRed leukemia) were transduced sorted and subsequently transplanted into sub-lethally irradiated recipient mice (FIG. 1(B)). The cells were allowed to engraft and then the relative representation of each shRNA in the leukemia cells was quantified from the bone marrow and spleen at day 0 and day 16 post transplantation. See FIG. 15 and FIG. 16. A pool of shRNAs with greater than 20 fold depletion was recovered, which indicated a strong selection against their expression during leukemia progression (FIG. 1(C) and FIGS. 8(C)-8(F)).

Figure 1F:
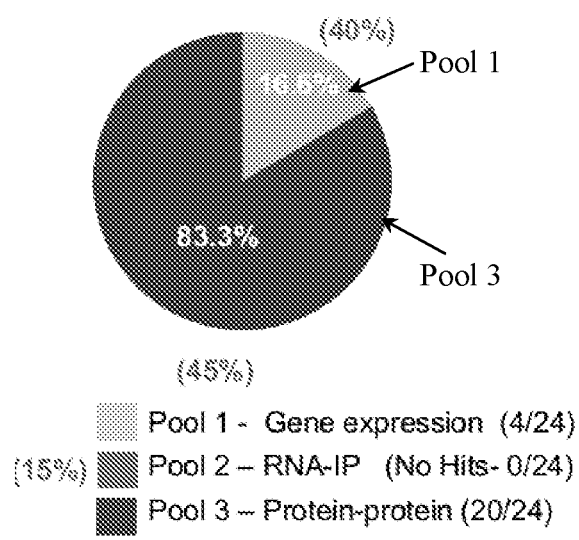
FIG. 1(F) shows a pie chart showing the scoring percentage of each screening pool in comparison to the predicted score based on pool representation.
Figure 1G:
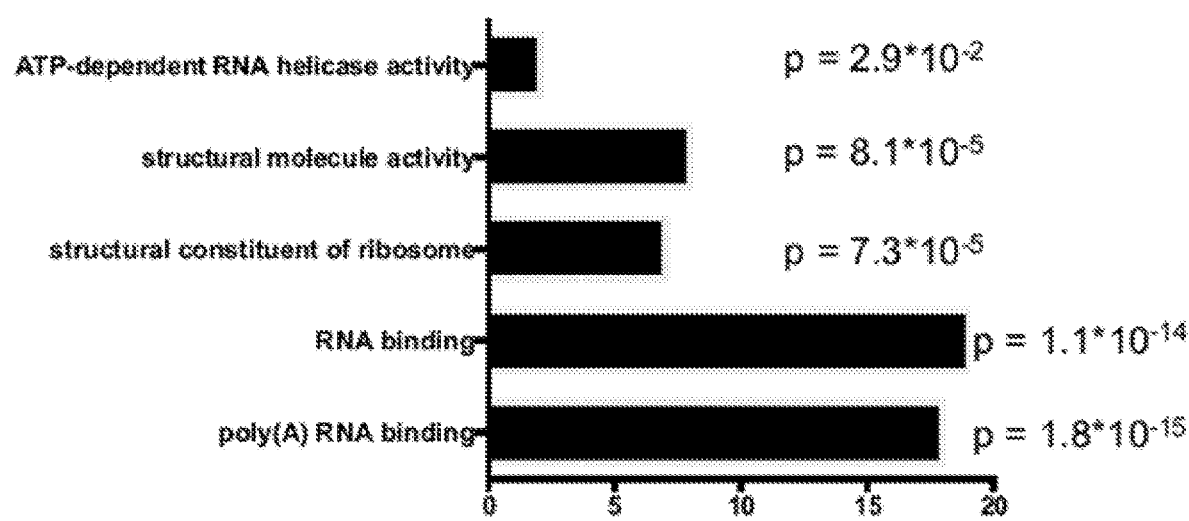
FIG. 1(G) shows Gene Ontology (GO) analysis of the top 24 genes scored in in vivo screen.
Figure 1H:
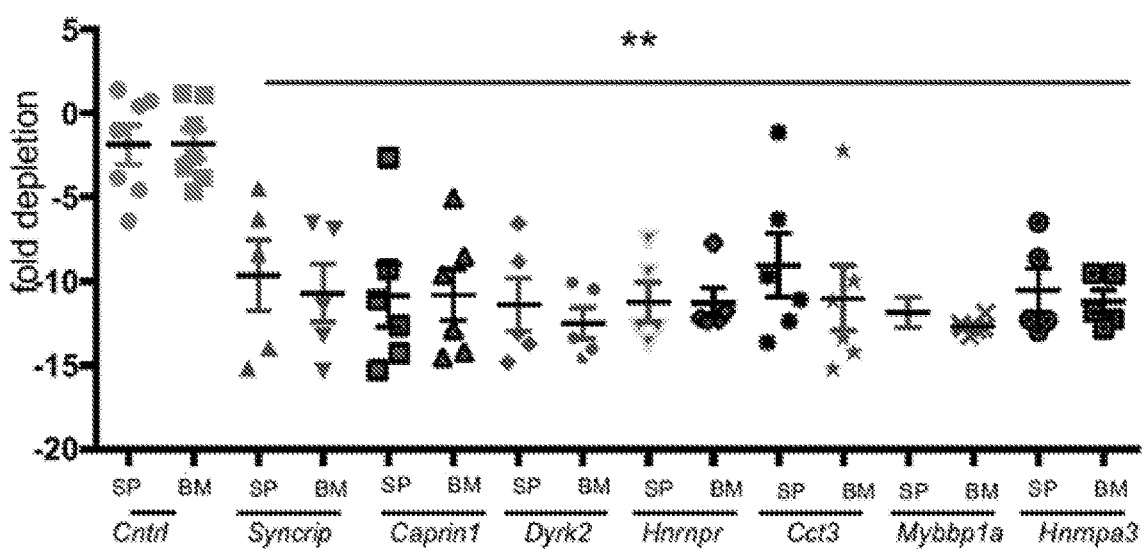
FIG. 1(H) shows $log_2$ fold depletion in the bone marrow (BM) and spleen (SP) of all the shRNAs against seven candidate genes in the pooled shRNA screen. error bars, s.e.m **$p<0.01$ two tailed t test.
Figure 1I:
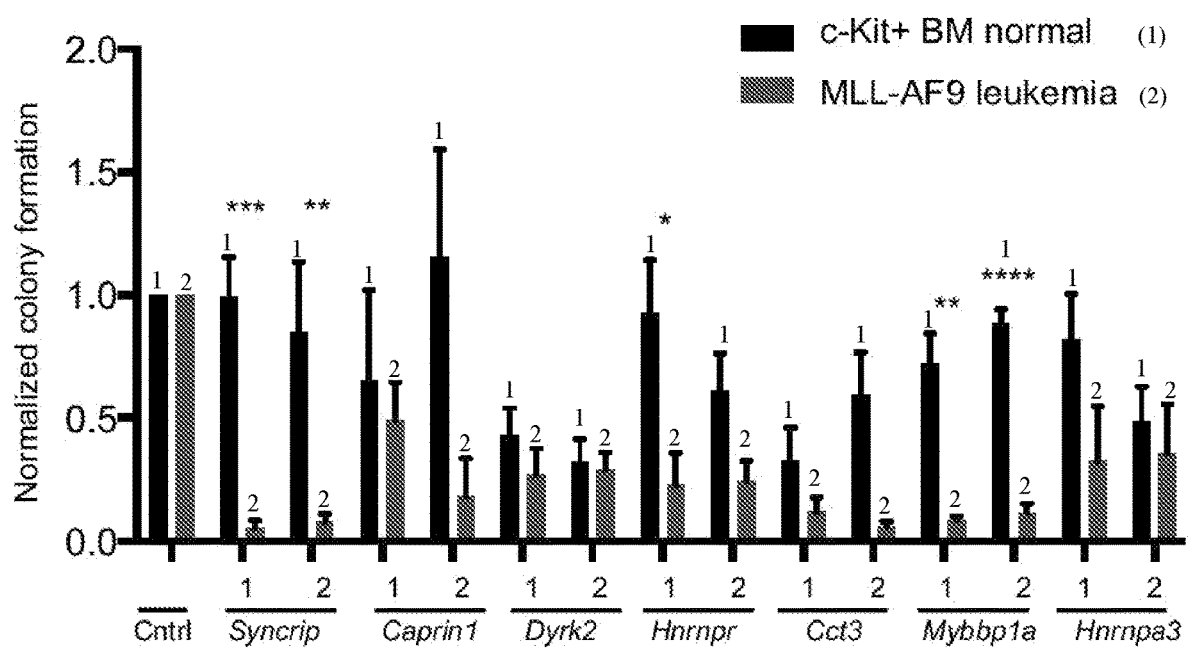
FIG. 1(I) shows colony formation was impaired in KD leukemia cells. The number of colonies formed was normalized to that of control MLL-AF9 leukemia cells or control normal c-kit enriched bone marrow cells. n=4 independent experiments; error bars, s.e.m. P value calculated by two tailed t test.
Figures 8G, 8H:
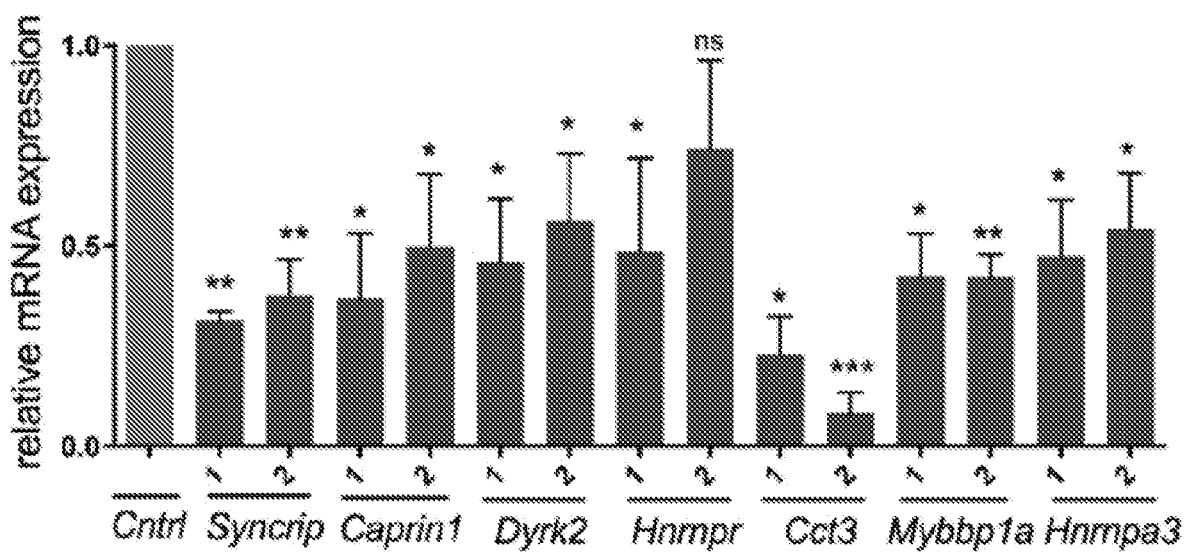
FIG. 8(G) shows summary of seven candidate genes.
FIG. 8(H) shows validation of efficient knockdown of target genes in mouse MLL-AF9 leukemia cells. Cells were selected under puromycin treatment for 48 hours prior to qRT-PCR assay. β-Actin serves as housekeeping gene control. All data represent the mean+s.e.m of at least three independent experiments. * p<0.05, p<0.01, * p<0.001 by two tailed t test.

The 24 top hits were prioritized; each hit had at least five hairpins that resulted in 20-fold depletion in both the bone marrow and spleen (FIGS. 1(D)-1(E), FIG. 15 and FIG. 16). GO analysis of the top genes revealed a significant enrichment for RBPs and mRNA binding proteins. The majority of the hits (20/24) were in the MSI2-protein-protein interaction group (Pool 3), demonstrating that these complexes were important for disease progression (FIGS. 1(F)-1(G)). Among the top 24 scored genes, seven genes were selected (of which four encode RBPs) for in vitro validation including: SYNCRIP, Caprin, Dyrk2, Hnrnpr, Cct3, Mybbp1, and Hnrnpa3 (FIG. 1(H) and FIG. 8(G)). In all of the genes tested, knock down was confirmed and a reduction in colony formation was observed (FIG. 1(I) and FIG. 8(H)). Additionally, MLL-AF9 leukemia cells were generally more sensitive to shRNA depletion compared to normal cells (c-kit+ enriched from bone marrow), except for Dyrk2, which was equally depleted (FIG. 1(I)). These data demonstrate that a dysregulated RBP network is differentially required for leukemia cell survival compared to normal cells.

Accordingly, the SYNCRIP-specific inhibitory nucleic acids disclosed herein are useful in methods for inhibiting leukemic cell proliferation and treating AML in a subject in need thereof.

Example 3: SYNCRIP is Required for Survival of Leukemia Cells

Figure 2A:
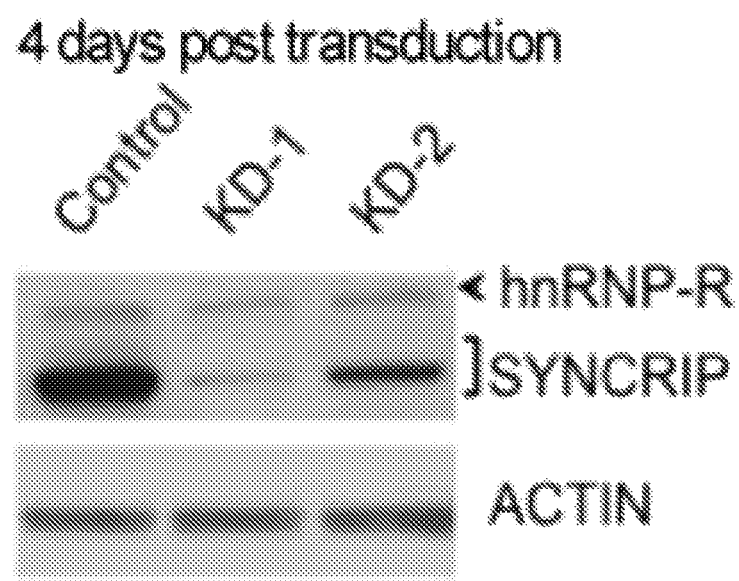
FIG. 2(A) shows the effects of SYNCRIP Knock Down (KD) in mouse MLL-AF9 leukemia cells.
Figure 2B:
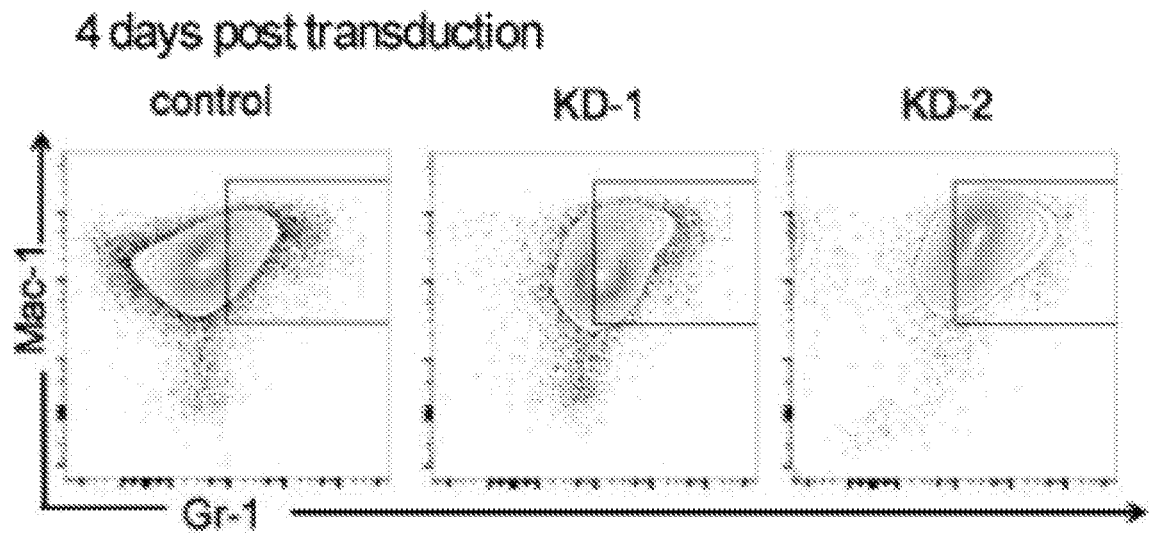
FIG. 2(B) shows that shRNA-mediated depletion of SYNCRIP promoted myeloid differentiation of leukemia cells. Representative FACS plot of control and SYNCRIP Knock Down (KD) leukemia cells.
Figure 2C:
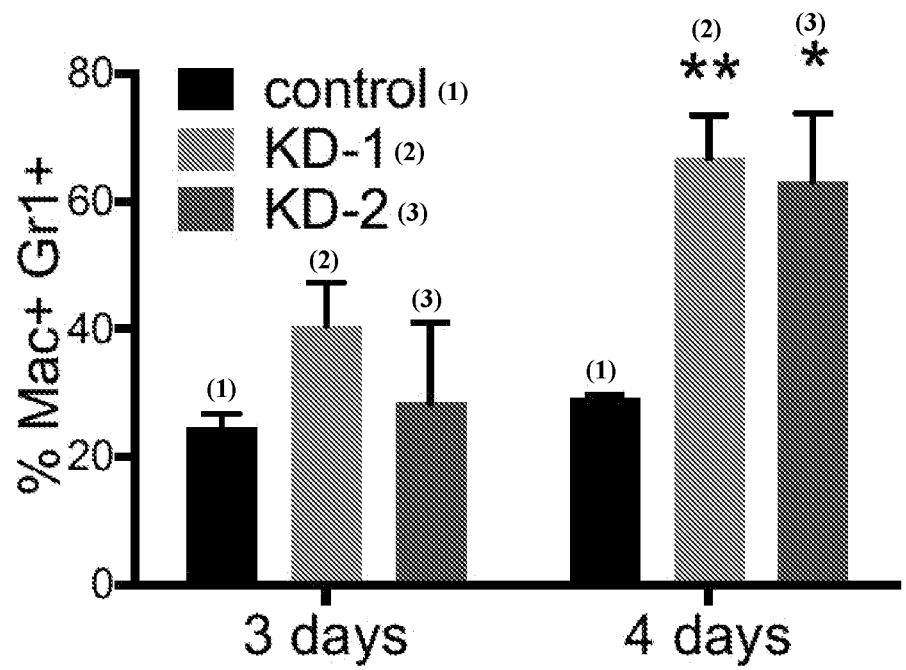
FIG. 2(C) shows the quantitative summary of FACS analysis of Gr-1 and Mac-1 expression in control and SYNCRIP Knock Down (KD) leukemia cells 3 days and 4 days post transduction, n=3 and n=5, respectively, independent experiments; error bars, s.e.m. ** $p<0.01$, * $p<0.05$ two sided t test.
Figure 2D:
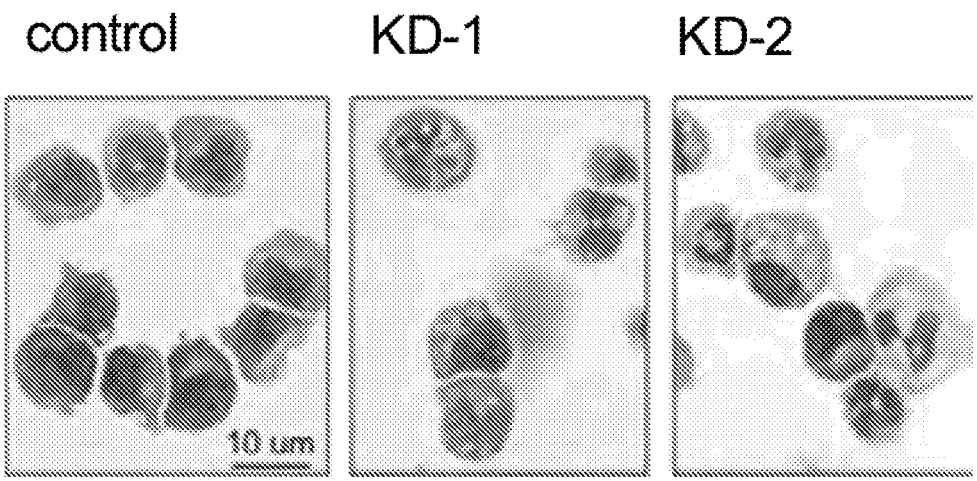
FIG. 2(D) shows Giemsa staining of control and SYNCRIP Knock Down (KD) leukemia cells at 4 days post transduction. Original magnification 63×, 1.4 NA Scale bars: 10 μM.
Figure 2E:
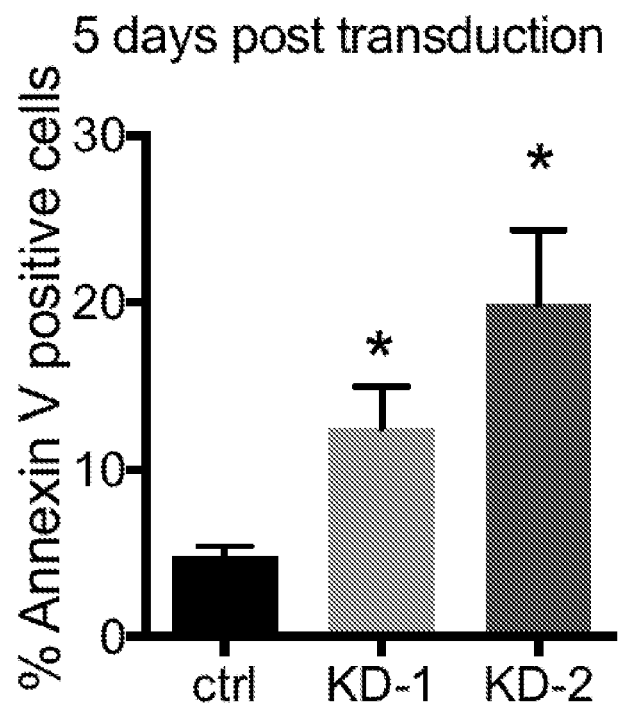
FIG. 2(E) shows Annexin-V expression assessed by flow cytometry 5 days post transduction. n=3 independent experiments; error bars, s.e.m. ** $p<0.01$, * $p<0.05$ two tailed t test.
Figure 2F:
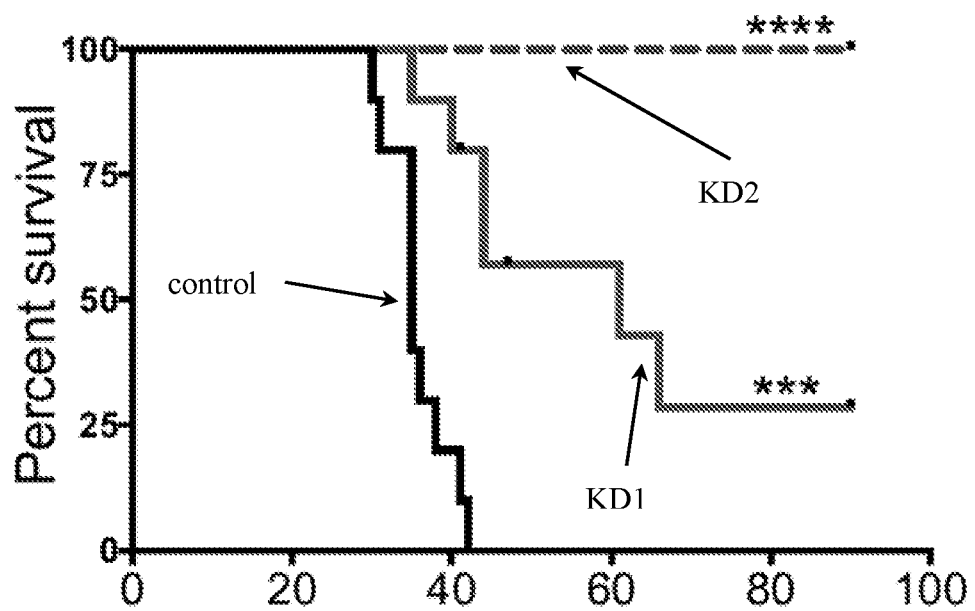
FIG. 2(F) shows Kaplan Meier analysis of leukemia-free survival outcomes after injection of SYNCRIP depleted or control cells into sub-lethally irradiated mice. n=10 for each group, Mantel-Cox test * $p<0.001$, ** $p<0.0001$.
Figure 2G:
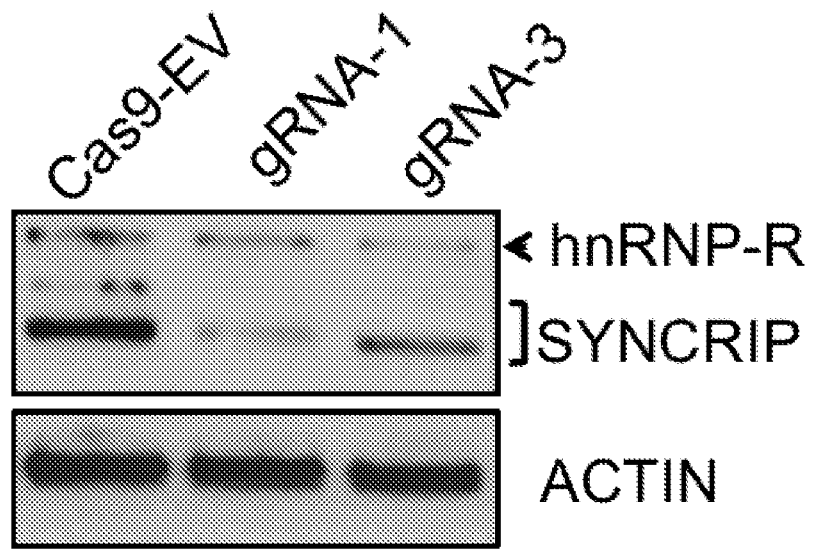
FIG. 2(G) shows the reduction of SYNCRIP expression in MLL-AF9 leukemia cells with mutant NRAS expressing a rtTA (RN2 cells) and transduced with tet(O)-inducible Cas9-GFP expressing guide RNAs specific for SYNCRIP (gRNA1 and gRNA3) or Cas9-GFP empty gRNA (Cas9-EV).
Figure 2H:
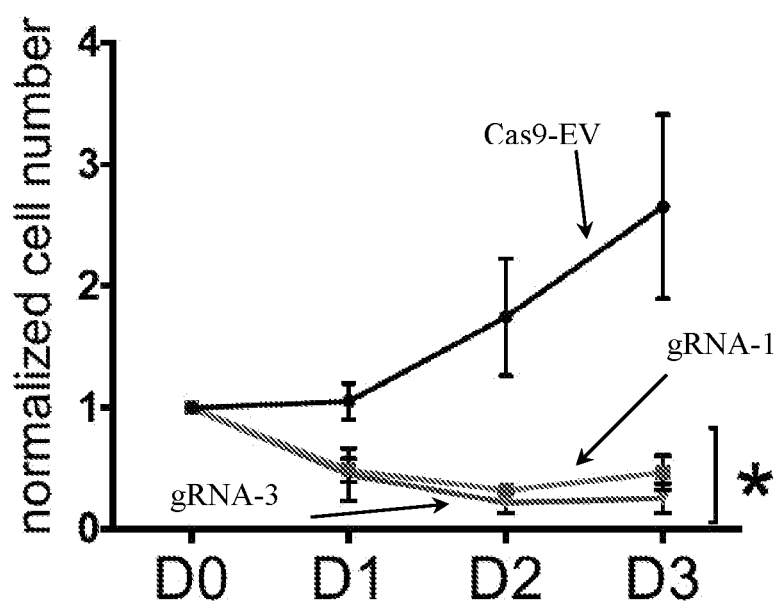
FIG. 2(H) shows cells from FIG. 2(g) plated and counted for cellular growth control and two gRNAs. n=3 independent experiments; error bars, s.e.m. * $p<0.05$ two tailed t test.
Figure 2I:
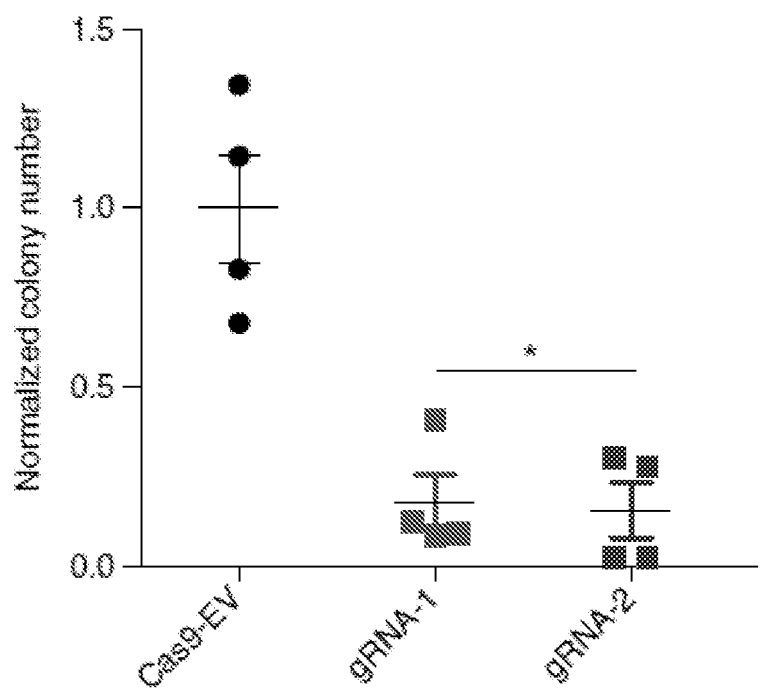
FIG. 2(I) shows cells from 2(G) were plated into methylcellulose colony assay. n=4 independent experiments; error bars, s.e.m. * $p<0.05$ two tailed t test.
Figure 9A:
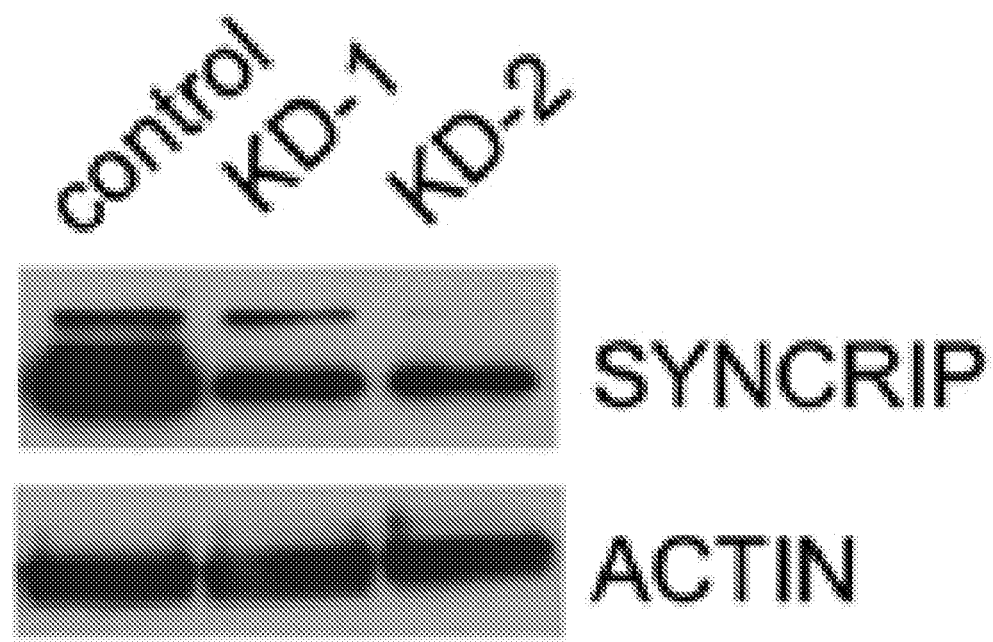
FIG. 9(A) shows knockdown of SYNCRIP in mouse MLL-AF9 leukemia cells. MLL-AF9 cells were transduced with lentiviruses expressing control shRNA (shRNA against Luciferase) or shRNAs directed against Syncrip (shRNA-1 and shRNA-2). Cells were selected under puromycin treatment for 24 hours prior to immunoblotting. Cells were harvested and assayed 3 days post viral transduction. Actin serves as loading control.
Figure 9B:
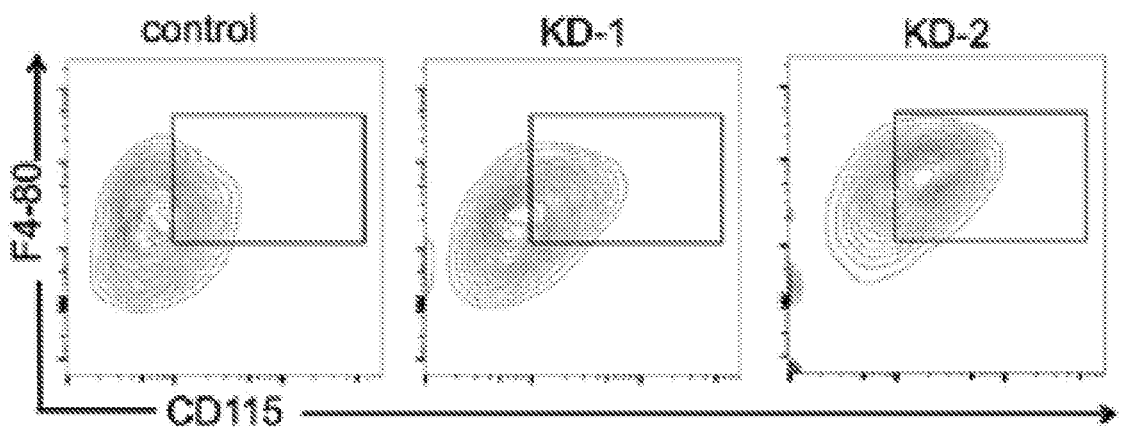
FIG. 9(B) shows shRNA depletion of SYNCRIP promoted myeloid differentiation of leukemia cells. Myeloid differentiation status was assayed by FACS analysis of F-480 and CD115 expression at 4 days post transduction. A representative FACS plot is shown for control and SYNCRIP-KD leukemia cells.
Figure 9C:
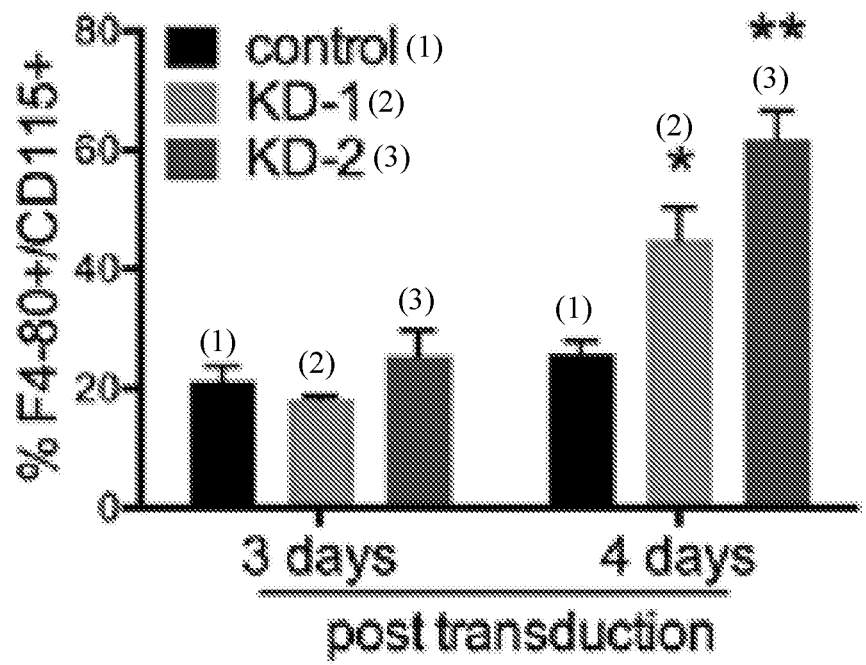
FIG. 9(C) shows quantitative summary of FACS analysis of F-480 and CD115 expression in control and SYNCRIP-KD leukemia cells 3 days and 4 days post transduction.
Figure 9D:
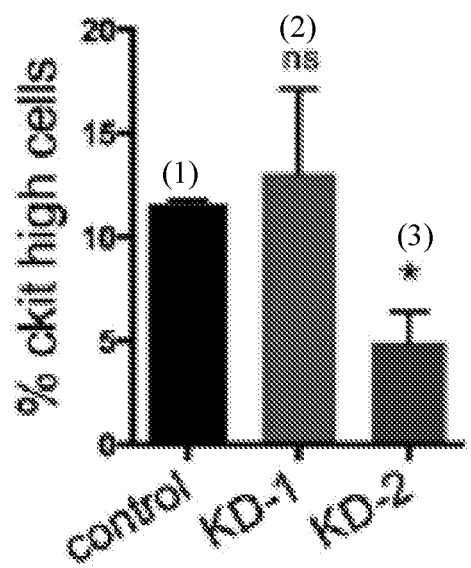
FIG. 9(D) shows quantitative summary of FACS analysis of percentage of c-kit$^{high}$ cells in control and SYNCRIP-KD leukemia cells 4 days post transduction.
Figure 9E:
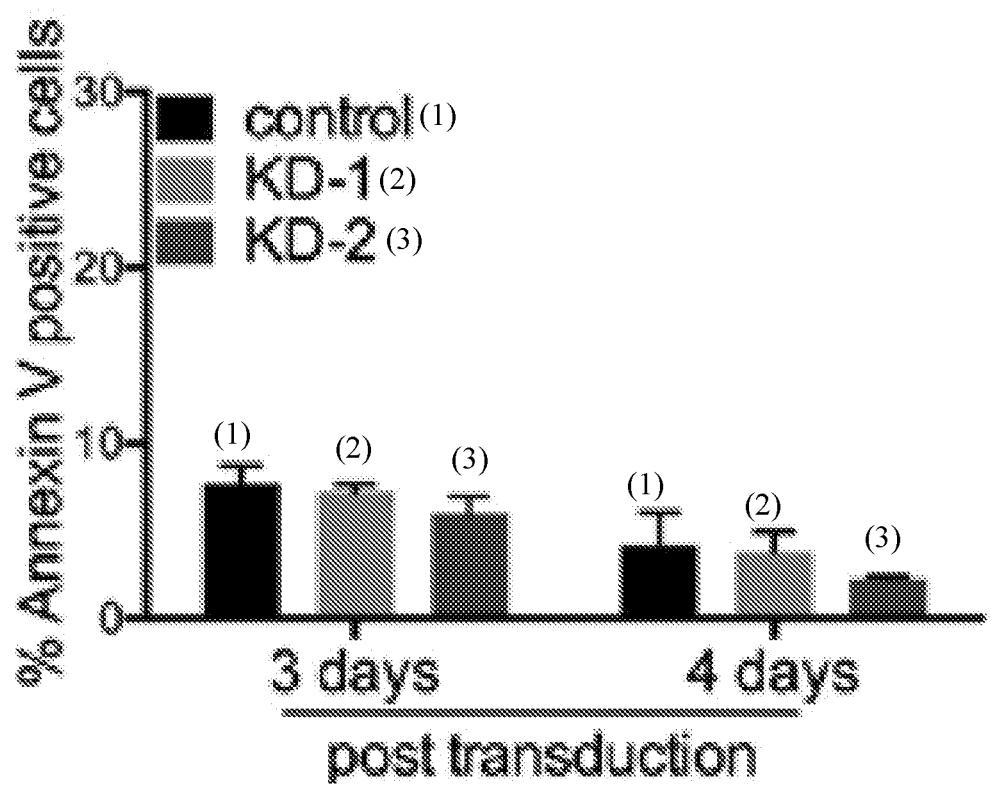
FIG. 9(E) shows increased apoptosis was not observed in SYNCRIP-KD leukemia cells at 3 days and 4 days post transduction. Quantitative summary of Annexin-V assessed by flow cytometry.
Figure 9F:
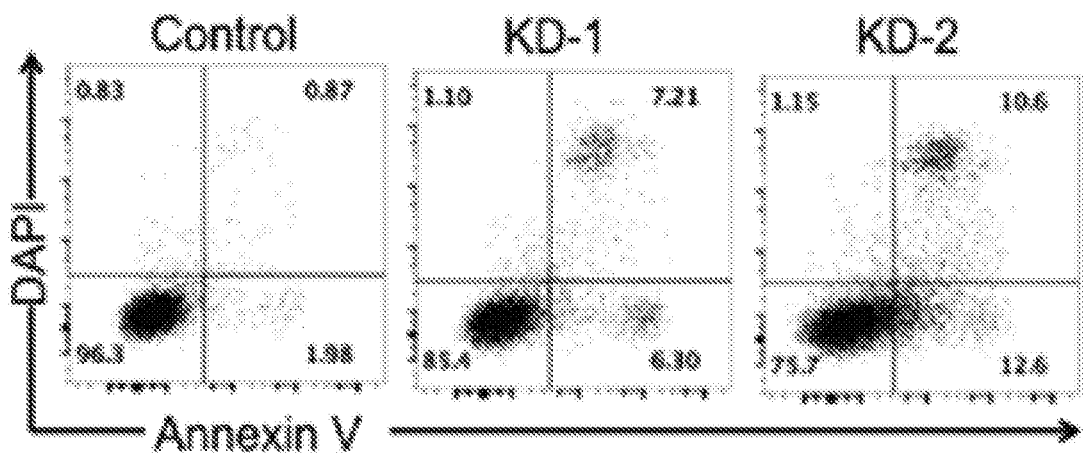
FIG. 9(F) shows Annexin-V expression assessed by flow cytometry 5 days post transduction of control and SYNCRIP-KD leukemia cells. A representative FACS analysis of FIG. 2(E) is shown.
Figure 9G:
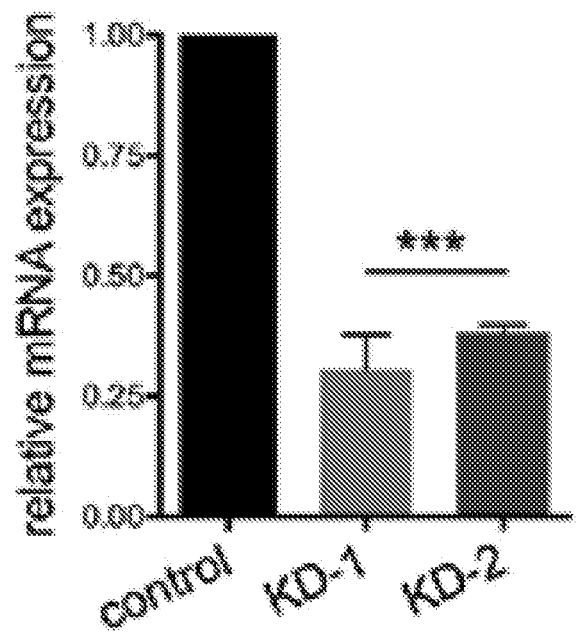
FIG. 9(G) shows quantitative qPCR demonstrating KD of SYNCRIP in mouse AML1-ETO9a driven leukemia cells. Cells were selected under puromycin treatment for 48 hours prior to qRT-PCR. β-Actin serves as housekeeping gene control.
Figure 9H:
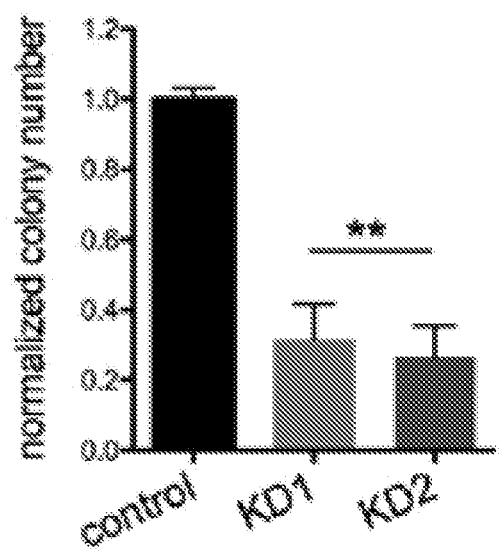
FIG. 9(H) shows cells from FIG. 9(G) were plated into methylcellulose and scored for number of colonies (average of three independent experiments).
Figure 9I:
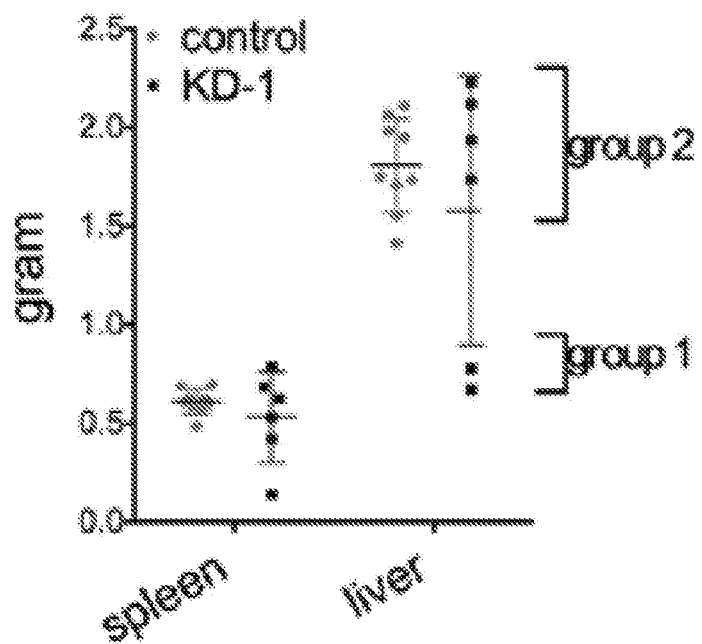
FIG. 9(I) shows the assessment of disease burden, including spleen weight and liver weight of recipient mice in FIG. 2(F).
Figure 9J:
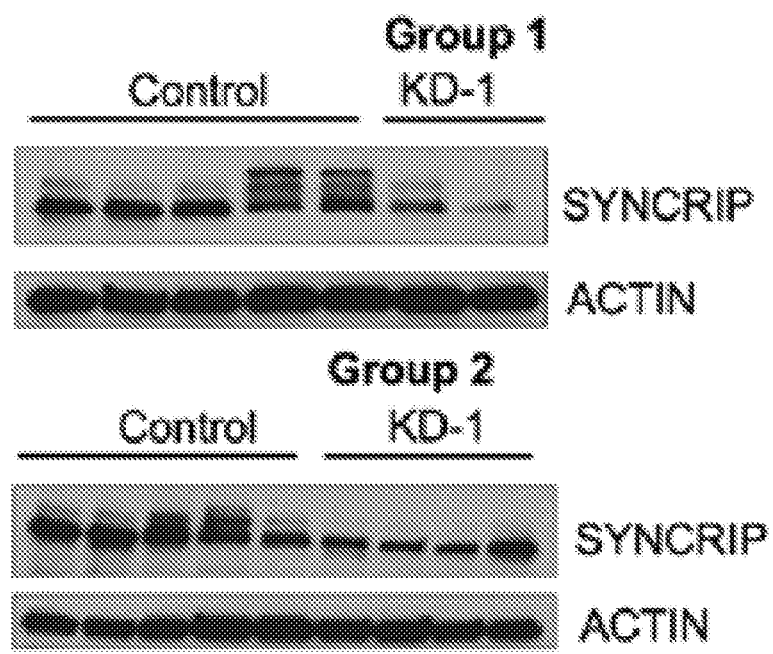
FIG. 9(J) shows SYNCRIP protein expression in bone marrow (as assessed by immunoblot analysis) of mice succumbed to disease in FIG. 2(F) and FIG. 9(I). Mice injected with SYNCRIP-KD1 with reduced disease burden (group 1) maintained better SYNCRIP knockdown level compared to mice (group 2), which manifested similar disease to control group.
Figure 9K:
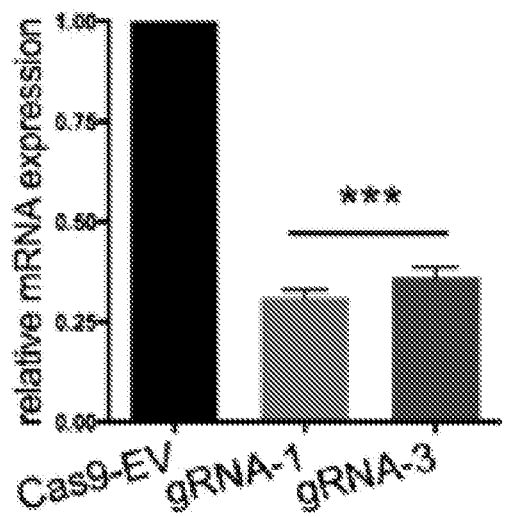
FIG. 9(K) shows quantitative qPCR showing KD of Syncrip assayed by primers designed for specific gRNA targeting regions (gRNA specific primers) in RN2 cells that were transduced for 24 hours with CRISPR/Cas9 containing tet-inducible guide RNAs specific for Syncrip (gRNA1-3) in comparison to control-Cas9-EV 24 hours.
Figure 9L:
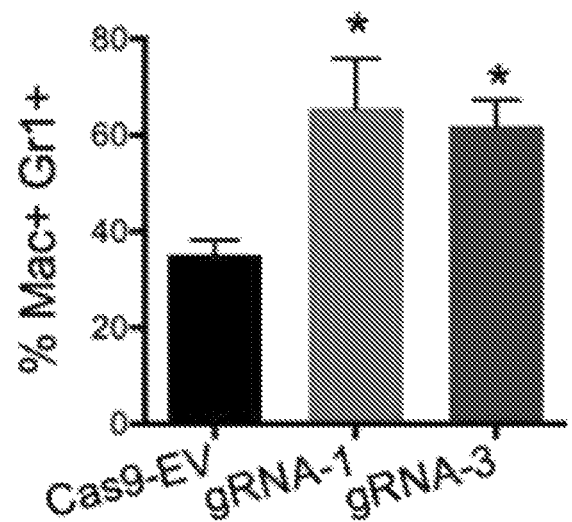
FIG. 9(L) shows quantitative summary of FACS analysis of the percentage of Gr-1$^+$ and Mac-1$^+$ positive cells in Cas9-EV and Syncrip-gRNAs transduced leukemia cells shown in FIG. 2(I).

Of the in vitro validated genes from Example 2, SYNCRIP demonstrated the most differential effect (10-fold) in colony forming ability between leukemia cells and normal c-kit+ enriched cells. To further evaluate the effects of SYNCRIP depletion, it was first confirmed that shRNAs specific for SYNCRIP resulted in the reduction of SYNCRIP by immunoblot in MLL-AF9 transformed leukemia cells (FIG. 2(A) and FIG. 9(A)). SYNCRIP depletion in leukemic cells resulted in rapid increase in myeloid differentiation based on increased Gr-1 and Mac-1, F480 and CD115 surface staining (FIGS. 2(B)-2(C) and FIGS. 9(B)-9(C)), and cellular morphology (FIG. 2(D)) at day 4 post transduction. Significant change in c-kit level was only observed for SYNCRIP-depleted cells with one hairpin shRNA (shRNA #2) but not the other shRNA (shRNA #1) (FIG. 9(D)). SYNCRIP-KD also resulted in apoptosis of leukemia cells at 5 days post transduction (FIG. 2(E) and FIGS. 9(E)-9(F)), demonstrating that differentiating cells subsequently underwent apoptosis. SYNCRIP function was not restricted to MLL-AF9 driven leukemia; a similar reduction in colony formation of AML-ETO9a driven leukemia cells depleted for SYNCRIP was also observed (FIGS. 9(G)-9(H)). shRNA mediated depletion in MLL-AF9 leukemia cells was performed, which demonstrated a requirement for leukemic disease in vivo, (FIG. 2(F)) since diseased mice with SYNCRIP-shRNA expressing leukemia cells selected for attenuated SYNCRIP-knockdown (FIGS. 9(I)-9(J)).

Figure 9M:
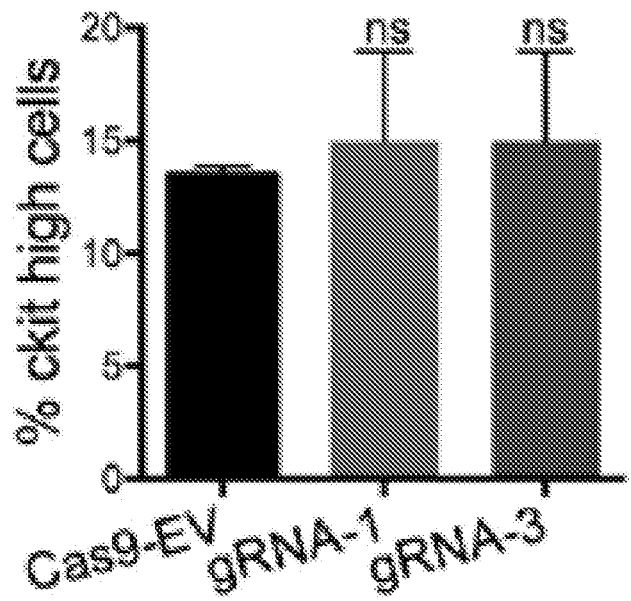
FIG. 9(M) shows the quantitative summary of FACS analysis of the percentage of c-kit$^{high}$ cells in Cas9-EV and SYNCRIP-gRNAs transduced leukemia cells shown in FIG. 2(I).

To rule out the potential for off-target effects from shRNA mediated knockdown and to test an additional leukemia cell line, SYNCRIP-guide RNAs (gRNAs) were developed for CRISPR/Cas9 mediated deletion. RN2-myeloid leukemia cells (MLL-AF9, NRASG12D and expressing rtTA-RN2 cells) were transduced with vectors expressing the inducible (tetO) Cas9 and gRNAs specific for SYNCRIP or an empty vector (Cas9-EV) and sorted based on GFP positivity after induction by Doxycycline (Dox). A reduction in colony formation and proliferation with an increase in differentiation (FIGS. 2(G)-2(I) and FIGS. 9(K)-9(L)) in SYNCRIP depleted RN2 cells was observed. No significant change in percentage of c-kit high cells was observed upon SYNCRIP depletion (FIG. 9(M)).

Figure 2J:
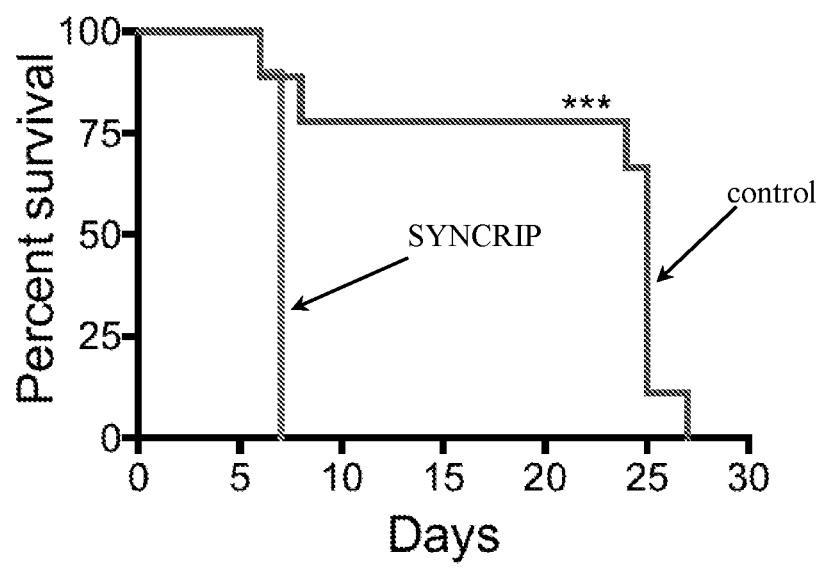
FIG. 2(J) shows Kaplan Meier analysis of leukemia-free survival outcomes after injection of RN2 cells overexpressing SYNCRIP or carrying control-empty vector into sub-lethally irradiated mice n=10 for each group, Mantel-Cox test *** $p<0.001$.
Figure 2K:
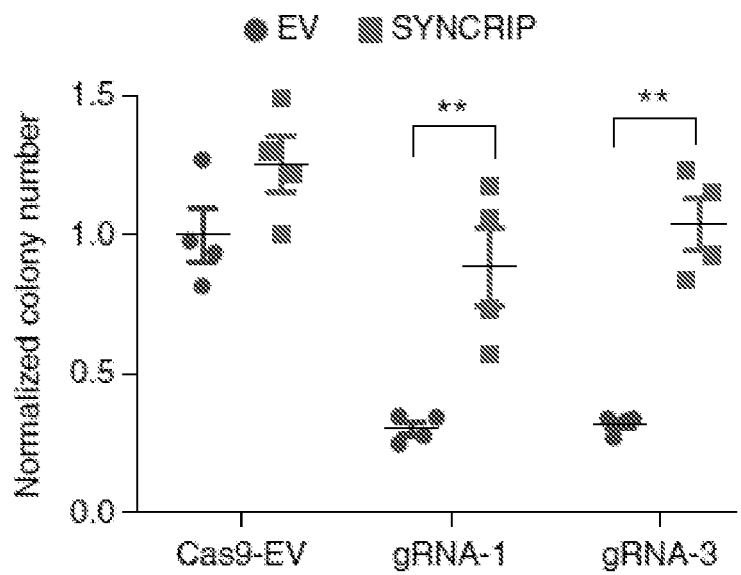
FIG. 2(K) shows that overexpression of SYNCRIP rescued colony forming ability of RN2 cells depleted of endogenous SYNCRIP. n=4 independent experiments; error bars, s.e.m. ** $p<0.01$ two tailed t test.
Figure 2L:
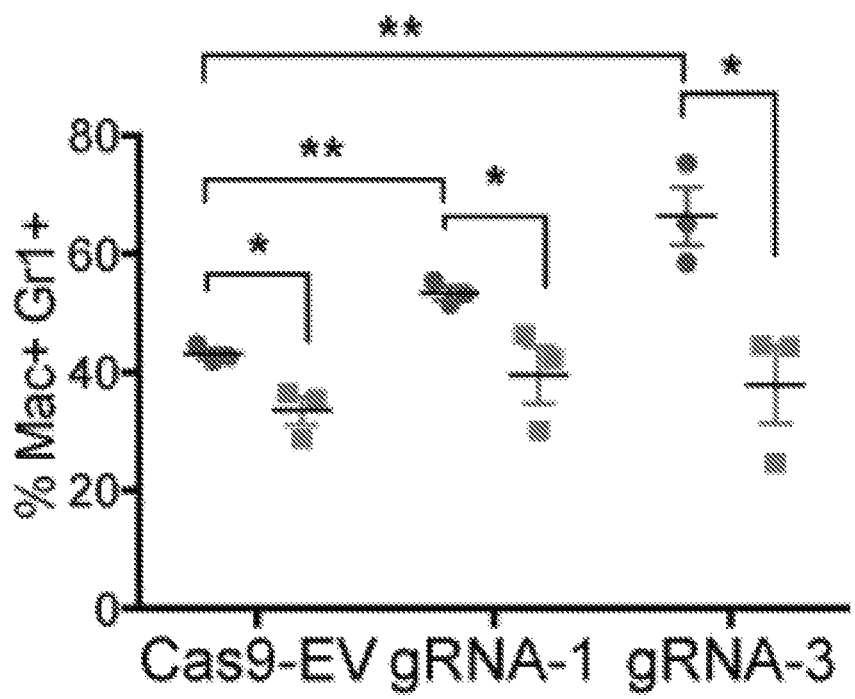
FIG. 2(L) shows the quantitative summary of FACS analysis of Gr-1 and Mac-1 expression in Cas9-EV and SYNCRIP-gRNAs transduced leukemia cells in FIG. 2(K), n=3 independent experiments; error bars, s.e.m. *$p<0.05$, ** $p<0.01$ two tailed t test.
Figure 9N:
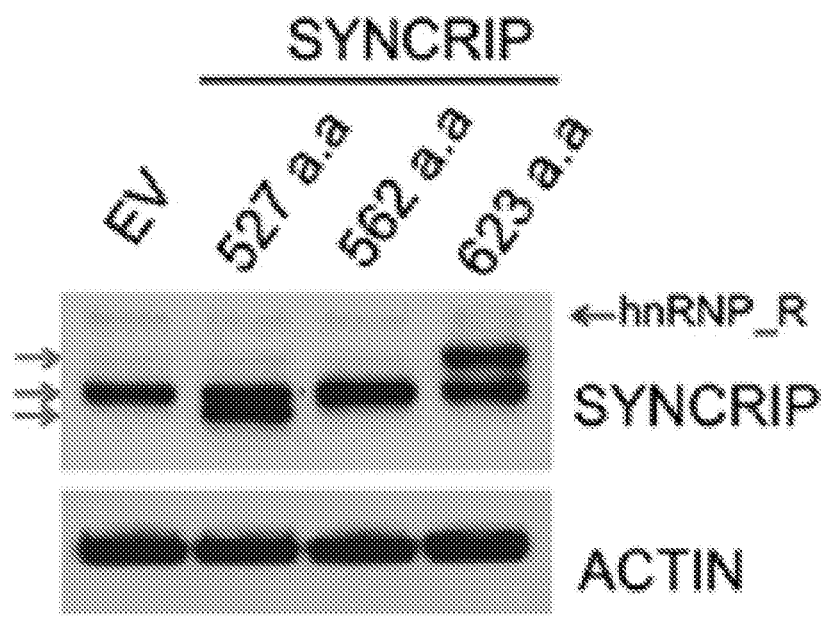
FIG. 9(N) shows immunoblot analysis of RN2 cells overexpressing different isoforms of SYNCRIP corresponding to proteins of 527 amino acids (aa), 562 aa and 623 aa. The SYNCRIP 562-aa isoform was the predominantly expressed isoform in leukemia cells. Actin serves as loading control.
Figure 9O:
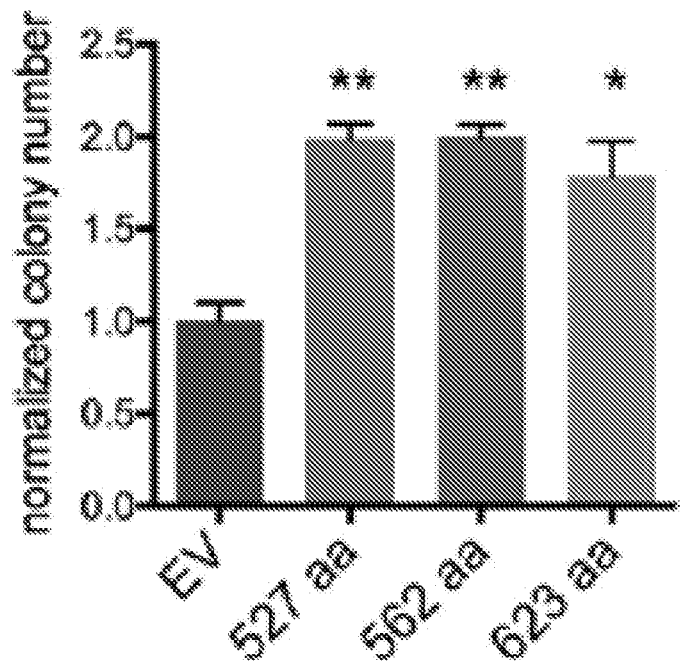
FIG. 9(O) shows that SYNCRIP overexpression in RN2 cells promotes colony formation (average of three independent experiments).
Figure 9P:
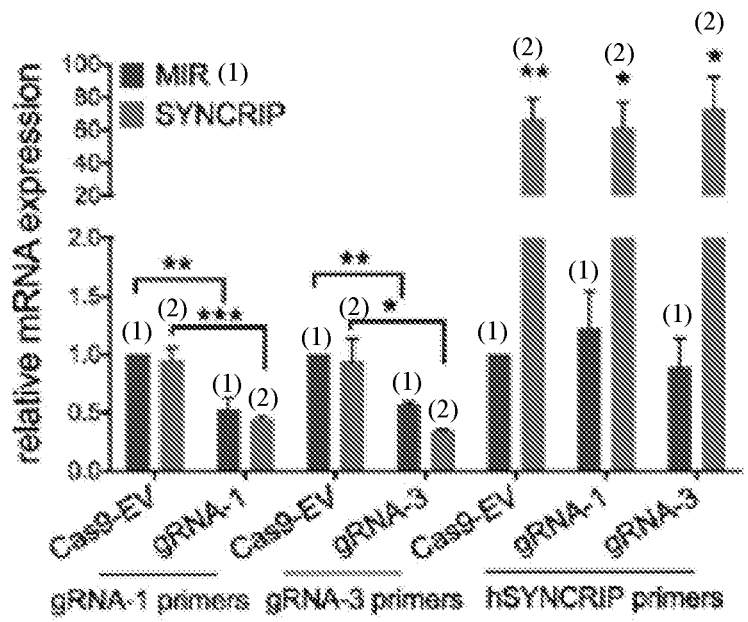
FIG. 9(P) shows mouse-Syncrip expression as assayed by qPCR using gRNA specific primers, and human-SYNCRIP expression for FIG. 2(K).
Figure 9Q:
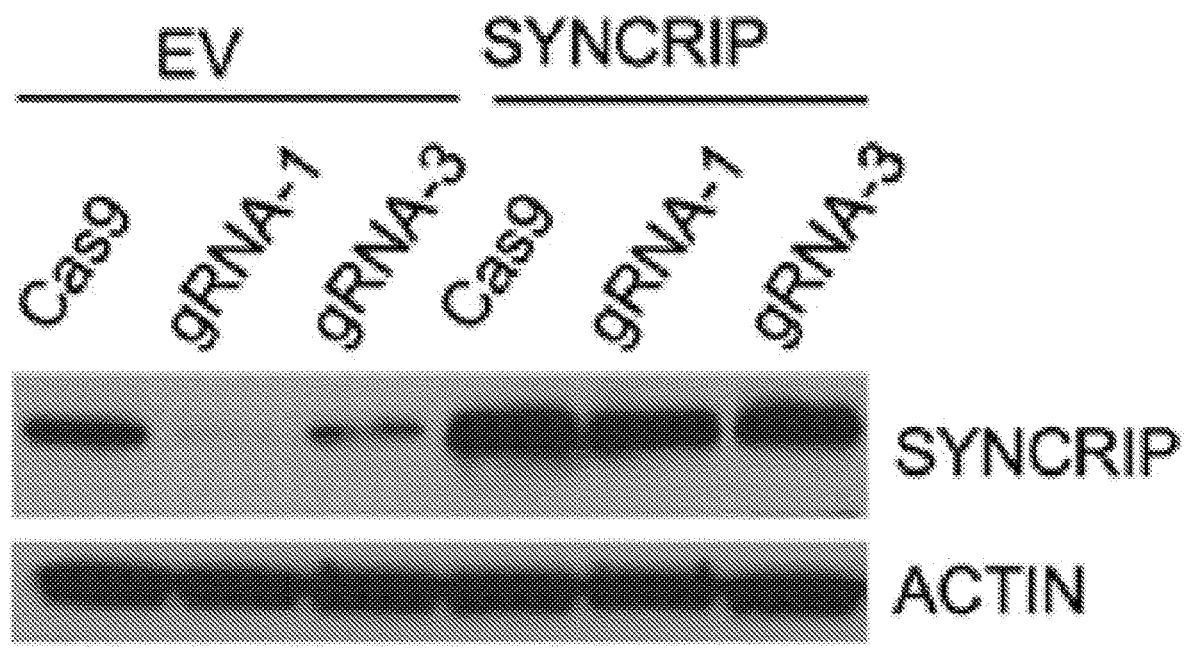
FIG. 9(Q) shows immunoblot analysis of RN2 cells overexpressing SYNCRIP or harboring control (empty vector (EV)) that were transduced for 24 hours with CRISPR/Cas9 containing tet-inducible gRNA1 and gRNA3 constructs or Cas9-EV in FIG. 2(J). All data represent the mean+s.e.m of at least three independent experiments. * $p<0.05$, $p<0.01$, * $p<0.001$ by two tailed t test.

Multiple isoforms of SYNCRIP (UniProtKB-O60506 human SYNCRIP/HNRNP Q) are expressed in mammalian cells. To identify the SYNCRIP isoforms in leukemia, cDNAs encoding 3 different isoforms of SYNCRIP were overexpressed (hnRNP_Q1: 562 amino acids, Q3: 623 amino acids, and Q4: 527 amino acids) in RN2 cells. Immunoblot analysis demonstrated the existence of 2 SYNCRIP isoforms with the dominant isoform being Q1 (562 aa) and the alternative, larger isoform Q3 (623 aa) (FIG. 9(N)). Despite the aggressiveness of the RN2 MLL-AF9 leukemia cells, SYNCRIP overexpression increased colony forming activity, demonstrating that SYNCRIP overexpression can potentiate leukemic cell growth (FIG. 9(O)). Additionally, overexpression of SYNCRIP dominant isoform (562 aa) in RN2 cells drove a more rapid leukemia in vivo (FIG. 2(J)).

Consistent with an on-target effect of CRISPR/Cas9 deletion for SYNCRIP, ectopic expression of non-target human SYNCRIP rescued the reduction in colony formation and reverse the increased differentiation from SYNCRIP depletion (FIGS. 2(K)-2(L) and FIGS. 9(P)-9(Q)). Therefore, the data shows that SYNCRIP is required for leukemic cell growth, cell survival, and maintenance of the undifferentiated state.

Accordingly, the SYNCRIP-specific inhibitory nucleic acids disclosed herein are useful in methods for inhibiting leukemic cell proliferation and treating AML in a subject in need thereof.

Figure 3A:
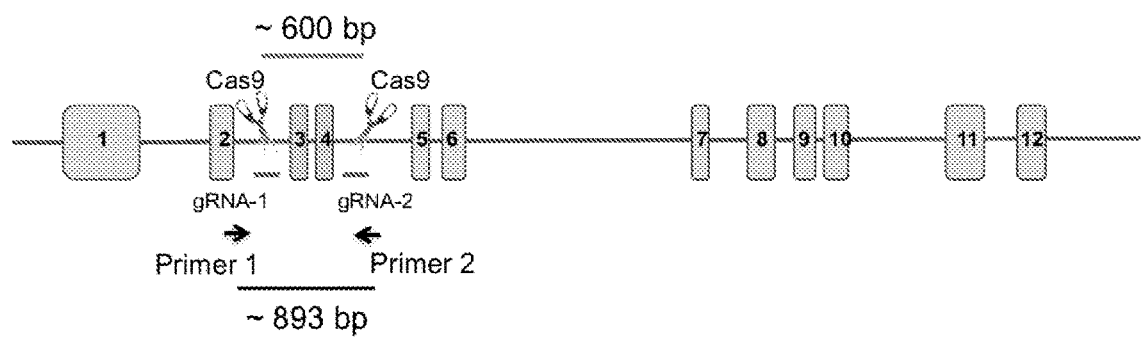
FIG. 3(A) shows the Syncrip locus and CRISPR/Cas9 targeting strategy for generation of Syncrip-CR-knockout (KO).
Figure 3B:
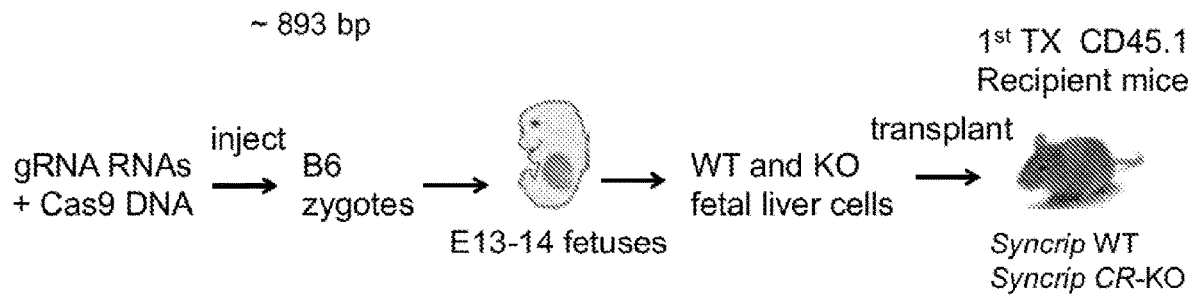
FIG. 3(B) shows the experimental scheme for generation of hematopoietic Syncrip-CR-KO using CRISPR/Cas9 approach and bone marrow transplantation of fetal liver cells.
Figure 3C:
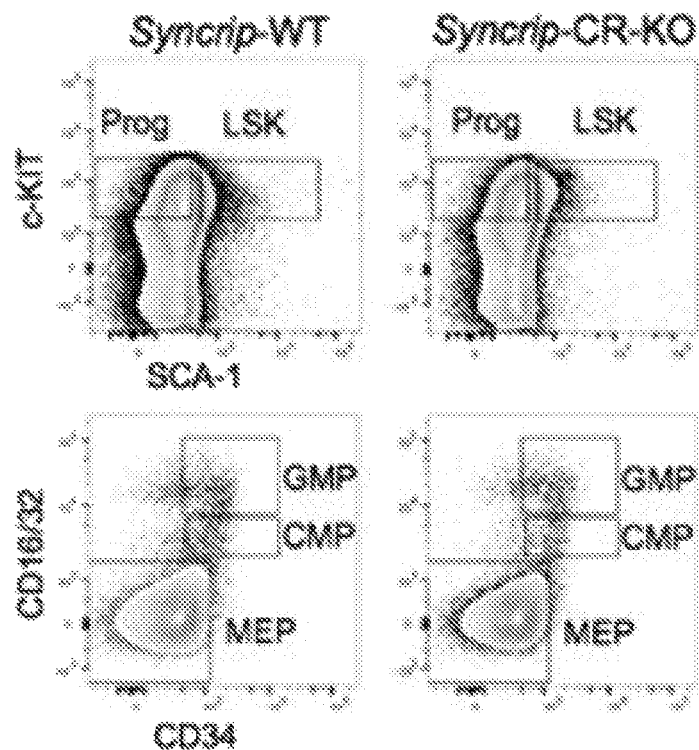
FIG. 3(C) shows FACS analysis of hematopoietic stem and progenitor cells in WT and Syncrip-CR-KO fetal livers.
Figure 10A:
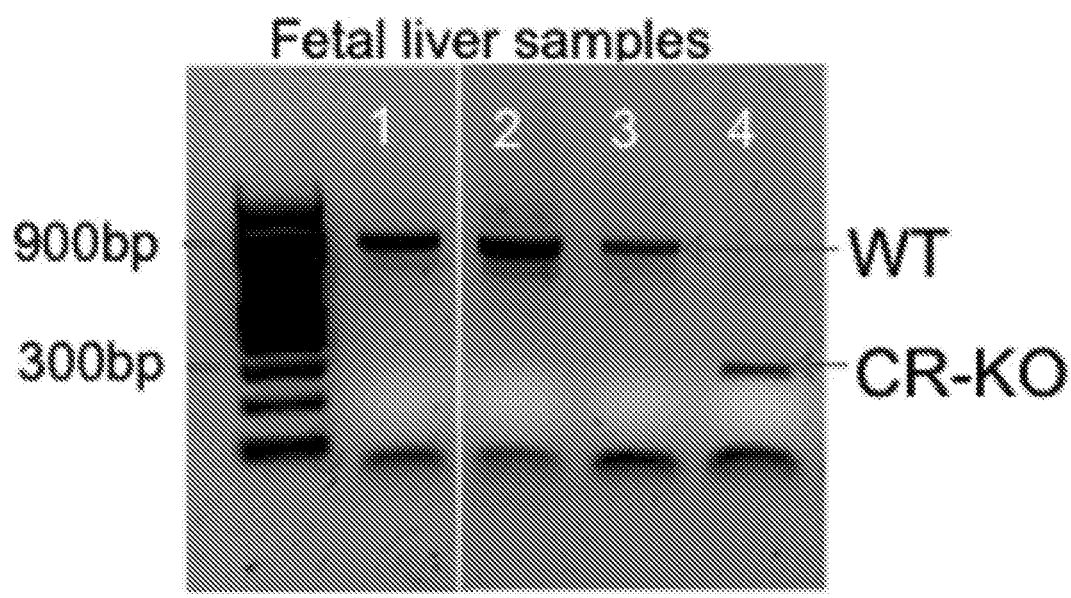
FIG. 10(A) shows representative PCR analysis for genotyping of Syncrip deletion in fetal liver cells.
Figure 10B:
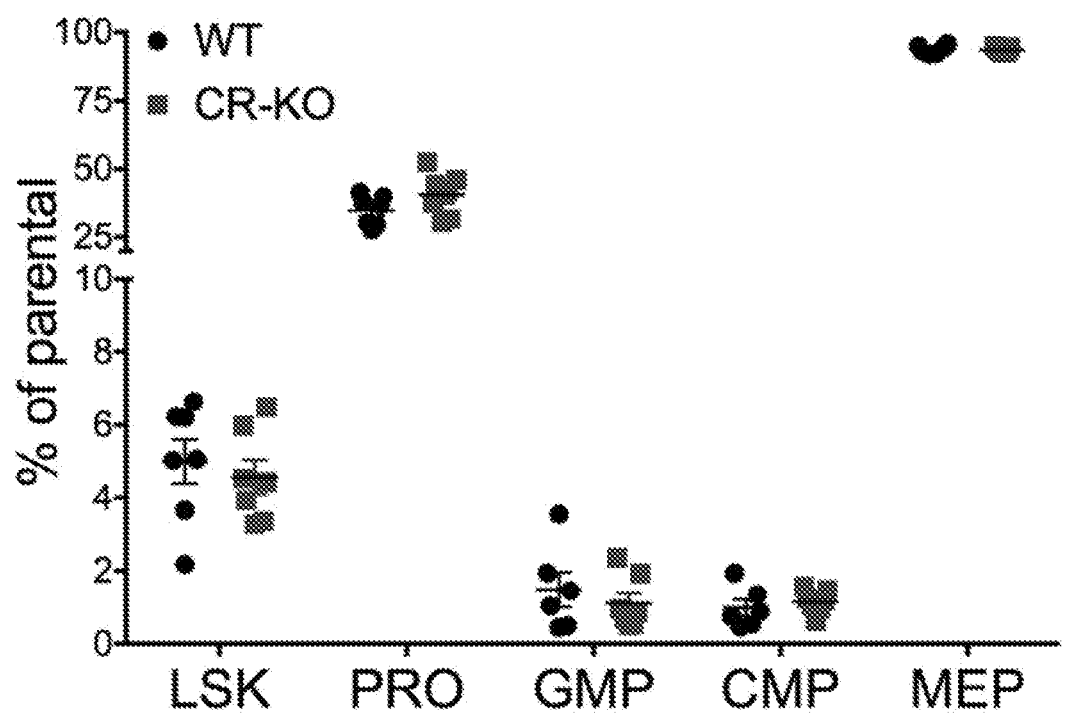
FIG. 10(B) shows a quantitative summary of FACS analysis of hematopoietic stem and progenitor cells in the WT and Syncrip-CR-KO fetal livers in FIG. 3(C) (WT n=7; CR-KO n=7).
Figure 10C:
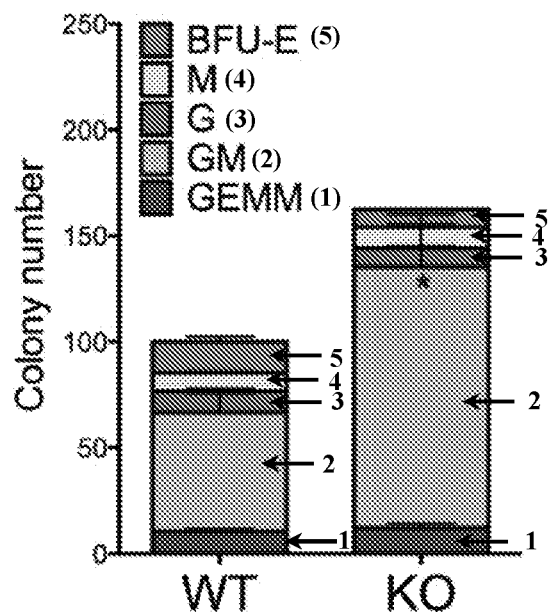
FIG. 10(C) shows a quantitative summary of the number of all colony types formed by WT and Syncrip-CR-KO fetal liver cells (average of 6 biological samples). BFU-E: burst-forming unit-erythroid, M: macrophage, G: granulocyte, GM: granulocyte, macrophage, GEMM: granulocyte, erythroid, macrophage, megakaryocyte.

Example 4: CRIPSR/Cas9 Deletion of SYNCRIP Differentially Impairs Leukemogenesis but not Normal Hematopoiesis To further assess SYNCRIP function in normal and malignant hematopoiesis in vivo, mice deficient for SYNCRIP were developed using CRISPR/Cas9 approach with co-injection of gRNAs and Cas9 mRNA into the pronucleus of mouse zygotes. Fetal liver cells were collected from developed embryos in pseudo moms at E14 and fetal liver genotypes were determined by PCR (FIGS. 3(A)-3(B) and FIG. 10(A)). Confirmed wild type (WT) and CRIPSR-knockout samples (CR-KO) were analyzed, and an equivalent frequency of phenotypic HSCs in WTs versus CR-KOs was found (FIG. 3(C) and FIG. 10(B)) along with a modest increase in colony forming units granulocyte-macrophage (CFU-GM) in the CR-KOs (FIG. 10(C)).

Figure 3D:
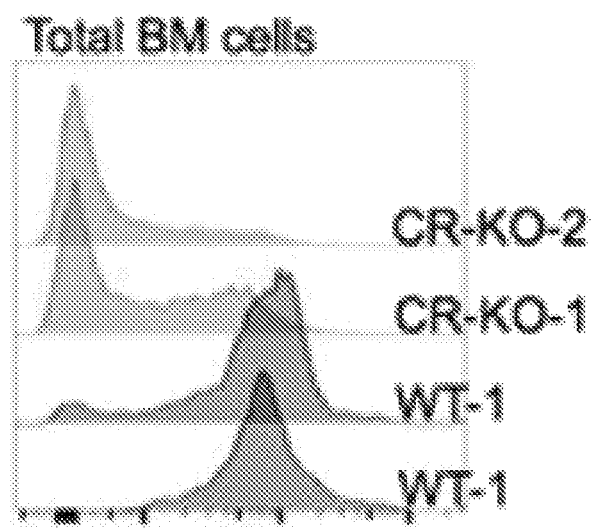
FIG. 3(D) shows FACS histograms of SYNCRIP intracellular staining of CD45.2 positive bone marrow cells isolated from WT and Syncrip-CR-KO recipient mice.
Figure 3E:
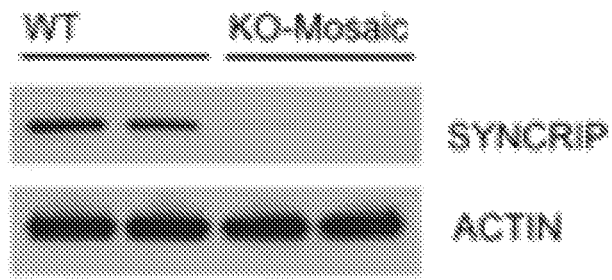
FIG. 3(E) shows immunoblot analysis of CD45.2 positive bone marrow cells isolated from WT and Syncrip-CR-KO recipient mice.
Figure 3F:
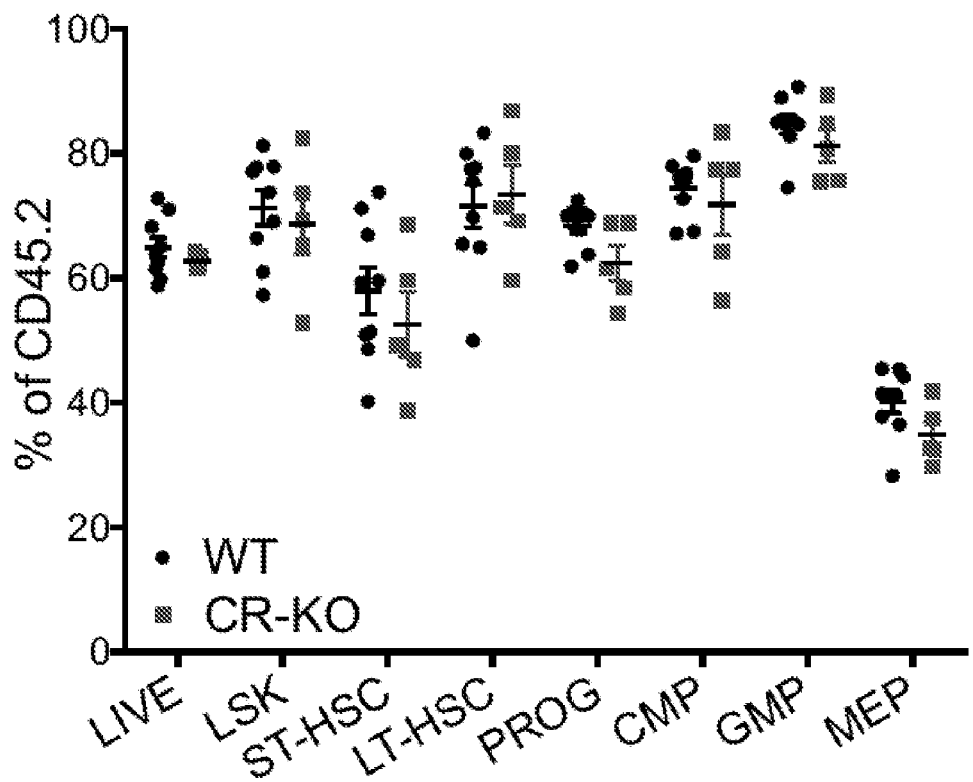
FIG. 3(F) shows quantitative summary of FACS analysis of hematopoietic stem and progenitor compartments in WT and Syncrip-CR-KO recipient mice. LIVE: total bone marrow cells; LSK: Lin$^-$Sca1$^+$Kit$^-$ cells; PROG: Progenitor cells; GMP: Granulocyte Macrophage progenitor; CMP: Common Myeloid progenitor; MEP: Megakaryocyte-Erythrocyte progenitor. WT n=9; CR-KO n=5.

Analysis of SYNCRIP functions during normal hematopoiesis in vivo was performed by monitoring the engraftment efficiency of WT vs. CR-KO cells in transplanted recipient mice. Reduction of SYNCRIP protein expression in engrafted bone marrow cells from CR-KO compared to WT recipient was confirmed (FIGS. 3(D)-3(E)). No defect in engraftment of CR-KO cells in primary transplant mice was observed (FIG. 3(F)).

Figure 3G:
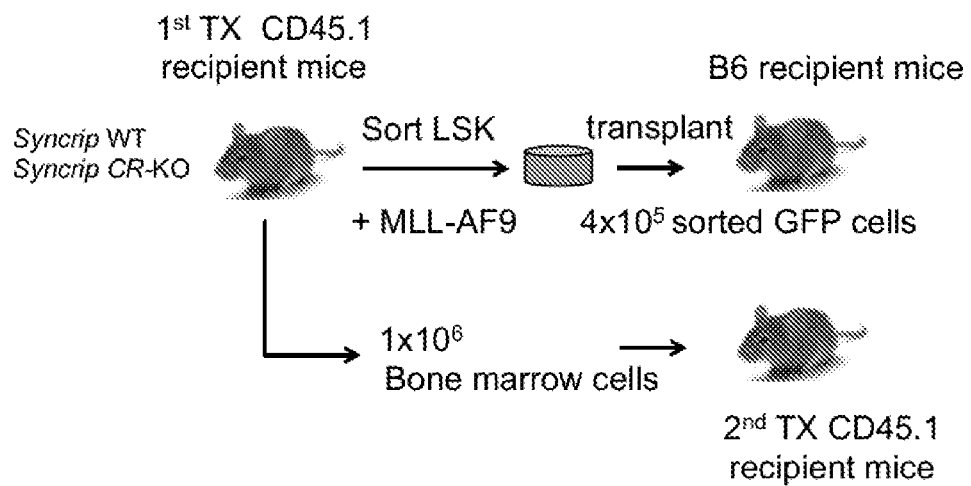
FIG. 3(G) shows an experimental scheme for LSK-derived MLL-AF9 leukemia transplantation model and secondary bone marrow transplantation.
Figure 3H:
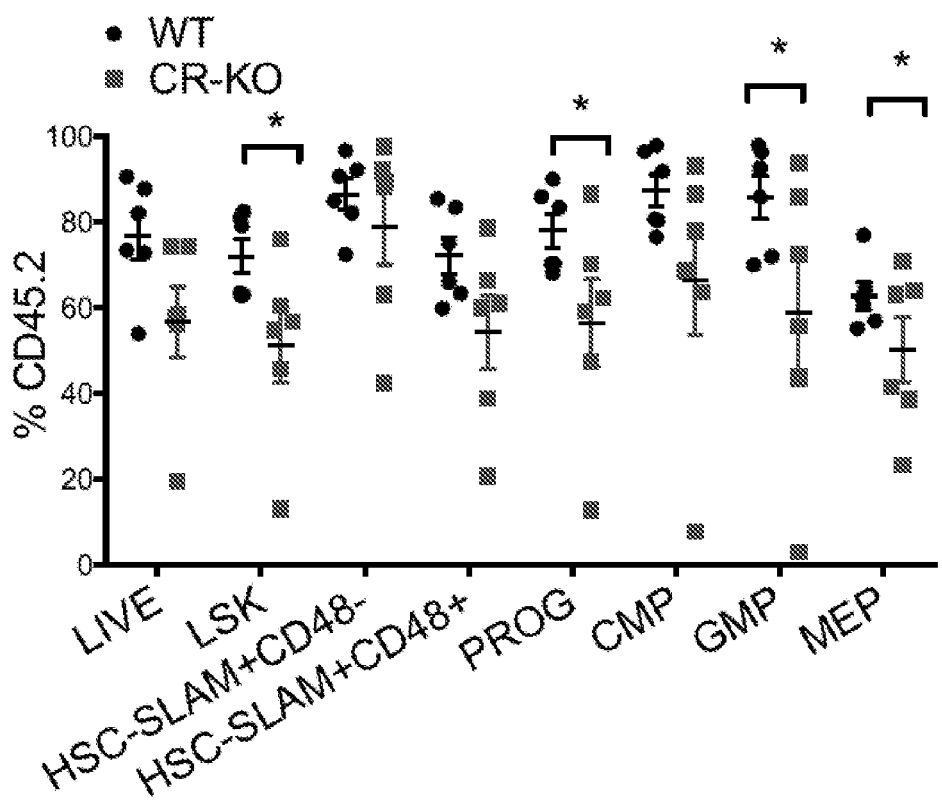
FIG. 3(H) shows the quantitative summary of FACS analysis of hematopoietic stem and progenitor compartments in WT and Syncrip-CR-KO secondary recipient mice. WT n=6; CR-KO n=6, error bars, s.e.m. *$p<0.05$ two tailed t test.
Figure 3I:
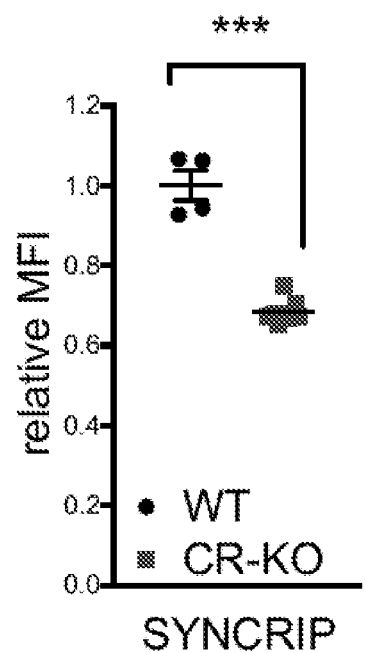
FIG. 3(I) shows the quantitative summary of relative median fluorescence intensity (MFI) analysis of SYNCRIP intracellular staining of engrafted CD45.2 cells in WT and Syncrip-CR-KO secondary recipient mice. WT n=4; CR-KO n=7 error bars, s.e.m. ***$p<0.001$ two tailed t test.
Figure 3J:
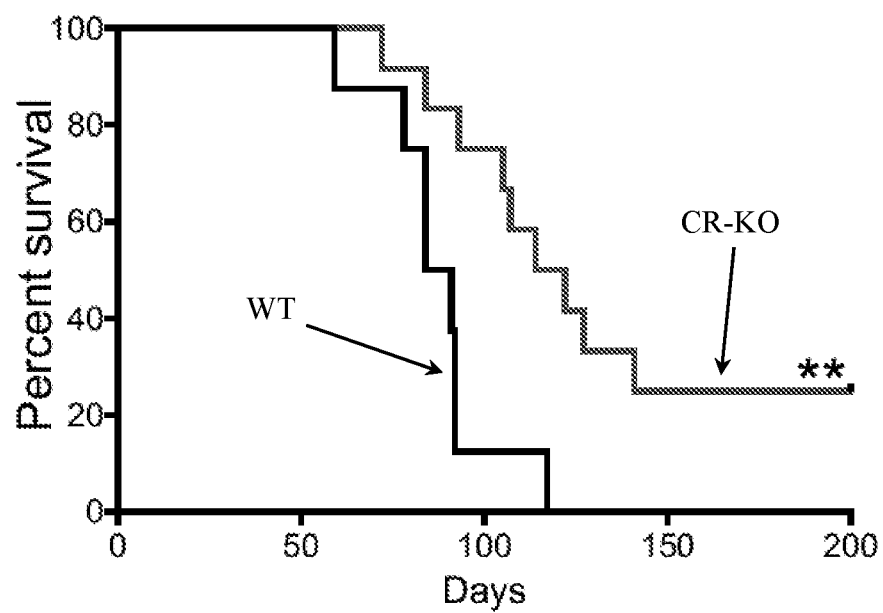
FIG. 3(J) shows Kaplan Meier analysis of leukemia free survival outcomes after injection of MLL-AF9 transformed WT and Syncrip-CR-KO cells into lethally irradiated mice WT n=8, Syncrip-CR-KO n=12; Mantel-Cox test ** $p<0.01$.
Figure 3K:
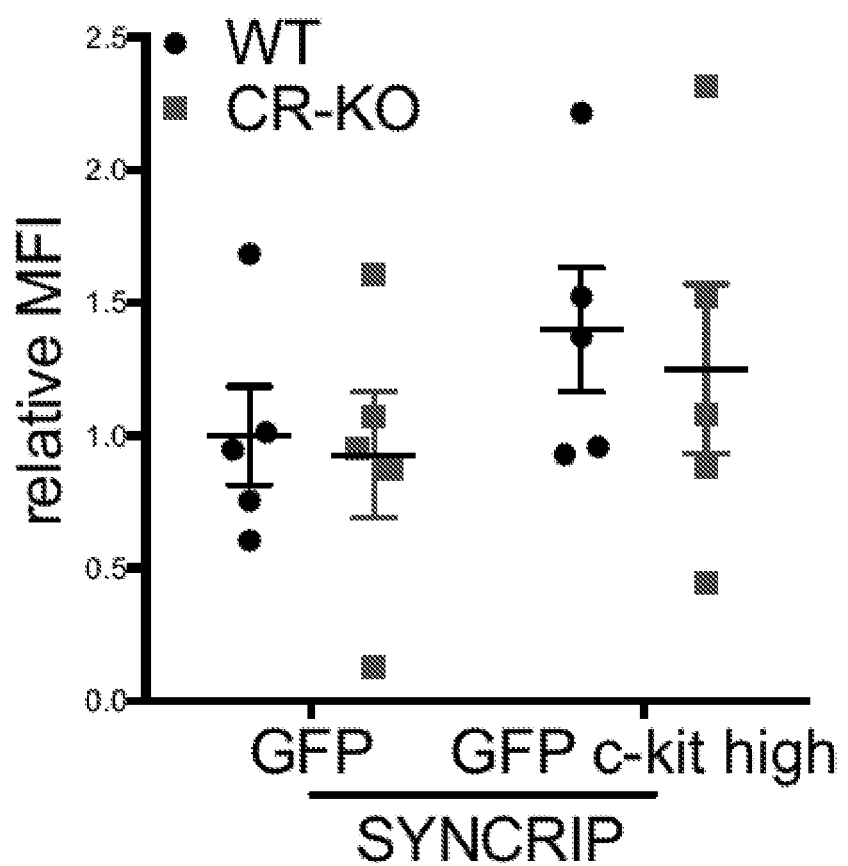
FIG. 3(K) shows the quantitative summary of relative MFI analysis of SYNCRIP intracellular staining of GFP positive and GFP positive c-kit high cells from mice succumbed to leukemia in WT vs. Syncrip-CR-KO. WT n=5; CR-KO n=5.
Figure 10D:
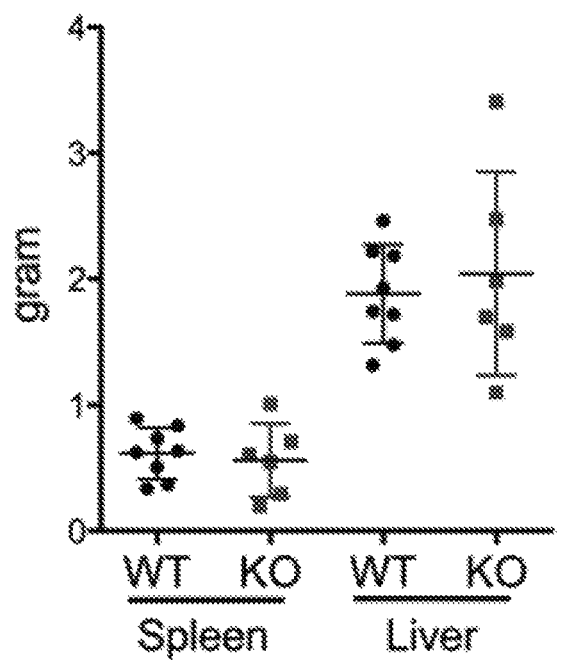
FIG. 10(D) shows the assessment of disease burden, including spleen weight and liver weight of recipient mice shown in FIG. 3(J). * $p<0.05$ by two tailed t test.

To determine whether SYNCRIP is required for development of leukemia in vivo, LSKs cells from bone marrow of SYNCRIP WT and CR-KO primary transplanted mice were isolated and transduced with MLL-AF9-GFP expressing viruses. MLL-AF9-GFP transformed cells were injected into recipient mice (FIG. 3(G)). Additionally, a secondary bone marrow transplantation of SYNCRIP WT and CR-KO bone marrow cells into lethally irradiated mice was performed, which resulted in a mild reduction in engraftment (FIGS. 3(H)-3(I)). MLL-AF9-GFP transformed LSK cells derived from CR-KO recipients showed a delay in leukemogenesis in vivo when compared to WT cells (FIG. 3(J)). It was determined that expression of SYNCRIP was maintained when the animals died of leukemia (FIG. 3(K) and FIG. 10(D)). This data shows that the CRISPR-driven KO fetal liver samples were mosaic for both WT and CR-KO SYNCRIP, resulting in the residual SYNCRIP-WT leukemia to grow out. Overall, this data show the requirement of SYNCRIP in the development of leukemia in a genetic mouse model.

Accordingly, the SYNCRIP-specific inhibitory nucleic acids disclosed herein are useful in methods for inhibiting leukemic cell proliferation and treating AML in a subject in need thereof.

Example 5: SYNCRIP is Highly Expressed and Essential for Human Leukemia Cells

Figure 11A:
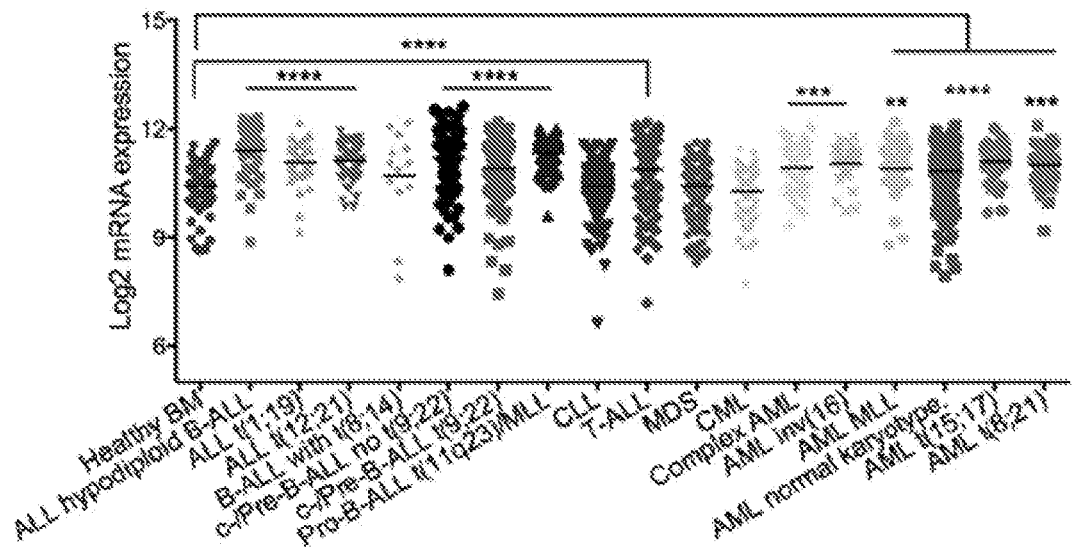
FIG. 11(A) shows a graph of the $\log_2$ expression of SYNCRIP from transcript profiling of bone marrow cells from patients with various types of hematological malignancies including ALLs, B-ALLs, CLL, MDS, CML and subtypes of AML and of healthy donors. Hypodiploid B-ALL, n=40; ALL with t(1;19), n=36; ALL with t(12;21), n=58; B-ALL with t(8;14), n=13; c-/pre-B-ALL without t(9;22), n=237; c-/pre-B-ALL with t(9;22), n=122; pro-B-ALL with t(11q23)/MLL, n=70; CLL, n=448; T-ALL, n=174; MDS, n=206; CML, n=76; complex AML, n=48; AML with inv(16), n=28; AML MLL, n=38; AML with a normal karyotype, n=351; AML with t(15;17), n=37; AML with t(8;21), n=40; healthy donors, n=73. $p<0.01$, *$p<0.001$, ****$p<0.0001$, Student's t test. (Hemaexplorer data for SYNCRIP probe 209024_s_at from the U133 and U133 Plus 2.0 arrays).
Figure 11B:
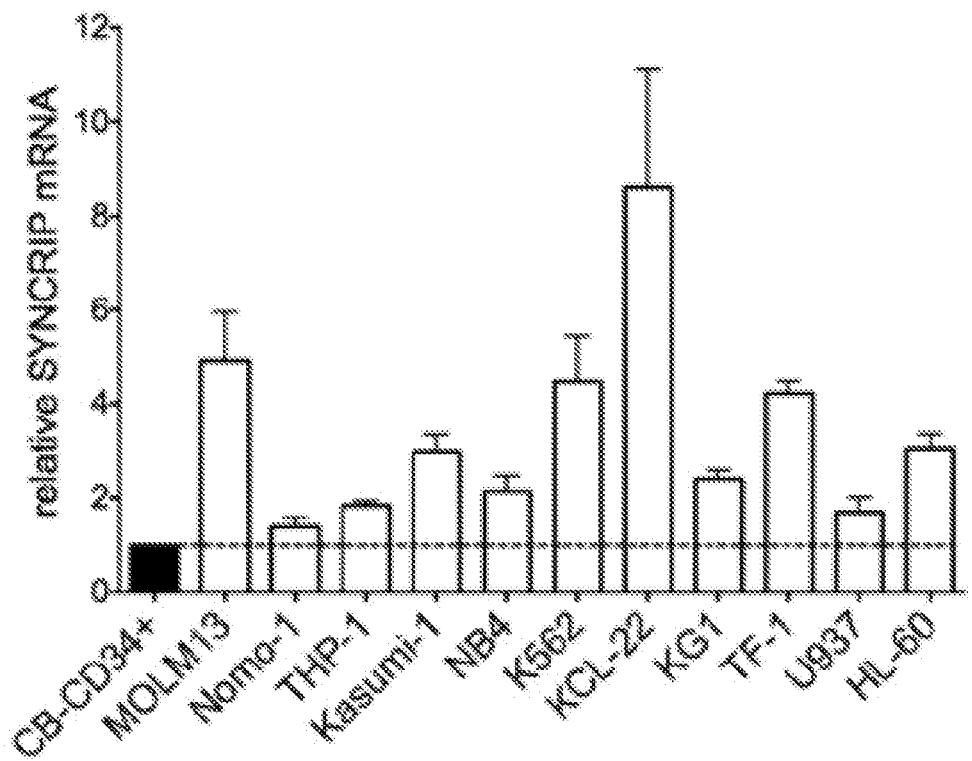
FIG. 11(B) shows qPCR of SYNCRIP mRNA levels in multiple human AML cell lines and normal cord blood derived CD34$^+$ cells (CB-CD34$^+$). β-actin served as a housekeeping gene control. Relative mRNA level was normalized to SYNCRIP mRNA in CB-CD34$^+$ cells.
Figure 11C:
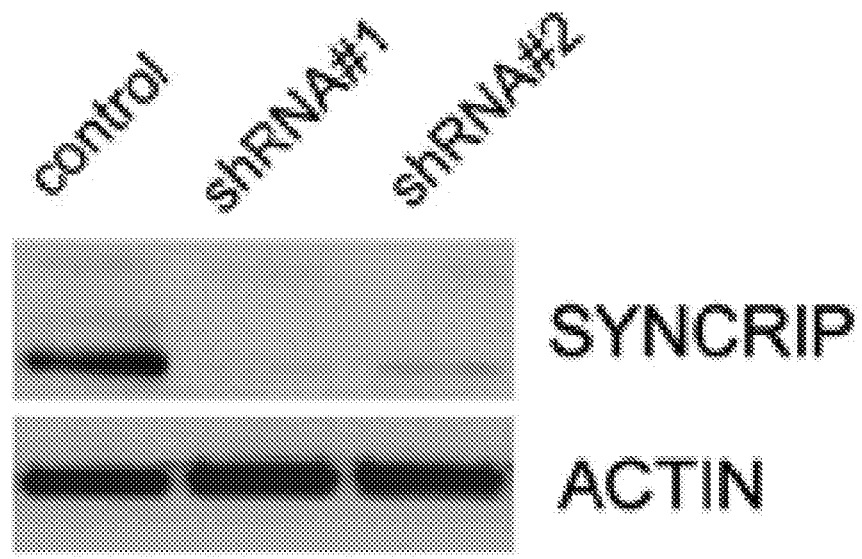
FIG. 11(C) shows SYNCRIP knockdown in MOLM13 AML cell line as assessed by immunoblot analysis.
Figure 11D:
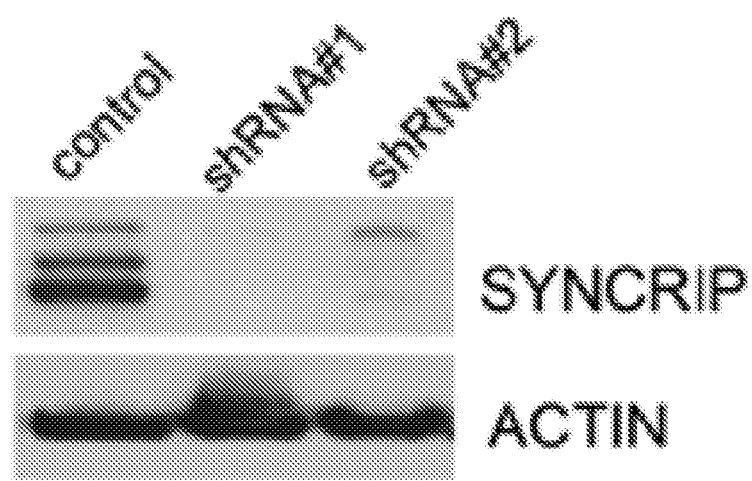
FIG. 11(D) shows SYNCRIP knockdown in NOMO-1 AML cell line as assessed by immunoblot analysis.
Figure 11E:
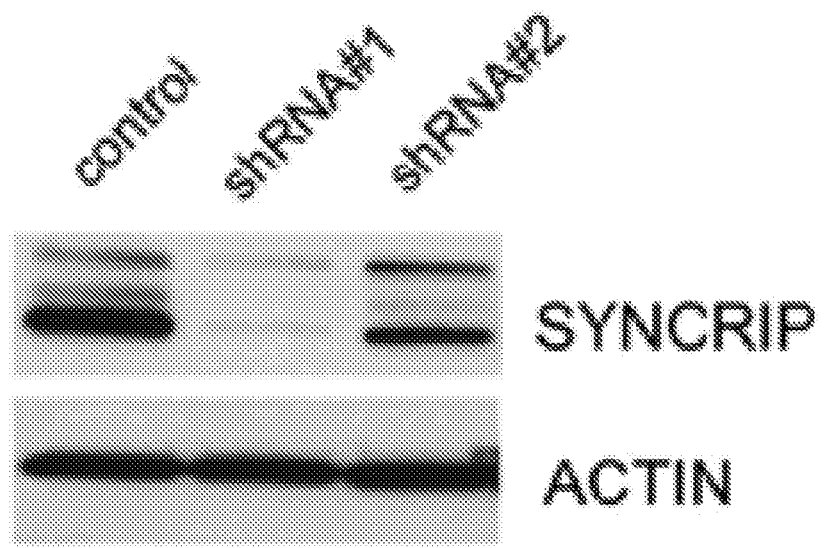
FIG. 11(E) shows SYNCRIP knockdown in KASUMI AML cell line as assessed by immunoblot analysis.
Figure 11F:
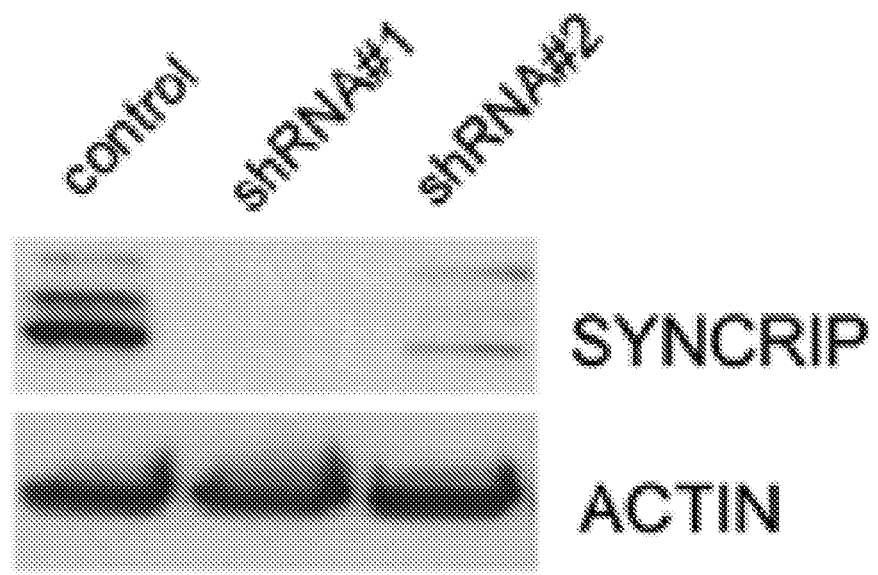
FIG. 11(F) shows SYNCRIP knockdown in NB4 AML cell line as assessed by immunoblot analysis.
Figure 11G:
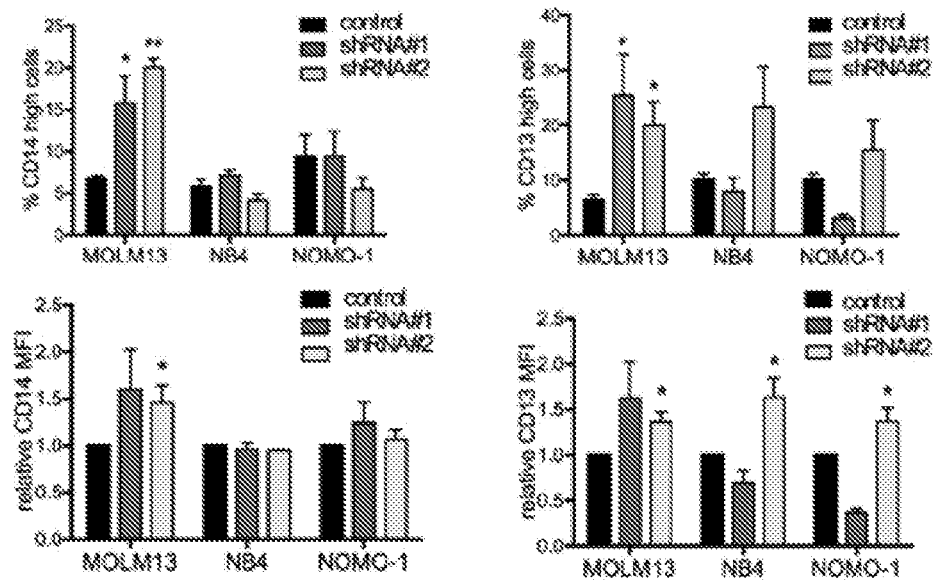
FIG. 11(G) shows a quantitative summary of CD14$^{high}$ and CD13$^{high}$ cells and CD14 and CD13 MFI in MOLM13, NB4 and NOMO-1 cells transduced with control shRNA or shRNAs against SYNCRIP (shRNA #1 and shRNA #2) 4 days post transduction.
Figure 11H:
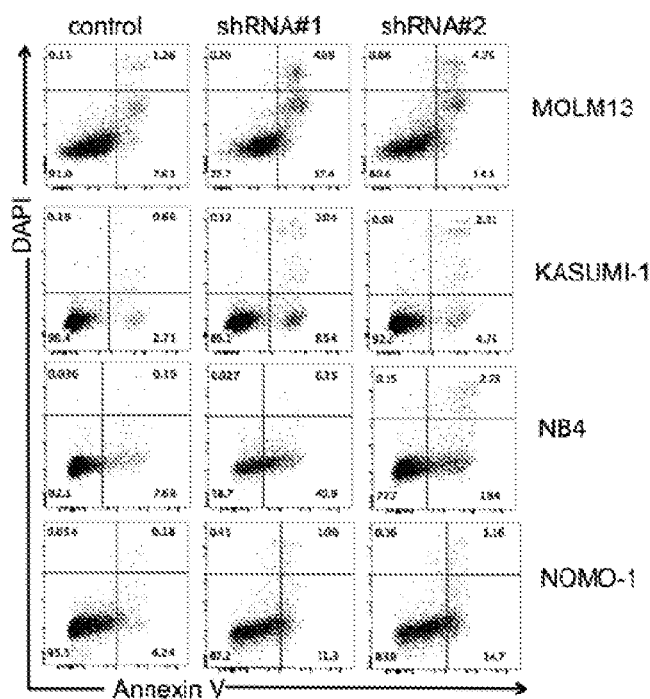
FIG. 11(H) shows representative FACS plots of cells in FIG. 4(H). All data represent the mean+s.e.m of at least three independent experiments. * $p<0.05$, $p<0.01$, * $p<0.001$ by two tailed t test.

To define SYNCRIP's role in human leukemia, a previously published expression dataset was surveyed (Bagger F O et al., *Nucleic Acids Res.* 41:D1034-9 (2013)). SYNCRIP expression was elevated in AML patients with diverse genetic alterations compared to normal hematopoietic stem and progenitor cells (FIG. 4(A)). Elevated expression of SYNCRIP in other hematological malignancies including T-ALL and B-ALLs with various genetic abnormalities was also determined (FIG. 11(A)). High levels of SYNCRIP expression were also observed across multiple human myeloid leukemia cell lines compared to normal human CD34 enriched cord blood cells (CB-CD34+ cells)(FIG. 11(B)). SYNCRIP was highly expressed at the protein level in human myeloid leukemia cell lines (10/11) and primary patient samples (5 patients) compared to CB-CD34 cells (FIGS. 4(B)-4(C)).

To test the functional role of the increased SYNCRIP expression in leukemic cells, myeloid leukemia cells (MOLM13, NOMO-1, KASUMI-1 and NB4) were transduced with lentiviral shRNA vectors targeting SYNCRIP and knock down of SYNCRIP with 2 independent hairpins was obtained. Depletion of SYNCRIP resulted in reduced cell proliferation and increased apoptosis coupled with increased myeloid differentiation, depending on the particular marker, in the AML cell lines (FIGS. 4(D)-4(H) and FIGS. 11(C)-11(H)). This data shows that SYNCRIP plays a role in different types of human myeloid leukemia driven by various oncogenic drivers.

Accordingly, the SYNCRIP-specific inhibitory nucleic acids disclosed herein are useful in methods for inhibiting leukemic cell proliferation and treating AML in a subject in need thereof.

Figure 5A:
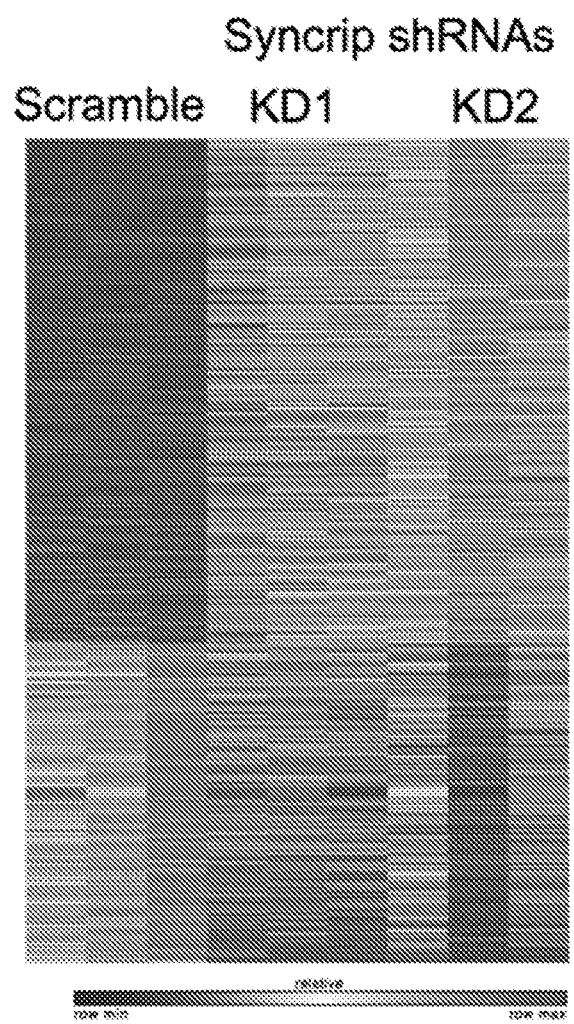
FIG. 5(A) shows a gene expression heat map of the top 191 upregulated and downregulated genes from RNA-sequencing analysis of MLL-AF9 leukemia cells transduced with control and shRNAs against SYNCRIP n=3 biological replicates.
Figure 5B:
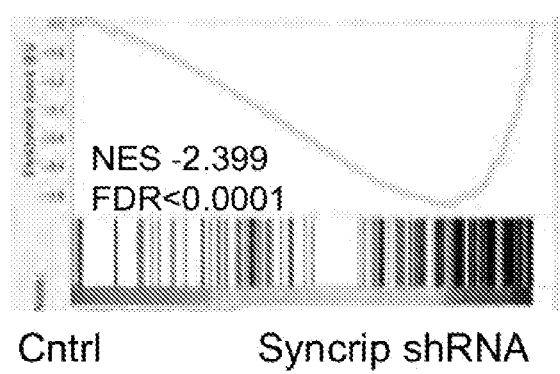
FIG. 5(B) shows Gene Set Enrichment Analysis (GSEA) results showing that the gene expression signature for genes enriched in hematopoietic stem cells was upregulated in SYNCRIP-KD cells.
Figure 5C:
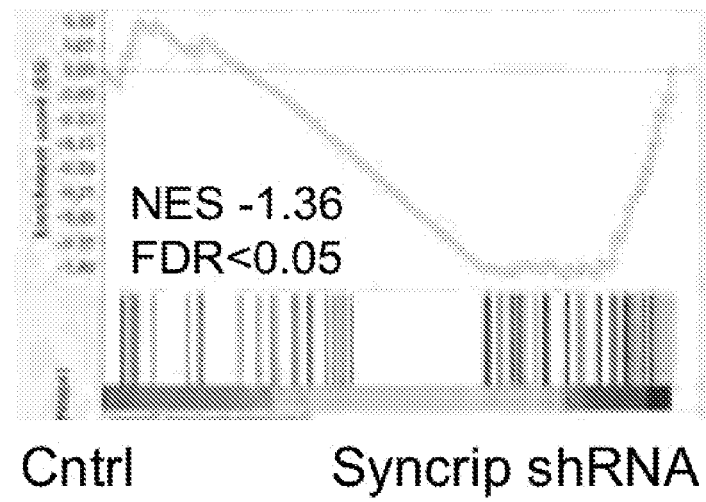
FIG. 5(C) shows GSEA results showing that the gene expression signature for genes enriched in leukemic stem cells was upregulated in SYNCRIP-KD cells.
Figure 5D:
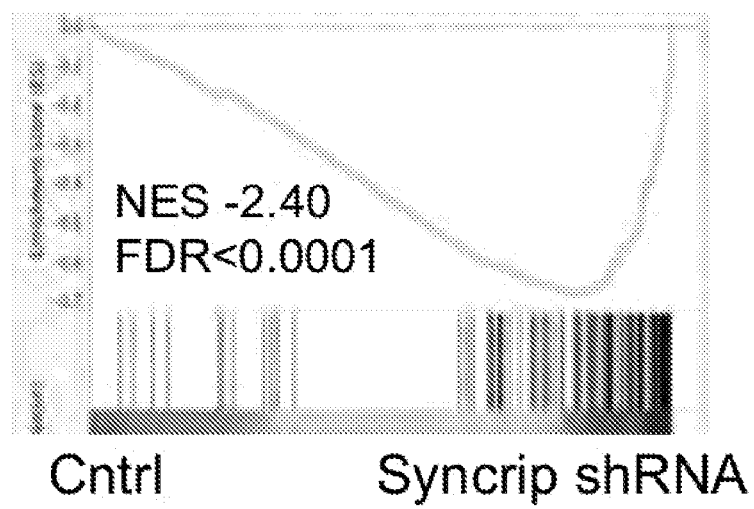
FIG. 5(D) shows GSEA results showing that the gene expression signature for genes enriched in myeloid development program was upregulated in SYNCRIP-KD cells.
Figure 12A:
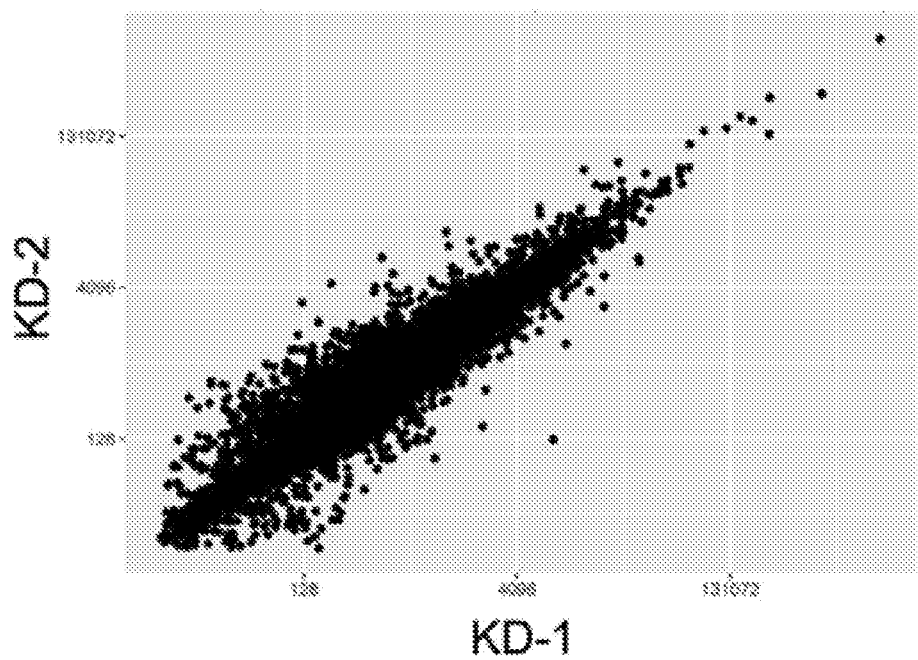
FIG. 12(A) shows plots representing the distribution of mean normalized counts of KD1 correlating with normalized mean counts of KD2 from RNA-sequencing data shown in FIG. 5(A).

Example 6: SYNCRIP and MSI2 Co-Regulate Leukemia Stem Cell Gene Expression Programs To understand the molecular function of SYNCRIP in leukemia, RNA-sequencing was performed on MLL-AF9 leukemia cells transduced with shRNAs against SYNCRIP four days post-transduction. The transcriptional profile of SYNCRIP-shRNA transduced cells was significantly altered and the results obtained from two independent shRNA hairpins were highly correlated (FIG. 12(A)). 282 genes were differentially expressed, where 57 were downregulated (SYNCRIP was ranked 9th most downregulated gene) and 225 were upregulated ($Log_2$ Fold change>1.5, FDR<0.01, FIGS. 5(A), and FIG. 17). The RNA-sequencing analysis was functionally annotated by performing Gene Set Enrichment Analysis (GSEA) on all curated gene sets in the Molecular Signatures Database (MSigDB, Broad Institute, Cambridge Mass.; 3,256 gene sets) combined with an additional set of relevant gene sets (92 gene sets from experimentally derived or published hematopoietic self-renewal and differentiation signatures) using the ranked list of differentially expressed genes in SYNCRIP-shRNA samples (Cntrl/SYNCRIP-shRNA). Genes upregulated after SYNCRIP depletion were enriched in 236 gene sets and downregulated genes were enriched in 172 gene sets. Set of genes downregulated in HSCs (CD133+ vs CD133−), LSC related gene signature associated with a good prognosis in AML and the myeloid development program were significantly enriched for upregulated genes in SYNCRIP depleted cells (FIGS. 5(B)-5(D)).

Figure 5E:
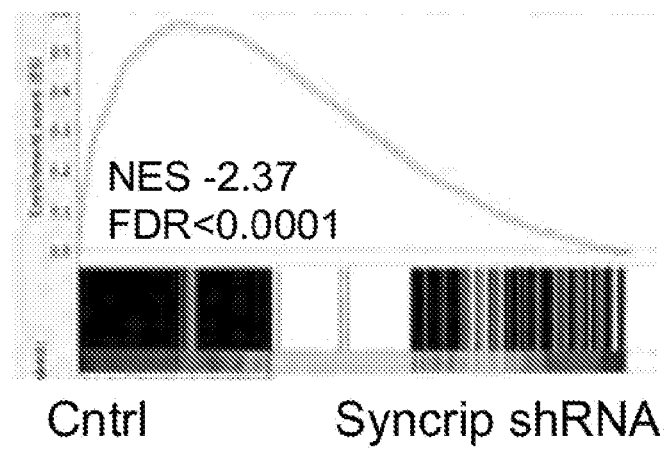
FIG. 5(E) shows GSEA results showing that the gene expression signature for MLL-AF9 directed target genes was downregulated in SYNCRIP-KD cells.
Figure 5F:
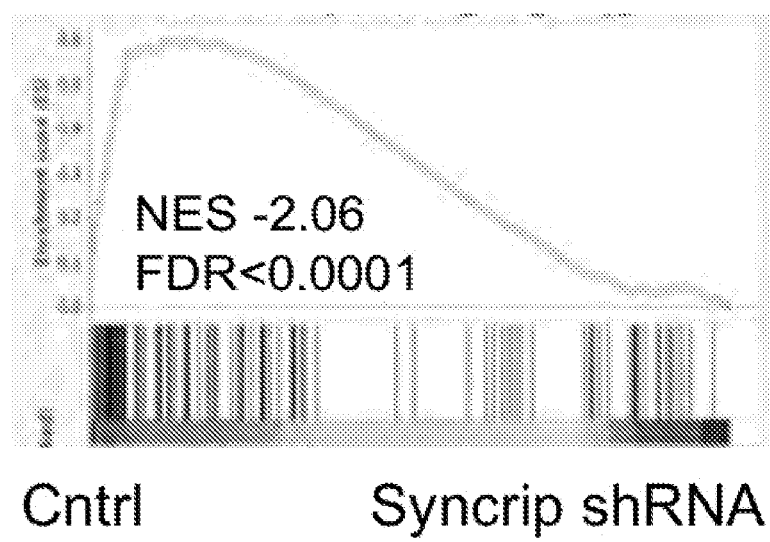
FIG. 5(F) shows GSEA results showing that the gene expression signature for MLL-AF9 directed target genes was downregulated in SYNCRIP-KD cells.
Figure 5G:
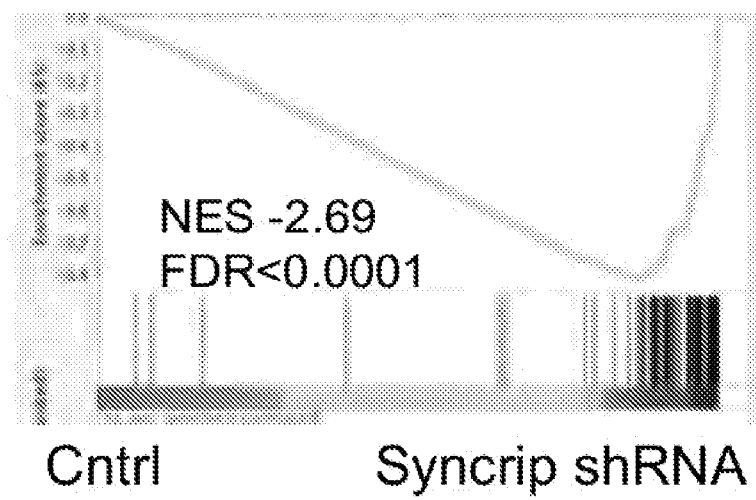
FIG. 5(G) shows GSEA results showing that the gene expression signature for HOXA9-MEIS1 target genes was downregulated in SYNCRIP-KD cells.
Figure 5H:
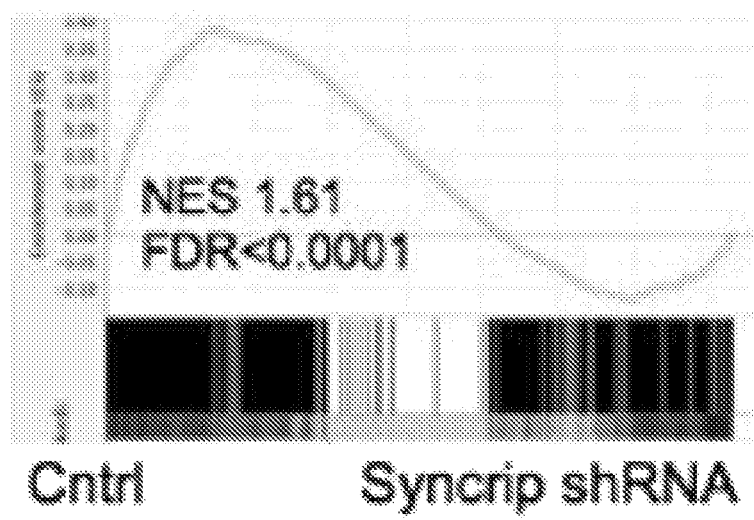
FIG. 5(H) shows enrichment of MSI2 target genes among SYNCRIP regulated genes.
Figure 5I:
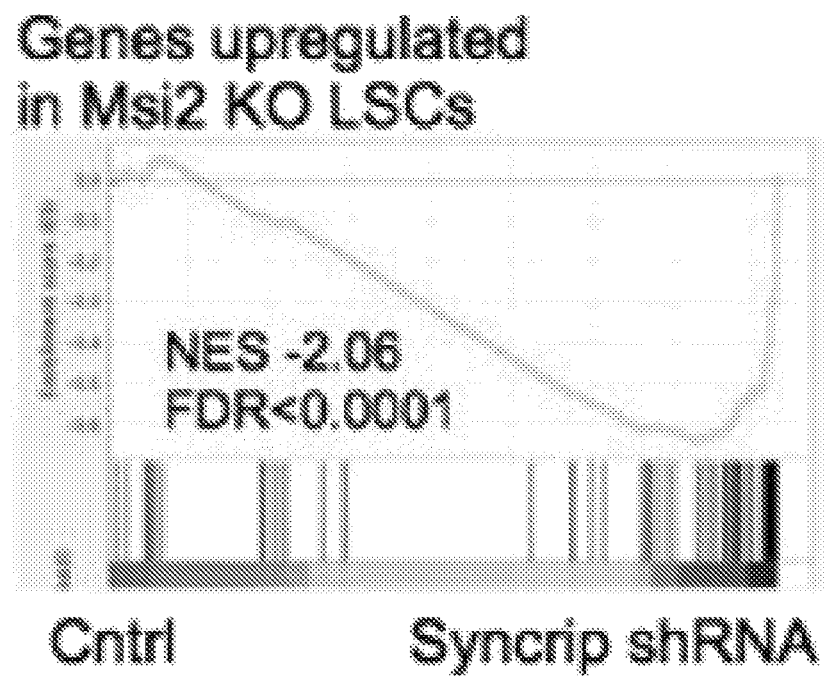
FIG. 5(I) shows enrichment of MSI2 target genes among SYNCRIP regulated genes.
Figure 12B:
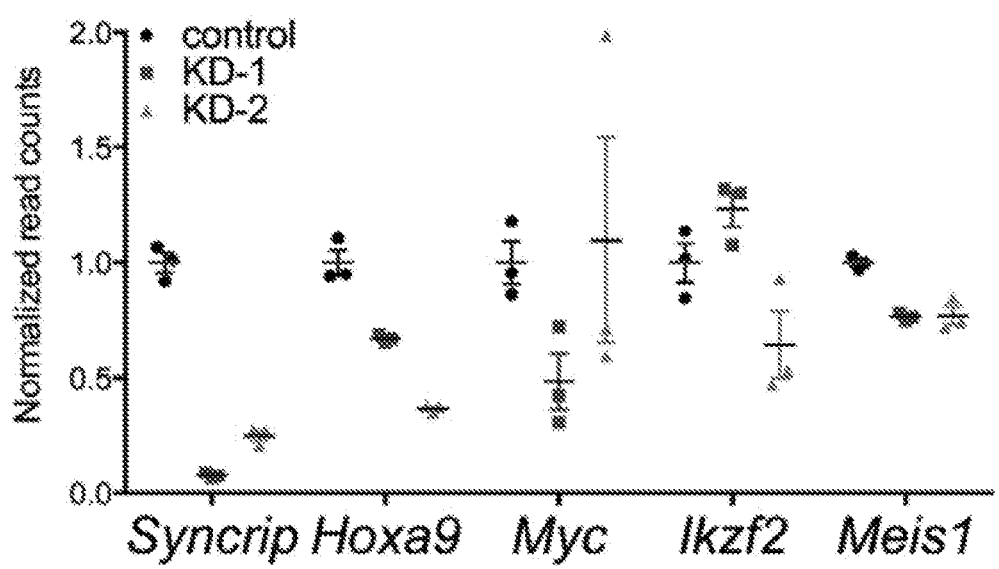
FIG. 12(B) shows normalized read counts of Syncrip, HoxA9, c-Myc, Ikzf2 and Meis1 from RNA-sequencing data shown in FIG. 5(A).
Figure 12C:
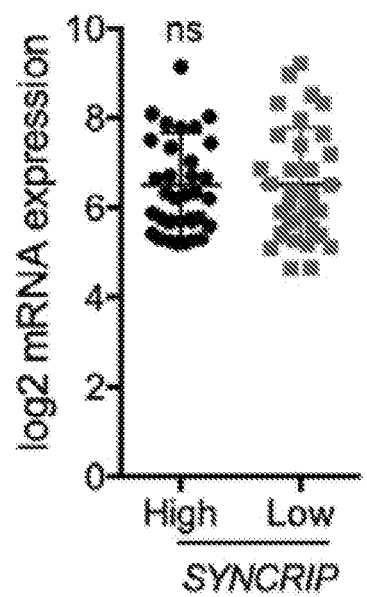
FIG. 12(C) shows $\log_2$ mRNA expression levels of MSI2 in patients with high vs. low SYNCRIP mRNA expression in AML patients reported in FIG. 4(A) (high SYNCRIP was defined as individuals with a value greater than the average+1 s.d. while low SYNCRIP was defined as individuals with a value greater than the average−1 s.d.). * $p<0.05$, $p<0.01$, * $p<0.001$ by two tailed t test.
Figure 12D:
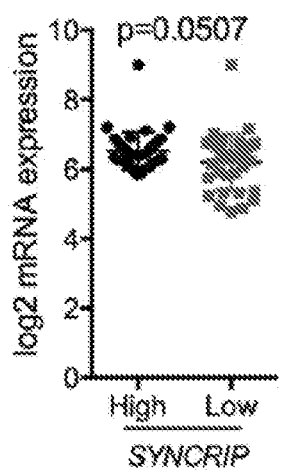
FIG. 12(D) shows $\log_2$ mRNA expression levels of target genes upregulated by HOXA9-MEIS in patients with high vs. low SYNCRIP mRNA expression in AML patients reported in FIG. 4(A) (high SYNCRIP was defined as individuals with a value greater than the average+1 s.d. while low SYNCRIP was defined as individuals with a value greater than the average−1 s.d.). * $p<0.05$, $p<0.01$, * $p<0.001$ by two tailed t test.
Figure 12E:
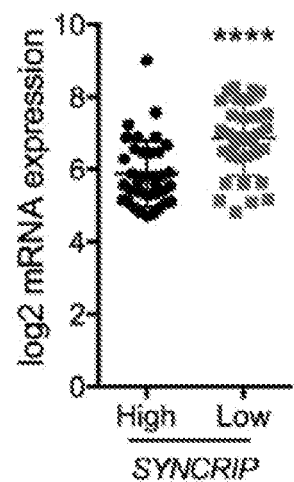
FIG. 12(E) shows $\log_2$ mRNA expression levels of target genes downregulated by HOXA9-MEIS in patients with high vs. low SYNCRIP mRNA expression in AML patients reported in FIG. 4(A) (high SYNCRIP was defined as individuals with a value greater than the average+1 s.d. while low SYNCRIP was defined as individuals with a value greater than the average−1 s.d.). * $p<0.05$, $p<0.01$, * $p<0.001$ by two tailed t test.
Figure 12F:
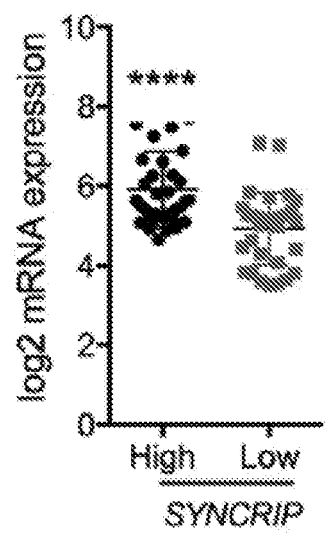
FIG. 12(F) shows $\log_2$ mRNA expression levels of IZKF2 in patients with high vs. low SYNCRIP mRNA expression in AML patients reported in FIG. 4(A) (high SYNCRIP was defined as individuals with a value greater than the average+1 s.d. while low SYNCRIP was defined as individuals with a value greater than the average−1 s.d.). * $p<0.05$, $p<0.01$, * $p<0.001$ by two tailed t test.
Figure 12G:
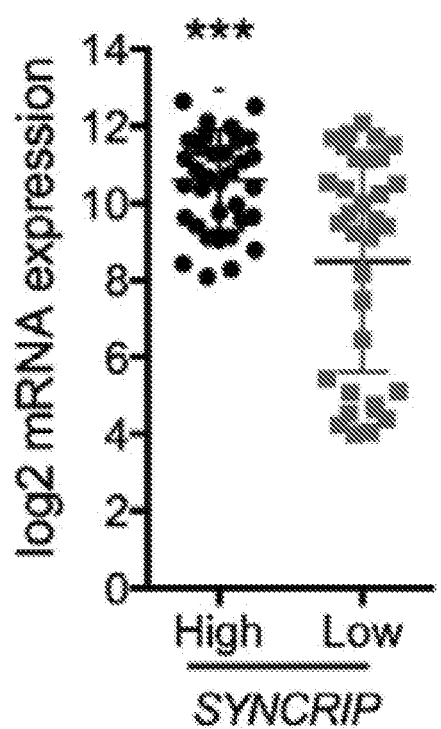
FIG. 12(G) shows $\log_2$ mRNA expression levels of c-MYC in patients with high vs. low SYNCRIP mRNA expression in AML patients reported in FIG. 4(A) (high SYNCRIP was defined as individuals with a value greater than the average+1 s.d. while low SYNCRIP was defined as individuals with a value greater than the average−1 s.d.). * $p<0.05$, $p<0.01$, * $p<0.001$ by two tailed t test.

Additionally, it was found that MLL-AF9 direct targets were enriched for genes downregulated after SYNCRIP depletion (FIGS. 5(E)-5(F)). Consistent with the MLL program being reversed upon SYNCRIP knockdown, genes negatively regulated by HOXA9/MEIS1 were enriched for genes suppressed by SYNCRIP (FIG. 5(G)). Overall, these data demonstrate that SYNCRIP depletion results in a loss of the HSC/LSC program and the MLL-AF9 gene expression program. The studies show that SYNCRIP and MSI2 coregulate the LSC/MLL epigenetic program. Consistent with this observation, genes downregulated after SYNCRIP depletion were significantly enriched for MSI2's direct mRNA binding targets (Top HITS-CLIP; Cross-linking immunoprecipitation followed by high throughput RNA-sequencing targets) (FIG. 5(H)). Furthermore, genes upregulated in SYNCRIP depleted cells were enriched for genes that were also upregulated in Msi2 deleted LSCs (FIG. 5(I)). Genes regulated by MSI2 including Hoxa9, c-Myc, Ikzf2, and Meis1 were found to be downregulated upon loss of SYNCRIP (FIG. 12(B)).

Figure 4A:
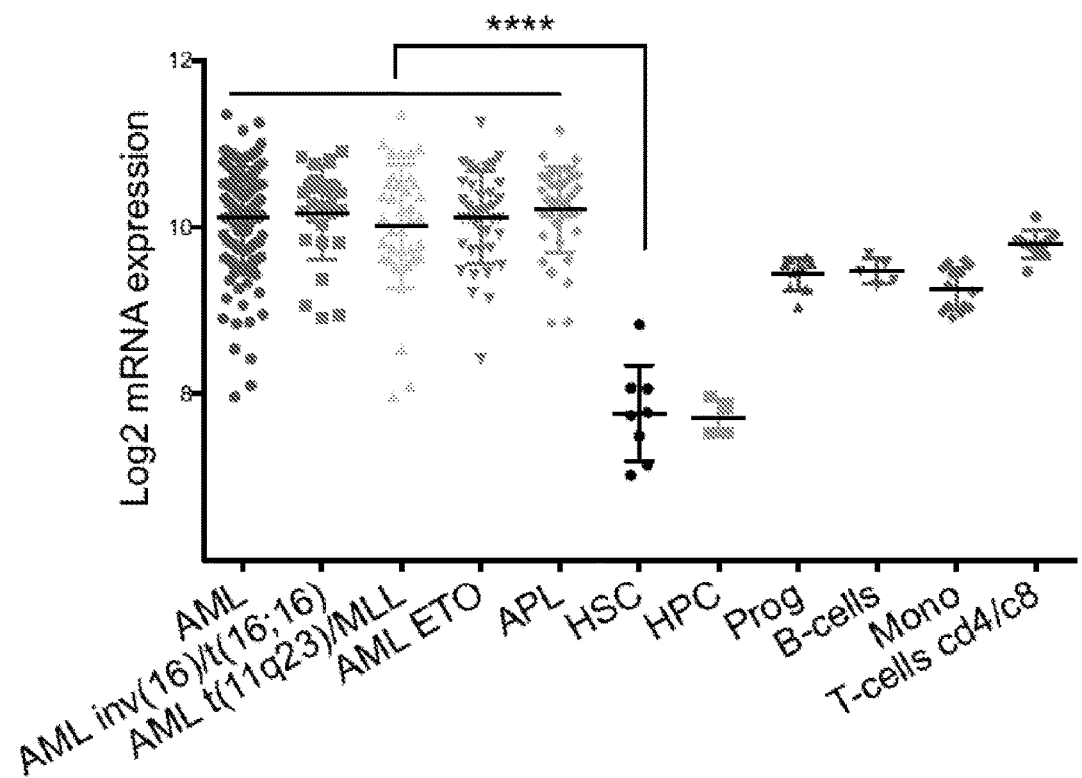
FIG. 4(A) shows that SYNCRIP is upregulated in AML patient samples. The graph shows the $\log_2$ expression of SYNCRIP from transcriptional profiling of bone marrow cells from patients with various subtypes of AML and of the normal hematopoietic stem/progenitor cells (HSPCs) from healthy donors. AML n=142; AML inv(16)/t(16;16) n=27; AML t(11q23)/MLL n=38; AML ETO n=39; APL n=37; HSC n=8; HPC n=4; Prog n=9; B-cells n=5; Mono n=14; T cell CD4/CD8 n=10. error bars, s.e.m. **** $p<0.0001$ two tailed t test. (Hemaexplorer data of SYNCRIP probe 209024_s_at from the U133 Plus 2.0 array).
Figure 4B:
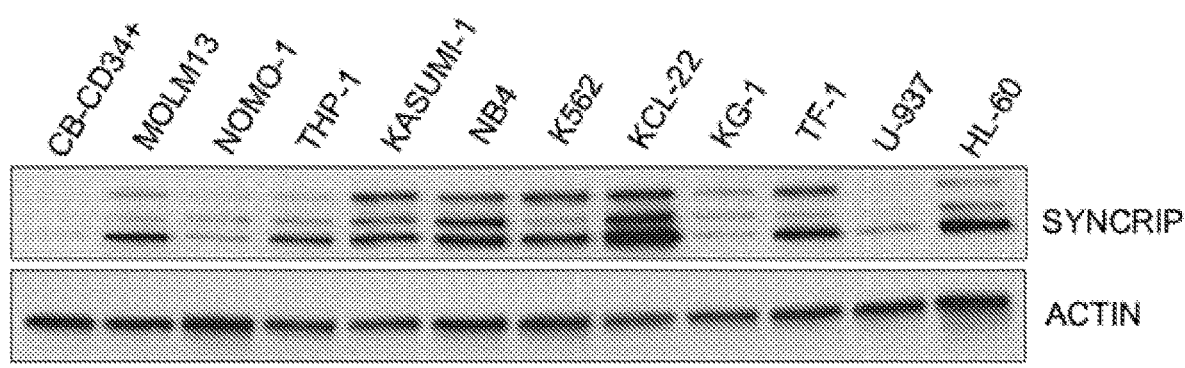
FIG. 4(B) shows high expression levels of SYNCRIP in multiple human AML cell lines. Immunoblot of various myeloid leukemia cell lines are compared to cord blood derived CD34$^+$ cells.
Figure 4C:
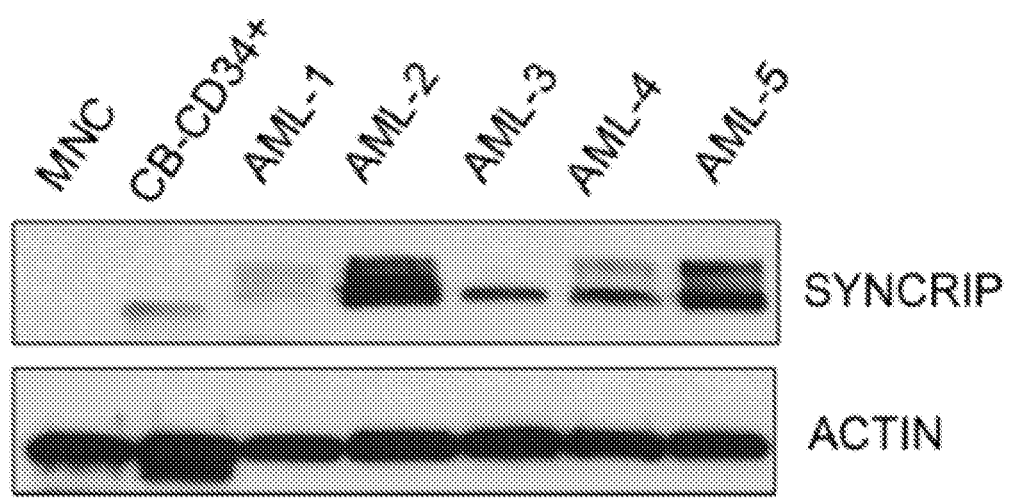
FIG. 4(C) shows SYNCRIP expression in primary AML patient samples. Actin serves as a loading control.
Figure 4D:
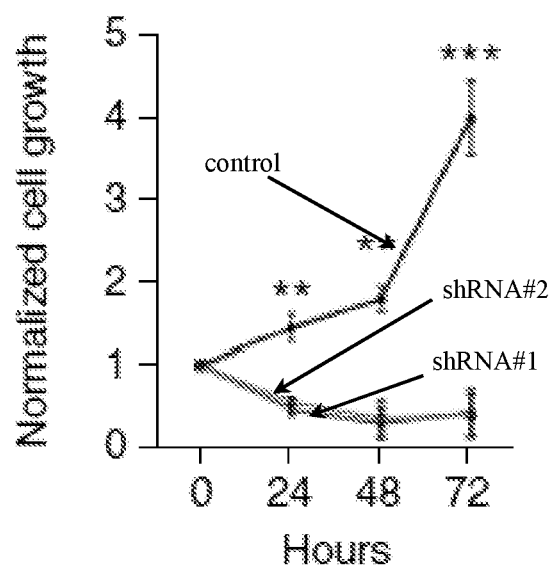
FIG. 4(D) shows cell proliferation in MOLM13 cell line after transduction with lentivirus expressing control or SYNCRIP-specific shRNAs. n=3 independent experiments per cell line; error bars, s.e.m. ***$p<0.001$ two tailed t test.
Figure 4E:
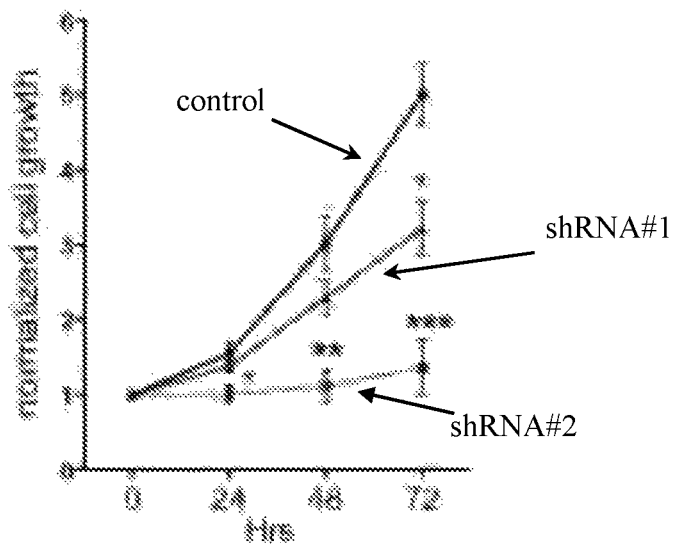
FIG. 4(E) shows cell proliferation in NOMO-1 cell line after transduction with lentivirus expressing control or SYNCRIP-specific shRNAs. n=3 independent experiments per cell line; error bars, s.e.m. ***$p<0.001$ two tailed t test.
Figure 4F:
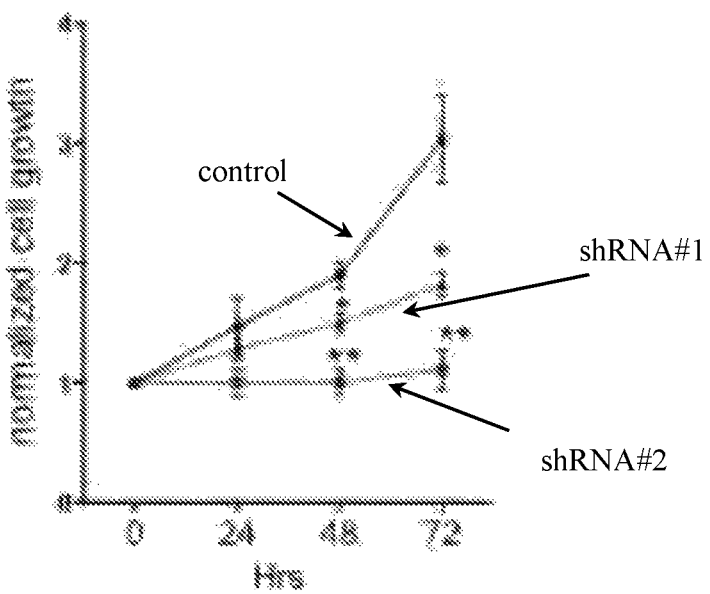
FIG. 4(F) shows cell proliferation in KASUMI-1 cell line after transduction with lentivirus expressing control or SYNCRIP-specific shRNAs. n=3 independent experiments per cell line; error bars, s.e.m. ***$p<0.001$ two tailed t test.
Figure 4G:
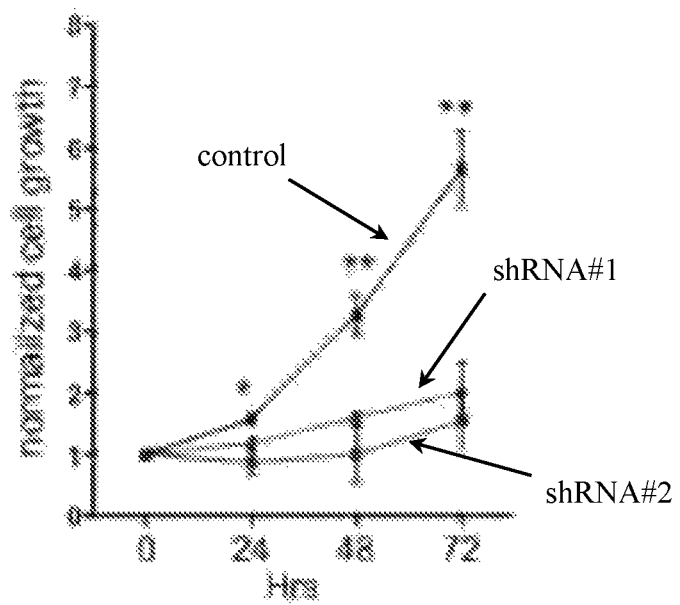
FIG. 4(G) shows cell proliferation in NB4 cell line after transduction with lentivirus expressing control or SYNCRIP-specific shRNAs. n=3 independent experiments per cell line; error bars, s.e.m. ***$p<0.001$ two tailed t test.
Figure 4H:
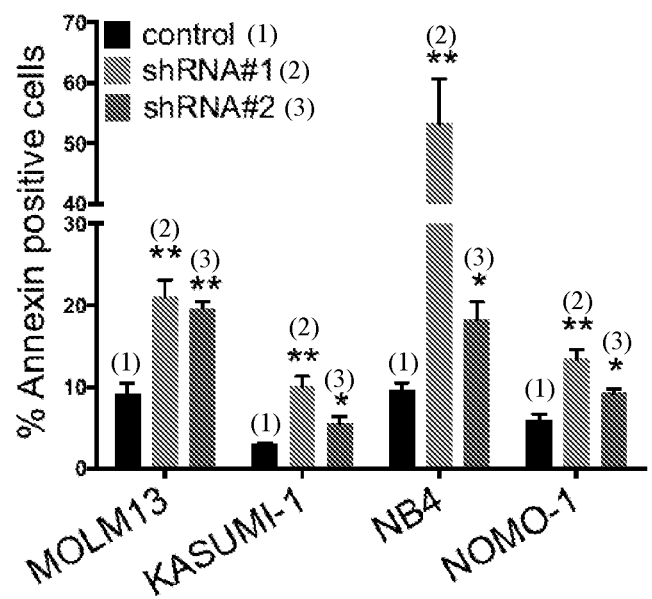
FIG. 4(H) shows Annexin-V expression assessed by flow cytometry 24 hours post puromycin selection. n=3 independent experiments per cell line; error bars, s.e.m.* $p<0.05$, **$p<0.001$ two tailed t test.

A human expression dataset was examined (FIG. 4(A)) and it was found that elevated SYNCRIP expression corresponded to an increase in HOXA9/MEIS1 target genes, IKZF2 and c-MYC, but without corresponding to altered MSI2 levels (FIGS. 12(C)-12(G)). Taken together, these data show that SYNCRIP and MSI2 coregulate a gene expression program that is essential for myeloid leukemia cells.

Accordingly, the SYNCRIP-specific inhibitory nucleic acids disclosed herein are useful in methods for inhibiting leukemic cell proliferation and treating AML in a subject in need thereof.

Example 7: SYNCRIP and MSI2 Interact Through Shared Common mRNA Targets

Figure 6A:
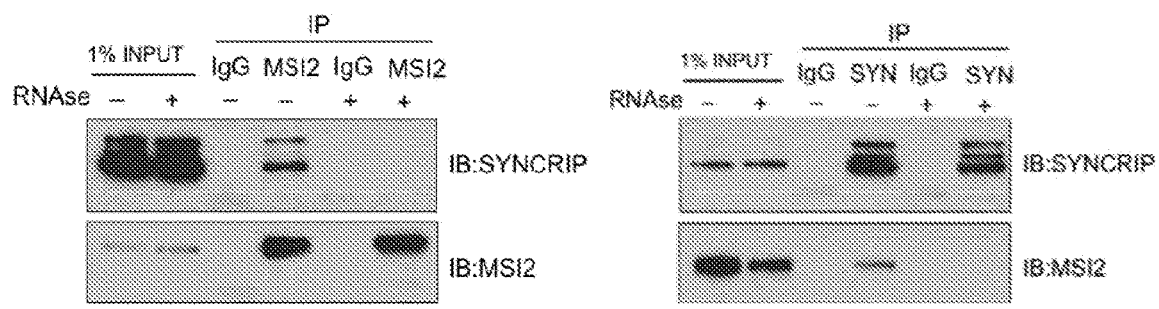
FIG. 6(A) shows immunoprecipitation of endogenous MSI2 and SYNCRIP in human myeloid leukemia K562 cells overexpressing MSI2. Lysates of K562 cells overexpressing MSI2 were incubated with RNase and immunoprecipitated.

To investigate the interaction between SYNCRIP and MSI2, reciprocal immunoprecipitations were performed in MSI2 overexpressing leukemia cell line (K562) to confirm SYNCRIP as an identified protein-protein interacting partner of MSI2 from the mass-spectrometry data. The interaction was detected by reciprocal immunoprecipitation using antibodies against either MSI2 or SYNCRIP. It was found that the interaction is RNA-dependent, as treatment of the lysate with RNase diminished the interaction between the two proteins (FIG. 6(A)).

Figure 6B:
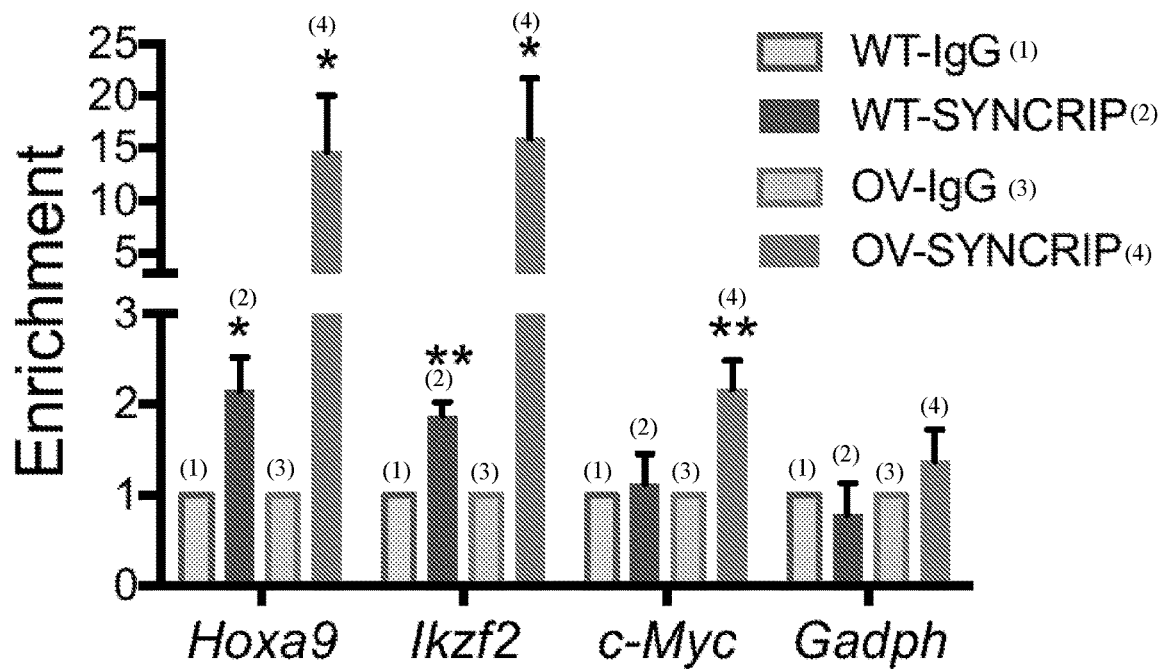
FIG. 6(B) shows immunoprecipitation of SYNCRIP with IgG or SYNCRIP antibody in either wild-type (WT) mouse RN2 MLL-AF9 leukemia cells or human SYNCRIP overexpressing (OV) mouse RN2 MLL-AF9 leukemia cells. n=4 independent experiments; error bars, s.e.m. * $p<0.05$, **$p<0.001$ two tailed t test.
Figure 6C:
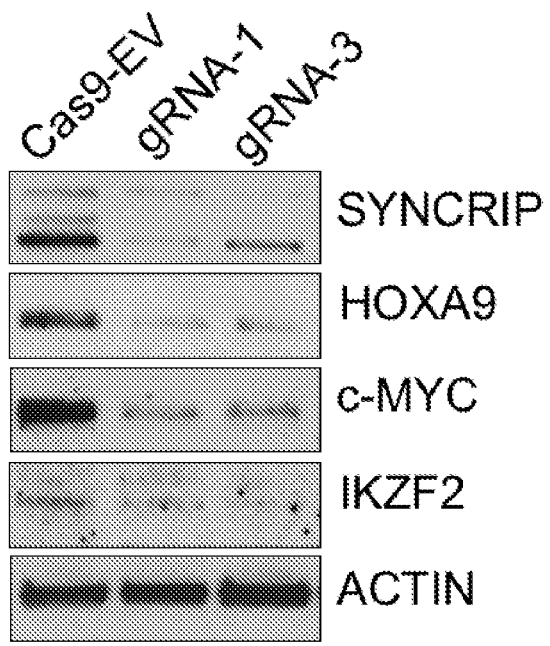
FIG. 6(C) shows downregulation of HOXA9, c-MYC and IKZF2 protein levels upon SYNCRIP knock down in RN2 cells 24 hours post induction with tetracycline with as assessed by immunoblot analysis.
Figure 6D:
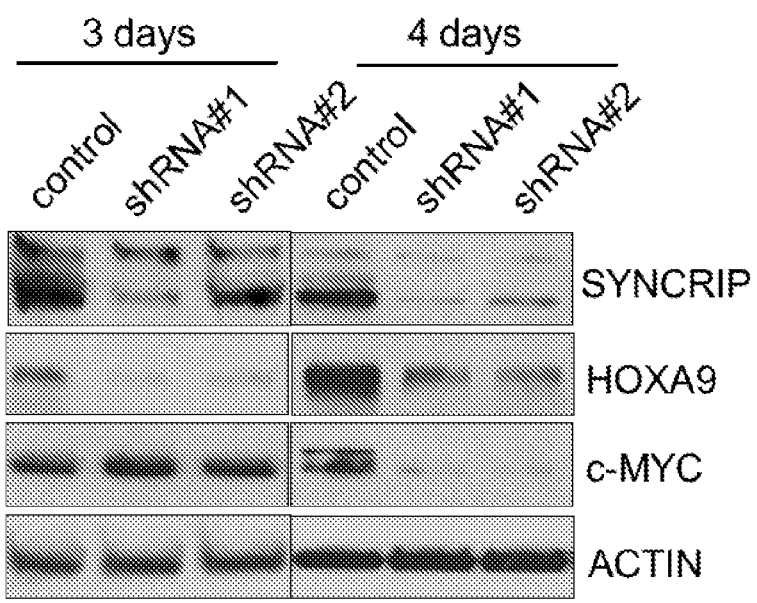
FIG. 6(D) shows expression levels of HOXA9 and c-MYC upon SYNCRIP-KD in human MOLM13 leukemia cells 3 and 4 days post transduction with viruses expressing control shRNA and SYNCRIP-shRNAs together with GFP as assessed by immunoblot analysis.

A similar interaction was observed in MOLM13, a myeloid leukemia cell line carrying MLL-AF9 fusion protein (FIG. 13(A)). This data shows that SYNCRIP and MSI2 bind to a common set of mRNA targets. To test if SYNCRIP and MSI2 share MSI2's previously validated targets in MLL-AF9 driven leukemia, RNA-IP was performed. AS shown in FIG. 6(B), SYNCRIP also binds Myc, Hoxa9, and Ikzf2 mRNA.

Example 8: SYNCRIP Post-Transcriptionally Regulates HOXA9 Expression

Targeted depletion of SYNCRIP with CRISPR/Cas9 or shRNA hairpins in multiple myeloid leukemia cells (RN2 cells, mouse dsRed MLL-AF9 cells and MOLM13 cells) significantly reduced HOXA9 (FIGS. 6(C)-6(D) and FIGS. 13(B)-13(C)). A decrease in c-MYC and IKZF2 was observed with CRISPR/Cas9 depletion of SYNCRIP in RN2 cells (FIG. 6(C)), while reduction in c-MYC was observed at 4 days post transduction compared to 3 days post transduction in both dsRed MLL-AF9 cells and MOLM13 cells (FIG. 6(D) and FIGS. 13(B)-13(C)). While these changes occurred at the protein level, variable reductions were also observed in mRNA levels of HoxA9, c-Myc, and Ikzf2 (FIGS. 13(D)-13(E), 13(H)-13(J)). MSI2 depletion reduced HOXA9 and c-MYC protein expression and downregulated HoxA9, c-Myc, and Ikzf2 mRNA levels at 4 days post transduction, similar to the phenotype observed in SYNCRIP knockdown cells (FIGS. 13(F)-13(G)).

Figure 6E:
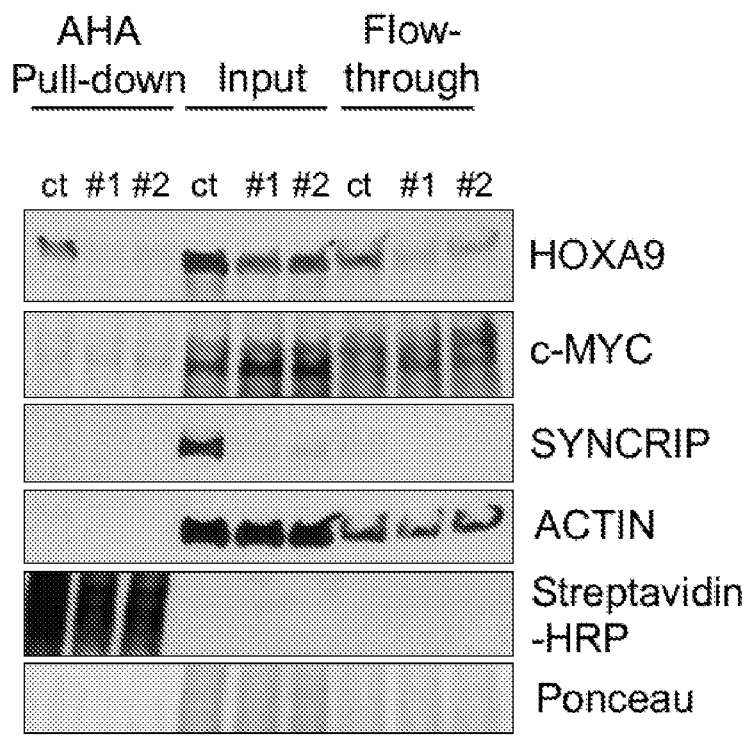
FIG. 6(E) shows protein expression levels of SYNCRIP, HOXA9 and c-MYC in AHA-pull down fraction, input and flow through fraction as assessed by immunoblot analysis. AHA incorporation into newly synthesized HOXA9 (but not c-MYC) proteins was reduced in SYNCRIP-KD cells. Streptavidin-HRP, Ponceau staining and Actin serve as control for total protein input and loading control.
Figure 6F:
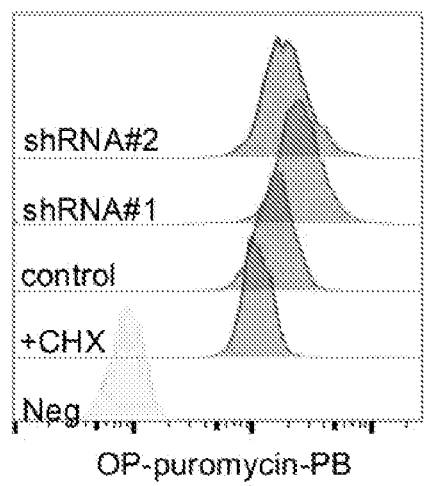
FIG. 6(F) shows representative histogram analysis of OP-Puro incorporation in control and SYNCRIP-KD MOLM13 cells (shRNA #1 and shRNA #2) at 3 days post transduction with viruses expressing control shRNA and SYNCRIP-shRNAs.
Figure 6G:
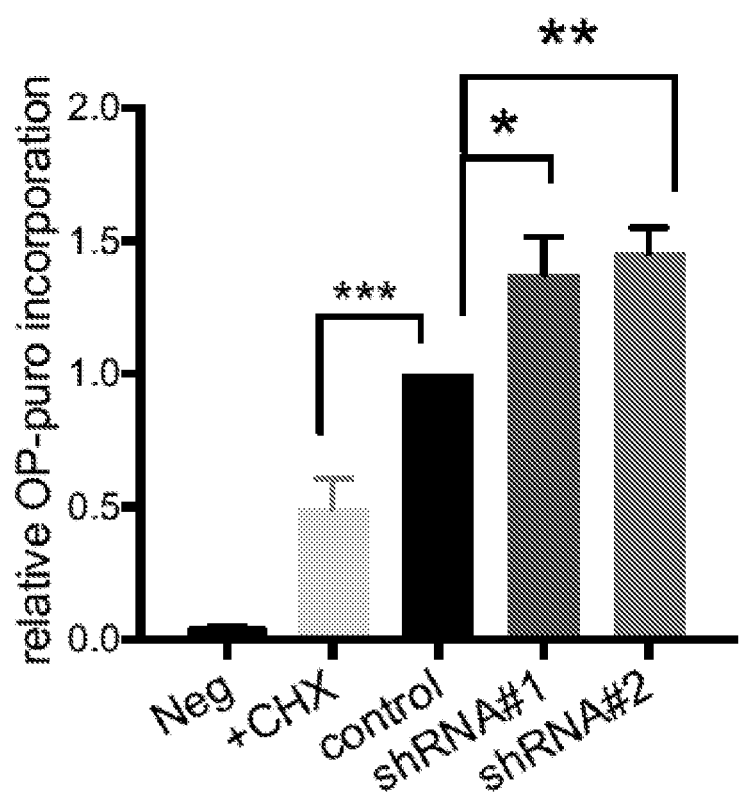
FIG. 6(G) shows quantitative summary of relative OP-Puro incorporation in cells described in FIG. 6(F). CHX-treated cells were used as negative control (n=3). Cells without OP-Puro incorporation served as staining control. n=4 independent experiments; error bars, s.e.m. *p<0.05, p<0.001, *p<0.0001 two tailed t test.

To further understand the mechanism for SYNCRIP regulation of HOXA9 expression, the effects of SYNCRIP depletion on total RNA was examined. There was no change in SYNCRIP depleted cells compared to control cells (FIG. 13(K)). Additionally, reduced HOXA9, c-MYC, and IKZF2 protein levels in SYNCRIP depleted cells were not due to an effect on mRNA stability, since mRNA levels of these genes were equivalent after the addition of actinomycin D to block transcription (FIGS. 13(L)-13(M)). Moreover, measurement of newly synthesized proteins based on AHA incorporation revealed a significant decrease in AHA labeled HOXA9 protein in SYNCRIP depleted cells. Despite its short half-life, c-MYC labeling at day 3 remained unchanged (FIG. 6(E)), and global peptide synthesis was modestly increased by quantifying total OP-Puro incorporation (FIGS. 6(F)-6(G)). This data shows that SYNCRIP, in part, controls translation of specific targets including HOXA9.

Accordingly, the SYNCRIP-specific inhibitory nucleic acids disclosed herein are useful in methods for inhibiting leukemic cell proliferation and treating AML in a subject in need thereof.

Figure 7A:
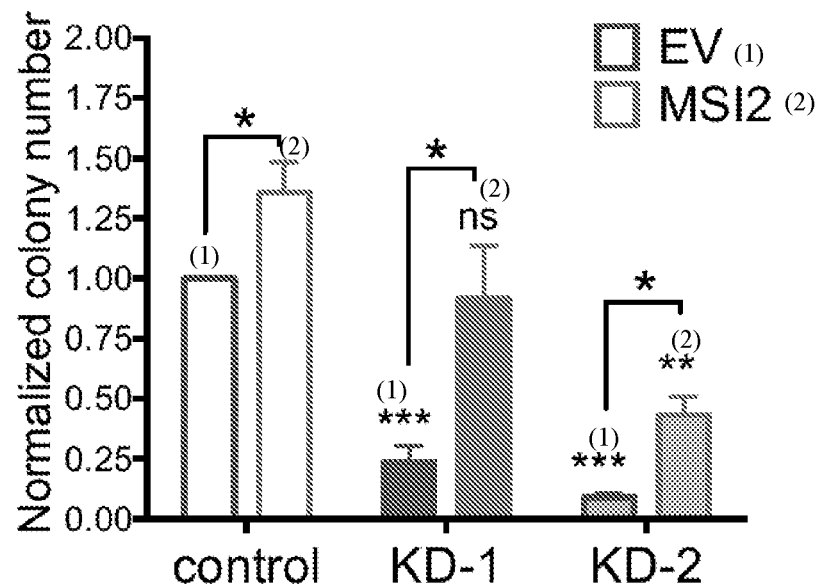
FIG. 7(A) shows colony formation was rescued in dsRed SYNCRIP-KD leukemia cells with MSI2 overexpression. n=3 independent experiments.
Figure 7B:
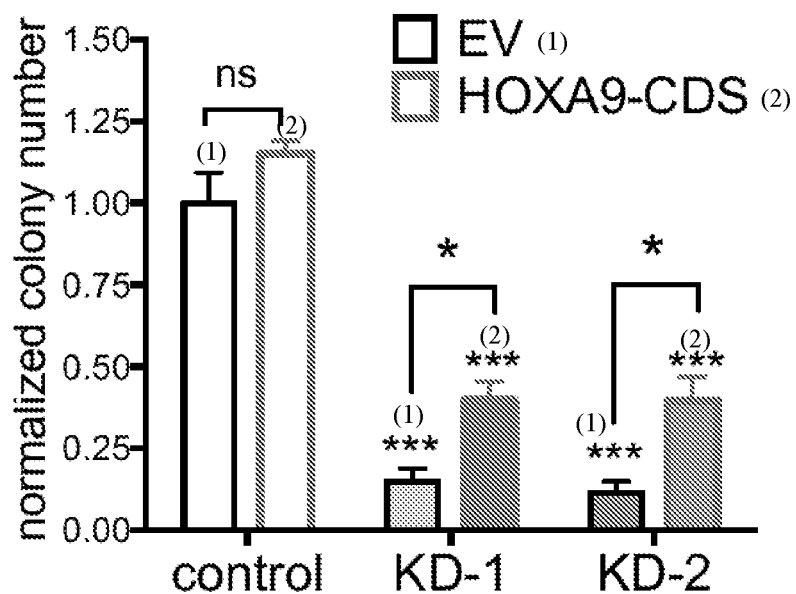
FIG. 7(B) shows colony formation was rescued in dsRed SYNCRIP-KD leukemia cells with HOXA9-CDS overexpression. n=4 independent experiments.
Figure 7C:
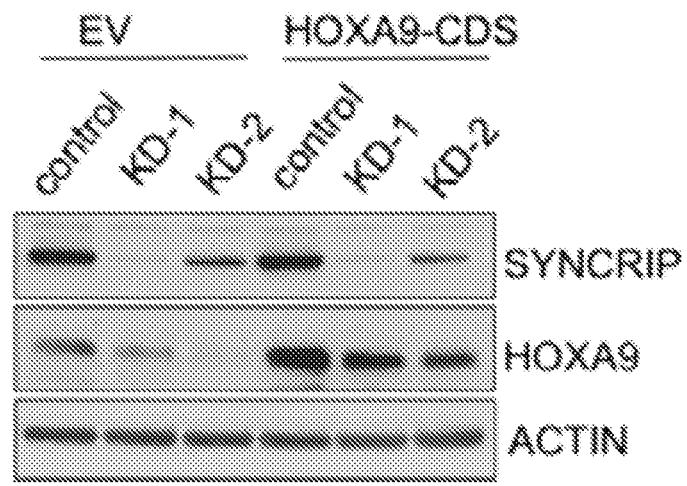
FIG. 7(C) shows depletion of SYNCRIP expression and expression of HOXA9 in dsRed SYNCRIP-KD leukemia cells that overexpress HOXA9-CDS as assessed by immunoblot analysis 4 days after transduction.
Figure 7D:
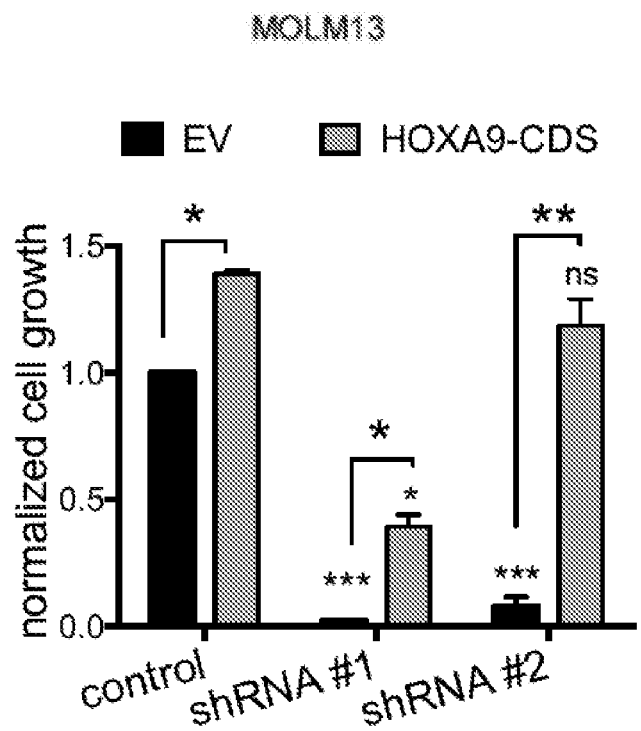
FIG. 7(D) shows rescue of cell growth in SYNCRIP-KD human MOLM13 leukemia cells with HOXA9 overexpression. n=3 independent experiments.
Figure 7E:
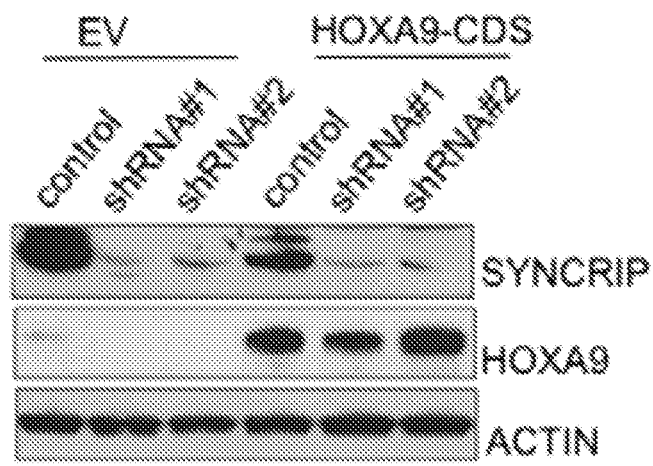
FIG. 7(E) shows depletion of SYNCRIP expression and expression of HOXA9 in SYNCRIP-KD human MOLM13 leukemia cells that overexpress HOXA9-CDS as assessed by immunoblot analysis 4 days after transduction.

Example 9: HOXA9 is a Functional Downstream Target of SYNCRIP in Leukemia Cells In support of SYNCRIP and MSI2 co-regulating the MLL-associated transcriptional program, MSI2 overexpression rescued the reduced colony formation and reversed the reduction of HOXA9 after shRNA-SYNCRIP depletion (FIG. 7(A) and FIGS. 14(A)-14(B)). Verifying the functional relationship between SYNCRIP and HOXA9, retroviral HOXA9 overexpression partially reversed the reduction in colony formation of dsRed MLL-AF9 cells after SYNCRIP depletion (FIGS. 7(B)-7(C) and FIGS. 14(C)-14(D)). Similarly, overexpression of HOXA9 also rescued the cell growth in SYNCRIP-KD MOLM13 cells (FIGS. 7(D)-7(E)). In contrast, forced MYC expression failed to rescue the effects of SYNCRIP depletion (FIGS. 14(E)-14(H)). MYC protein levels were also reduced after SYNCRIP depletion but remained higher than the controls after shRNA depletion. This data shows that SYNCRIP maintains translation of the MLL and LSC program in part through its control of HOXA9 expression.

Figure 7F:
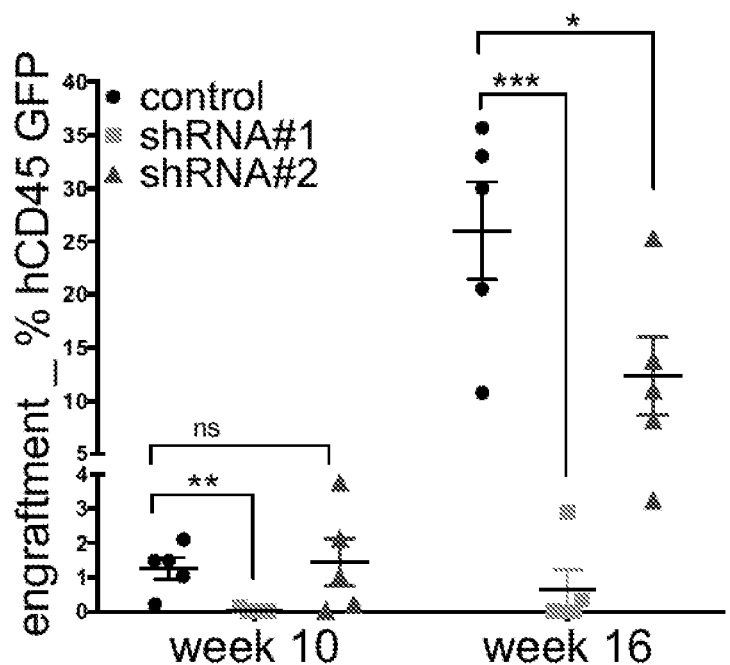
FIG. 7(F) shows quantitative summary of percentage of engrafted hCD45$^+$ GFP$^+$ cells in recipient mice transplanted with primary AML patient cells transduced with control shRNA or shRNAs against SYNCRIP (shRNA #1 and shRNA #2) at week 10 and week 16 post transplantation. n=5 for each group.
Figure 7G:
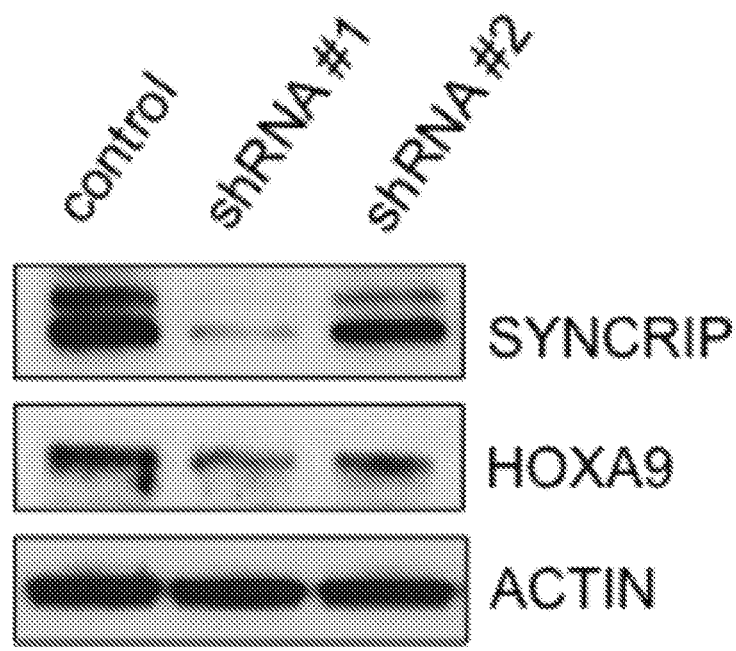
FIG. 7(G) shows depletion of SYNCRIP expression in primary AML patient cells and downregulation of HOXA9 expression as assessed by immunoblots analysis. All data: error bars, s.e.m. ns: *p<0.05, p<0.001, *p<0.0001 two tailed t test.
Figure 7H:
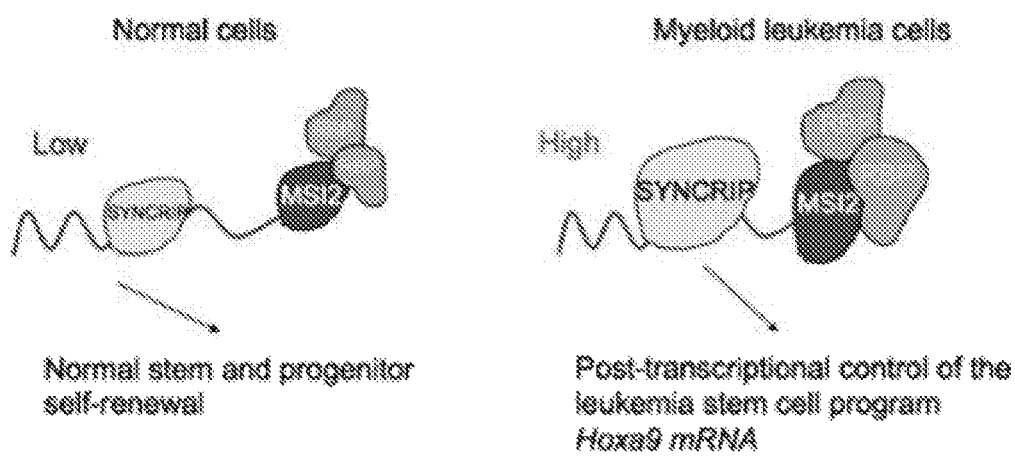
FIG. 7(H) shows a schematic depicting the dominant function of SYNCRIP when its expression is elevated in LSCs in comparison to normal HSCs. In LSCs, SYNCRIP and MSI2 binds and increases expression of the mRNA transcripts associated with the MLL self-renewal program, including Hoxa9 thus driving the LSC program instead of normal hematopoietic development.

To directly demonstrate the relevance of SYNCRIP function in human leukemia, SYNCRIP expression was knocked down in leukemia cells derived from a primary AML patient by transducing cells with control shRNA or SYNCRIP-shRNAs. Engraftment of the cells in vivo was monitored after transplantation of sorted GFP positive transduced cells into recipient mice. Depletion of SYNCRIP protein expression resulted in a marked reduction in engraftment of human CD45 GFP positive leukemia cells at week 10 (for shRNA #1) and week 16 (for both shRNA #1 and #2) (FIG. 7(F)). HOXA9 expression in the primary AML patient cells correlated with extent of SYNCRIP shRNA depletion (FIG. 7(G)). This data shows that SYNCRIP regulates myeloid leukemia cell survival at least in part through regulating expression of HOXA9, a critical target in leukemia. FIG. 7(H) shows a schematic depicting the dominant function of SYNCRIP when its expression is elevated in LSCs in comparison to normal HSCs. In LSCs, SYNCRIP and MSI2 binds and increases expression of the mRNA transcripts associated with the MLL self-renewal program, including Hoxa9 thus driving the LSC program instead of normal hematopoietic development.

Accordingly, the SYNCRIP-specific inhibitory nucleic acids disclosed herein are useful in methods for inhibiting leukemic cell proliferation and treating AML in a subject in need thereof.

Example 10: Effects of SYNCRIP Depletion on Normal Hematopoietic Stem Cells Function and Leukemia Stem Cell Function Using SYNCRIP Conditional Knockout (cKO) Mouse Model Using the Syncrip cKO mouse model described herein, the Cre transgene will be activated by injecting the mice with polyinositol-polycytosine (pIpC) three times. Deletion of Syncrip will be determined by PCR, quantitative real time PCR (qPCR) and western blot analysis within the hematopoietic stem and progenitor cells (HSPCs; LSK: Lineage$^{lo}$ c-kit$^+$ Sca$^+$). Cohorts of 10 animals of Syncrip deleted mice Syncrip$^{\Delta/\Delta}$ and control Syncrip$^{flox/flox}$ mice will be sacrificed and assessed for hematopoietic phenotypes. Complete analysis will include peripheral blood counts, histopathology, flow cytometry for terminally differentiated cells using Mac1, Gr1, B220, CD3, CD4 and CD8; multiparametric flow cytometry analysis to characterize the size and distribution of the stem and progenitor compartments; cell cycle analysis of stem and progenitor compartments using Hoechst and pyronin Y staining, and apoptosis analysis using Annexin V staining.

Stem cell function will be assayed using in vitro colony forming assays in methylcellulose, and in vivo long-term repopulating potential in non-competitive and competitive repopulation and serial transplantation assays (primary, secondary and tertiary). See FIG. 25(B). It is anticipated that SYNCRIP depletion will not adversely impact hematopoietic homeostasis in normal hematopoietic stem cells.

As demonstrated herein, depletion of SYNCRIP with shRNAs and CRIPSR-sgRNAs resulted in apoptosis and growth inhibition of leukemia cells. To determine if SYNCRIP is required for LSC function and leukemia initiation and maintenance, retroviral transductions of MLL-AF9 oncogene to LSK cells isolated from 3 SYNCRIP deficient Syncrip$^{\Delta/\Delta}$ and 3 control mice will be performed. Transformed cells from each donor will be injected into 6 recipients mice. Survival of recipient mice will be monitored and a complete analysis will be performed at the time of sacrifice. Complete analysis will include peripheral blood counts, histopathology, flow cytometry for terminally differentiated cells using Mac1, Gr1, B220, CD3, CD4 and CD8; multi-parametric flow cytometry analysis to characterize the size and distribution of the stem and progenitor compartments; cell cycle analysis of stem and progenitor compartments using Hoechst and pyronin Y staining, and apoptosis analysis using Annexin V staining.

To evaluate requirement of SYNCRIP for maintenance of leukemia in vivo, LSK isolated from Syncrip$^{flox/flox}$:Mx1-Cre and control Syncrip$^{flox/flox}$ mice will be transformed with MLL-AF9 oncogene and the cells will be transplanted into recipient mice. Prior to onset of leukemia, pIpC injection will be initiated at week 12 and the animals will be evaluated as described above to determine whether loss of SYNCRIP will attenuate disease penetrance and/or latency or alter the disease phenotype. Frequency and number of LSCs will be determined by frequency of c-kit$^{high}$ cells and limiting-dilution transplantation of leukemia formed in recipient mice (FIG. 25(C)). It is anticipated that SYNCRIP depletion will adversely impact LSC function and leukemia initiation and maintenance.

Accordingly, the SYNCRIP-specific inhibitory nucleic acids disclosed herein are useful in methods for inhibiting leukemic cell proliferation and treating AML in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for treating or preventing Acute Myeloid Leukemia (AML) in a subject in need thereof, comprising administering to the subject a therapeutically effective amount of at least one SYNCRIP-specific inhibitory nucleic acid that inhibits synaptotagmin-binding, cytoplasmic RNA-interacting protein (SYNCRIP) expression levels or activity in the subject,
wherein the at least one SYNCRIP-specific inhibitory nucleic acid is a siRNA, an antisense oligonucleotide, or a sgRNA,
wherein the at least one SYNCRIP-specific inhibitory nucleic acid is about 20-30 nucleotides in length; and
wherein the at least one SYNCRIP-specific inhibitory nucleic acid has 100% complementarity to a coding region of a SYNCRIP nucleic acid sequence.

2. The method of claim 1, wherein the at least one SYNCRIP-specific inhibitory nucleic acid comprises a nucleic acid sequence selected from the group consisting of: SEQ ID NO: 1, SEQ ID NO: 2, SEQ ID NO: 18, SEQ ID NO: 19, SEQ ID NO: 20, SEQ ID NO: 21, and any complement thereof.

3. The method of claim 1, wherein the subject displays elevated expression levels of SYNCRIP protein in leukemic cells prior to treatment.

4. The method of claim 1, wherein treatment with the at least one SYNCRIP-specific inhibitory nucleic acid results in a decrease in SYNCRIP and/or HOXA9 levels in the subject compared to that observed prior to treatment.

5. The method of claim 1, wherein the subject has been diagnosed as having AML.

6. The method of claim 5, wherein the signs or symptoms of AML comprise one or more of leukemic cell proliferation, enlarged lymph nodes, anemia, neutropenia, leukopenia, leukostasis, chloroma, granulocytic sarcoma, myeloid sarcoma, fatigue, weakness, dizziness, chills, headaches, shortness of breath, thrombocytopenia, excess bruising and bleeding, frequent or severe nosebleeds, bleeding gums, gum pain and swelling, headache, weakness in one side of the body, slurred speech, confusion, sleepiness, blurry vision, vision loss, deep venous thrombosis (DVT), pulmonary embolism, bone or joint pain, swelling in the abdomen, seizures, vomiting, facial numbness, defects in balance, weight loss, fever, night sweats, and loss of appetite.

7. The method of claim 1, wherein the subject harbors one or more point mutations in NRAS, DNMT3A, FLT3, KIT, IDH1, IDH2, CEBPA and NPM1 or wherein the subject harbors one or more gene fusions selected from the group consisting of CBFB-MYH11, DEK-NUP214, MLL-MLLT3, PML-RARA, RBM15-MKL1, RPN1-EVI1 and RUNX1-RUNX1T1.

8. The method of claim 1, wherein the subject is human.

9. The method of claim 1, wherein the at least one SYNCRIP-specific inhibitory nucleic acid is administered orally, topically, intranasally, systemically, intravenously, subcutaneously, intraperitoneally, intradermally, intraocularly, iontophoretically, transmucosally, or intramuscularly.

10. The method of claim 1, further comprising separately, sequentially or simultaneously administering one or more additional therapeutic agents to the subject.

11. The method of claim 10, wherein the additional therapeutic agents are selected from the group consisting of cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacnne, etoposide phosphate, teniposide, azacitidine (Vidaza), decitabine, accatin III, 10-deacetyl-taxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, or combinations thereof.

12. The method of claim 1, wherein the at least one SYNCRIP-specific inhibitory nucleic acid is administered daily for 6 weeks or more or for 12 weeks or more.

13. A method for inhibiting leukemic cell proliferation in a subject in need thereof, comprising administering to the subject a therapeutically effective amount of a SYNCRIP-specific inhibitory nucleic acid,
  wherein the SYNCRIP-specific inhibitory nucleic acid is a siRNA, an antisense oligonucleotide, or a sgRNA,
  wherein the SYNCRIP-specific inhibitory nucleic acid is about 20-30 nucleotides in length; and
  wherein the SYNCRIP-specific inhibitory nucleic acid has 100% complementarity to a coding region of a SYNCRIP nucleic acid sequence.

14. The method of claim 13, wherein the SYNCRIP-specific inhibitory nucleic acid comprises a nucleic acid sequence selected from the group consisting of: SEQ ID NO: 1, SEQ ID NO: 2, SEQ ID NO: 18, SEQ ID NO: 19, SEQ ID NO: 20, SEQ ID NO: 21, and any complement thereof.

* * * * *

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtacctgtat tacccaatgc                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 2
caatttggaa ttgaccgcac                                                    20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtgttcag gactacttgg acac                                               24

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtctatgctt tccatagatg gttgtag                                            27

<210> SEQ ID NO 5
<211> LENGTH: 6716
<212> TYPE: DNA
<213> ORGANISM: Homo sapiens

<400> SEQUENCE: 5
ctccactcgc gccggacaca gggagcagcg agcacgcgtt tcccgcaacc cgataccatc        60
ggacaggatt tctccgcctc agcccaacgg ggagggctag ttgcacatag tgatttagat       120
gaaagagcta ttgaagcttt aaaagaattc aatgaagacg tgcattggc agttcttcaa        180
cagtttaaag acagtgatct ctctcatgtt cagaacaaaa gtgcctttttt atgtggagtc     240
atgaagactt acaggcagag agaaaaacaa gggaccaaag tagcagattc tagtaaagga       300
ccagatgagg caaaaattaa ggcactcttg gaaagaacag gctacacact tgatgtgacc       360
actggacaga ggaagtatgg aggaccacct ccagattccg tttattcaga tatttgtggg       420
aaagatccca agagatctat ttgaggatga acttgttcca ttatttgaga agctggacc       480
tatatgggat cttcgtctaa tgatggatcc actcactggt ctcaatagag gttatgcgtt       540
tgtcactttt tgtacaaaag aagcagctca ggaggctgtt aaactgtata ataatcatga       600
aattcgttct ggaaaacata ttggtgtctg catctcagtt gccaacaata ggcttttttgt      660
gggctctatt cctaagagta aaaccaagga acagattctt gaagaattta gcaaagtaac       720
agagggtctt acagacgtca ttttataccca ccaaccggat gacaagaaaa aaacagagg       780
cttttgcttt cttgaatatg aagatcacaa aacagctgcc caggcaaggc gtaggttaat       840
gagtggtaaa gtcaaggtct gggggaatgt tggaactgtt gaatgggctg atcctataga       900
agatcctgat cctgaggtta tggcaaaggt aaaagtgctg tttgtacgca accttgccaa       960
tactgtaaca gaagagattt tagaaaaggc atttagtcag tttgggaaac tggaacgagt      1020
gaagaagtta aaagattatg cgttcattca ttttgatgag cgagatggtg ctgtcaaggc      1080
tatggaagaa atgaatggca aagacttgga ggggagaaaa ttgaaattg ttttttgccaa      1140
gccaccagat cagaaaagga agaaagaaa agctcagagg caagcagcaa aaaatcaaat      1200

```
gtatgacgat tactactatt atggtccacc tcatatgccc cctccaacaa gaggtcgagg    1260
gcgtggaggt agaggtggtt atggatatcc tccagattat tatggatatg aagattatta    1320
tgattattat ggttatgatt accataacta tcgtggtgga tatgaagatc catactatgg    1380
ttatgaagat tttcaagttg gagctagagg aaggggtggt agaggagcaa ggggtgctgc    1440
tccatccaga ggtcgtgggg ctgctcctcc ccgcggtaga gccggttatt cacagagagg    1500
aggtcctgga tcagcaagag gcgttcgagg tgcgagagga ggtgcccaac aacaaagagg    1560
ccgcgggcag ggaaaagggg tcgaggccgg tcctgacctg ttacaatgaa gactgacttg    1620
ctatgtggga ttacaccaga agcttgcagt ggagtaatgg taaggaaatc aagcaacctt    1680
aaatatgtcg gctgtatagg agcatattct attgcagaag accttcctat gaagatcatg    1740
gaatcaaata cgggacattg aactaatact tggactttga tatgaatttc tttaacaatt    1800
ttctctgcag tgcaagttat taaactaaag ctactctatt ttcaaaatgt gttccaacag    1860
aaatccttca taactcctag catggtatct taataaagaa taaagttctt ttaaaaatct    1920
gctctaagta gattttttccc cttttttaaa ttaaggatcc caacagtggt attttgaaat    1980
attctcttga atttgtgcat ttaaatttta ttgcagtggt atagatgaat gccactgatg    2040
gtatccttaa attttatttc tgctcaccaa ggttaatcat gattgtctat atcttttta     2100 tagtgatcac ttttgaattg tgttcagata tgcagtttca ggtgtaatca tcagagctgg    2160
ttagtcaggc attccagata gtggttcttt tcagaacctt tttaaagggg ttggttaact    2220
acctcagtag cagaggattg aactataccc tgtctgtact gtacatagaa aatctttgta    2280
gataaaagca aggcttgtta aatatgatat gagggtaaga ttttaatata ccaaatgtaa    2340
cattcttagt tgcctttagt ttcagaggct tgtaagactt cctcatgacc atcataacag    2400
gccttgcttt tgtcgtattt tgtggctgaa aaagcagcct tgcttcttca gatattgtag    2460
ttatttggat gtataatagt ttagcaagat gttacttttg taagacatca gatgttcaaa    2520
aaagtgcatc cgaacttgta ctaaatactg cagtgtccct ttataaaaag tcagactaaa    2580
actgacaatt gtacagcgaa gcctgacatt tggatatttt gaagttttt cataaatcat     2640 agaaattagt atatggctgt agtttagctt tttaggtaaa aggtatgttt cattagtgca    2700
tttcttcctg ctgatcactg taaacatgtg aatcagcttt ccatttctta tgcaggtcat    2760
gataacttgt agagtagagt acaatcattt gtgctatgtt tttaattttc taaagcacct    2820
tgatgacagt gagtgtccag tggtgaagca tcctctattg aaccaccctc aaaaattttt    2880
ttgccaagtc ctaagttgat agcttaaagt aaaaagtgaa aattatagtt tcattaggac    2940
ttggtgtaaa gaaatcccct ccccccttcc ccaagggat actgcagtta tatcacatac      3000
ccaataggca ccacgatgaa gatcagagct tatacttaat taaggtttta tacacaccag    3060
ttccccagta aatgcaaatt taacaagaaa atcagacatg tcatatgttc aaaatgctca    3120
tggcaaacaa tcattttgca ttcctgcaaa taaaattgtt ttatactgta agctggaggc    3180
gagtgtaact tattttgta ataaagtttt tattttttt atgtgtcatt aatataaatg       3240
tgtgttagtg tagaaatctt ctggtttaaa aacttagaat tgcacacatt tcagtatgtt    3300
tatttgtact tacataattt tagaatagtg gttgccaata gcctgtatgt ttcacattaa    3360
ttggtttttt gttatctaaa taaatcattt tagtatgttg tatgtcagtt actgggatag    3420
ctgggacata gagtgtaatt taaaatttgt caataagtat tcattggaat atatgtaaat    3480
gtgccttgcc ggttattgaa acttatctac aaaatgagta tggggtgaca aaaattagtt    3540
```

```
cctggtgctt aatgaaactt tctgccactg attttatata ttaccccgtg cttttttaaa    3600
gtacatctct ctcaaaactt agtgtaagtt tgagggctac acaaaacatt tacatttcat    3660
tctaacataa tgaatataat aggttgtgga aagtgggtaa actaaatgta gccttcagta    3720
aaattgaatc tcagtgtaat ccttggtgct ggcatttctc agttccgagg agttaaatga    3780
tcccatctaa gaggtcattg ccatgcctat tggcacttta ctgtcatagc attttaagg     3840
gacactgtca aggtgtttaa gttctcagaa ttacttgttg ggattttagg acaggtttgt    3900
ttacttaaag taagaactgc attgtcaaag ttgaaagagg aacacttttg tgagttcaca    3960
aatgtgttct taagaaaaca ttaaaatatg gagctctggg ttttcaagac tatttggcat    4020
tcttaatttg gggacttggg agggaaactg ataaaaagaa attgaagaat tgatggttat    4080
acttaaagaa gggtaatgta aacagtggtg atgaaatata tacacatcaa gtgaaattac    4140
ttgacagtgt tcatttgaat gactttgaat tcaagccatt ataattactt ttaaaattaa    4200
atatcatttg cactgttctg ataatgggtg cagttttga gcaatataat cagagctaaa     4260
tatgcatgta gtgattagtg atgtgaacaa ttaacgttct gagaagaaat actaactgtg    4320
gtattttcaa acttaaattt ctgtagtaaa atcagtatca aagtcttatc agatcaagga    4380
aaaacaggca atgcatataa acatactttt gaatgttgtg tggcctataa agcaataatg    4440
caatttatat ggaatgtcat gggatatgag aaatggaaat gcaaaaataa ctaatccttt    4500
agtaaaaatg tcaacatgtt aaagggggaa tgttaactaa tgtaggttat tgctatttgt    4560
gatttgttta tgggttcttg gctttgacag cttcaaagaa tggacagtga taagttaaaa    4620
gaaattttgt atattgtcaa ggaaagggtc ttaaatccga gtcaagtccc ttccttgggg    4680
taaaaaatgt attcttaaag cattctgatg ttaaaaagaa aacttaagtt atctaaccaa    4740
aacagacgca agattttgtt tctgcagact acttggcaat caaaagtgat cataaattta    4800
ggttatcagt tttcagaaag ttgctttgtg agaaaatttt gttagatata ttctcccaag    4860
catgcttttt gtggaaggtt ttcagccatt gccactgaat cagatgttaa aaatgaaggg    4920
aaaattgagt gtgcacacac acaactgttg tacactcatg attgcagttt ttagcttaag    4980
aaactttct accagttact gtgaatctga cttaaaatgt aaagtttcct catgataaaa      5040
taggaacaac atagaaatgg attgatgggg tgatctgagt tattgtatat aaaagttttt    5100
aaagaataga atgaacatca agctagatag gcaaaaattg acacattcag aacagctttt    5160
ttgactgcga agccaaaagt tgtcagaaac agcaaaagat cccttattat tacagagtat    5220
tttacgtagt ctctatttta aggagagaaa ttaaatagaa gggcttcatg catttagggg    5280
agggtgctaa aacttctcaa gttcgtcaaa cttacaggaa tacccaccat gatcattttc    5340
tctctaatta tgtataccac aaaattttca tctggccata ggaattcact ggtgggtgta    5400
aaattaatga ctaaagaaat taagtgacaa atacataaaa gaaacagact tgtggggata    5460
ttgtttttaag gtgtattaat tactcagtga tgataccact caatagggca tgccactact    5520
tttcttaaga tgctaattat gaagcagtgc tcacaggcat tttttaacta gcaaattagt    5580
agatggactt ttggggtctg tcacttttta aaagtattta agacttaaat tctattagca    5640
ccacagtctg ccttcagtaa tacacctaaa atattttca ggaccagaag cattcagttt      5700
gaaaatttgc agatgcaaac cagtattatt actaacgctc tgggtcaaag attaggtttt    5760
taatattaac agtagtctgg taaatattta gaagtctggc attgagaaac aaaagcttgt    5820
acctgactag tattttttatt taaaaaaatt agttctgtta gcttatttaa attgtgtttt    5880
atttatccgt agaatttata tttatttcat tcctttcatc tcactgaaaa ctgtctgcag    5940
```

```
gcccttttgat ttggattaga gtgtgaagt actgtctttt gccaaaaacc tcaaattacc    6000
tgttcttttc aacgtagtgg gtttgtgctt gtttggagat cagttcaaaa actatctgta    6060
ctatctgtac tgcctctgat gttaagattt tatgtatagc ataaggaagc tagctctgac    6120
tatattttcc taagaataaa gacctatttt tgtagcatgt cttaggatct ccaggagtcc    6180
aagaattatt gtgggtgtcc tccaattcat cactcttcac ttaacagctt ttaagtagac    6240
acttggaatc tttagaggtc tgtcgccctt tgattatcca tacattcgaa gtaactagcc    6300
aatggtgaaa aattcctcaa gatatcctca gttgcaatca cattactgga agatgaatag    6360
aataaatgta ttaggctggt cttaattttt gatggaaata ttctgttgtc ccgtacttgc    6420
cattggattt gataaagtta gtggtaattt ggaagaatc ggggacttgc caatatattt     6480
gtgggtttta gcttataccc ctaggatttc ttggttgcgg gacgagcagt tttggccact    6540
tccatcagga caagactttt taggtcactt agtgcaggtt ttagtttcta ttttggatta    6600
acaacattta tattgattat cgaaaagaag ctttcatcat ttcagaacag tcctggaagt    6660
ttgactttga gtgtgggaga agtcctaata aaccattttg gaaattaaaa aaaaaa       6716

<210> SEQ ID NO 6
<211> LENGTH: 7337
<212> TYPE: DNA
<213> ORGANISM: Homo sapiens

<400> SEQUENCE: 6
agcgcgggag agagaaagag aggagccgac tcggcaggga ctgggggacc gggccgagag      60
tgcgagcgag cgagggaggg agtgagggag cgtgcgagcc agaagggggaa aggcggccac    120 tcgtgcctga gcgaccgcag aggggagtgg gagcagtggg gtaaaggagc ggggggcggg    180
aataagaaag gccgagagaa ggcggacaga ggctagtggt ggtggtggtg gtaggggggag   240 aaggaggagc tggaggaggg caggggctga gggagtgagt gaagcggacg cgcgagggag    300
gggagggaag ggaagggaag ggaaggggg gtcacgcggg ggcgcgcgcg cgcaccggga     360
gcgcgctcgg aggcgagtgg aactggatcg ggtttgctgc cagcggcgtg agcttcggcc    420
gccattttac aacagctcca ctcgcgccgg acacagggag cagcgagcac gcgtttcccg    480
caacccgata ccatcggaca ggatttctcc gcctcagccc aacggggaga tctctggaaa    540
catggctaca gaacatgtta atggaaatgg tactgaagag cccatggata ctacttctgc    600
agttatccat tcagaaaatt ttcagacatt gcttgatgct ggtttaccac agaaagttgc    660
tgaaaaacta gatgaaattt acgttgcagg gctagttgca catagtgatt tagatgaaag    720
agctattgaa gctttaaaag aattcaatga agacggtgca ttggcagttc ttcaacagtt    780
taaagacagt gatctctctc atgttcagaa caaaagtgcc tttttatgtg gagtcatgaa    840
gacttacagg cagagagaaa acaagggac caaagtagca gattctagta aaggaccaga    900
tgaggcaaaa attaaggcac tcttggaaag aacaggctac acacttgatg tgaccactgg    960
acagaggaag tatggaggac cacctccaga ttccgtttat tcaggtcagc agccttctgt   1020
tggcactgag atatttgtgg gaaagatccc aagagatcta tttgaggatg aacttgttcc   1080
attatttgag aaagctggac ctatatggga tcttcgtcta atgatggatc cactcactgg   1140
tctcaataga ggttatgcgt ttgtcacttt ttgtacaaaa gaagcagctc aggaggctgt   1200
taaactgtat aataatcatg aaattcgttc tggaaaacat attggtgtct gcatctcagt   1260
tgccaacaat aggctttttg tgggctctat tcctaagagt aaaaccaagg aacagattct   1320
```

-continued

```
tgaagaattt agcaaagtaa cagagggtct tacagacgtc attttatacc accaaccgga      1380
tgacaagaaa aaaaacagag gcttttgctt tcttgaatat gaagatcaca aaacagctgc      1440
ccaggcaagg cgtaggttaa tgagtggtaa agtcaaggtc tgggggaatg ttggaactgt      1500
tgaatgggct gatcctatag aagatcctga tcctgaggtt atggcaaagg taaaagtgct      1560
gtttgtacgc aaccttgcca atactgtaac agaagagatt ttagaaaagg catttagtca      1620
gtttgggaaa ctggaacgag tgaagaagtt aaaagattat gcgttcattc attttgatga      1680
gcgagatggt gctgtcaagg ctatggaaga aatgaatggc aaagacttgg agggagaaaa      1740
tattgaaatt gttttttgcca agccaccaga tcagaaaagg aaagaaagaa agctcagag      1800 gcaagcagca aaaaatcaaa tgtatgacga ttactactat tatggtccac ctcatatgcc      1860
ccctccaaca agaggtcgag ggcgtggagg tagaggtggt tatggatatc ctccagatta      1920
ttatggatat gaagattatt atgattatta tggttatgat taccataact atcgtggtgg      1980
atatgaagat ccatactatg ttatgaagat ttttcaagtt ggagctagag gaaggggtgg      2040
tagaggagca agggtgctg ctccatccag aggtcgtggg gctgctcctc cccgcggtag      2100
agccggttat tcacagagag gaggtcctgg atcagcaaga ggcgttcgag gtgcgagagg      2160
aggtgcccaa caacaagag gccgcgggca gggaaaaggg gtcgaggccg gtcctgacct      2220
gttacaatga agactgactt gctatgtggg attacaccag aagcttgcag tggagtaatg      2280
gtaaggaaat caagcaacct taaatatgtc ggctgtatag gagcatattc tattgcagaa      2340
gaccttccta tgaagatcat ggaatcaaat acgggacatt gaactaatac ttggactttg      2400
atatgaattt ctttaacaat tttctctgca gtgcaagtta ttaaactaaa gctactctat      2460
tttcaaaatg tgttccaaca gaaatccttc ataactccta gcatggtatc ttaataaaga      2520
ataaagttct tttaaaaatc tgctctaagt agattttcc ccttttttaa attaaggatc      2580
ccaacagtgg tattttgaaa tattctcttg aatttgtgca tttaaatttt attgcagtgg      2640
tatagatgaa tgccactgat ggtatcctta aattttattt ctgctcacca aggttaatca      2700
tgattgtcta tatcttttt atagtgatca cttttgaatt gtgttcagat atgcagtttc      2760
aggtgtaatc atcagagctg gttagtcagg cattccagat agtggttctt ttcagaacct      2820
ttttaaaagg gttggttaac tacctcagta gcagaggatt gaactatacc ctgtctgtac      2880
tgtacataga aaatctttgt agataaaagc aaggcttgtt aaatatgata tgagggtaag      2940
attttaatat accaaatgta acattcttag ttgcctttag tttcagaggc ttgtaagact      3000
tcctcatgac catcataaca ggccttgctt tgtcgtatt tgtggctga aaaagcagcc      3060 ttgcttcttc agatattgta gttatttgga tgtataatag tttagcaaga tgttactttt      3120 gtaagcatc agatgttcaa aaaagtgcat ccgaacttgt actaaatact gcagtgtccc      3180
tttataaaaa gtcagactaa aactgacaat tgtacagcga agcctgacat ttggatattt      3240
tgaagttttt tcataaatca tagaaattag tatatggctg tagtttagct ttttaggtaa      3300
aaggtatgtt tcattagtgc atttcttcct gctgatcact gtaaacatgt gaatcagctt      3360
tccatttctt atgcaggtca tgataacttg tagagtagag tacaatcatt tgtgctatgt      3420
ttttaatttt ctaaagcacc ttgatgcacag tgagtgtcca gtggtgaagc atcctctatt      3480
gaaccaccct caaaaatttt tttgccaagt cctaagttga tagcttaaag taaaaagtga      3540
aaattatagt ttcattagga cttggtgtaa agaaatcccc tccccccttc cccaagggaa      3600
tactgcagtt atatcacata cccaataggc accacgatga agatcagagc ttatacttaa      3660
ttaaggtttt atacacacca gttccccagt aaatgcaaat ttaacaagaa aatcagacat      3720
```

```
gtcatatgtt caaaatgctc atggcaaaca atcattttgc attcctgcaa ataaaattgt    3780
tttatactgt aagctggagg cgagtgtaac ttattttgt aataaagttt ttattttttt    3840
tatgtgtcat taatataaat gtgtgttagt gtagaaatct tctggtttaa aaacttagaa    3900
ttgcacacat ttcagtatgt ttatttgtac ttacataatt ttagaatagt ggttgccaat    3960
agcctgtatg tttcacatta attggttttt tgttatctaa ataaatcatt ttagtatgtt    4020
gtatgtcagt tactgggata gctgggacat agagtgtaat ttaaaatttg tcaataagta    4080
ttcattggaa tatatgtaaa tgtgccttgc cggttattga aacttatcta caaaatgagt    4140
atggggtgac aaaaattagt tcctggtgct taatgaaact ttctgccact gattttatat    4200 attacccgt gcttttttaa agtacatctc tctcaaaact tagtgtaagt ttgagggcta    4260
cacaaaacat ttacatttca ttctaacata atgaatataa taggttgtgg aaagtgggta    4320
aactaaatgt agccttcagt aaaattgaat ctcagtgtaa tccttggtgc tggcatttct    4380
cagttccgag gagttaaatg atcccatcta agaggtcatt gccatgccta ttggcacttt    4440
actgtcatag catttttaag ggacactgtc aaggtgttta agttctcaga attacttgtt    4500
gggattttag gacaggtttg tttacttaaa gtaagaactg cattgtcaaa gttgaaagag    4560
gaacactttt gtgagttcac aaatgtgttc ttaagaaaac attaaaatat ggagctctgg    4620
gttttcaaga ctatttggca ttcttaattt ggggacttgg gagggaaact gataaaaaga    4680
aattgaagaa ttgatggtta tacttaaaga agggtaatgt aaacagtggt gatgaaatat    4740
atacacatca agtgaaatta cttgacagtg ttcatttgaa tgactttgaa ttcaagccat    4800
tataattact tttaaaatta aatatcattt gcactgttct gataatgggt gcagttttg    4860 agcaatataa tcagagctaa atatgcatgt agtgattagt gatgtgaaca attaacgttc    4920
tgagaagaaa tactaactgt ggtattttca aacttaaatt tctgtagtaa aatcagtatc    4980
aaagtcttat cagatcaagg aaaaacaggc aatgcatata aacatacttt tgaatgttgt    5040
gtggcctata aagcaataat gcaatttata tggaatgtca tgggatatga gaaatggaaa    5100
tgcaaaaata actaatcctt tagtaaaaat gtcaacatgt taagggggga atgttaacta    5160
atgtaggtta ttgctatttg tgatttgttt atgggttctt ggctttgaca gcttcaaaga    5220
atggacagtg ataagttaaa agaaattttg tatattgtca aggaaagggt cttaaatccg    5280
agtcaagtcc cttccttggg gtaaaaaatg tattcttaaa gcattctgat gttaaaaga    5340 aaacttaagt tatctaacca aaacagacgc aagattttgt ttctgcagac tacttggcaa    5400
tcaaaagtga tcataaattt aggttatcag ttttcagaaa gttgctttgt gagaaaattt    5460
tgttagatat attctcccaa gcatgctttt tgtggaaggt tttcagccat tgccactgaa    5520
tcagatgtta aaaatgaagg gaaaattgag tgtgcacaca cacaactgtt gtacactcat    5580
gattgcagtt tttagcttaa gaaacttttc taccagttac tgtgaatctg acttaaaatg    5640
taaagtttcc tcatgataaa ataggaacaa catagaaatg gattgatggg gtgatctgag    5700
ttattgtata taaaagtttt taaagaatag aatgaacatc aagctagata ggcaaaaatt    5760
gacacattca gaacagcttt tttgactgcg aagccaaaag ttgtcagaaa cagcaaaaga    5820
tcccttatta ttacagagta ttttacgtag tctctatttt aaggagagaa attaaataga    5880
agggcttcat gcatttaggg gagggtgcta aaacttctca agttcgtcaa acttacagga    5940
atacccacca tgatcatttt ctctctaatt atgtatacca caaaattttc atctggccat    6000
aggaattcac tggtgggtgt aaaattaatg actaaagaaa ttaagtgaca aatacataaa    6060
```

| | |
|---|---|
| agaaacagac ttgtggggat attgttttaa ggtgtattaa ttactcagtg atgataccac | 6120 |
| tcaatagggc atgccactac ttttcttaag atgctaatta tgaagcagtg ctcacaggca | 6180 |
| ttttttaact agcaaattag tagatggact tttggggtct gtcactttt aaaagtattt | 6240 |
| aagacttaaa ttctattagc accacagtct gccttcagta atacacctaa aatattttc | 6300 |
| aggaccagaa gcattcagtt tgaaaatttg cagatgcaaa ccagtattat tactaacgct | 6360 |
| ctgggtcaaa gattaggttt ttaatattaa cagtagtctg gtaaatattt agaagtctgg | 6420 |
| cattgagaaa caaaagcttg tacctgacta gtatttttat ttaaaaaaat tagttctgtt | 6480 |
| agcttattta aattgtgttt tatttatccg tagaatttat atttatttca ttcctttcat | 6540 |
| ctcactgaaa actgtctgca ggccctttga tttggattag atgtgtgaag tactgtcttt | 6600 |
| tgccaaaaac ctcaaattac ctgttctttt caacgtagtg ggtttgtgct tgtttggaga | 6660 |
| tcagttcaaa aactatctgt actatctgta ctgcctctga tgttaagatt ttatgtatag | 6720 |
| cataaggaag ctagctctga ctatattttc ctaagaataa agacctattt ttgtagcatg | 6780 |
| tcttaggatc tccaggagtc caagaattat tgtgggtgtc ctccaattca tcactcttca | 6840 |
| cttaacagct tttaagtaga cacttggaat ctttagaggt ctgtcgccct ttgattatcc | 6900 |
| atacattcga gtaactagc caatggtgaa aaattcctca agatatcctc agttgcaatc | 6960 |
| acattactgg aagatgaata gaataaatgt attaggctgg tcttaatttt tgatggaaat | 7020 |
| attctgttgt cccgtacttg ccattggatt tgataaagtt agtggtaatt tggaaagaat | 7080 |
| cggggacttg ccaatatatt tgtgggtttt agcttatacc cctaggattt cttggttgcg | 7140 |
| ggacgagcag ttttggccac ttccatcagg acaagacttt ttaggtcact tagtgcaggt | 7200 |
| tttagtttct attttggatt aacaacattt atattgatta tcgaaagaa gctttcatca | 7260 |
| tttcagaaca gtcctggaag tttgactttg agtgtgggag aagtcctaat aaaccatttt | 7320 |
| ggaaattaaa aaaaaaa | 7337 |

<210> SEQ ID NO 7
<211> LENGTH: 6774
<212> TYPE: DNA
<213> ORGANISM: Homo sapiens

<400> SEQUENCE: 7

| | |
|---|---|
| cggcgtgagc ttcggccgcc attttacaac agctccactc gcgccggaca cagggagcag | 60 |
| cgagcacgcg tttcccgcaa cccgatacca tcggacagga tttctccgcc tcagcccaac | 120 |
| ggggagggct agttgcacat agtgatttag atgaaagagc tattgaagct ttaaaagaat | 180 |
| tcaatgaaga cggtgcattg gcagttcttc aacagtttaa agacagtgat ctctctcatg | 240 |
| ttcagaacaa aagtgccttt ttatgtggag tcatgaagac ttacaggcag agagaaaaac | 300 |
| aagggaccaa agtagcagat tctagtaaag gaccagatga ggcaaaaatt aaggcactct | 360 |
| tggaaagaac aggctacaca cttgatgtga ccactggaca gaggaagtat ggaggaccac | 420 |
| ctccagattc cgtttattca ggtcagcagc cttctgttgg cactgagata tttgtgggaa | 480 |
| agatcccaag agatctattt gaggatgaac ttgttccatt atttgagaaa gctggaccta | 540 |
| tatgggatct tcgtcaatg atggatccac tcactggtct caatagaggt tatgcgtttg | 600 |
| tcactttttg tacaaaagaa gcagctcagg aggctgttaa actgtataat aatcatgaaa | 660 |
| ttcgttctgg aaaacatatt ggtgtctgca tctcagttgc caacaatagg cttttttgtgg | 720 |
| gctctattcc taagagtaaa accaaggaac agattcttga agaatttagc aaagtaacag | 780 |
| agggtcttac agacgtcatt ttataccacc aaccggatga caagaaaaaa aacagaggct | 840 |

-continued

```
tttgctttct tgaatatgaa gatcacaaaa cagctgccca ggcaaggcgt aggttaatga    900
gtggtaaagt caaggtctgg gggaatgttg aactgttga atgggctgat cctatagaag     960
atcctgatcc tgaggttatg gcaaaggtaa aagtgctgtt tgtacgcaac cttgccaata   1020
ctgtaacaga agagattta gaaaaggcat ttagtcagtt tgggaaactg aacgagtga    1080
agaagttaaa agattatgcg ttcattcatt ttgatgagcg agatggtgct gtcaaggcta   1140
tggaagaaat gaatggcaaa gacttggagg gagaaaatat tgaaattgtt tttgccaagc   1200
caccagatca gaaaaggaaa gaaagaaaag ctcagaggca agcagcaaaa aatcaaatgt   1260
atgacgatta ctactattat ggtccacctc atatgccccc tccaacaaga ggtcgagggc   1320
gtggaggtag aggtggttat ggatatcctc cagattatta tggatatgaa gattattatg   1380
attattatgg ttatgattac cataactatc gtggtggata tgaagatcca tactatggtt   1440
atgaagattt tcaagttgga gctagaggaa ggggtggtag aggagcaagg ggtgctgctc   1500
catccagagg tcgtggggct gctcctcccc gcggtagagc cggttattca cagagaggag   1560
gtcctggatc agcaagaggc gttcgaggtg cgagaggagg tgcccaacaa caaagaggcc   1620
gcggcaggga aaaggggtc gaggccggtc ctgacctgtt acaatgaaga ctgacttgct   1680
atgtgggatt acaccagaag cttgcagtgg agtaatggta aggaaatcaa gcaaccttaa   1740
atatgtcggc tgtataggag catattctat tgcagaagac cttcctatga agatcatgga   1800
atcaaatacg ggacattgaa ctaatacttg gactttgata tgaatttctt taacaatttt   1860
ctctgcagtg caagttatta aactaaagct actctatttt caaatgtgt tccaacagaa    1920
atccttcata actcctagca tggtatctta ataaagaata aagttctttt aaaaatctgc   1980
tctaagtaga ttttccccct tttttaaatt aaggatccca acagtggtat tttgaaatat   2040
tctcttgaat ttgtgcattt aaattttatt gcagtggtat agatgaatgc cactgatggt   2100
atccttaaat tttatttctg ctcaccaagg ttaatcatga ttgtctatat cttttttata   2160
gtgatcactt ttgaattgtg ttcagatatg cagtttcagg tgtaatcatc agagctggtt   2220
agtcaggcat tccagatagt ggttcttttc agaaccttt taaaagggtt ggttaactac    2280
ctcagtagca gaggattgaa ctatacctg tctgtactgt acatagaaaa tctttgtaga    2340
taaaagcaag gcttgttaaa tatgatatga gggtaagatt ttaatatacc aaatgtaaca   2400
ttcttagttg ccttagtttt cagaggcttg taagacttcc tcatgaccat cataacaggc   2460
cttgcttttg tcgtattttg tggctgaaaa agcagccttg cttcttcaga tattgtagtt   2520
atttggatgt ataatagttt agcaagatgt tacttttgta agacatcaga tgttcaaaaa   2580
agtgcatccg aacttgtact aaatactgca gtgtcccttt ataaaaagtc agactaaaac   2640
tgacaattgt acagcgaagc ctgacatttg gatattttga agtttttttca taaatcatag   2700
aaattagtat atggctgtag tttagctttt taggtaaaag gtatgtttca ttagtgcatt   2760
tcttcctgct gatcactgta acatgtgaa tcagctttcc atttcttatg caggtcatga    2820
taacttgtag agtagagtac aatcatttgt gctatgtttt taattttcta aagcaccttg   2880
atgacagtga gtgtccagtg gtgaagcatc ctctattgaa ccaccctcaa aaatttttt    2940
gccaagtcct aagttgatag cttaaagtaa aaagtgaaaa ttatagtttc attaggactt   3000
ggtgtaaaga aatcccctcc ccccttcccc aaagggatac tgcagttata tcacataccc   3060
aataggcacc acgatgaaga tcagagctta tacttaatta aggttttata cacaccagtt   3120
ccccagtaaa tgcaaattta acaagaaaat cagacatgtc atatgttcaa aatgctcatg   3180
```

-continued

```
gcaaacaatc attttgcatt cctgcaaata aaattgtttt atactgtaag ctggaggcga    3240
gtgtaactta ttttttgtaat aaagttttta tttttttttat gtgtcattaa tataaatgtg   3300
tgttagtgta gaaatcttct ggtttaaaaa cttagaattg cacacatttc agtatgttta    3360
tttgtactta cataatttta gaatagtggt tgccaatagc ctgtatgttt cacattaatt    3420
ggttttttgt tatctaaata aatcatttta gtatgttgta tgtcagttac tgggatagct    3480
gggacataga gtgtaattta aaatttgtca ataagtattc attggaatat atgtaaatgt    3540
gccttgccgg ttattgaaac ttatctacaa aatgagtatg gggtgacaaa aattagttcc    3600
tggtgcttaa tgaaactttc tgccactgat tttatatatt accccgtgct ttttaaagt     3660
acatctctct caaaacttag tgtaagtttg agggctacac aaaacattta catttcattc    3720
taacataatg aatataatag gttgtggaaa gtgggtaaac taaatgtagc cttcagtaaa    3780
attgaatctc agtgtaatcc ttggtgctgg catttctcag ttccgaggag ttaaatgatc    3840
ccatctaaga ggtcattgcc atgcctattg gcactttact gtcatagcat ttttaaggga    3900
cactgtcaag gtgtttaagt tctcagaatt acttgttggg attttaggac aggtttgttt    3960
acttaaagta agaactgcat tgtcaaagtt gaaagaggaa cacttttgtg agttcacaaa    4020
tgtgttctta agaaaacatt aaaatatgga gctctgggtt ttcaagacta tttggcattc    4080
ttaatttggg gacttgggag ggaaactgat aaaaagaaat tgaagaattg atggttatac    4140
ttaaagaagg gtaatgtaaa cagtggtgat gaaatatata cacatcaagt gaaattactt    4200
gacagtgttc atttgaatga ctttgaattc aagccattat aattactttt aaaattaaat    4260
atcatttgca ctgttctgat aatgggtgca gttttttgagc aatataatca gagctaaata  4320
tgcatgtagt gattagtgat gtgaacaatt aacgttctga aagaaatac taactgtggt    4380
attttcaaac ttaaatttct gtagtaaaat cagtatcaaa gtcttatcag atcaaggaaa    4440
aacaggcaat gcatataaac atacttttga atgttgtgtg gcctataaag caataatgca    4500
atttatatgg aatgtcatgg gatatgagaa atggaaatgc aaaaataact aatcctttag    4560
taaaaatgtc aacatgttaa agggggaatg ttaactaatg taggttattg ctatttgtga    4620
tttgtttatg ggttcttggc tttgacagct tcaaagaatg gacagtgata agttaaaaga    4680
aattttgtat attgtcaagg aaagggtctt aaatccgagt caagtcccctt ccttggggta   4740
aaaaatgtat tcttaaagca ttctgatgtt aaaaagaaaa cttaagttat ctaaccaaaa    4800
cagacgcaag attttgtttc tgcagactac ttggcaatca aaagtgatca taaatttagg   4860
ttatcagttt tcagaaagtt gctttgtgag aaaattttgt tagatatatt ctcccaagca   4920
tgcttttttgt ggaaggtttt cagccattgc cactgaatca gatgttaaaa atgaagggaa  4980
aattgagtgt gcacacacac aactgttgta cactcatgat tgcagttttt agcttaagaa   5040
acttttctac cagttactgt gaatctgact taaaatgtaa agtttcctca tgataaaata   5100
ggaacaacat agaaatggat tgatggggtg atctgagtta ttgtatataa agttttttaa   5160
agaatagaat gaacatcaag ctagataggc aaaaattgac acattcagaa cagctttttt   5220
gactgcgaag ccaaaagttg tcagaaacag caaaagatcc cttattatta cagagtattt   5280
tacgtagtct ctattttaag gagagaaatt aaatagaagg gcttcatgca tttaggggag   5340
ggtgctaaaa cttctcaagt tcgtcaaact tacaggaata cccaccatga tcattttctc    5400
tctaattatg tataccacaa aattttcatc tggccatagg aattcactgg tgggtgtaaa   5460
attaatgact aaagaaatta agtgacaaat acataaaaga aacagacttg tggggatatt    5520
gttttaaggt gtattaatta ctcagtgatg ataccactca atagggcatg ccactacttt   5580
```

```
tcttaagatg ctaattatga agcagtgctc acaggcattt tttaactagc aaattagtag    5640
atggactttt ggggtctgtc actttttaaa agtatttaag acttaaattc tattagcacc    5700
acagtctgcc ttcagtaata cacctaaaat attttcagg  accagaagca ttcagtttga    5760
aaatttgcag atgcaaacca gtattattac taacgctctg ggtcaaagat taggttttta    5820
atattaacag tagtctggta aatatttaga agtctggcat tgagaaacaa agcttgtac    5880 ctgactagta ttttattta  aaaaaattag ttctgttagc ttatttaaat tgtgttttat    5940
ttatccgtag aatttatatt tatttcattc ctttcatctc actgaaaact gtctgcaggc    6000
cctttgattt ggattagatg tgtgaagtac tgtcttttgc caaaaacctc aaattacctg    6060
ttcttttcaa cgtagtgggt ttgtgcttgt ttggagatca gttcaaaaac tatctgtact    6120
atctgtactg cctctgatgt taagatttta tgtatagcat aaggaagcta gctctgacta    6180
tattttccta agaataaaga cctatttttg tagcatgtct taggatctcc aggagtccaa    6240
gaattattgt gggtgtcctc caattcatca ctcttcactt aacagctttt aagtagacac    6300
ttggaatctt tagaggtctg tcgccctttg attatccata cattcgaagt aactagccaa    6360
tggtgaaaaa ttcctcaaga tatcctcagt tgcaatcaca ttactggaag atgaatagaa    6420
taaatgtatt aggctggtct taattttga  tggaaatatt ctgttgtccc gtacttgcca    6480
ttggatttga taaagttagt ggtaatttgg aaagaatcgg ggacttgcca atatatttgt    6540
gggttttagc ttatacccct aggatttctt ggttgcggga cgagcagttt tggccacttc    6600
catcaggaca agactttta  ggtcacttag tgcaggtttt agtttctatt ttggattaac    6660
aacatttata ttgattatcg aaaagaagct ttcatcattt cagaacagtc ctggaagttt    6720
gactttgagt gtgggagaag tcctaataaa ccatttggga aattaaaaaa aaaa          6774
```

<210> SEQ ID NO 8
<211> LENGTH: 6805
<212> TYPE: DNA
<213> ORGANISM: Homo sapiens

<400> SEQUENCE: 8

```
atctctggaa acatggctac agaacatgtt aatggaaatg gtactgaaga gcccatggat      60
actacttctg cagttatcca ttcagaaaat tttcagacat tgcttgatgc tggtttacca     120
cagaaagttg ctgaaaaact agatgaaatt tacgttgcag ggctagttgc acatagtgat     180
ttagatgaaa gagctattga agctttaaaa gaattcaatg aagacggtgc attggcagtt     240
cttcaacagt ttaaagacag tgatctctct catgttcaga acaaaagtgc cttttttatgt     300 ggagtcatga agacttacag gcagagagaa aaacaaggga ccaaagtagc agattctagt     360
aaaggaccag atgaggcaaa aattaaggca ctccttgaaa gaacaggcta cacacttgat     420
gtgaccactg gacagaggaa gtatggagga ccacctccag attccgttta ttcaggtcag     480
cagccttctg ttggcactga gatatttgtg ggaaagatcc aagagatct  atttgaggat     540 gaacttgttc cattatttga gaaagctgga cctatatggg atcttcgtct aatgatggat     600
ccactcactg gtctcaatag aggttatgcg tttgtcactt tttgtacaaa agaagcagct     660
caggaggctg ttaaactgta taataatcat gaaattcgtt ctggaaaaca tattggtgtc     720
tgcatctcag ttgccaacaa taggcttttt gtgggctcta ttcctaagag taaaaccaag     780
gaacagattc ttgaagaatt tagcaaagta acagagggtc ttacagacgt catttttatac     840 caccaaccgg atgacaagaa aaaaaacaga ggcttttgct ttcttgaata tgaagatcac     900
```

```
aaaacagctg cccaggcaag gcgtaggtta atgagtggta aagtcaaggt ctgggggaat    960
gttggaactg ttgaatgggc tgatcctata aagatcctg  atcctgaggt tatggcaaag   1020
gtaaaagtgc tgtttgtacg caaccttgcc aatactgtaa cagaagagat tttagaaaag   1080
gcatttagtc agtttgggaa actggaacga gtgaagaagt taaaagatta tgcgttcatt   1140
cattttgatg agcgagatgg tgctgtcaag gctatggaag aaatgaatgg caaagacttg   1200
gagggagaaa atattgaaat tgttttttgcc aagccaccag atcagaaaag gaaagaaaga   1260
aaagctcaga ggcaagcagc aaaaaatcaa atgtatgacg attactacta ttatggtcca   1320
cctcatatgc cccctccaac aagaggtcga gggcgtggag gtagaggtgg ttatggatat   1380
cctccagatt attatggata tgaagattat tatgattatt atggttatga ttaccataac   1440
tatcgtggtg gatatgaaga tccatactat ggttatgaag attttcaagt tggagctaga   1500
ggaaggggtg gtagaggagc aaggggtgct gctccatcca gaggtcgtgg ggctgctcct   1560
ccccgcggta gagccggtta ttcacagaga ggaggtcctg gatcagcaag aggcgttcga   1620
ggtgcgagag gaggtgccca acaacaaaga ggccgcgggg gaaaagggt  cgaggccggt   1680
cctgacctgt tacaatgaag actgacttgc tatgtgggat tacaccagaa gcttgcagtg   1740
gagtaatggt aaggaaatca agcaacctta aatatgtcgg ctgtatagga gcatattcta   1800
ttgcagaaga ccttcctatg aagatcatgg aatcaaatac gggacattga actaatactt   1860
ggactttgat atgaatttct ttaacaattt tctctgcagt gcaagttatt aaactaaagc   1920
tactctattt tcaaaatgtg ttccaacaga aatccttcat aactcctagc atggtatctt   1980
aataaagaat aaagttcttt taaaaatctg ctctaagtag atttttcccc tttttttaaat  2040
taaggatccc aacagtggta ttttgaaata ttctcttgaa tttgtgcatt taaatttat   2100
tgcagtggta tagatgaatg ccactgatgg tatccttaaa ttttatttct gctcaccaag   2160
gttaatcatg attgtctata tcttttttat agtgatcact tttgaattgt gttcagatat   2220
gcagtttcag gtgtaatcat cagagctggt tagtcaggca ttccagatag tggttctttt   2280
cagaaccttt ttaaaagggt tggttaacta cctcagtagc agaggattga actatacct   2340
gtctgtactg tacatagaaa atctttgtag ataaaagcaa ggcttgttaa atatgatatg   2400
agggtaagat tttaatatac caaatgtaac attcttagtt gcctttagtt tcagaggctt   2460
gtaagacttc ctcatgacca tcataacagg ccttgctttt gtcgtatttt gtggctgaaa   2520
aagcagcctt gcttcttcag atattgtagt tatttggatg tataatagtt tagcaagatg   2580
ttactttgt  aagacatcag atgttcaaaa aagtgcatcc gaacttgtac taaatactgc   2640
agtgtccctt tataaaaagt cagactaaaa ctgacaattg tacagcgaag cctgacattt   2700
ggatattttg aagttttttc ataaatcata gaaattagta tatggctgta gtttagcttt   2760
ttaggtaaaa ggtatgtttc attagtgcat ttcttcctgc tgatcactgt aaacatgtga   2820
atcagctttc catttcttat gcaggtcatg ataacttgta gagtagagta caatcatttg   2880
tgctatgttt ttaattttct aaagcacctt gatgacagta agtgtccagt ggtgaagcat   2940
cctctattga accaccctca aaattttttt tgccaagtcc taagttgata gcttaaagta   3000
aaaagtgaaa attatagttt cattaggact tggtgtaaag aaatcccctc ccccttccc   3060
caaagggata ctgcagttat atcacatacc caataggcac cacgatgaag atcagagctt   3120
atacttaatt aaggttttat acacaccagt tccccagtaa atgcaaattt aacaagaaaa   3180
tcagacatgt catatgttca aaatgctcat ggcaaacaat cattttgcat tcctgcaaat   3240
aaaattgttt tatactgtaa gctggaggcg agtgtaactt attttttgtaa taaagttttt   3300
```

```
attttttta tgtgtcatta atataaatgt gtgttagtgt agaaatcttc tggtttaaaa    3360
acttagaatt gcacacattt cagtatgttt atttgtactt acataatttt agaatagtgg    3420
ttgccaatag cctgtatgtt tcacattaat tggttttttg ttatctaaat aaatcattt     3480 agtatgttgt atgtcagtta ctgggatagc tgggacatag agtgtaattt aaaatttgtc    3540
aataagtatt cattggaata tatgtaaatg tgccttgccg gttattgaaa cttatctaca    3600
aaatgagtat ggggtgacaa aaattagttc ctggtgctta atgaaacttt ctgccactga    3660
ttttatatat taccccgtgc ttttttaaag tacatctctc tcaaaactta gtgtaagttt    3720
gagggctaca caaaacattt acatttcatt ctaacataat gaatataata ggttgtggaa    3780
agtgggtaaa ctaaatgtag ccttcagtaa aattgaatct cagtgtaatc cttggtgctg    3840
gcatttctca gttccgagga gttaaatgat cccatctaag aggtcattgc catgcctatt    3900
ggcactttac tgtcatagca ttttaaggg acactgtcaa ggtgtttaag ttctcagaat     3960
tacttgttgg gattttagga caggtttgtt tacttaaagt aagaactgca ttgtcaaagt    4020
tgaaagagga acacttttgt gagttcacaa atgtgttctt aagaaaacat taaaatatgg    4080
agctctgggt tttcaagact atttggcatt cttaatttgg ggacttggga gggaaactga    4140 taaaagaaa ttgaagaatt gatggttata cttaaagaag ggtaatgtaa acagtggtga     4200
tgaaatatat acacatcaag tgaaattact tgacagtgtt catttgaatg actttgaatt    4260
caagccatta taattacttt taaaattaaa tatcatttgc actgttctga taatgggtgc    4320 agttttgag caatataatc agagctaaat atgcatgtag tgattagtga tgtgaacaat     4380
taacgttctg agaagaaata ctaactgtgg tattttcaaa cttaaatttc tgtagtaaaa    4440
tcagtatcaa agtcttatca gatcaaggaa aaacaggcaa tgcatataaa catacttttg    4500
aatgttgtgt ggcctataaa gcaataatgc aatttatatg gaatgtcatg ggatatgaga    4560
aatggaaatg caaaaataac taatccttta gtaaaaatgt caacatgtta aaggggaat     4620 gttaactaat gtaggttatt gctatttgtg atttgtttat gggttcttgg ctttgacagc    4680
ttcaaagaat ggacagtgat aagttaaaag aaatttgta tattgtcaag gaaagggtct     4740
taaatccgag tcaagtccct tccttggggt aaaaaatgta ttcttaaagc attctgatgt    4800 taaaagaaa acttaagtta tctaaccaaa acagacgcaa gattttgttt ctgcagacta     4860
cttggcaatc aaagtgatc ataaatttag gttatcagtt ttcagaaagt tgctttgtga    4920
gaaaattttg ttagatatat tctcccaagc atgcttttg tggaaggttt tcagccattg     4980
ccactgaatc agatgttaaa aatgaaggga aaattgagtg tgcacacaca caactgttgt    5040
acactcatga ttgcagtttt tagcttaaga aacttttcta ccagttactg tgaatctgac    5100
ttaaaatgta agtttcctc atgataaaat aggaacaaca tagaaatgga ttgatgggt     5160 gatctgagtt attgtatata aaagttttta agaatagaa tgaacatcaa gctagatagg    5220 caaaattga cacattcaga acagcttttt tgactgcgaa gccaaagtt gtcagaaaca     5280 gcaaagatc ccttattatt acagagtatt ttacgtagtc tctattttaa ggagagaaat    5340
taaatagaag gcttcatgc atttagggga gggtgctaaa acttctcaag ttcgtcaaac     5400
ttacaggaat acccaccatg atcattttct ctctaattat gtataccaca aaattttcat    5460
ctggccatag gaattcactg gtgggtgtaa aattaatgac taaagaaatt aagtgacaaa    5520
tacataaaag aaacagactt gtggggatat tgttttaagg tgtattaatt actcagtgat    5580
gataccactc aatagggcat gccactactt ttcttaagat gctaattatg aagcagtgct    5640
```

| | |
|---|---|
| cacaggcatt ttttaactag caaattagta gatggacttt tggggtctgt cactttttaa | 5700 |
| aagtatttaa gacttaaatt ctattagcac cacagtctgc cttcagtaat acacctaaaa | 5760 |
| tattttcag gaccagaagc attcagtttg aaaatttgca gatgcaaacc agtattatta | 5820 |
| ctaacgctct gggtcaaaga ttaggttttt aatattaaca gtagtctggt aaatatttag | 5880 |
| aagtctggca ttgagaaaca aaagcttgta cctgactagt attttattt aaaaaaatta | 5940 |
| gttctgttag cttatttaaa ttgtgtttta tttatccgta gaatttatat ttatttcatt | 6000 |
| cctttcatct cactgaaaac tgtctgcagg ccctttgatt tggattagat gtgtgaagta | 6060 |
| ctgtcttttg ccaaaaacct caaattacct gttcttttca acgtagtggg tttgtgcttg | 6120 |
| tttggagatc agttcaaaaa ctatctgtac tatctgtact gcctctgatg ttaagatttt | 6180 |
| atgtatagca taaggaagct agctctgact atattttcct aagaataaag acctattttt | 6240 |
| gtagcatgtc ttaggatctc caggagtcca agaattattg tgggtgtcct ccaattcatc | 6300 |
| actcttcact taacagcttt taagtagaca cttggaatct ttagaggtct gtcgcccttt | 6360 |
| gattatccat acattcgaag taactagcca atggtgaaaa attcctcaag atatcctcag | 6420 |
| ttgcaatcac attactggaa gatgaataga ataaatgtat taggctggtc ttaattttttg | 6480 |
| atggaaatat tctgttgtcc cgtacttgcc attggatttg ataaagttag tggtaatttg | 6540 |
| gaaagaatcg gggacttgcc aatatatttg tgggttttag cttataccc taggatttct | 6600 |
| tggttgcggg acgagcagtt ttggccactt ccatcaggac aagactttt aggtcactta | 6660 |
| gtgcaggttt tagtttctat tttggattaa caacatttat attgattatc gaaaagaagc | 6720 |
| tttcatcatt tcagaacagt cctggaagtt tgactttgag tgtgggagaa gtcctaataa | 6780 |
| accatttttgg aaattaaaaa aaaaa | 6805 |

<210> SEQ ID NO 9
<211> LENGTH: 3194
<212> TYPE: DNA
<213> ORGANISM: Homo sapiens

<400> SEQUENCE: 9

| | |
|---|---|
| agcgcgggag agagaaagag aggagccgac tcggcaggga ctgggggacc gggccgagag | 60 |
| tgcgagcgag cgagggaggg agtgagggag cgtgcgagcc agaagggaa aggcggccac | 120 |
| tcgtgcctga cgaccgcag aggggagtgg gagcagtggg gtaaaggagc ggggggcggg | 180 |
| aataagaaag gccgagagaa ggcggacaga ggctagtggt ggtggtggtg gtaggggag | 240 |
| aaggaggagc tggaggaggg caggggctga gggagtgagt gaagcggacg cgcgagggac | 300 |
| gggagggaag ggaagggaag ggaaggggg gtcacgcggg ggcgcgcgcg cgcaccggga | 360 |
| gcgcgctcgg aggcgagtgg aactggatcg ggtttgctgc cagcggcgtg agcttcggcc | 420 |
| gccattttac aacagctcca ctcgcgccgg acacagggag cagcgagcac gcgtttcccg | 480 |
| caacccgata ccatcggaca ggatttctcc gcctcagccc aacggggaga tctctggaaa | 540 |
| catggctaca gaacatgtta atggaaatgg tactgaagag cccatggata ctacttctgc | 600 |
| agttatccat tcagaaaatt ttcagacatt gcttgatgct ggttttaccac agaaagttgc | 660 |
| tgaaaaacta gatgaaattt acgttgcagg gctagttgca catagtgatt tagatgaaag | 720 |
| agctattgaa gctttaaaag aattcaatga agacggtgca ttggcagttc ttcaacagtt | 780 |
| taaagacagt gatctctctc atgttcagaa caaaagtgcc ttttttatgtg gagtcatgaa | 840 |
| gacttacagg cagagagaaa acaagggac caaagtagca gattctagta aaggaccaga | 900 |
| tgaggcaaaa attaaggcac tcttggaaag aacaggctac acacttgatg tgaccactgg | 960 |

```
acagaggaag tatggaggac cacctccaga ttccgtttat tcaggtcagc agccttctgt    1020
tggcactgag atatttgtgg gaaagatccc aagagatcta tttgaggatg aacttgttcc    1080
attatttgag aaagctggac ctatatggga tcttcgtcta atgatggatc cactcactgg    1140
tctcaataga ggttatgcgt tgtcactttt ttgtacaaaa gaagcagctc aggaggctgt    1200
taaactgtat aataatcatg aaattcgttc tggaaaacat attggtgtct gcatctcagt    1260
tgccaacaat aggcttttg tgggctctat tcctaagagt aaaaccaagg aacagattct    1320
tgaagaattt agcaaagtaa cagagggtct tacagacgtc attttatacc accaaccgga    1380
tgacaagaaa aaaacagag gcttttgctt tcttgaatat aagatcaca aaacagctgc    1440 ccagcaagg cgtaggttaa tgagtggtaa agtcaaggtc tgggggaatg ttggaactgt    1500
tgaatgggct gatcctatag aagatcctga tcctgaggtt atggcaaagg taaaagtgct    1560
gtttgtacgc aaccttgcca atactgtaac agaagagatt ttagaaaagg catttagtca    1620
gtttgggaaa ctggaacgag tgaagaagtt aaaagattat gcgttcattc attttgatga    1680
gcgagatggt gctgtcaagg ctatggaaga aatgaatggc aaagacttgg agggagaaaa    1740
tattgaaatt gtttttgcca agccaccaga tcagaaaagg aaagaaagaa aagctcagag    1800
gcaagcagca aaaaatcaaa tgtatgacga ttactactat tatggtccac ctcatatgcc    1860
ccctccaaca agaggtcgag ggcgtggagg tagaggtggt tatggatatc ctccagatta    1920
ttatggatat gaagattatt atgattatta tggttatgat taccataact atcgtggtgg    1980
atatgaagat ccatactatg gttatgaaga ttttcaagtt ggagctagag aaggggtgg    2040 tagaggagca aggggtgctg ctccatccag aggtcgtggg gctgctcctc ccgcggtag    2100 agccggttat tcacagagag gaggtcctgg atcagcaaga ggcgttcgag gtgcgagagg    2160
aggtgcccaa caacaaagag gccgcggggt acgtggtgcg aggggtggcc gcggtggaaa    2220
tgtaggagga aagcgcaaag ctgatgggta caaccagcca gattccaagc ggcgccagac    2280
caataatcag aactggggct cccaacccat tgctcagcaa ccgctccaag gtggtgatca    2340
ttctggtaac tatggttaca aatctgaaaa ccaggagttt tatcaggata cttttgggca    2400
acagtggaag tagaaacagt agggcctctg taaaattgga gactgatagg ttgatcagaa    2460
actcacccta atctgaacg ggtgccgcta taatttgtga catctggcaa gatttccctt    2520
tatgtatata ttttaacaat ccgcttggac acgaacaaag ccacacttct aactgcttct    2580
ggcgaactga ttttattttt aattttttc aataaagata ttcttagata ctgaaagaaa    2640
tagttaatga gtttgcattt gtgcttgaga aaatttggct caagtccatt tggctgtagt    2700
gtcaacgatg tttccagtag tgtttagatt tggtgtcttc aaaggtagtt gattaaaacc    2760
aagtgtgtct ttaatatctt gtatcagaat aactttgtat gttaccaact taaattgcta    2820
gaataaggta aattgataca caactgctat ttttaattta gaactttgac ctaatttggg    2880
ttttcaaaac catttggct acttgtattc tttatgctgt tgtttatttc aataaaaaat    2940
tcacacctaa atgtatactt actaaaattg tgtttacaat tcgttttca caaaatttcc    3000 tgcaaatttg gttcaaattg tatagcatgt caaggccaat taagggtttt tgtgccttgt    3060
taattcttgt gtggaatatg tctgcacatt acacaacact gatttattgc agttttctgc    3120
ttctggttta aagtgctatt ttacaacaga cttcatgttc ccatcaaaaa taaaagata    3180 atacatgtag taag                                                     3194
```

<210> SEQ ID NO 10

<211> LENGTH: 6797
<212> TYPE: DNA
<213> ORGANISM: Homo sapiens

<400> SEQUENCE: 10

```
ctccactcgc gccggacaca gggagcagcg agcacgcgtt tcccgcaacc cgataccatc      60
ggacaggatt tctccgcctc agcccaacgg ggagatctct ggaaacatgg ctacagaaca     120
tgttaatgga aatggtactg aagagcccat ggatactact tctgcagtta tccattcaga     180
aaattttcag acattgcttg atgctggttt accacagaaa gttgctgaaa actagatga     240
aatttacgtt gcagggctag ttgcacatag tgatttagat gaaagagcta ttgaagcttt     300
aaaagaattc aatgaagacg gtgcattggc agttcttcaa cagtttaaag acagtgatct     360
ctctcatgtt cagaacaaaa gtgccttttt atgtggagtc atgaagactt acaggcagag     420
agaaaaacaa gggaccaaag tagcagattc tagtaaagga ccagatgagg caaaaattaa     480
ggcactcttg gaaagaacag gctacacact tgatgtgacc actggacaga ggaagtatgg     540
aggaccacct ccagattccg tttattcagg tcagcagcct tctgttggca ctgagatatt     600
tgtgggaaag atcccaagag atctatttga ggatgaactt gttccattat ttgagaaagc     660
tggacctata tgggatcttc gtctaatgat ggatccactc actggtctca atagaggtta     720
tgcgtttgtc actttttgta caaaagaagc agctcaggag gctgttaaac tgtataataa     780
tcatgaaatt cgttctggaa acatattggg tgtctgcatc tcagttgcca acaataggct     840
ttttgtgggc tctattccta agagtaaaac caaggaacag attcttgaag aatttagcaa     900
agtaacagag ggtcttacag acgtcatttt ataccaccaa ccggatgaca agaaaaaaaa     960
cagaggcttt tgcttcttg aatatgaaga tcacaaaaca gctgcccagg taaaagtgct    1020
gtttgtacgc aaccttgcca atactgtaac agaaagagatt ttagaaaagg catttagtca    1080
gtttgggaaa ctggaacgag tgaagaagtt aaaagattat gcgttcattc attttgatga    1140
gcgagatggt gctgtcaagg ctatggaaga aatgaatggc aaagacttgg agggagaaaa    1200
tattgaaatt gtttttgcca agccaccaga tcagaaaagg aaagaaagaa aagctcagag    1260
gcaagcagca aaaaatcaaa tgtatgacga ttactactat tatggtccac tcatatgcc    1320
ccctccaaca agaggtcgag ggcgtggagg tagaggtggt tatggatatc ctccagatta    1380
ttatggatat gaagattatt atgattatta tggttatgat taccataact atcgtggtgg    1440
atatgaagat ccatactatg gttatgaaga ttttcaagtt ggagctagag aaggggtgg    1500
tagaggagca aggggtgctg ctccatccag aggtcgtggg gctgctcctc cccgcggtag    1560
agccggttat tcacagagag aggtcctgg atcagcaaga ggcgttcgag gtgcgagagg    1620
aggtgcccaa caacaaagag gccgcgggca gggaaaaggg gtcgaggccg gtcctgacct    1680
gttacaatga agactgactt gctatgtggg attacaccag aagcttgcag tggagtaatg    1740
gtaaggaaat caagcaaccc taaatatgtc ggctgtatag gagcatattc tattgcagaa    1800
gaccttccta tgaagatcat ggaatcaaat acgggacatt gaactaatac ttggactttg    1860
atatgaattt ctttaacaat tttctctgca gtgcaagtta ttaaactaaa gctactctat    1920
tttcaaaatg tgttccaaca gaaatccttc ataactccta gcatggtatc ttaataaga    1980
ataaagttct tttaaaaatc tgctctaagt agattttcc ccttttttaa attaaggatc    2040
ccaacagtgg tattttgaaa tattctcttg aatttgtgca tttaaatttt attgcagtgg    2100
tatagatgaa tgccactgat ggtatcctta aatttattt ctgctcacca aggttaatca    2160
tgattgtcta tatcttttt atagtgatca cttttgaatt gtgttcagat atgcagtttc    2220
```

```
aggtgtaatc atcagagctg gttagtcagg cattccagat agtggttctt ttcagaacct    2280
ttttaaaagg gttggttaac tacctcagta gcagaggatt gaactatacc ctgtctgtac    2340
tgtacataga aaatctttgt agataaaagc aaggcttgtt aaatatgata tgagggtaag    2400
attttaatat accaaatgta acattcttag ttgcctttag tttcagaggc ttgtaagact    2460
tcctcatgac catcataaca ggccttgctt ttgtcgtatt ttgtggctga aaaagcagcc    2520
ttgcttcttc agatattgta gttatttgga tgtataatag tttagcaaga tgttactttt    2580
gtaagacatc agatgttcaa aaaagtgcat ccgaacttgt actaaatact gcagtgtccc    2640
tttataaaaa gtcagactaa aactgacaat tgtacagcga agcctgacat ttggatattt    2700
tgaagttttt tcataaatca tagaaattag tatatggctg tagtttagct ttttaggtaa    2760
aaggtatgtt tcattagtgc atttcttcct gctgatcact gtaaacatgt gaatcagctt    2820
tccatttctt atgcaggtca tgataacttg tagagtagag tacaatcatt tgtgctatgt    2880
ttttaatttt ctaaagcacc ttgatgacag tgagtgtcca gtggtgaagc atcctctatt    2940
gaaccaccct caaaaatttt tttgccaagt cctaagttga tagcttaaag taaaaagtga    3000
aaattatagt ttcattagga cttggtgtaa agaaatcccc tcccccttc cccaaaggga     3060
tactgcagtt atatcacata cccaataggc accacgatga agatcagagc ttatacttaa    3120
ttaaggtttt atacacacca gttccccagt aaatgcaaat ttaacaagaa aatcagacat    3180
gtcatatgtt caaaatgctc atggcaaaca atcattttgc attcctgcaa ataaaattgt    3240
tttatactgt aagctggagg cgagtgtaac ttatttttgt aataaagttt ttatttttt    3300
tatgtgtcat taatataaat gtgtgttagt gtagaaatct tctggtttaa aaacttagaa    3360
ttgcacacat ttcagtatgt ttatttgtac ttacataatt ttagaatagt ggttgccaat    3420
agcctgtatg tttcacatta attggttttt tgttatctaa ataaatcatt ttagtatgtt    3480
gtatgtcagt tactgggata gctgggacat agagtgtaat ttaaaatttg tcaataagta    3540
ttcattggaa tatatgtaaa tgtgccttgc cggttattga aacttatcta caaaatgagt    3600
atggggtgac aaaaattagt tcctggtgct taatgaaact ttctgccact gattttatat    3660
attacccgt gcttttttaa agtacatctc tctcaaaact tagtgtaagt ttgagggcta     3720
cacaaaacat ttcatttca ttctaacata atgaatataa taggttgtgg aaagtgggta     3780
aactaaatgt agccttcagt aaaattgaat ctcagtgtaa tccttggtgc tggcatttct    3840
cagttccgag gagttaaatg atcccatcta agaggtcatt gccatgccta ttggcacttt    3900
actgtcatag catttttaag ggacactgtc aaggtgttta agttctcaga attacttgtt    3960
gggattttag acaggtttg tttacttaaa gtaagaactg cattgtcaaa gttgaaagag     4020
gaacactttt gtgagttcac aaatgtgttc ttaagaaaac attaaaatat ggagctctgg    4080
gttttcaaga ctatttggca ttcttaattt ggggacttgg gagggaaact gataaaaaga    4140
aattgaagaa ttgatggtta tacttaaaga agggtaatgt aaacagtggt gatgaaatat    4200
atacacatca agtgaaatta cttgacagtg ttcatttgaa tgactttgaa ttcaagccat    4260
tataattact tttaaaatta aatatcattt gcactgttct gataatgggt gcagttttg     4320
agcaatataa tcagagctaa atatgcatgt agtgattagt gatgtgaaca attaacgttc    4380
tgagaagaaa tactaactgt ggtattttca aacttaaatt tctgtagtaa aatcagtatc    4440
aaagtcttat cagatcaagg aaaaacaggc aatgcatata aacatacttt tgaatgttgt    4500
gtggcctata aagcaataat gcaatttata tggaatgtca tgggatatga gaaatggaaa    4560
```

```
tgcaaaaata actaatcctt tagtaaaaat gtcaacatgt taaaggggga atgttaacta      4620
atgtaggtta ttgctatttg tgatttgttt atgggttctt ggctttgaca gcttcaaaga      4680
atggacagtg ataagttaaa agaaattttg tatattgtca aggaaagggt cttaaatccg      4740
agtcaagtcc cttccttggg gtaaaaaatg tattcttaaa gcattctgat gttaaaaaga      4800
aaacttaagt tatctaacca aaacagacgc aagattttgt ttctgcagac tacttggcaa      4860
tcaaaagtga tcataaattt aggttatcag ttttcagaaa gttgctttgt gagaaaattt      4920
tgttagatat attctcccaa gcatgctttt tgtggaaggt tttcagccat tgccactgaa      4980
tcagatgtta aaaatgaagg gaaaattgag tgtgcacaca cacaactgtt gtacactcat      5040
gattgcagtt tttagcttaa gaaacttttc taccagttac tgtgaatctg acttaaaatg      5100
taaagtttcc tcatgataaa ataggaacaa catagaaatg gattgatggg gtgatctgag      5160
ttattgtata taaaagttttt taaagaatag aatgaacatc aagctagata ggcaaaaatt      5220
gacacattca gaacagcttt tttgactgcg aagccaaaag ttgtcagaaa cagcaaaaga      5280
tcccttatta ttacagagta ttttacgtag tctctatttt aaggagagaa attaaataga      5340
agggcttcat gcatttaggg gagggtgcta aaacttctca agttcgtcaa acttacagga      5400
atacccacca tgatcatttt ctctctaatt atgtatacca caaaattttc atctggccat      5460
aggaattcac tggtgggtgt aaaattaatg actaaagaaa ttaagtgaca aatacataaa      5520
agaaacagac ttgtggggat attgttttaa ggtgtattaa ttactcagtg atgataccac      5580
tcaatagggc atgccactac ttttcttaag atgctaatta tgaagcagtg ctcacaggca      5640
ttttttaact agcaaattag tagatggact tttggggtct gtcactttt aaaagtattt       5700 aagacttaaa ttctattagc accacagtct gccttcagta atacacctaa atatttttc       5760 aggaccagaa gcattcagtt tgaaaatttg cagatgcaaa ccagtattat tactaacgct      5820
ctgggtcaaa gattaggttt ttaatattaa cagtagtctg gtaaatattt agaagtctgg      5880
cattgagaaa caaaagcttg tacctgacta gtatttttat ttaaaaaaat tagttctgtt      5940
agcttattta aattgtgttt tatttatccg tagaatttat attatttca ttcctttcat       6000 ctcactgaaa actgtctgca ggcccttga tttggattag atgtgtgaag tactgtcttt       6060
tgccaaaaac ctcaaattac ctgttctttt caacgtagtg ggtttgtgct tgtttggaga      6120
tcagttcaaa aactatctgt actatctgta ctgcctctga tgttaagatt ttatgtatag      6180
cataaggaag ctagctctga ctatatttc ctaagaataa agacctattt ttgtagcatg       6240
tcttaggatc tccaggagtc caagaattat tgtgggtgtc ctccaattca tcactcttca     6300
cttaacagct tttaagtaga cacttggaat ctttagaggt ctgtcgccct ttgattatcc      6360
atacattcga gtaactagc caatggtgaa aaattcctca agatatcctc agttgcaatc       6420
acattactgg aagatgaata gaataaatgt attaggctgg tcttaattt tgatggaaat       6480 attctgttgt cccgtacttg ccattggatt tgataaagtt agtggtaatt tggaaagaat      6540
cggggacttg ccaatatatt tgtgggtttt agcttatacc cctaggattt cttggttgcg      6600
ggacgagcag ttttggccac ttccatcagg acaagacttt ttaggtcact tagtgcaggt      6660
tttagtttct attttggatt aacaacattt atattgatta tcgaaaagaa gctttcatca      6720
tttcagaaca gtcctggaag tttgactttg agtgtgggag aagtcctaat aaaccatttt      6780
ggaaattaaa aaaaaaa                                                     6797
```

<210> SEQ ID NO 11
<211> LENGTH: 2560

<212> TYPE: DNA
<213> ORGANISM: Homo sapiens

<400> SEQUENCE: 11

| | | | | | |
|---|---|---|---|---|---|
| atctctggaa | acatggctac | agaacatgtt | aatggaaatg | gtactgaaga | gcccatggat | 60 |
| actacttctg | cagttatcca | ttcagaaaat | tttcagacat | tgcttgatgc | tggtttacca | 120 |
| cagaaagttg | ctgaaaaact | agatgaaatt | tacgttgcag | ggctagttgc | acatagtgat | 180 |
| ttagatgaaa | gagctattga | agctttaaaa | gaattcaatg | aagacggtgc | attggcagtt | 240 |
| cttcaacagt | ttaaagacag | tgatctctct | catgttcaga | acaaaagtgc | cttttttatgt | 300 |
| ggagtcatga | agacttacag | gcagagagaa | aaacaaggga | ccaaagtagc | agattctagt | 360 |
| aaaggaccag | atgaggcaaa | aattaaggca | ctcttggaaa | gaacaggcta | cacacttgat | 420 |
| gtgaccactg | gacagaggaa | gtatggagga | ccacctccag | attccgttta | ttcaggtcag | 480 |
| cagccttctg | ttggcactga | gatatttgtg | ggaaagatcc | caagagatct | atttgaggat | 540 |
| gaacttgttc | cattatttga | gaaagctgga | cctatatggg | atcttcgtct | aatgatggat | 600 |
| ccactcactg | gtctcaatag | aggttatgcg | tttgtcactt | tttgtacaaa | agaagcagct | 660 |
| caggaggctg | ttaaactgta | taataatcat | gaaattcgtt | ctggaaaaca | tattggtgtc | 720 |
| tgcatctcag | ttgccaacaa | taggcttttt | gtgggctcta | ttcctaagag | taaaaccaag | 780 |
| gaacagattc | ttgaagaatt | tagcaaagta | acagagggtc | ttacagacgt | catttttatac | 840 |
| caccaaccgg | atgacaagaa | aaaaaacaga | ggcttttgct | ttcttgaata | tgaagatcac | 900 |
| aaaacagctg | cccaggtaaa | agtgctgttt | gtacgcaacc | ttgccaatac | tgtaacagaa | 960 |
| gagattttag | aaaaggcatt | tagtcagttt | gggaaactgg | aacgagtgaa | gaagttaaaa | 1020 |
| gattatgcgt | tcattcattt | tgatgagcga | gatggtgctg | tcaaggctat | ggaagaaatg | 1080 |
| aatggcaaag | acttggaggg | agaaaatatt | gaaattgttt | ttgccaagcc | accagatcag | 1140 |
| aaaaggaaag | aaagaaaagc | tcagaggcaa | gcagcaaaaa | atcaaatgta | tgacgattac | 1200 |
| tactattatg | gtccacctca | tatgcccccct | ccaacaagag | gtcgagggcg | tggaggtaga | 1260 |
| ggtggttatg | gatatcctcc | agattattat | ggatatgaag | attattatga | ttattatggt | 1320 |
| tatgattacc | ataactatcg | tggtggatat | gaagatccat | actatggtta | tgaagatttt | 1380 |
| caagttggag | ctagaggaag | gggtggtaga | ggagcaaggg | gtgctgctcc | atccagaggt | 1440 |
| cgtgggggctg | ctcctccccg | cggtagagcc | ggttattcac | agagaggagg | tcctggatca | 1500 |
| gcaagaggcg | ttcgaggtgc | gagaggaggt | gcccaacaac | aaagaggccg | cggggtacgt | 1560 |
| ggtgcgaggt | gtgccgcgg | tggaaatgta | ggaggaaagc | gcaaagctga | tgggtacaac | 1620 |
| cagccagatt | ccaagcggcg | ccagaccaat | aatcagaact | ggggctccca | acccattgct | 1680 |
| cagcaaccgc | tccaaggtgg | tgatcattct | ggtaactatg | gttacaaatc | tgaaaaccag | 1740 |
| gagttttatc | aggatacttt | tgggcaacag | tggaagtaga | aacagtaggg | cctctgtaaa | 1800 |
| attggagact | gataggttga | tcagaaactc | accctaaatc | tgaacgggtg | ccgctataat | 1860 |
| ttgtgacatc | tggcaagatt | tcccttttatg | tatatatttt | aacaatccgc | ttggacacga | 1920 |
| acaaagccac | acttctaact | gcttctggcg | aactgatttt | atttttaatt | tttttcaata | 1980 |
| aagatattct | tagatactga | aagaaatagt | taatgagttt | gcatttgtgc | ttgagaaaat | 2040 |
| ttggctcaag | tccatttggc | tgtagtgtca | acgatgtttc | cagtagtgtt | tagatttggt | 2100 |
| gtcttcaaag | gtagttgatt | aaaaccaagt | gtgtctttaa | tatcttgtat | cagaataact | 2160 |
| ttgtatgtta | ccaacttaaa | ttgctagaat | aaggtaaatt | gatacacaac | tgctattttt | 2220 |

-continued

```
aatttagaac tttgacctaa tttgggtttt caaaaccatt ttggctactt gtattcttta      2280
tgctgttgtt tatttcaata aaaaattcac acctaaatgt atacttacta aaattgtgtt      2340
tacaattcgt ttttcacaaa atttcctgca aatttggttc aaattgtata gcatgtcaag      2400
gccaattaaa gggttttgtg ccttgttaat tcttgtgtgg aatatgtctg cacattacac      2460
aacactgatt tattgcagtt ttctgcttct ggtttaaagt gctatttac aacagacttc       2520 atgttcccat caaaaataaa aagataaatac atgtagtaag                           2560
```

<210> SEQ ID NO 12
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 12

```
nnnnnnnnnn nnnnnnnnnn gttttgtac tctcaagatt tagaaataaa tcttgcagaa       60
gctacaaaga taaggcttca tgccgaaatc aacaccctgt cattttatgg cagggtgttt      120
tcgttattta attttt                                                     137
```

<210> SEQ ID NO 13
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 13

```
nnnnnnnnnn nnnnnnnnnn gttttgtac tctcagaaat gcagaagcta caaagataag       60
gcttcatgcc gaaatcaaca ccctgtcatt ttatggcagg gtgttttcgt tatttaattt      120
ttt                                                                    123
```

<210> SEQ ID NO 14
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 14

```
nnnnnnnnnn nnnnnnnnnn gttttgtac tctcagaaat gcagaagcta caaagataag       60
gcttcatgcc gaaatcaaca ccctgtcatt ttatggcagg gtgttttttt                 110
```

<210> SEQ ID NO 15
<211> LENGTH: 102
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 16
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gttttagagc tagaaatagc aagttaaaat aaggctagtc    60
cgttatcaac ttgaaaaagt gttttttt                                       88

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc    60
cgttatcatt tttttt                                                    76

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcagcacaag aggctgttaa a                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcaaccttaa atatctcgga t                                              21

<210> SEQ ID NO 20

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcacatagtg atttagatga a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccaaagtagc agattctagt a                                              21
```